(12) United States Patent
Hatakeyama et al.

(10) Patent No.: US 11,460,773 B2
(45) Date of Patent: Oct. 4, 2022

(54) RESIST COMPOSITION AND PATTERNING PROCESS

(71) Applicant: Shin-Etsu Chemical Co., Ltd., Tokyo (JP)

(72) Inventors: Jun Hatakeyama, Joetsu (JP); Takayuki Fujiwara, Joetsu (JP); Masaki Ohashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 458 days.

(21) Appl. No.: 16/729,643

(22) Filed: Dec. 30, 2019

(65) Prior Publication Data
US 2020/0241417 A1  Jul. 30, 2020

(30) Foreign Application Priority Data

Jan. 25, 2019  (JP) .............. JP2019-010892

(51) Int. Cl.
| | | |
|---|---|---|
| *G03F 7/004* | (2006.01) |
| *G03F 7/039* | (2006.01) |
| *G03F 7/038* | (2006.01) |
| *C08F 220/18* | (2006.01) |
| *C08F 212/14* | (2006.01) |
| *C07C 49/175* | (2006.01) |
| *G03F 7/32* | (2006.01) |
| *G03F 7/16* | (2006.01) |
| *G03F 7/20* | (2006.01) |
| *G03F 7/38* | (2006.01) |

(52) U.S. Cl.
CPC .......... *G03F 7/0392* (2013.01); *C07C 49/175* (2013.01); *C08F 212/24* (2020.02); *C08F 220/1802* (2020.02); *C08F 220/1805* (2020.02); *G03F 7/0045* (2013.01); *G03F 7/0382* (2013.01); *G03F 7/162* (2013.01); *G03F 7/168* (2013.01); *G03F 7/2004* (2013.01); *G03F 7/2006* (2013.01); *G03F 7/2037* (2013.01); *G03F 7/322* (2013.01); *G03F 7/38* (2013.01)

(58) Field of Classification Search
CPC .................................................... C07C 49/175
See application file for complete search history.

(56) References Cited

U.S. PATENT DOCUMENTS

| 10,539,870 B2* | 1/2020 | Williams, III ........ C07C 269/04 |
| 11,281,101 B2* | 3/2022 | Hatakeyama ......... G03F 7/0392 |
| 2006/0147836 A1* | 7/2006 | Hatakeyama ......... G03F 7/0046 |
| | | 430/921 |

FOREIGN PATENT DOCUMENTS

| JP | 2001-194776 A | 7/2001 |
| JP | 2002-226470 A | 8/2002 |
| JP | 2002-363148 A | 12/2002 |
| JP | 2018-97356 A | 6/2018 |
| WO | 2008/066011 A1 | 6/2008 |

\* cited by examiner

Primary Examiner — Amanda C. Walke
(74) Attorney, Agent, or Firm — WHDA, LLP

(57) ABSTRACT

A resist composition comprising a base polymer and a quencher in the form of an amine compound having an iodized aromatic ring and a tertiary ester structure offers a high sensitivity and minimal LWR or improved CDU, independent of whether it is of positive or negative tone.

12 Claims, No Drawings

RESIST COMPOSITION AND PATTERNING PROCESS

CROSS-REFERENCE TO RELATED APPLICATION

This non-provisional application claims priority under 35 U.S.C. § 119(a) on Patent Application No. 2019-010892 filed in Japan on Jan. 25, 2019, the entire contents of which are hereby incorporated by reference.

TECHNICAL FIELD

This invention relates to a resist composition and a pattern forming process.

BACKGROUND ART

To meet the demand for higher integration density and operating speed of LSIs, the effort to reduce the pattern rule is in rapid progress. In particular, the enlargement of the logic memory market to comply with the wide-spread use of smart phones drives forward the miniaturization technology. As the advanced miniaturization technology, manufacturing of microelectronic devices at the 10-nm node by double patterning of the ArF immersion lithography has been implemented in a mass scale. Manufacturing of 7-nm node devices as the next generation by the double patterning technology is approaching to the verge of high-volume application. The candidate for 5-nm node devices as the next generation but one is EUV lithography.

As the pattern feature size is reduced, approaching to the diffraction limit of light, light contrast lowers. In the case of positive resist film, a lowering of light contrast leads to reductions of resolution and focus margin of hole and trench patterns. For mitigating the influence of reduced resolution of resist pattern due to a lowering of light contrast, an attempt is made to enhance the dissolution contrast of resist film.

Chemically amplified resist compositions comprising an acid generator capable of generating an acid upon exposure to light or EB include chemically amplified positive resist compositions wherein deprotection reaction takes place under the action of acid and chemically amplified negative resist compositions wherein polarity switch or crosslinking reaction takes place under the action of acid. Quenchers are often added to these resist compositions for the purpose of controlling the diffusion of the acid to unexposed region to improve the contrast. The addition of quenchers is fully effective to this purpose. A number of amine quenchers were proposed as disclosed in Patent Documents 1 to 3.

With respect to the acid labile group used in (meth) acrylate polymers for the ArF lithography resist material, deprotection reaction takes place when a photoacid generator capable of generating a sulfonic acid having fluorine substituted at α-position (referred to "α-fluorinated sulfonic acid") is used, but not when an acid generator capable of generating to a sulfonic acid not having fluorine substituted at α-position (referred to "α-non-fluorinated sulfonic acid") or carboxylic acid is used. If a sulfonium or iodonium salt capable of generating an α-fluorinated sulfonic acid is combined with a sulfonium or iodonium salt capable of generating an α-non-fluorinated sulfonic acid, the sulfonium or iodonium salt capable of generating an α-non-fluorinated sulfonic acid undergoes ion exchange with the α-fluorinated sulfonic acid. Through the ion exchange, the α-fluorinated sulfonic acid thus generated by light exposure is converted back to the sulfonium or iodonium salt while the sulfonium or iodonium salt of an α-non-fluorinated sulfonic acid or carboxylic acid functions as a quencher. Patent Document 4 discloses a resist composition comprising a sulfonium or iodonium salt capable of generating carboxylic acid as a quencher.

Patent Document 5 discloses a resist composition comprising an iodized aniline as a quencher. The aniline has a low basicity which is insufficient to suppress acid diffusion.

Sulfonium and iodonium salt type quenchers are photo-decomposable like photoacid generators. That is, the amount of quencher in the exposed region is reduced. Since acid is generated in the exposed region, the reduced amount of quencher leads to a relatively increased concentration of acid and hence, an improved contrast. However, the acid diffusion in the exposed region is not suppressed, indicating the difficulty of acid diffusion control.

Lowering the PEB temperature is effective for suppressing acid diffusion. However, the dissolution contrast is reduced, inviting degradations of resolution and LWR. There is the need for a resist composition of new concept featuring controlled acid diffusion and a high contrast.

CITATION LIST

Patent Document 1: JP-A 2001-194776
Patent Document 2: JP-A 2002-226470
Patent Document 3: JP-A 2002-363148
Patent Document 4: WO 2008/066011
Patent Document 5: JP-A 2018-097356

DISCLOSURE OF INVENTION

For the acid-catalyzed chemically amplified resist, it is desired to develop a quencher capable of reducing the LWR of line patterns or the CDU of hole patterns and improving sensitivity. To this end, it is necessary to reduce the distance of acid diffusion significantly and to increase the contrast at the same time, that is, to improve ambivalent properties at the same time.

An object of the invention is to provide a resist composition which exhibits a high sensitivity and a reduced LWR or improved CDU, independent of whether it is of positive tone or negative tone; and a pattern forming process using the same.

The inventors have found that using an amine compound having an iodized aromatic ring and a tertiary ester structure as the quencher, a resist material having a reduced LWR, improved CDU, high contrast, improved resolution, and wide process margin is obtainable.

In one aspect, the invention provides a resist composition comprising a base polymer and a quencher, the quencher containing at least one compound selected from amine compounds having the formula (A-1) and amine compounds having the formula (A-2).

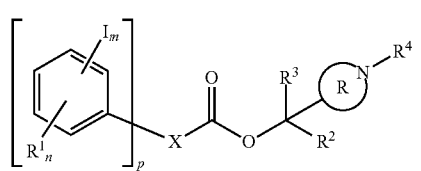

-continued

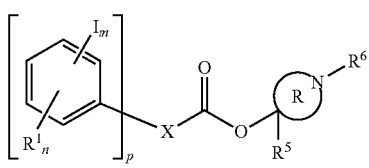
(A-2)

Herein X is a single bond or a $C_1$-$C_{20}$ divalent linking group which may contain an ether bond, carbonyl moiety, ester bond, amide bond, sultone ring, lactam ring, carbonate bond, halogen, hydroxyl moiety or carboxyl moiety. $R^1$ is hydrogen, hydroxyl, an optionally halo-substituted $C_1$-$C_6$ alkyl group, optionally halo-substituted $C_1$-$C_6$ alkoxy group, optionally halo-substituted $C_2$-$C_6$ acyloxy group, optionally halo-substituted $C_1$-$C_4$ alkylsulfonyloxy group, fluorine, chlorine, bromine, amino, nitro, cyano, —$NR^{1A}$—C(=O)—$R^{1B}$, or —$NR^{1A}$—C(=O)—O—$R^{1B}$, $R^{1A}$ is hydrogen or a $C_1$-$C_6$ alkyl group, $R^{1B}$ is a $C_1$-$C_6$ alkyl group or $C_2$-$C_8$ alkenyl group. $R^2$ and $R^3$ are each independently a $C_1$-$C_6$ alkyl group, $R^2$ and $R^3$ may bond together to form a ring with the carbon atom to which they are attached. $R^4$ and $R^6$ are each independently hydrogen, a $C_1$-$C_4$ straight or branched alkyl group, $C_2$-$C_{12}$ straight or branched alkoxycarbonyl group. $C_6$-$C_{15}$ aryloxycarbonyl group, or $C_6$-$C_{14}$ aralkyloxycarbonyl group. $R^5$ is a $C_1$-$C_6$ alkyl group, $C_2$-$C_6$ alkenyl group, $C_2$-$C_6$ alkynyl group, or $C_6$-$C_{12}$ aryl group. R is a $C_2$-$C_{10}$ alicyclic group to form a ring with the nitrogen atom, m is an integer of 1 to 5, n is an integer of 0 to 4, and 1≤m+n≤5, and p is 1 or 2.

The resist composition may further comprise an acid generator capable of generating a sulfonic acid, imide acid or methide acid, and an organic solvent.

In a preferred embodiment, the base polymer comprises recurring units having the formula (a1) or recurring units having the formula (a2).

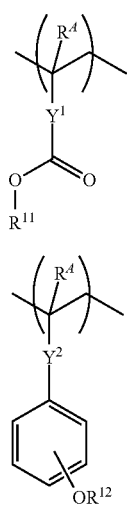

Herein $R^A$ is each independently hydrogen or methyl, $R^{11}$ and $R^{12}$ each are an acid labile group, $Y^1$ is a single bond, phenylene group, naphthylene group, or $C_1$-$C_{12}$ linking group containing at least one moiety selected from ester bond and lactone ring, and $Y^2$ is a single bond or ester bond.

Typically, the resist composition is a chemically amplified positive resist composition.

In another embodiment, the base polymer is free of an acid labile group. Typically, the resist composition is a chemically amplified negative resist composition.

The resist composition may further comprise a surfactant.

In a preferred embodiment, the base polymer further comprises recurring units of at least one type selected from recurring units having the formulae (f1) to (f3).

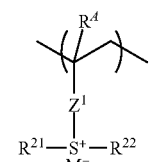
(f1)

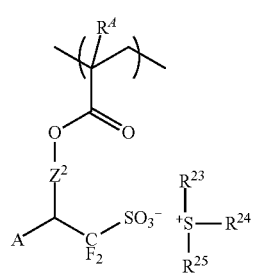
(f2)

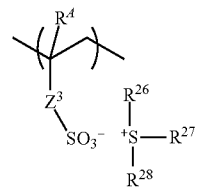
(f3)

Herein $R^A$ is each independently hydrogen or methyl. $Z^1$ is a single bond, phenylene group, —O—$Z^{11}$—, —C(=O)—O—$Z^{11}$— or —C(=O)—NH—$Z^{11}$—, $Z^{11}$ is a $C_1$-$C_6$ alkanediyl group, $C_2$-$C_6$ alkenediyl group, or phenylene group, which may contain a carbonyl, ester bond, ether bond or hydroxyl moiety. $Z^2$ is a single bond, —$Z^{21}$—C(=O)—O—, —$Z^{21}$—O— or —$Z^{21}$—O—C(=O)—, $Z^{21}$ is a $C_1$-$C_{12}$ alkanediyl group which may contain a carbonyl moiety, ester bond or ether bond. $Z^3$ is a single bond, methylene, ethylene, phenylene, fluorinated phenylene, —O—$Z^{31}$—, —C(=O)—O—$Z^{31}$—, or —C(=O)—NH—$Z^{31}$—, $Z^{31}$ is a $C_1$-$C_6$ alkanediyl group, $C_2$-$C_6$ alkenediyl group, phenylene group, fluorinated phenylene group, or trifluoromethyl-substituted phenylene group, which may contain a carbonyl moiety, ester bond, ether bond or hydroxyl moiety. $R^{21}$ to $R^{28}$ are each independently a $C_1$-$C_{20}$ monovalent hydrocarbon group which may contain a heteroatom, any two of $R^{23}$, $R^{24}$ and $R^{25}$ or any two of $R^{26}$, $R^{27}$ and $R^{28}$ may bond together to form a ring with the sulfur atom to which they are attached. "A" is hydrogen or trifluoromethyl. $M^-$ is a non-nucleophilic counter ion.

In another aspect, the invention provides a process for forming a pattern comprising the steps of applying the resist composition defined herein to form a resist film on a substrate, exposing the resist film to high-energy radiation, and developing the exposed resist film in a developer.

Typically, the high-energy radiation is ArF excimer laser radiation of wavelength 193 nm, KrF excimer laser radiation of wavelength 248 nm, EB, or EUV of wavelength 3 to 15 nm.

Advantageous Effects of Invention

The amine compound having an iodized aromatic ring is fully absorptive to EUV due to iodine, has a sensitizing effect, and is quite effective for suppressing acid diffusion by virtue of the large atomic weight of iodine. Since the amine compound also has an acid-decomposable tertiary ester structure, it is decomposed with acid in the exposed region and converted to an amine compound having a lower molecular weight. As a result, the acid in the exposed region becomes more active and the contrast is improved. There are obtained advantages including low diffusion, high contrast, high sensitivity, low LWR, and improved CDU. Thus a resist composition having a high sensitivity, low LWR and improved CDU is designed.

DESCRIPTION OF EMBODIMENTS

As used herein, the singular forms "a," "an" and "the" include plural referents unless the context clearly dictates otherwise. The notation ($C_n$-$C_m$) means a group containing from n to m carbon atoms per group. As used herein, the term "iodized" compound means an iodine-substituted compound. In chemical formulae, Me stands for methyl, and Ac for acetyl.

The abbreviations and acronyms have the following meaning.
EB: electron beam
EUV: extreme ultraviolet
Mw: weight average molecular weight
Mn: number average molecular weight
Mw/Mn: molecular weight dispersity
GPC: gel permeation chromatography
PEB: post-exposure bake
PAG: photoacid generator
LWR: line width roughness
CDU: critical dimension uniformity Resist Composition The resist composition of the invention is defined as comprising a base polymer and a quencher containing an amine compound having an iodized aromatic ring and a tertiary ester structure.

Amine Compound

The quencher contains an amine compound having an iodized aromatic ring and a tertiary ester structure. Specifically the amine compound has the formula (A-1) or (A-2).

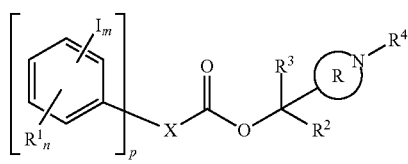

(A-1)

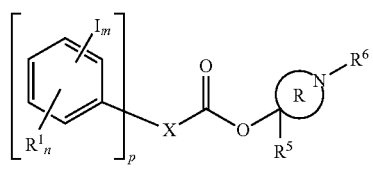

(A-2)

In formulae (A-1) and (A-2), X is a single bond or a $C_1$-$C_{20}$ divalent linking group. The divalent linking group may be straight, branched or cyclic. Examples include straight or branched alkanediyl groups such as methylene, ethylene, propane-1,2-diyl, propane-1,3-diyl, butane-1,2-diyl, butane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, and dodecane-1,12-diyl; $C_3$-$C_{20}$ divalent saturated cyclic hydrocarbon groups such as cyclopentanediyl, cyclohexanediyl, norbornanediyl, and adamantanediyl; $C_2$-$C_{20}$ divalent unsaturated aliphatic hydrocarbon groups such as vinylene and propene-1,3-diyl; $C_6$-$C_{20}$ divalent aromatic hydrocarbon groups such as phenylene and naphthylene; and mixtures thereof. The divalent linking group may contain an ether bond, carbonyl moiety, ester bond, amide bond, sultone ring, lactam ring, carbonate bond, halogen, hydroxyl moiety or carboxyl moiety.

In formulae (A-1) and (A-2), $R^1$ is hydrogen, hydroxyl, an optionally halo-substituted $C_1$-$C_6$ alkyl group, optionally halo-substituted $C_1$-$C_6$ alkoxy group, optionally halo-substituted $C_2$-$C_6$ acyloxy group, optionally halo-substituted $C_1$-$C_4$ alkylsulfonyloxy group, fluorine, chlorine, bromine, amino, nitro, cyano, —$NR^{1A}$—C(=O)—$R^{1B}$, or —$NR^{1A}$—C(=O)—O—$R^{1B}$, wherein $R^{1A}$ is hydrogen or a $C_1$-$C_6$ alkyl group, and $R^{1B}$ is a $C_1$-$C_6$ alkyl group or $C_2$-$C_5$ alkenyl group.

The $C_1$-$C_6$ alkyl group may be straight, branched or cyclic, and examples thereof include methyl, ethyl, n-propyl, isopropyl, cyclopropyl, n-butyl, isobutyl, sec-butyl, tert-butyl, cyclobutyl, n-pentyl, cyclopentyl, n-hexyl, and cyclohexyl. Examples of the alkyl moiety in the $C_1$-$C_6$ alkoxy, $C_2$-$C_6$ acyloxy or $C_1$-$C_4$ alkylsulfonyloxy group are as exemplified above for the alkyl group of 1 to 6, 1 to 5, or 1 to 4 carbon atoms.

The $C_2$-$C_8$ alkenyl group may be straight, branched or cyclic, and examples thereof include vinyl, 1-propenyl, 2-propenyl, butenyl, hexenyl and cyclohexenyl.

Among others, $R^1$ is preferably fluorine, chlorine, bromine, hydroxyl, amino, $C_1$-$C_3$ alkyl, $C_1$-$C_3$ alkoxy, $C_2$-$C_4$ acyloxy, —$NR^{1A}$—C(=O)—$R^{1B}$ or —$NR^{1A}$—C(=O)—O—$R^{1B}$. When m is 2 or more, a plurality of groups $R^1$ may be the same or different.

In formulae (A-1) and (A-2), $R^2$ and $R^3$ are each independently a $C_1$-$C_6$ alkyl group, $R^2$ and $R^3$ may bond together to form a ring with the carbon atom to which they are attached. $R^4$ and $R^6$ are each independently hydrogen, a $C_1$-$C_4$ straight or branched alkyl group, $C_2$-$C_{12}$ straight or branched alkoxycarbonyl group, $C_6$-$C_{15}$ aryloxycarbonyl group, or $C_6$-$C_{14}$ aralkyloxycarbonyl group. $R^5$ is a $C_1$-$C_6$ alkyl group, $C_2$-$C_6$ alkenyl group, $C_2$-$C_6$ alkynyl group, or $C_6$-$C_{12}$ aryl group.

The $C_1$-$C_6$ alkyl and $C_2$-$C_6$ alkenyl groups may be straight, branched or cyclic, and examples thereof are as exemplified above. Examples of the $C_1$-$C_4$ straight or branched alkyl group include those exemplified above which are straight or branched and have 1 to 4 carbon atoms. The $C_2$-$C_6$ alkynyl group may be straight, branched or cyclic and examples thereof include ethynyl, propynyl, and butynyl. Examples of the $C_6$-$C_{12}$ aryl group include phenyl, tolyl, xylyl, 1-naphthyl and 2-naphthyl.

Examples of the $C_2$-$C_{12}$ straight or branched alkoxycarbonyl group include methoxycarbonyl, ethoxycarbonyl, n-propyloxycarbonyl, isopropyloxycarbonyl, n-butyloxycarbonyl, isobutyloxycarbonyl, sec-butyloxycarbonyl, tert-butyloxycarbonyl, n-pentyloxycarbonyl, sec-pentyloxycarbonyl, tert-pentyloxycarbonyl, neopentyloxycarbonyl, n-hexyloxycarbonyl, n-heptyloxycarbonyl, n-octyloxycarbonyl, 2-ethylhexyloxycarbonyl, n-nonyloxycarbonyl, n-decyloxycarbonyl, n-undecyloxycarbonyl, n-dodecyloxycarbonyl, n-tridecyloxycarbonyl, n-pentadecyloxycarbonyl, vinyloxycarbonyl, 1-propenyloxycarbonyl, and 2-propenyloxycarbonyl.

Among others, $R^2$ and $R^3$ are preferably $C_1$-$C_3$ alkyl groups. $R^5$ is preferably a $C_1$-$C_6$ alkyl, $C_2$-$C_4$ alkenyl, or $C_2$-$C_4$ alkynyl group. $R^4$ and $R^6$ are preferably hydrogen, $C_1$-$C_4$ straight or branched alkyl groups, or $C_2$-$C_6$ straight or branched alkoxycarbonyl groups.

In formulae (A-1) and (A-2), R is a $C_2$-$C_{10}$ alicyclic group to form a ring with the nitrogen atom in the formula. Examples of the ring R include cyclic hydrocarbons such as cyclopropane, cyclopentane, cyclohexane, norbornane and adamantane, in which one carbon atom is replaced by nitrogen atom.

In formulae (A-1) and (A-2), m is an integer of 1 to 5, n is an integer of 0 to 4, and $1 \leq m+n \leq 5$, preferably m is an integer of 2 to 4 and n is 0 or 1; and p is 1 or 2.

Examples of the amine compound having formula (A-1) are shown below, but not limited thereto.

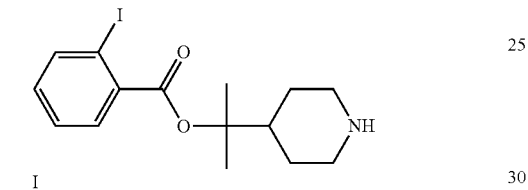

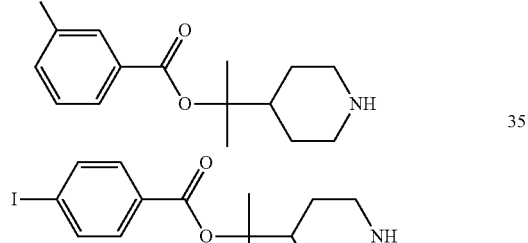

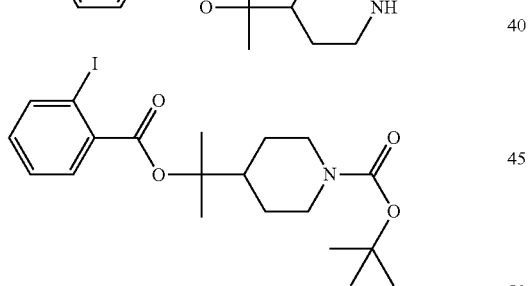

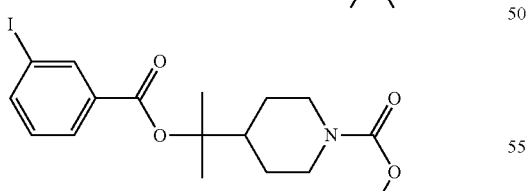

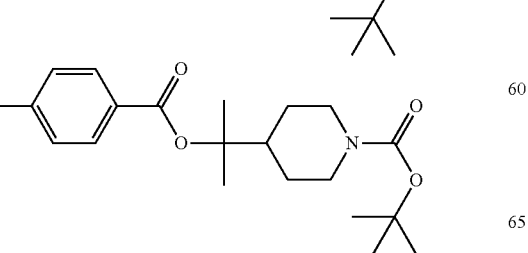

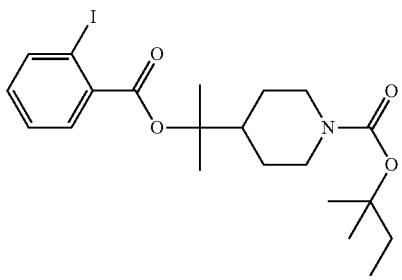

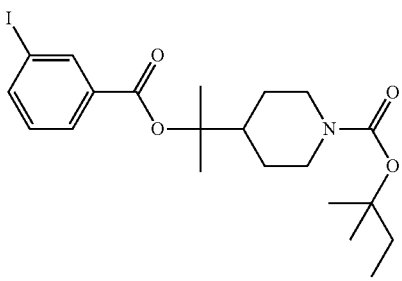

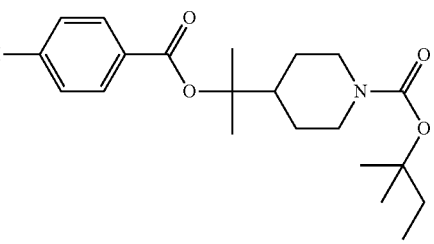

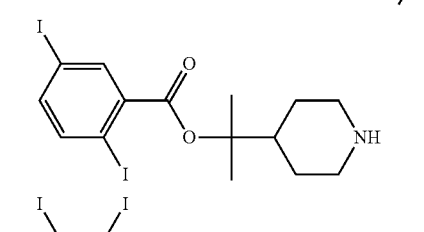

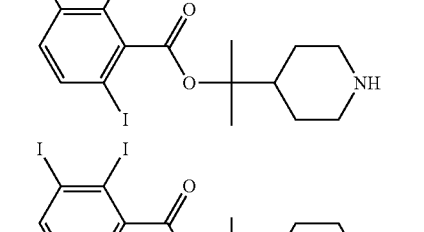

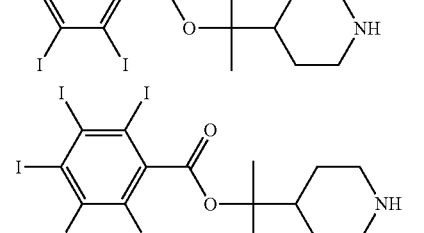

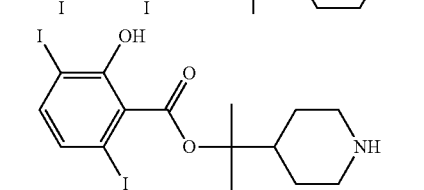

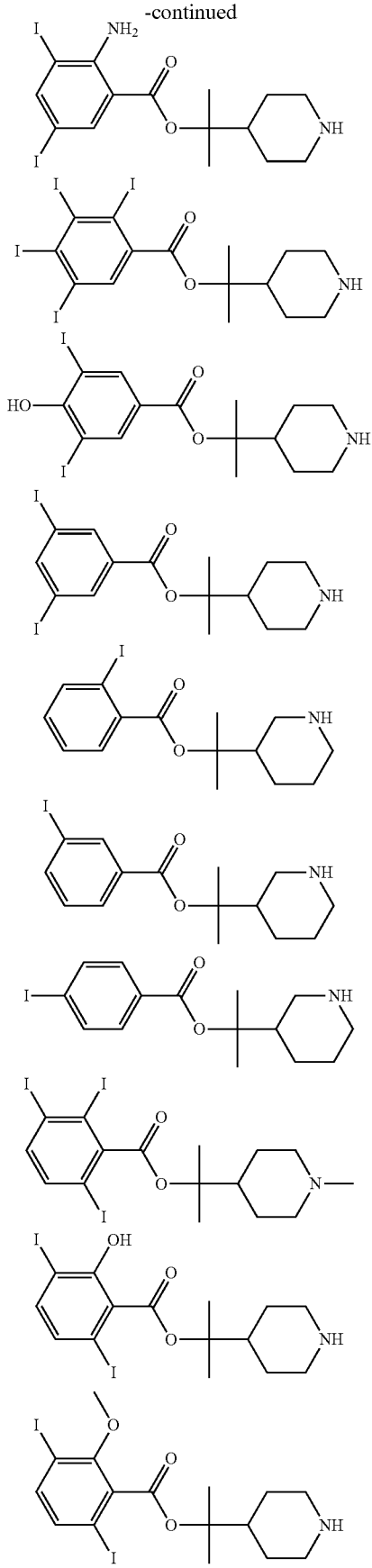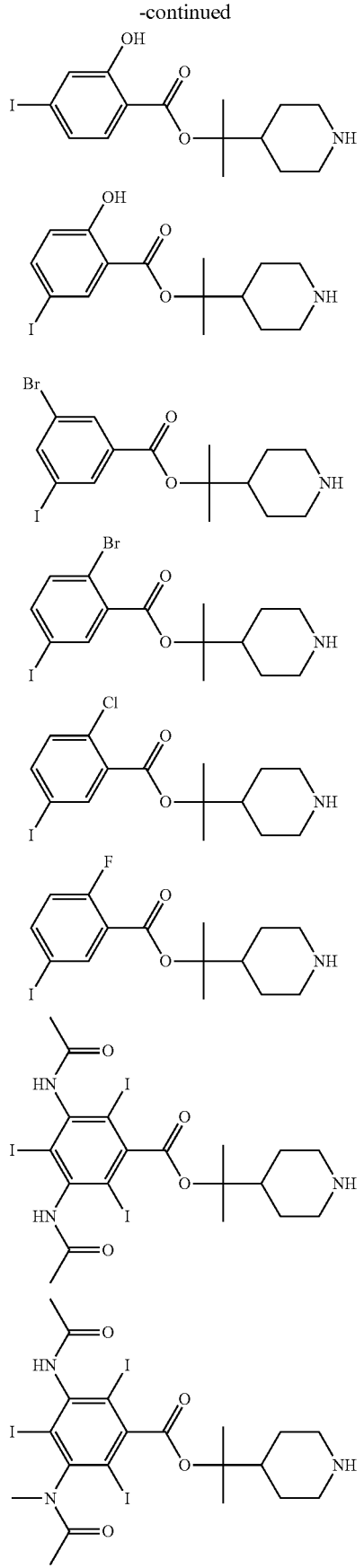

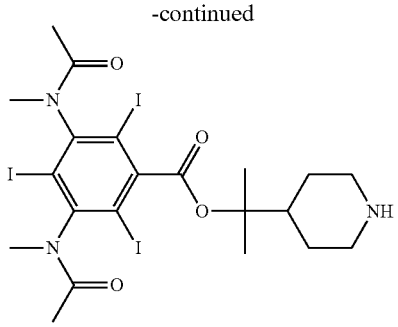
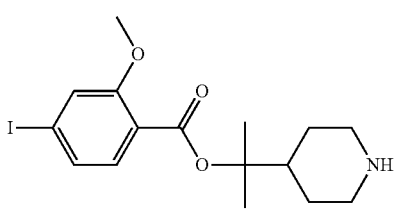
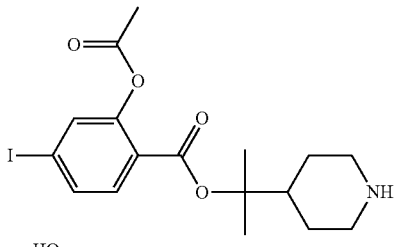
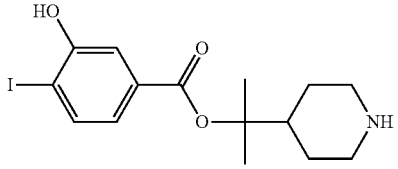
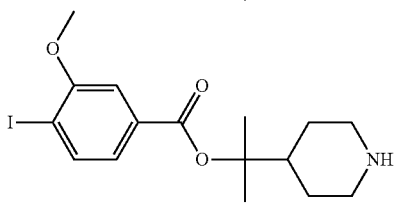
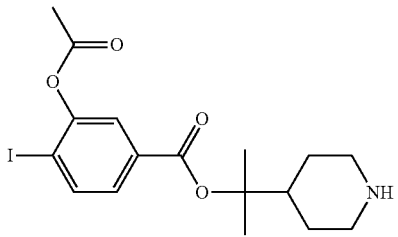
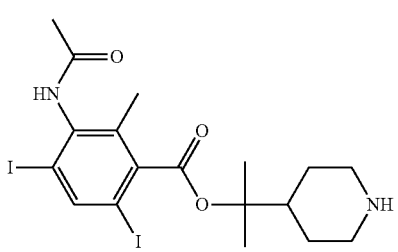
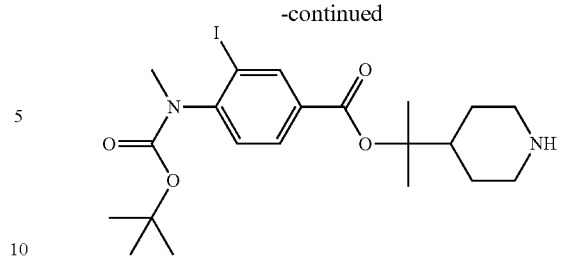
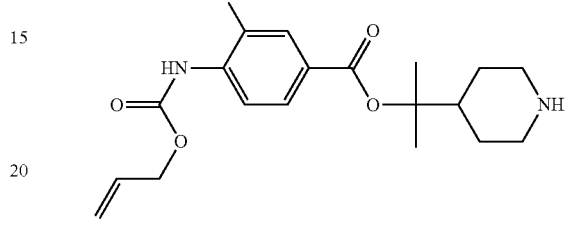
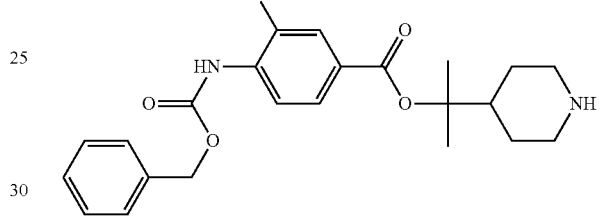
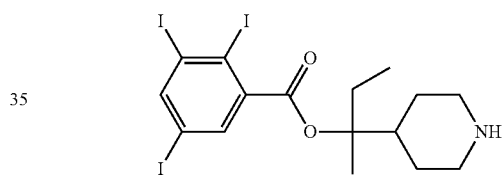
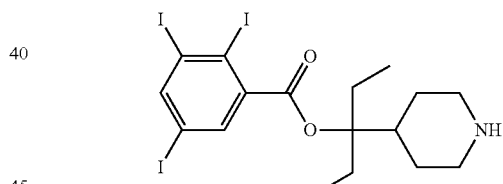
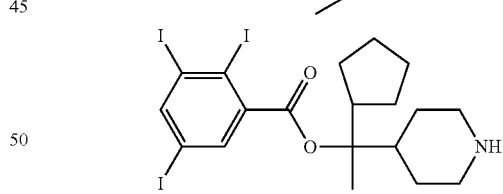
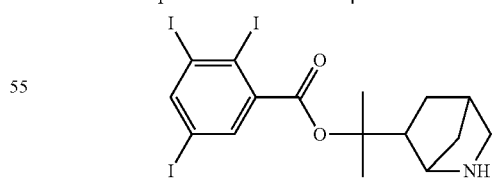
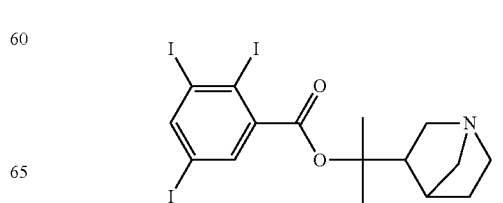

-continued
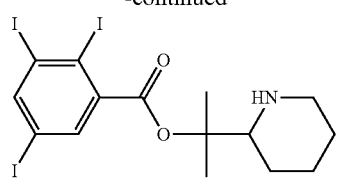
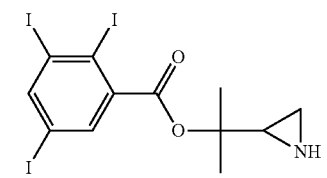
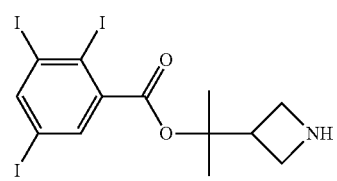
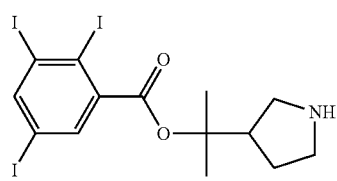
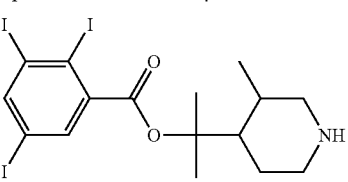
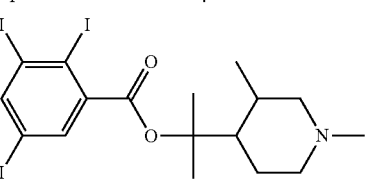
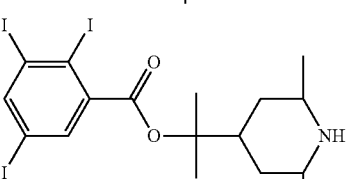
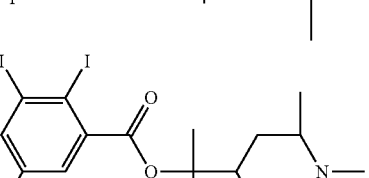
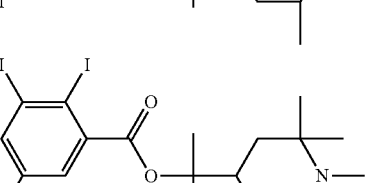
-continued
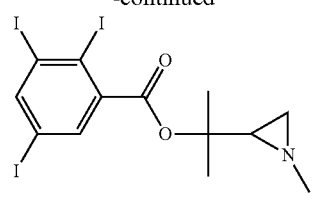
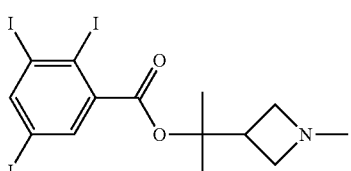
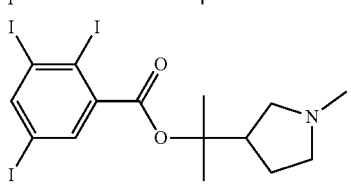
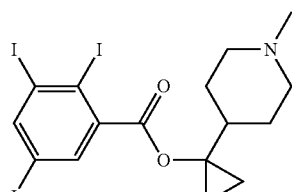
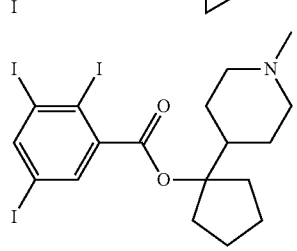
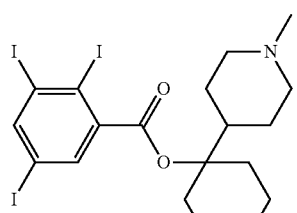
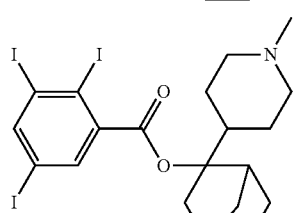
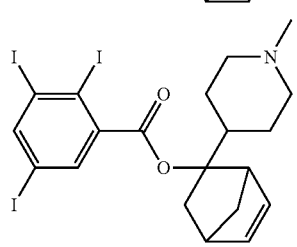

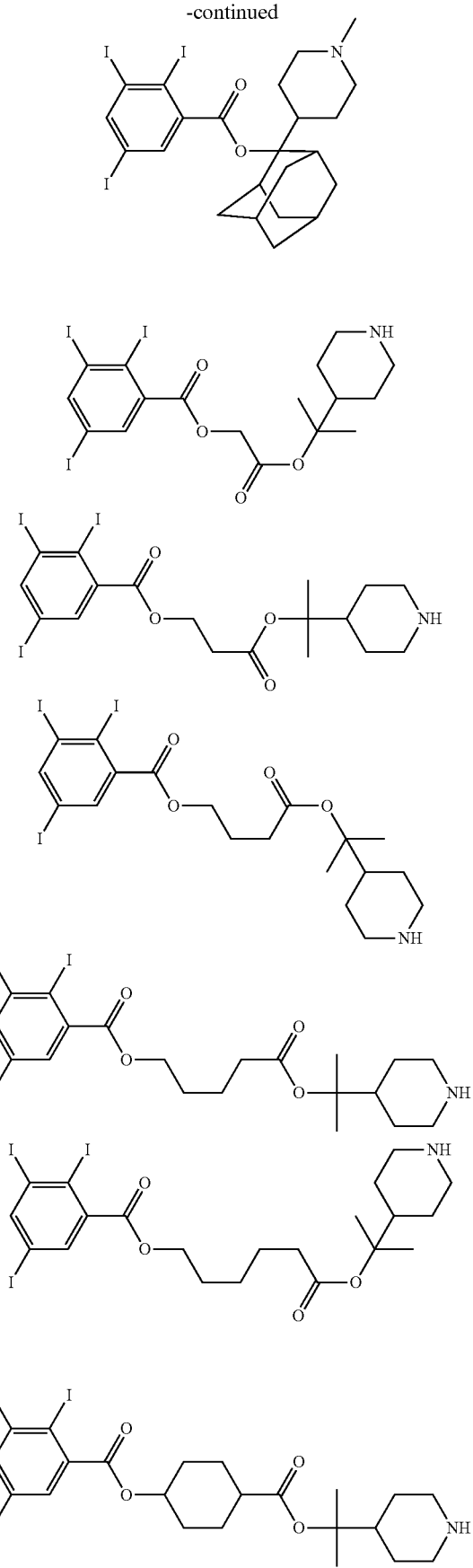

17
-continued
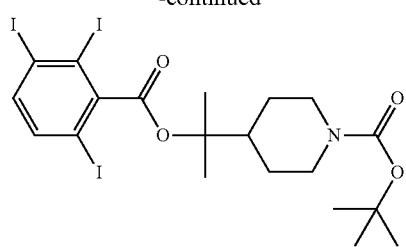
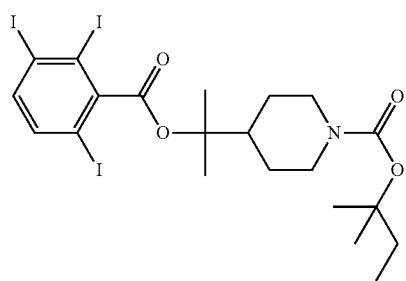
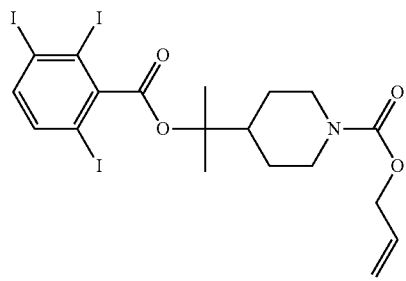
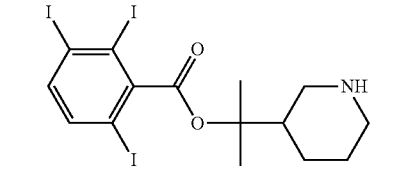
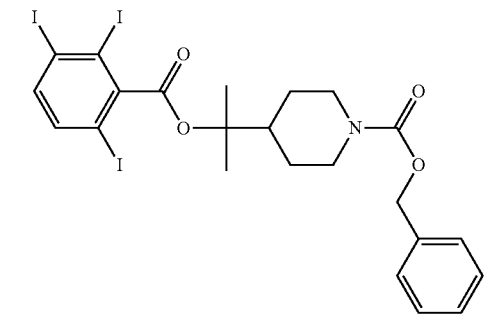
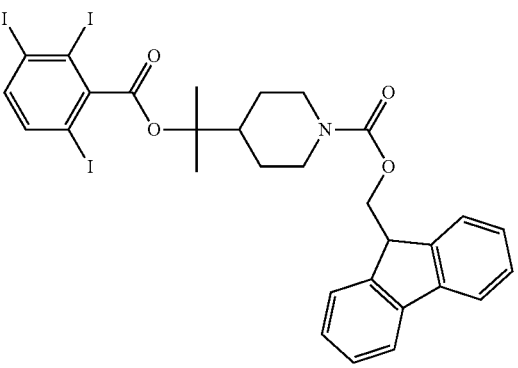
18
-continued
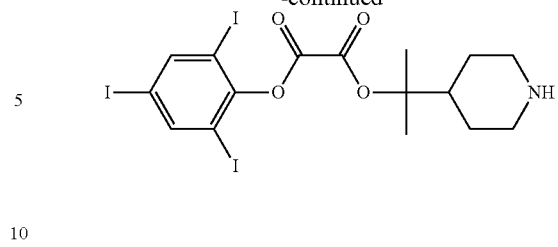
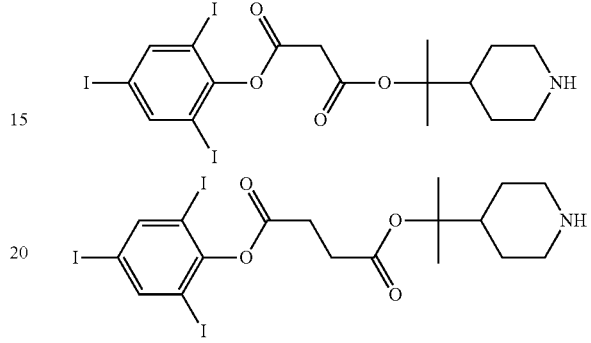
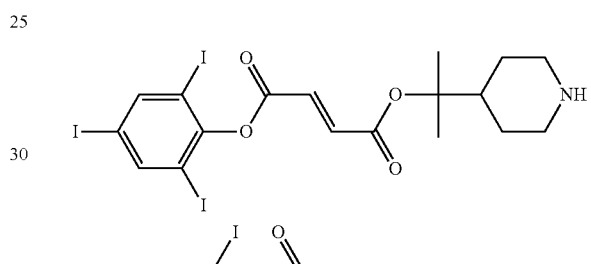
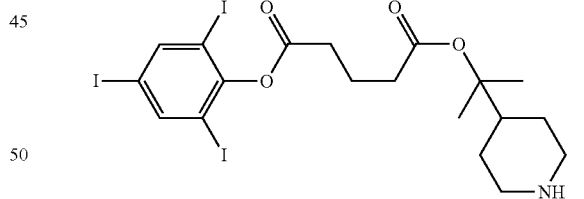
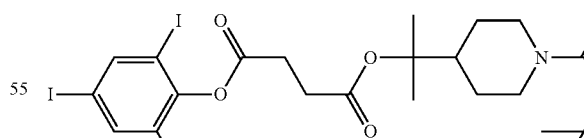
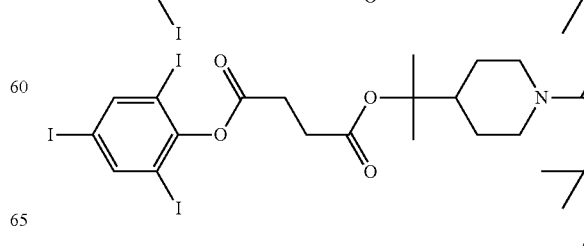

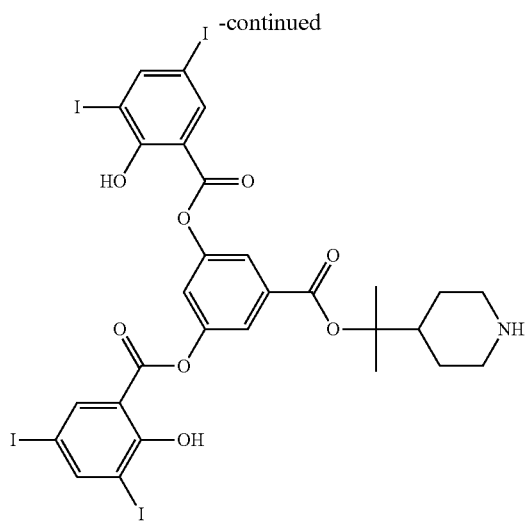
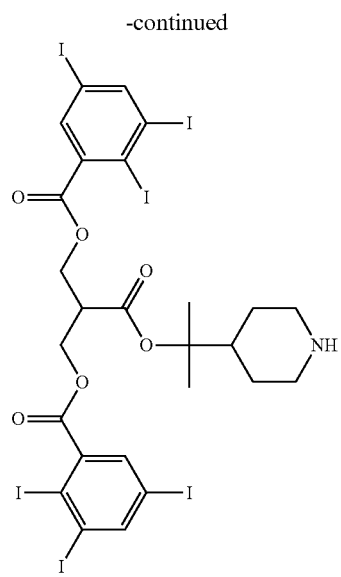
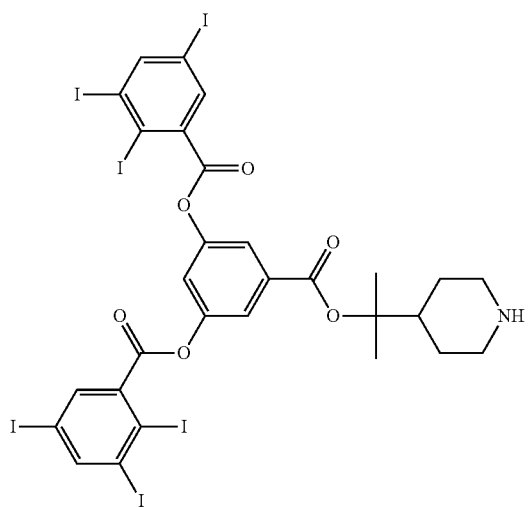
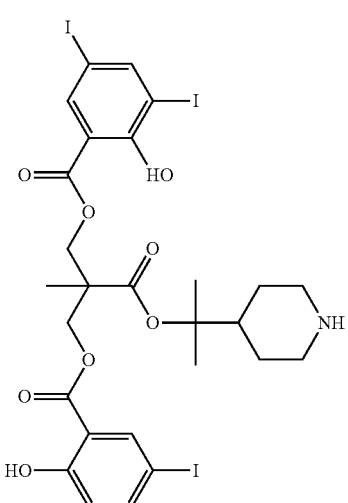
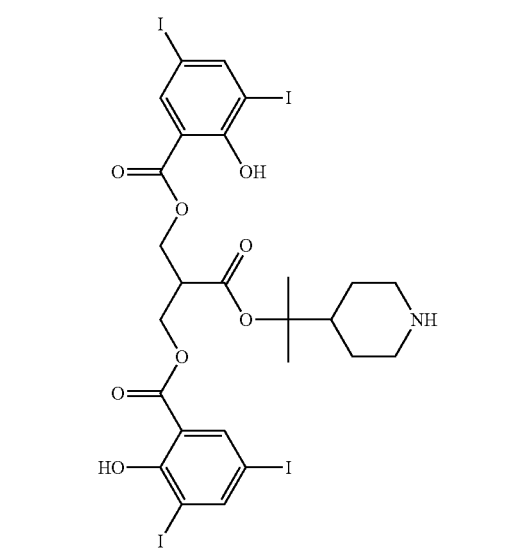
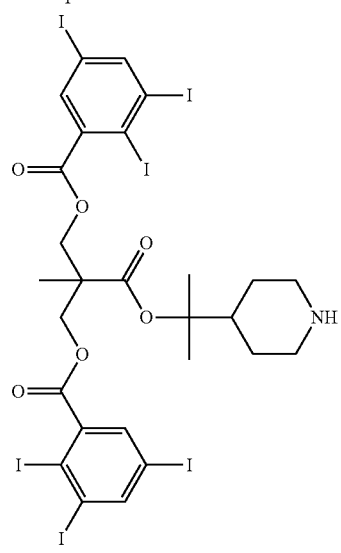

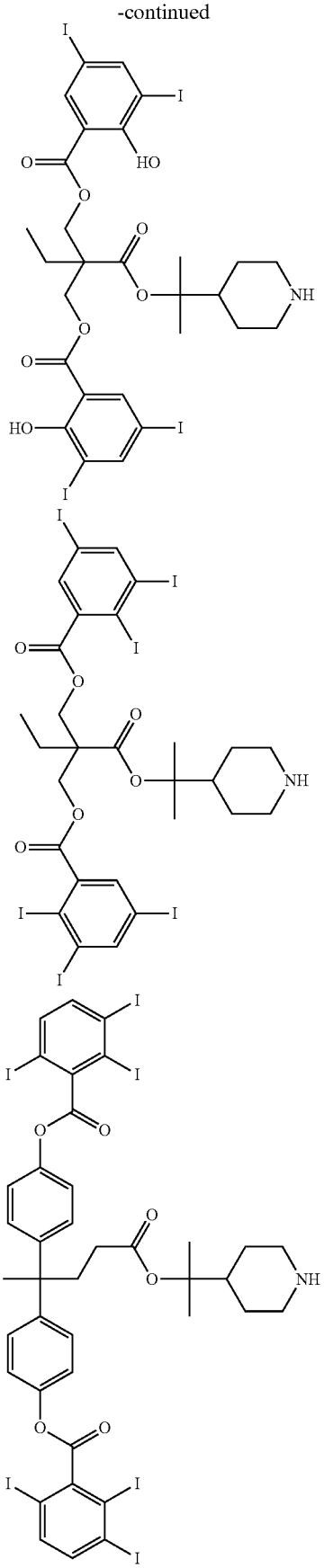
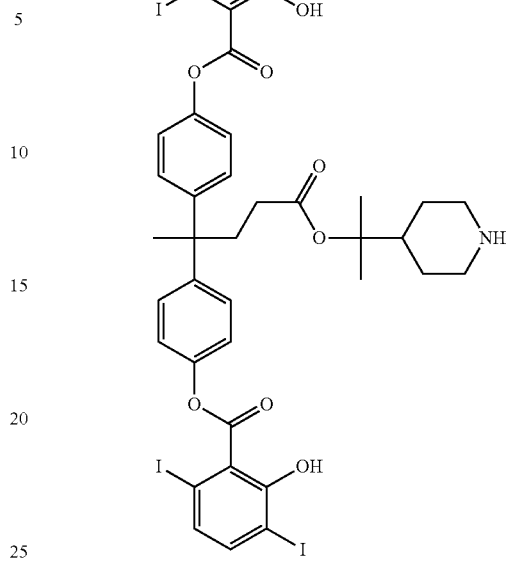
Examples of the amine compound having formula (A-2) are shown below, but not limited thereto.
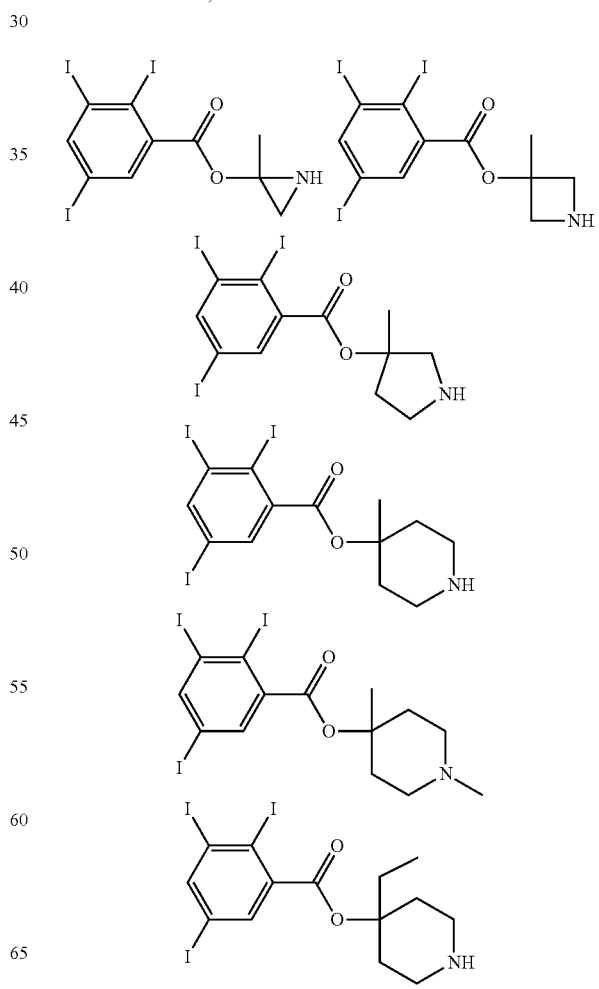

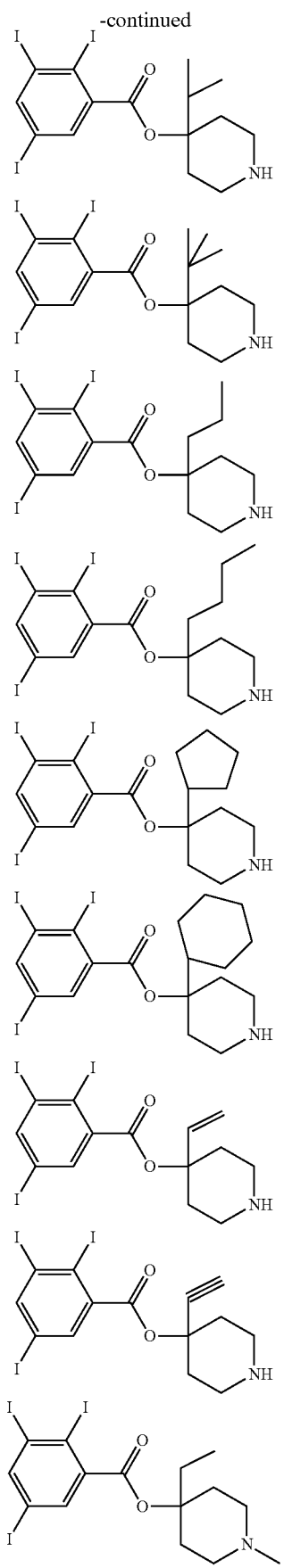

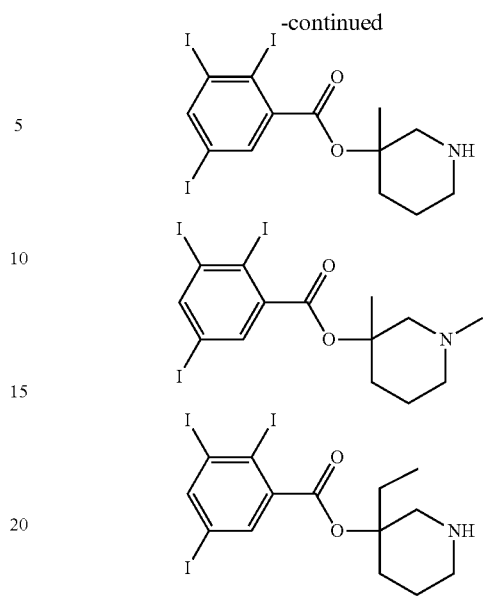

The amine compound may be synthesized, for example, by esterification reaction of a carboxylic acid chloride having an iodized aromatic ring with a tertiary amine compound having a hydroxyl group.

The inventive amine compound functions as a quencher having a sensitizing effect in a resist composition. While a conventional quencher functions to control acid diffusion to endow a resist material with a lower sensitivity for thereby reducing LWR or CDU, the inventive amine compound has an acid diffusion controlling effect owing to the amino group and iodine having a large atomic weight, and a sensitizing effect due to the inclusion of a plurality of iodine atoms with substantial EUV absorption, contributing to a high sensitivity.

Since the inventive amine compound has an acid-decomposable tertiary ester structure, it is decomposed with acid to a lower molecular weight. As the amino group-containing compound reduces its molecular weight, its acid diffusion ability decreases and its acid reactivity increases. It occurs in the exposed region that the amine compound reduces its molecular weight under the action of acid. An acid diffusion control ability is retained in the unexposed region whereas acid diffusion is promoted in the exposed region. Thus the difference in reactivity between the exposed region and the unexposed region is exaggerated, leading to an improvement in reaction contrast. It is thus possible to improve a contrast while suppressing acid diffusion.

U.S. Pat. No. 10,095,109 (JP-A 2018-172640) discloses a methacrylate having a tertiary ester structure and an iodized benzene ring. In the presence of an acid catalyst, it generates iodized isopropenylbenzene, for example. Because of a high boiling point, the iodized benzene compound does not evaporate, but remains within the resist film during PEB. Since the iodized benzene compound is not dissolved in the alkaline developer, it can cause defect formation.

In the inventive amine compound, the direction of ester bond bonding to iodized benzene ring is reverse to the compound of U.S. Pat. No. 10,095,109. As a result of deprotection, the amine compound generates an iodized benzoic acid, which causes no development defects because it is highly alkaline soluble.

In the resist composition, the amine compound is preferably present in an amount of 0.001 to 50 parts by weight, more preferably 0.01 to 40 parts by weight per 100 parts by weight of the base polymer, as viewed from sensitivity and acid diffusion suppressing effect. The amine compound may be used alone or in admixture.

In the unexposed region or prior to acid decomposition, the amine compound is highly lipophilic and least dissolvable in alkaline developer. After acid decomposition, it releases an amine compound having a low molecular weight and an iodized aromatic carboxylic acid. Thus alkali solubility is increased, and any pattern film thickness loss is restrained. The amine compound is thus effective for preventing pattern defects which can form in the exposed region when a highly lipophilic amine quencher is added.

Base Polymer

Where the resist composition is of positive tone, the base polymer comprises recurring units containing an acid labile group, preferably recurring units having the formula (a1) or recurring units having the formula (a2). These units are simply referred to as recurring units (a1) and (a2).

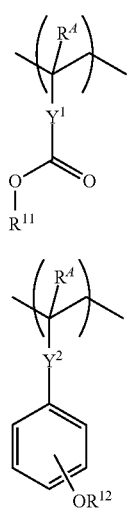

(a1)

(a2)

In formulae (a1) and (a2), $R^A$ is each independently hydrogen or methyl. $R^{11}$ and $R^{12}$ each are an acid labile group. $Y^1$ is a single bond, phenylene or naphthylene group, or $C_1$-$C_{12}$ linking group containing at least one moiety selected from ester bond and lactone ring. $Y^2$ is a single bond or ester bond. When the base polymer contains both recurring units (a1) and (a2), $R^{11}$ and $R^{12}$ may be the same or different.

Examples of the monomer from which the recurring units (a1) are derived are shown below, but not limited thereto. $R^A$ and $R^{11}$ are as defined above.

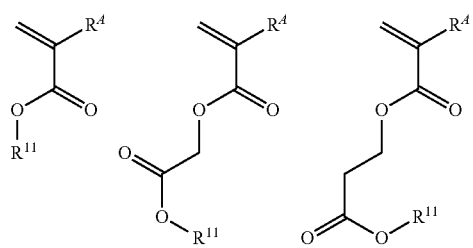

-continued

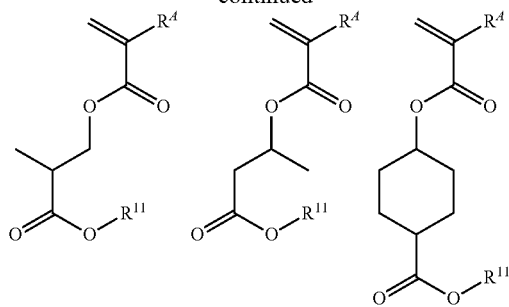

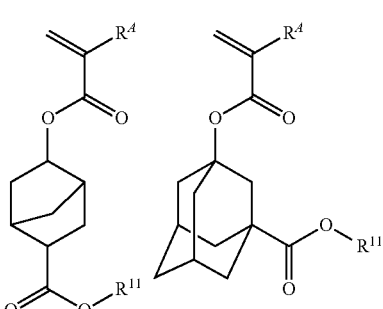

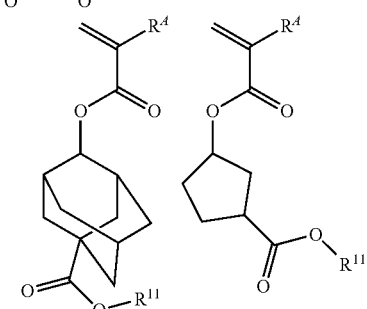

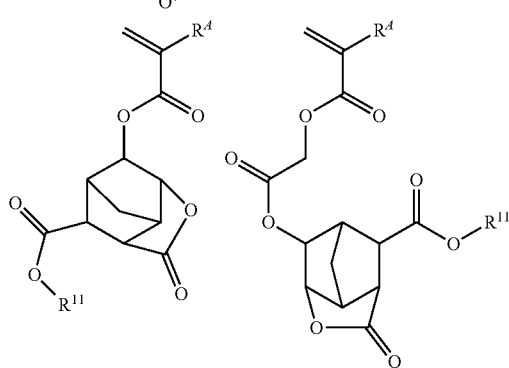

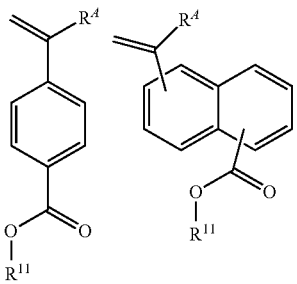

Examples of the monomer from which the recurring units (a2) are derived are shown below, but not limited thereto. $R^A$ and $R^{12}$ are as defined above.

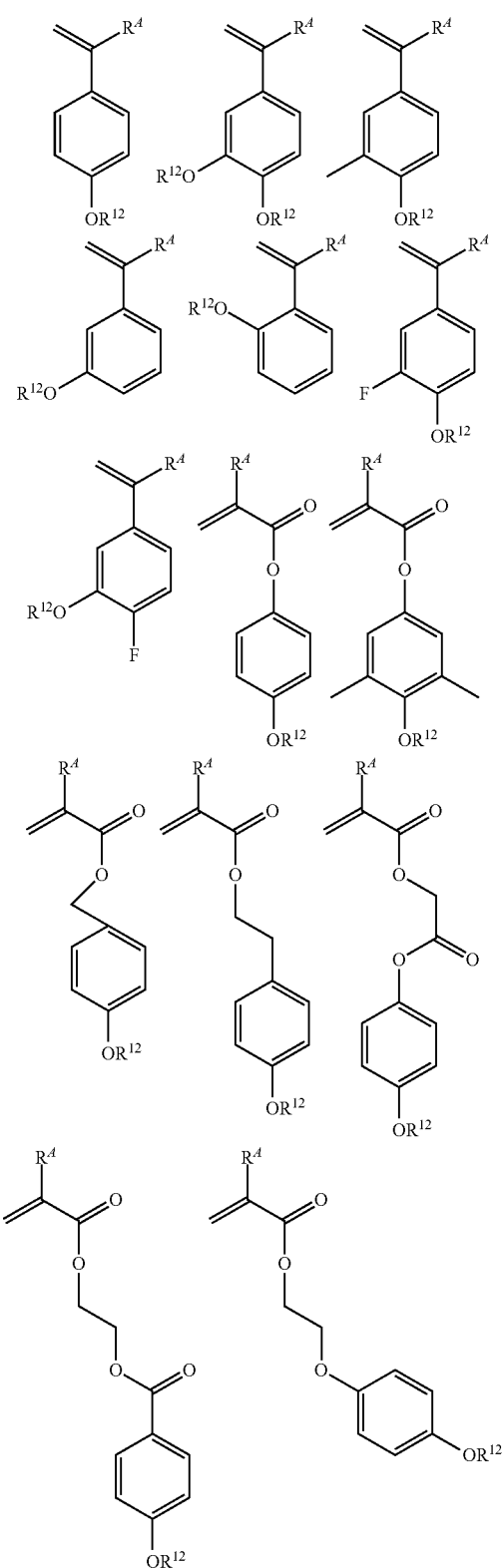

The acid labile groups represented by $R^{11}$ and $R^{12}$ in formulae (a1) and (a2) may be selected from a variety of such groups, for example, those groups described in JP-A 2013-080033 (U.S. Pat. No. 8,574,817) and JP-A 2013-083821 (U.S. Pat. No. 8,846,303).

Typical of the acid labile group are groups of the following formulae (AL-1) to (AL-3).

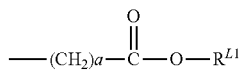

(AL-1)

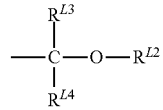

(AL-2)

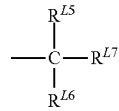

(AL-3)

In formulae (AL-1) and (AL-2), $R^{L1}$ and $R^{L2}$ are each independently a $C_1$-$C_{40}$ monovalent hydrocarbon group which may contain a heteroatom such as oxygen, sulfur, nitrogen or fluorine. The monovalent hydrocarbon groups may be straight, branched or cyclic while $C_1$-$C_{40}$ alkyl groups are preferred, and $C_1$-$C_{20}$ alkyl groups are more preferred. In formula (AL-1), "a" is an integer of 0 to 10, preferably 1 to 5.

In formula (AL-2), $R^{L3}$ and $R^{L4}$ are each independently hydrogen or a $C_1$-$C_{20}$ monovalent hydrocarbon group which may contain a heteroatom such as oxygen, sulfur, nitrogen or fluorine. The monovalent hydrocarbon groups may be straight, branched or cyclic while $C_1$-$C_{20}$ alkyl groups are preferred. Any two of $R^{L2}$, $R^{L3}$ and $R^{L4}$ may bond together to form a ring, typically alicyclic, with the carbon atom or carbon and oxygen atoms to which they are attached, the ring containing 3 to 20 carbon atoms, preferably 4 to 16 carbon atoms.

In formula (AL-3), $R^{L5}$, $R^{L6}$ and $R^{L7}$ are each independently a $C_1$-$C_{20}$ monovalent hydrocarbon group which may contain a heteroatom such as oxygen, sulfur, nitrogen or fluorine. The monovalent hydrocarbon groups may be straight, branched or cyclic while $C_1$-$C_{20}$ alkyl groups are preferred. Any two of $R^{L5}$, $R^{L6}$ and $R^{L7}$ may bond together to form a ring, typically alicyclic, with the carbon atom to which they are attached, the ring containing 3 to 20 carbon atoms, preferably 4 to 16 carbon atoms.

The base polymer may further comprise recurring units (b) having a phenolic hydroxyl group as an adhesive group. Examples of suitable monomers from which recurring units (b) are derived are given below, but not limited thereto. Herein $R^A$ is as defined above.

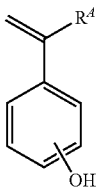 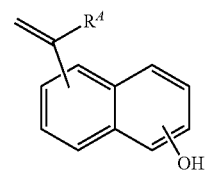 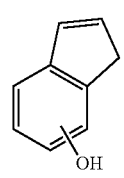

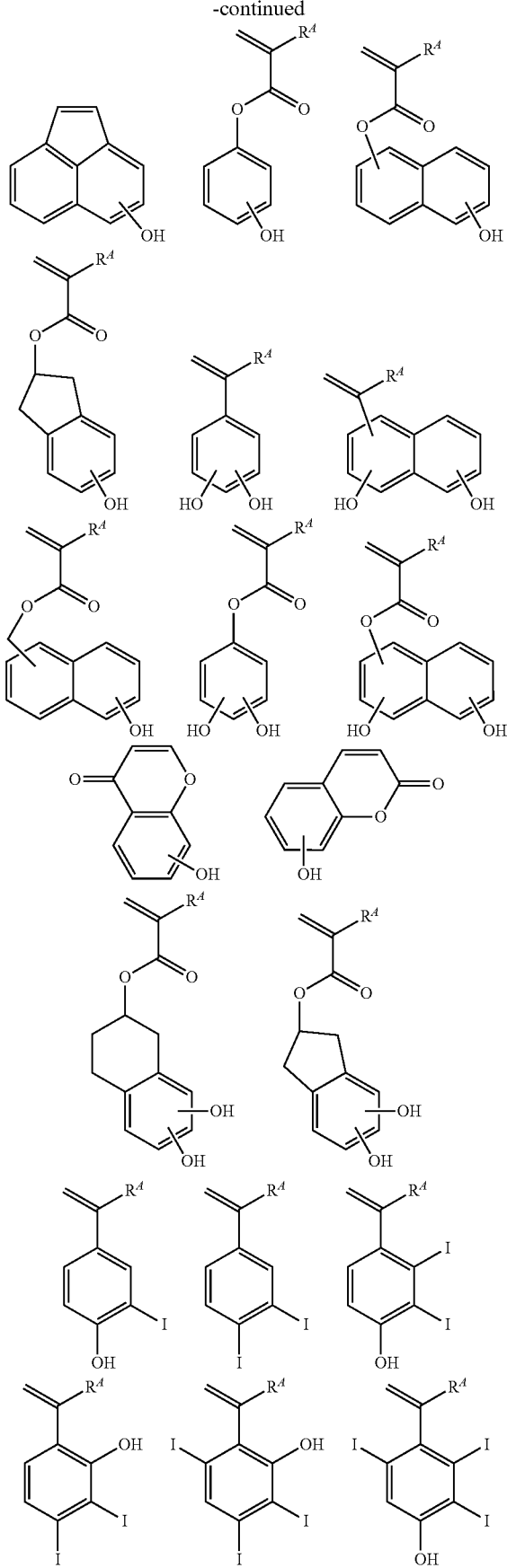
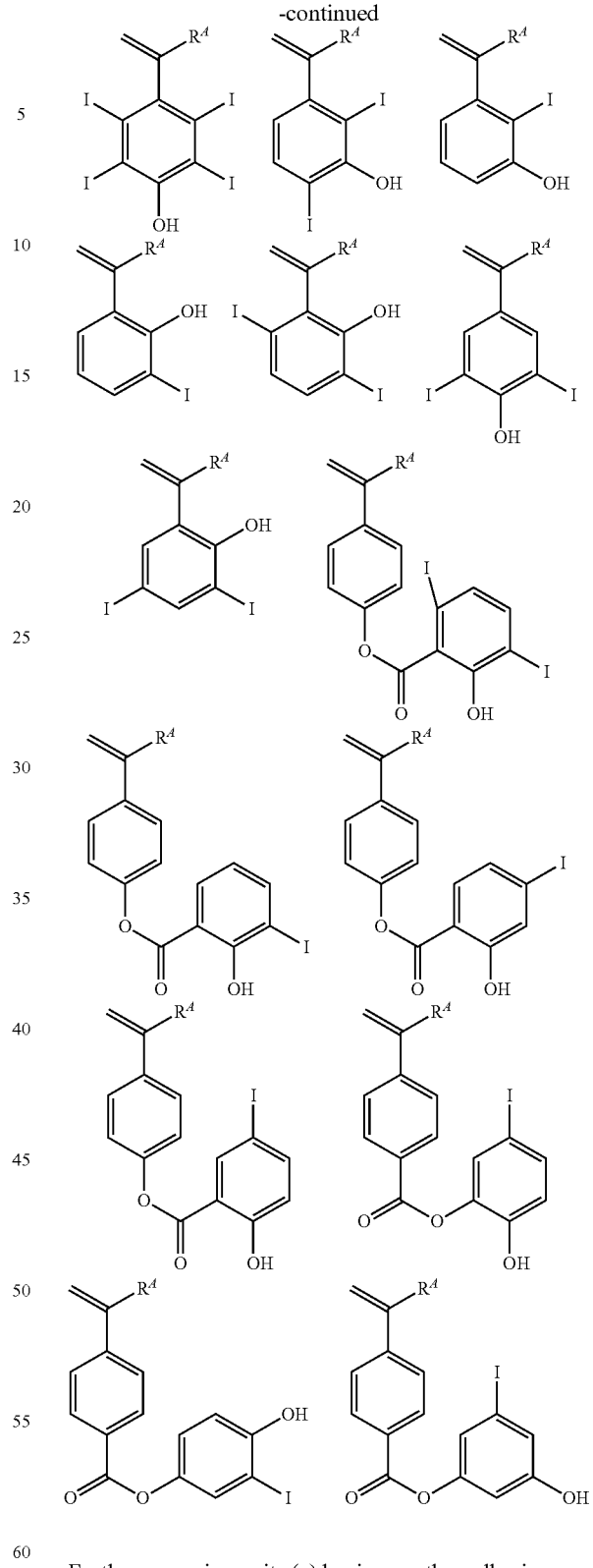

Further, recurring units (c) having another adhesive group selected from hydroxyl (other than the foregoing phenolic hydroxyl), lactone ring, ether bond, ester bond, carbonyl, cyano, and carboxyl groups may also be incorporated in the base polymer. Examples of suitable monomers from which recurring units (c) are derived are given below, but not limited thereto. Herein $R^A$ is as defined above.

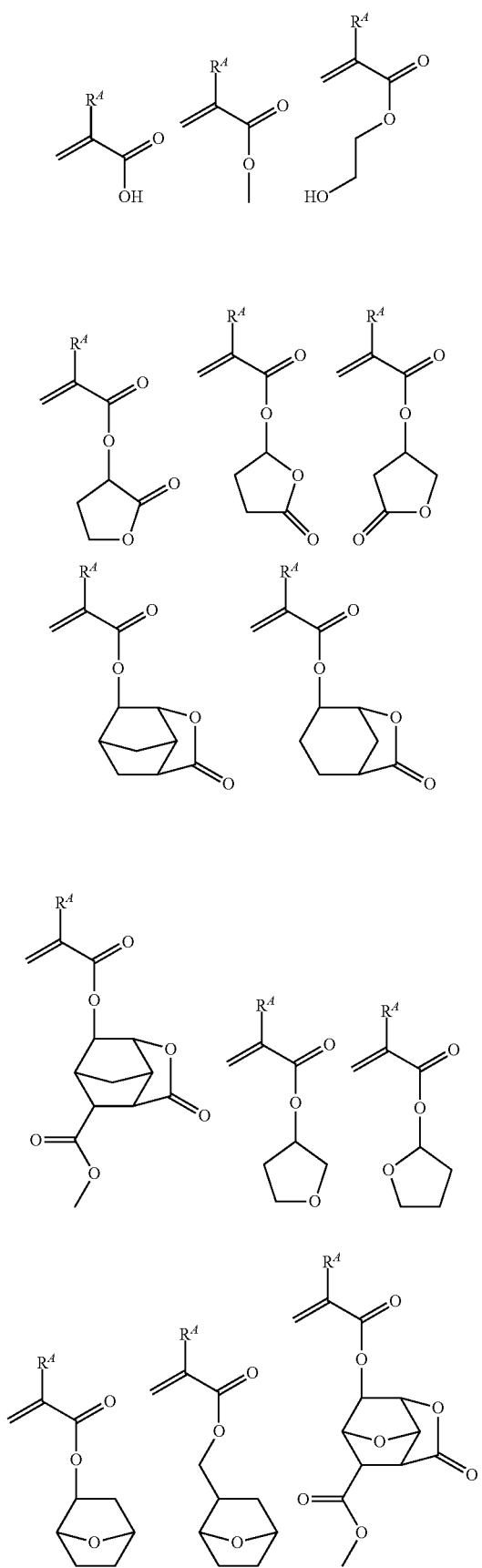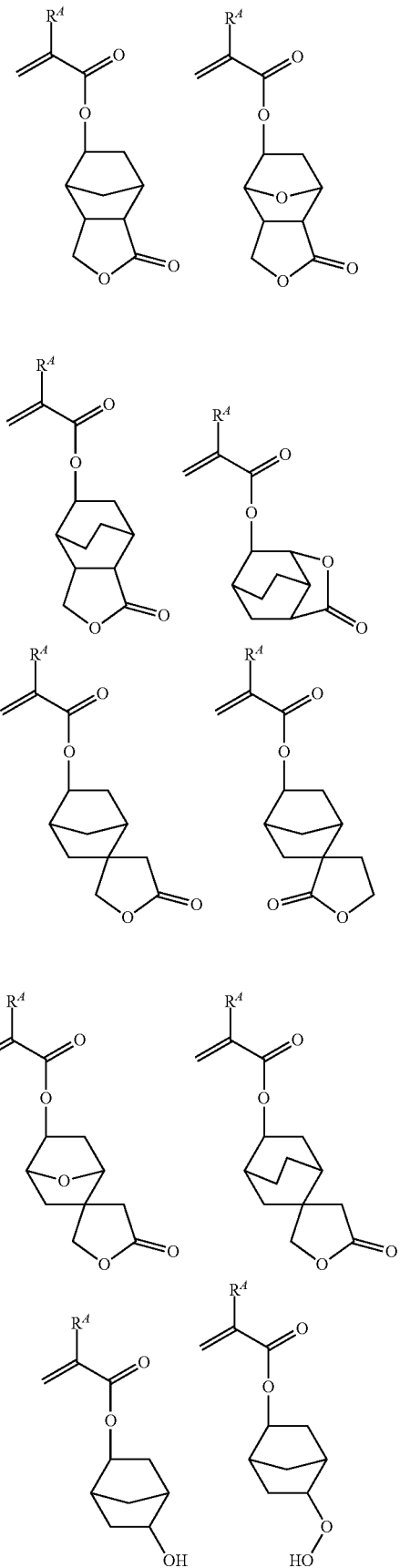
-continued

-continued
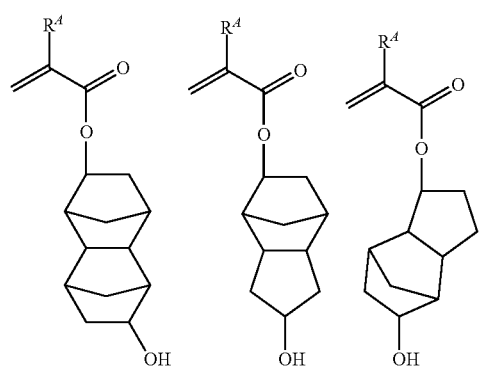
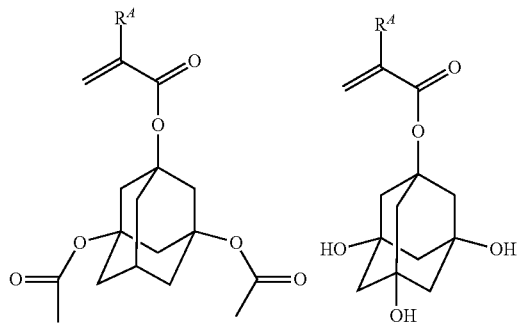
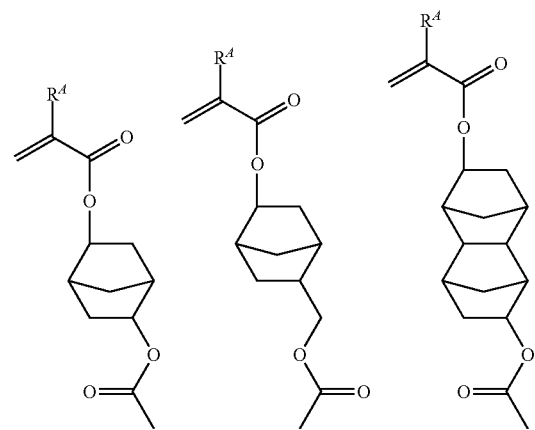
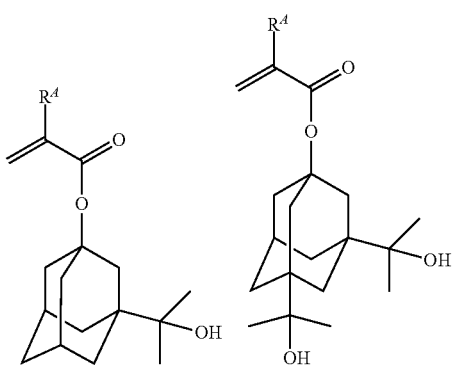
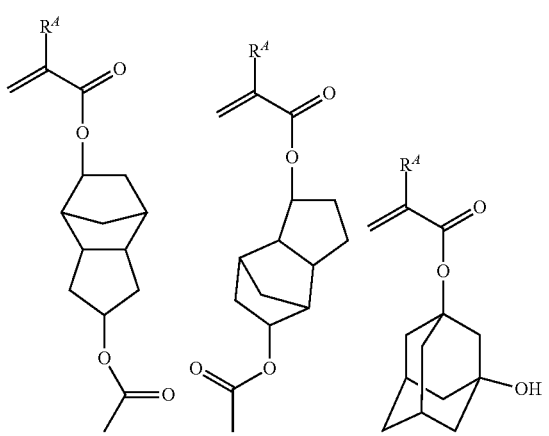
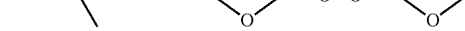
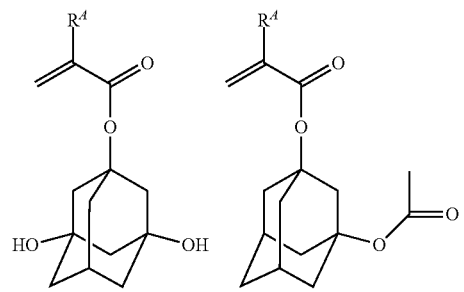
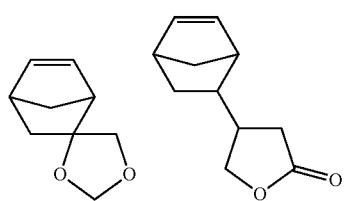

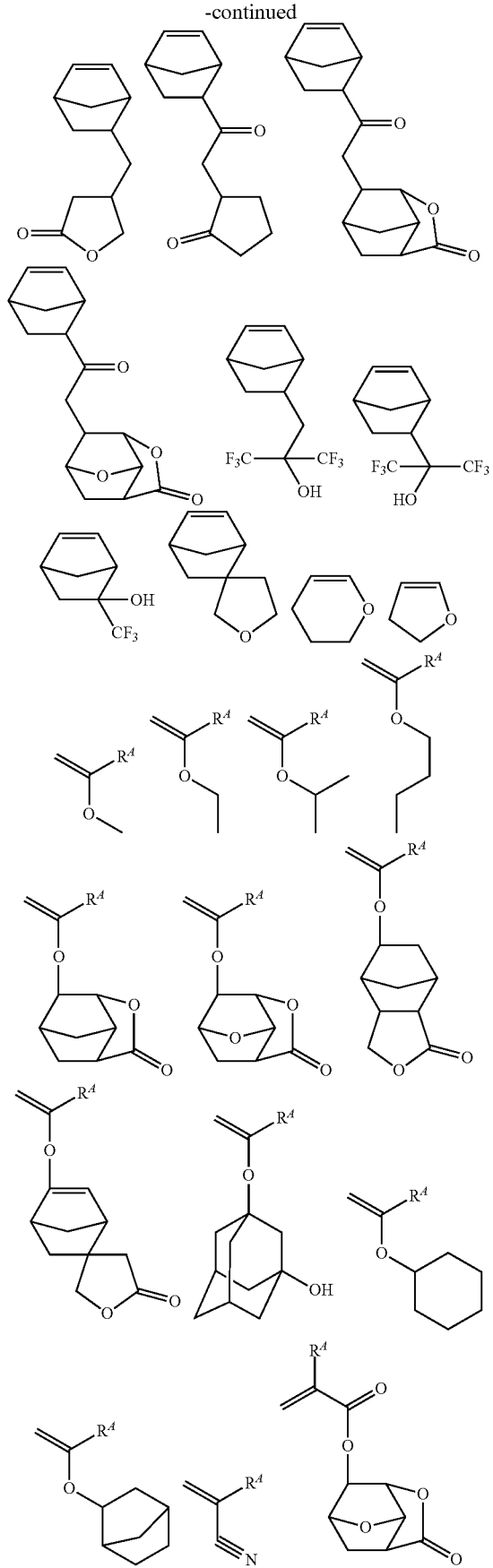
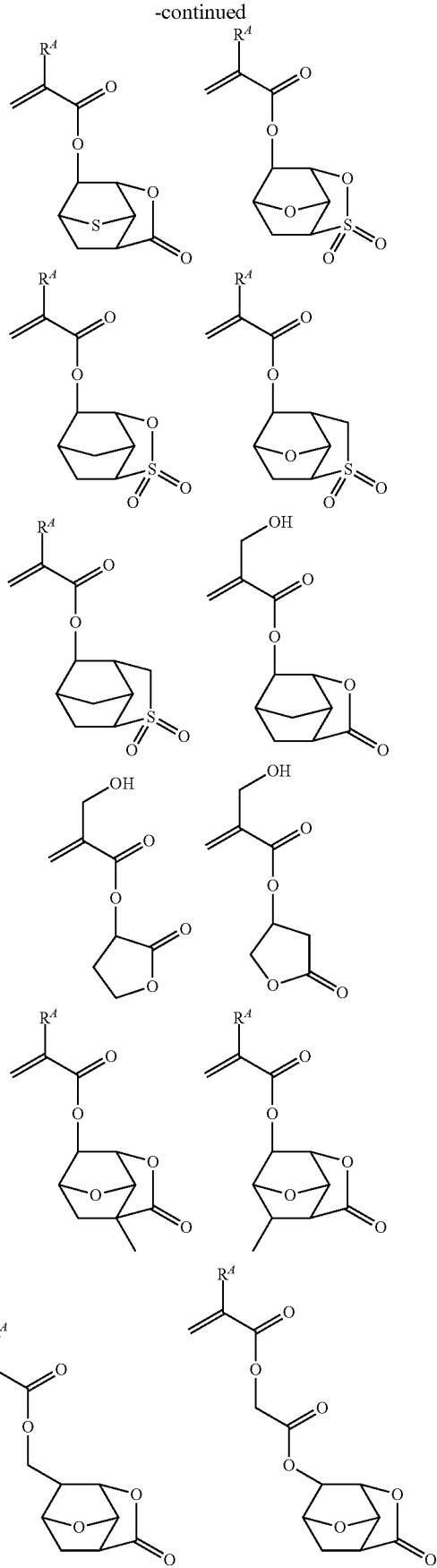

37
-continued
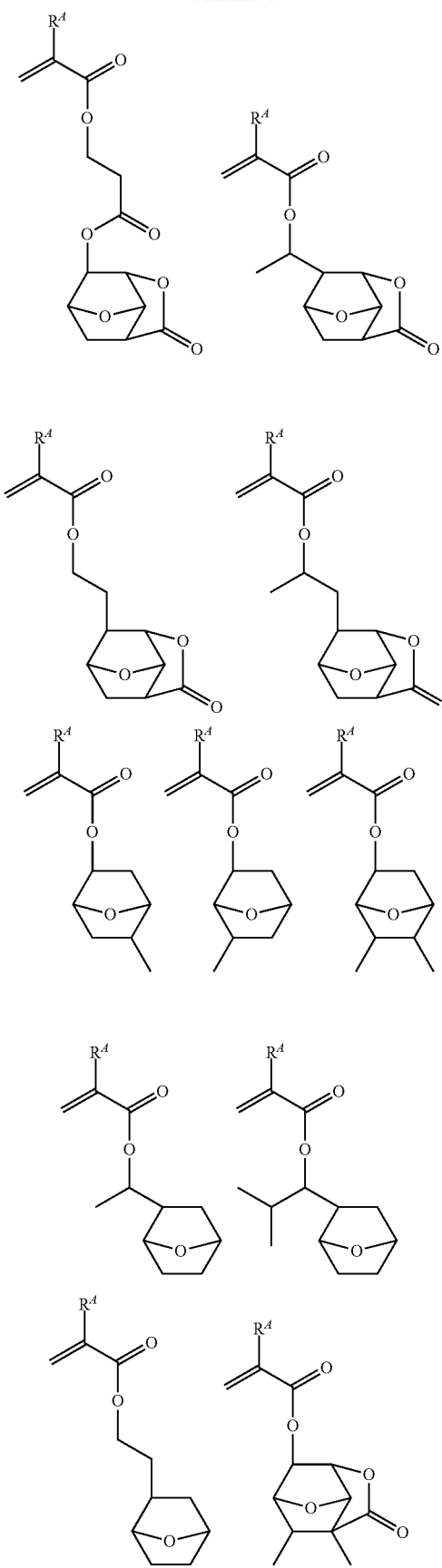
38
-continued
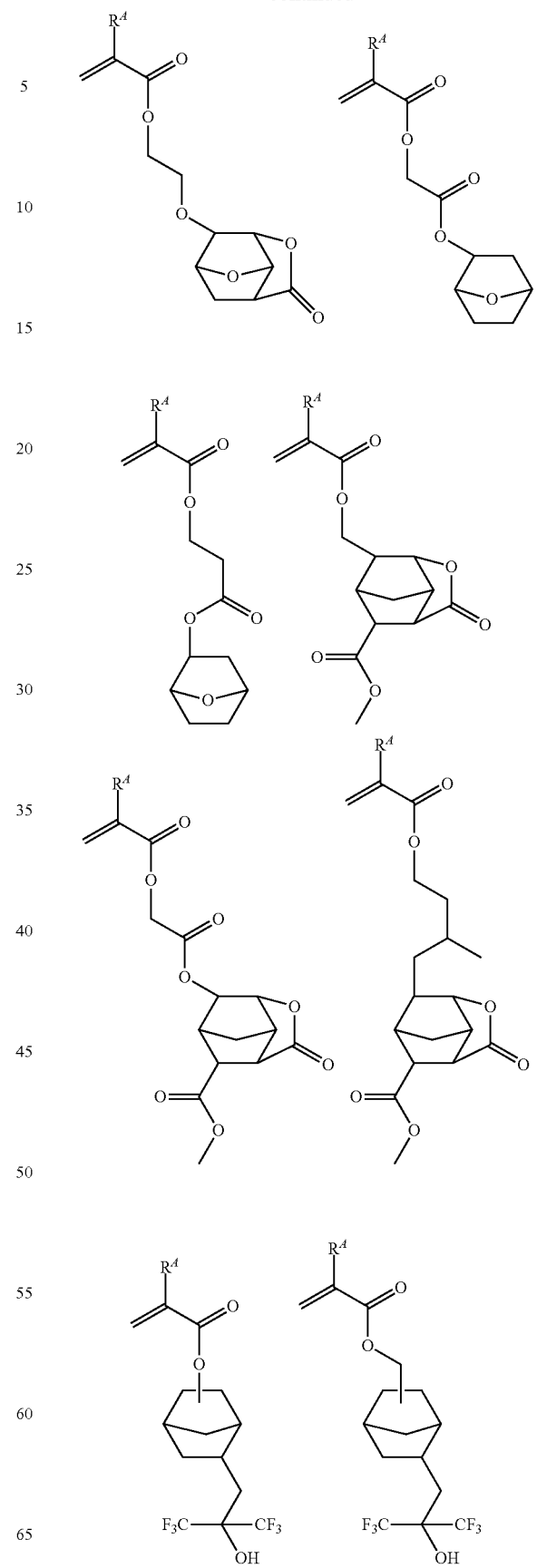

-continued
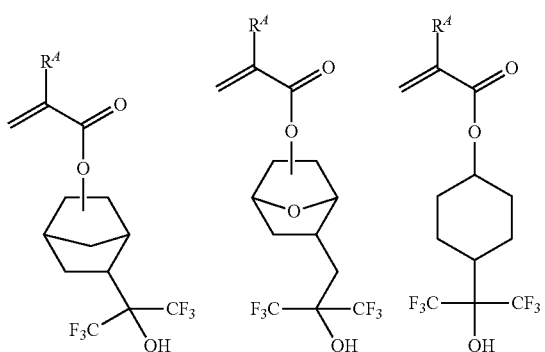
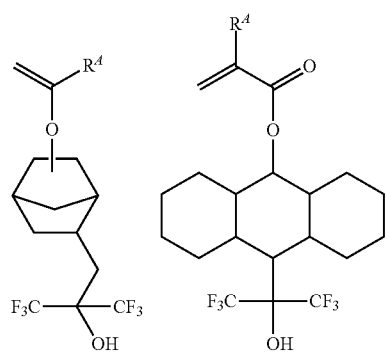
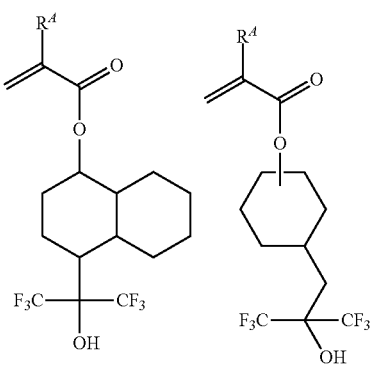
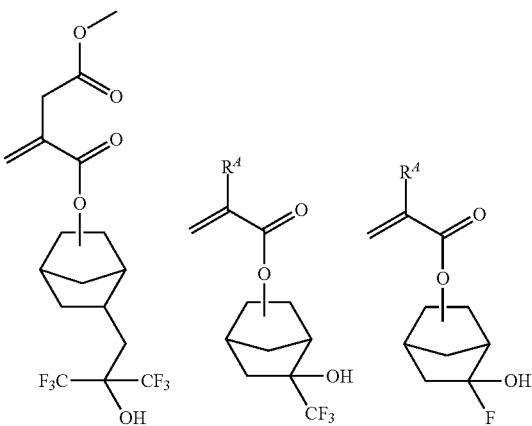
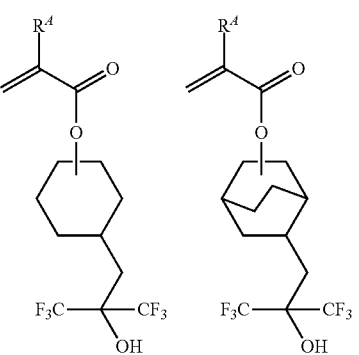
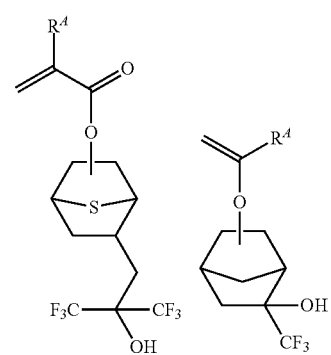
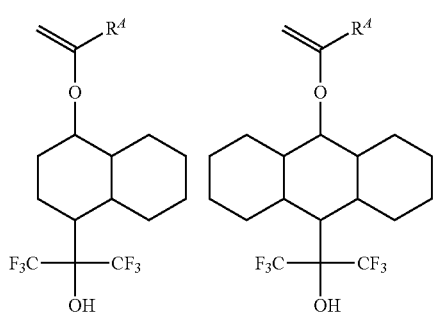

-continued
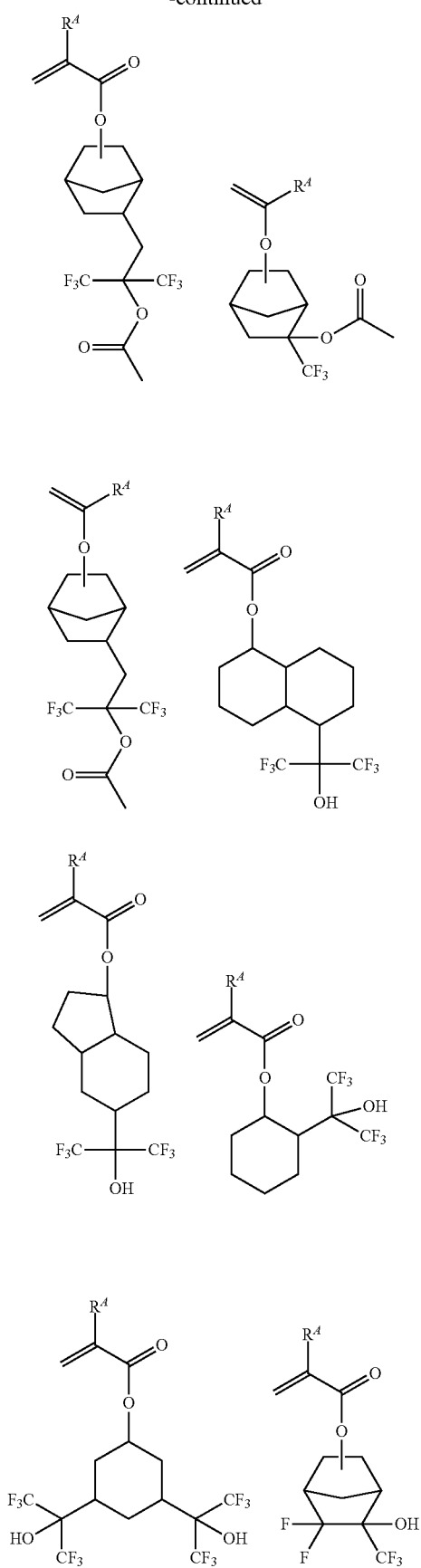
-continued
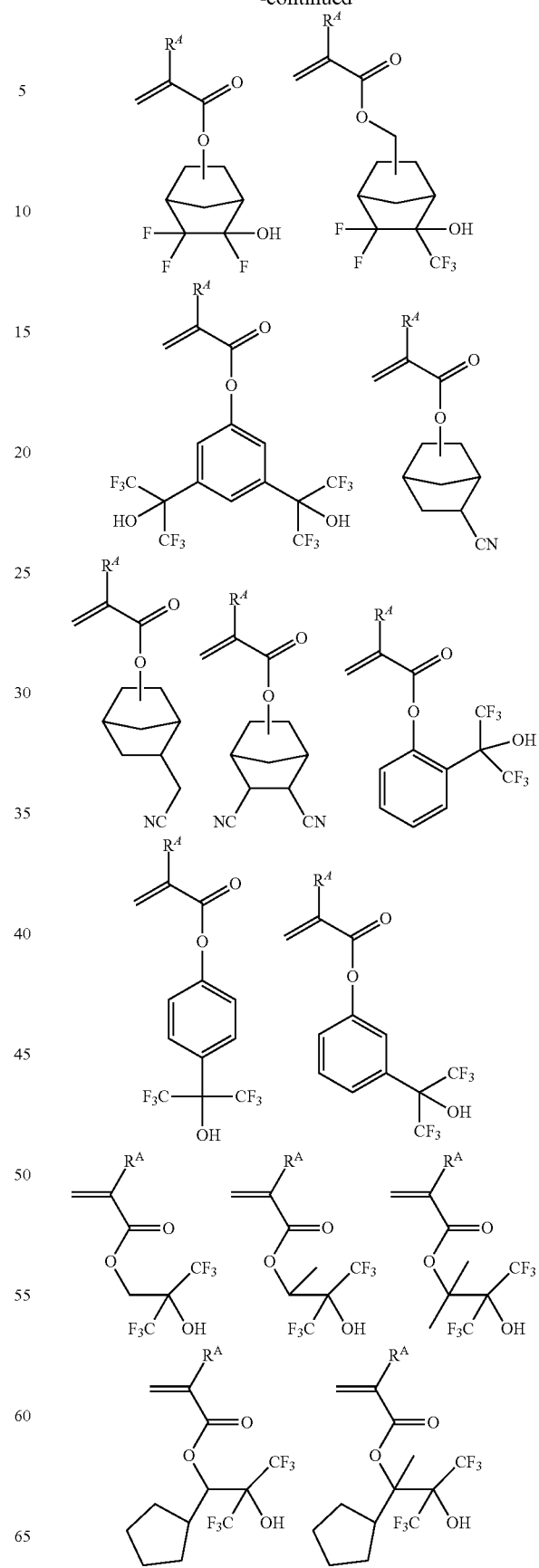

-continued
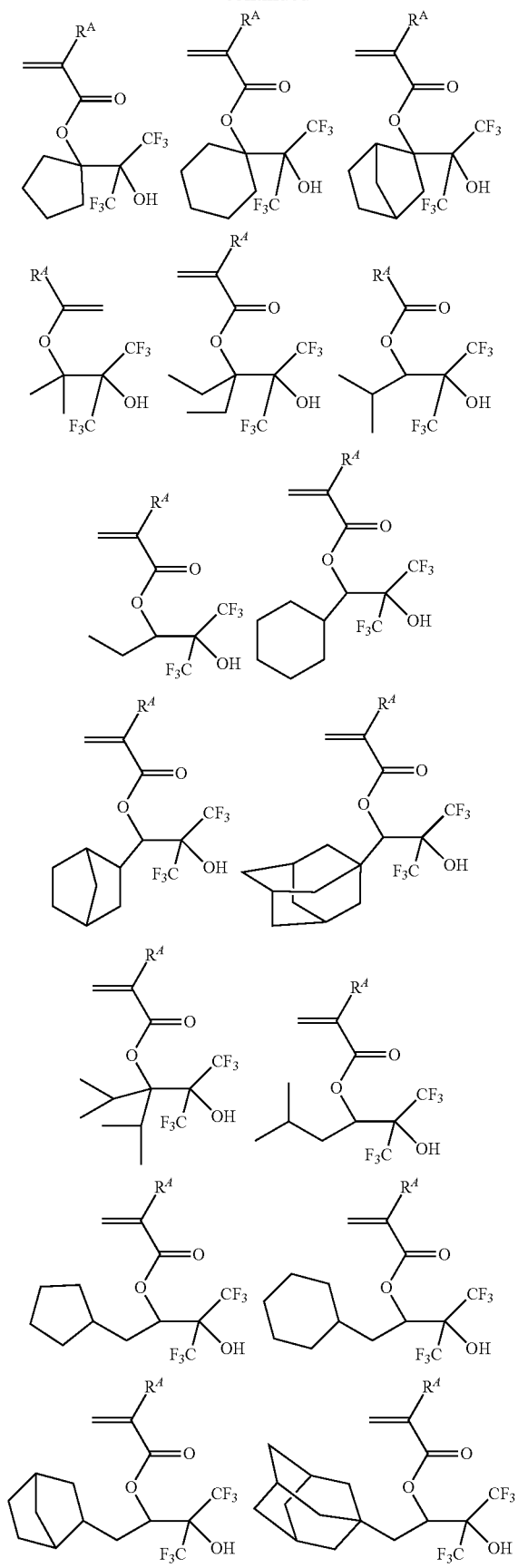
-continued
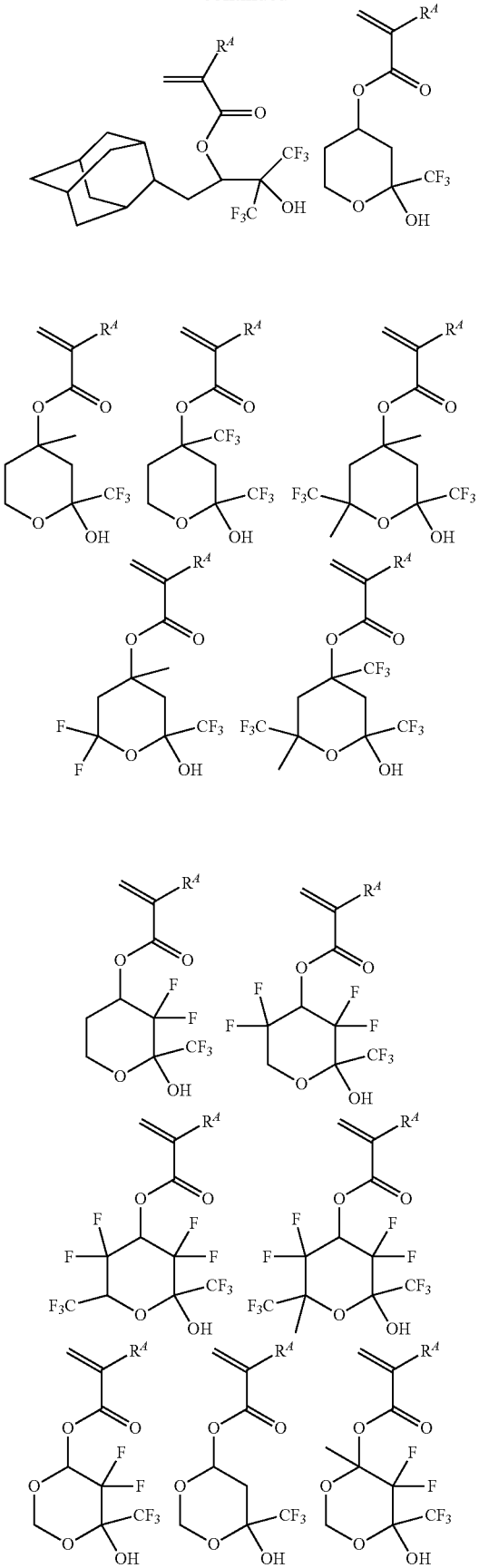

-continued
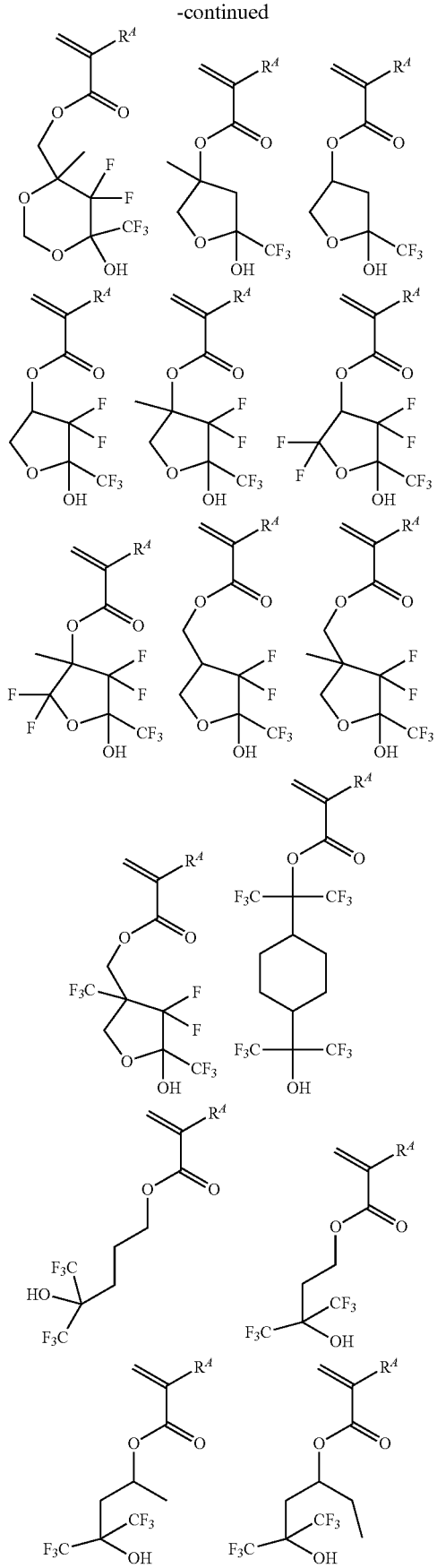
-continued
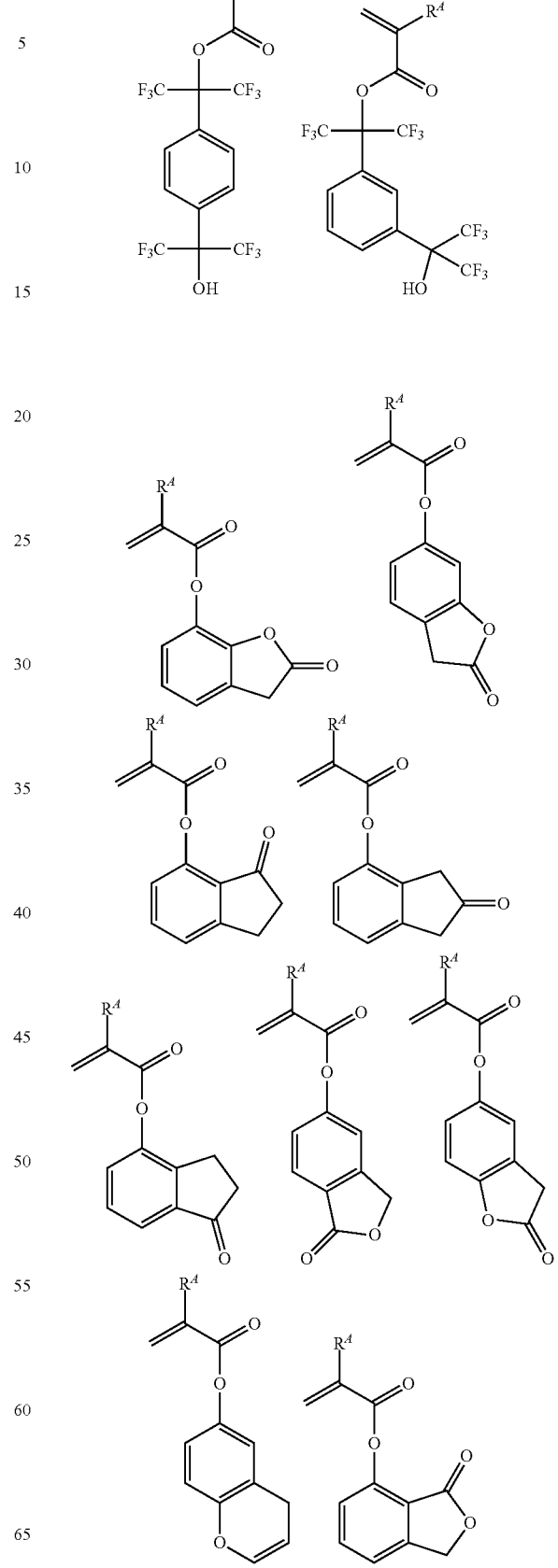

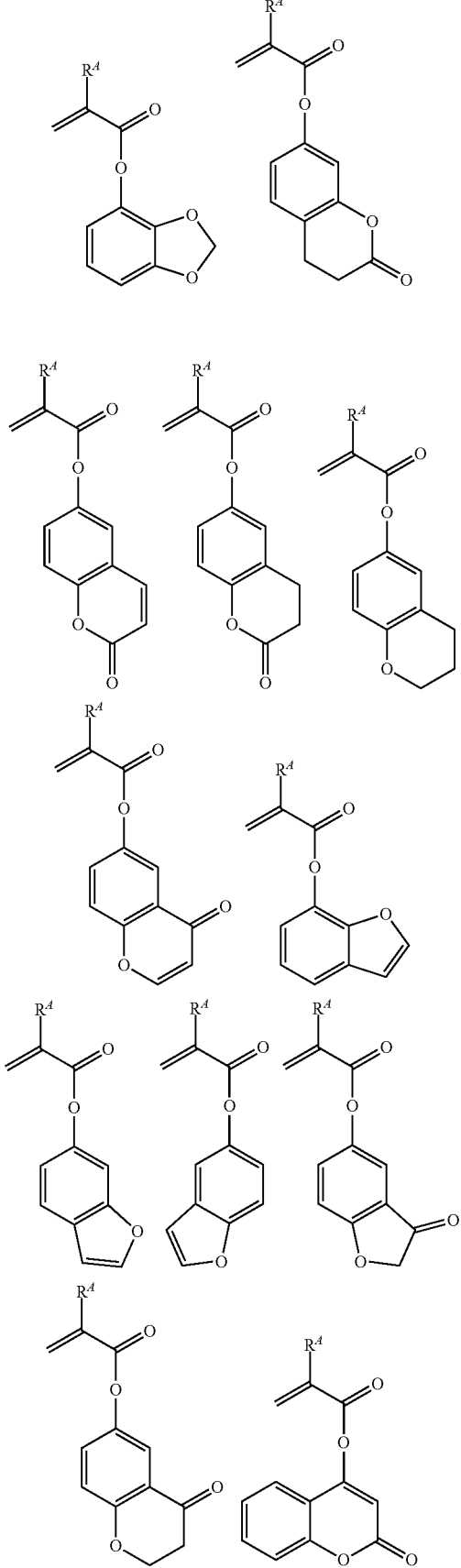
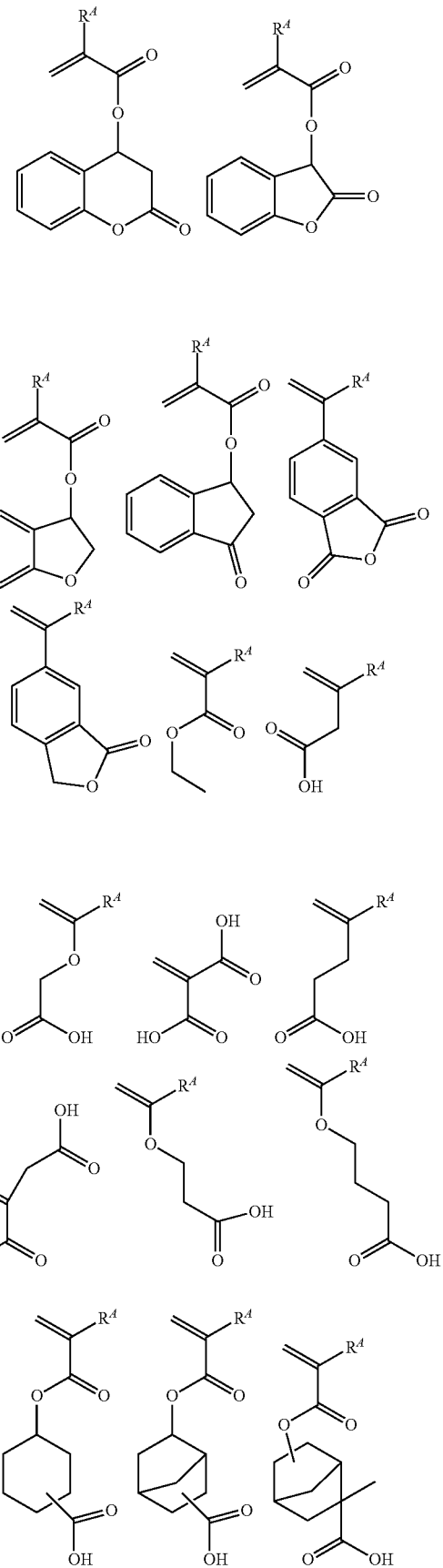

49
-continued
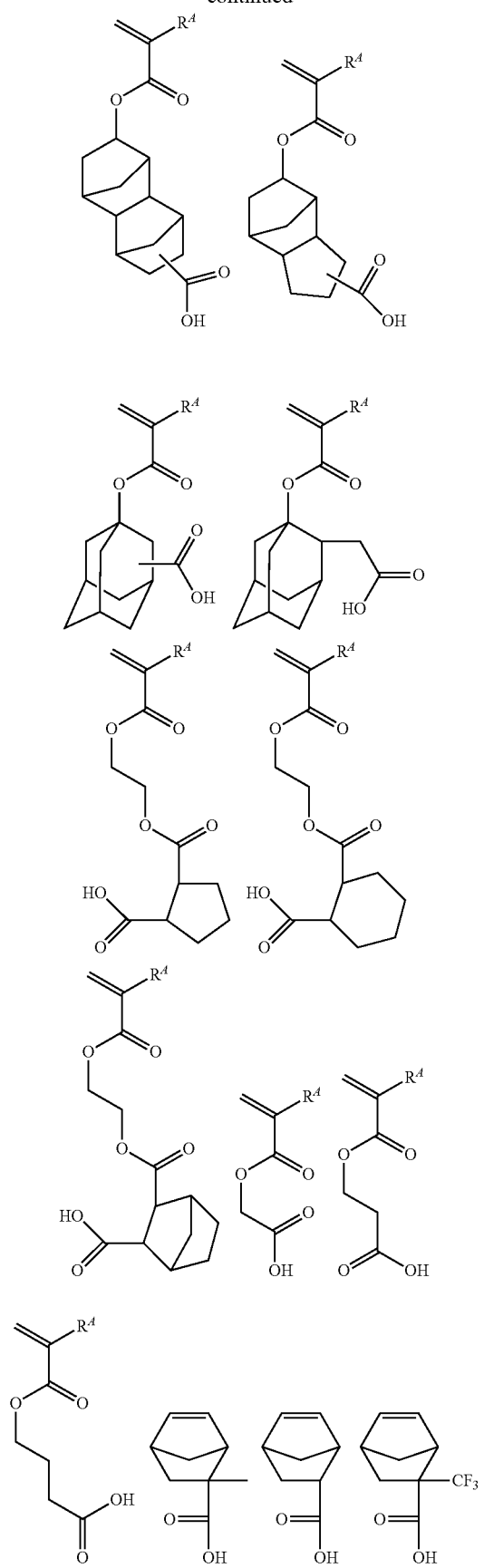
50
-continued
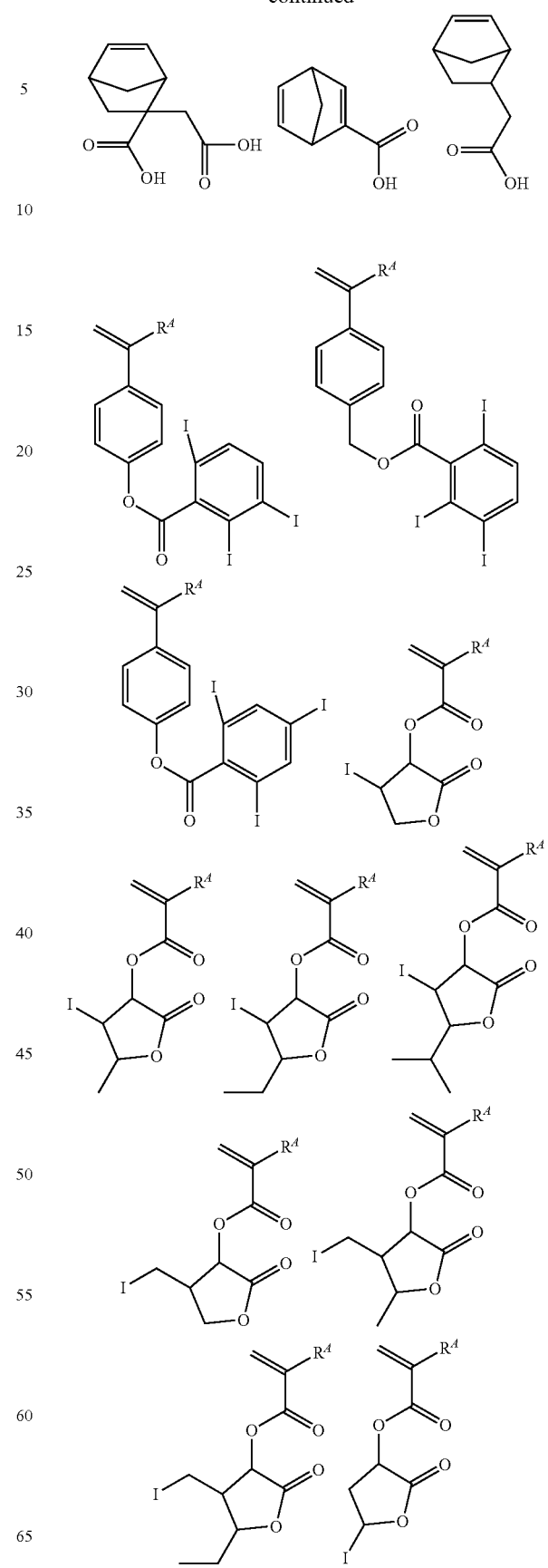

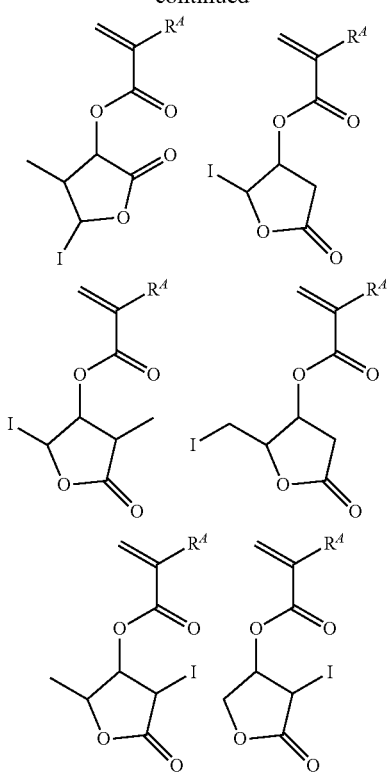

In another preferred embodiment, the base polymer may further comprise recurring units (d) selected from units derived from indene, benzofuran, benzothiophene, acenaphthylene, chromone, coumarin, and norbornadiene, or derivatives thereof. Suitable monomers are exemplified below.

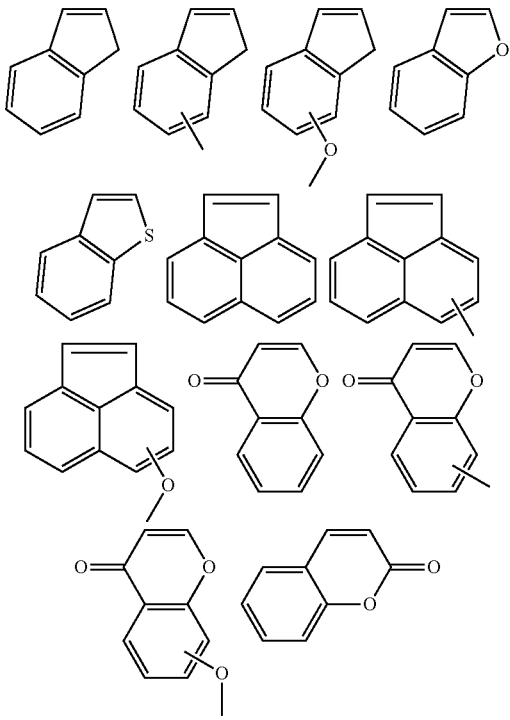

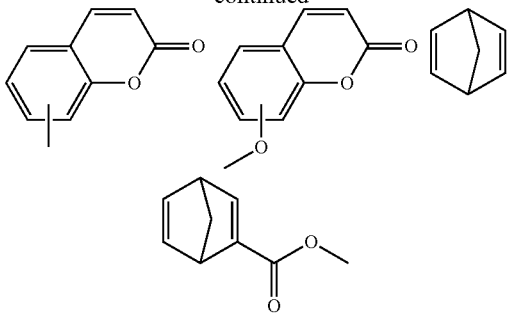

Furthermore, recurring units (e) may be incorporated in the base polymer, which are derived from styrene, vinylnaphthalene, vinylanthracene, vinylpyrene, methyleneindene, vinylpyridine, and vinylcarbazole.

In a further embodiment, recurring units (f) derived from an onium salt having a polymerizable unsaturated bond may be incorporated in the base polymer. Specifically, the base polymer may comprise recurring units of at least one type selected from formulae (f1), (f2) and (f3). These units are simply referred to as recurring units (f1), (f2) and (f3), which may be used alone or in combination of two or more types.

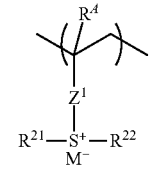

(f1)

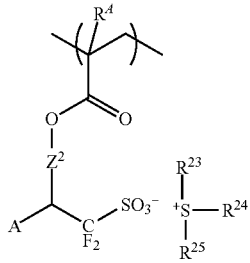

(f2)

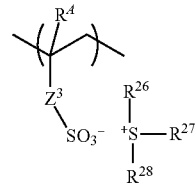

(f3)

In formulae (f1) to (f3). $R^A$ is independently hydrogen or methyl. $Z^1$ is a single bond, phenylene group, —O—$Z^{11}$—, —C(=O)—O—$Z^{11}$—, or —C(=O)—NH—$Z^{11}$—, wherein $Z^{11}$ is a $C_1$-$C_6$ alkanediyl group, $C_2$-$C_6$ alkenediyl group, or phenylene group, which may contain a carbonyl, ester bond, ether bond or hydroxyl moiety. $Z^2$ is a single bond, —$Z^{21}$—C(=O)—O—, —$Z^{21}$—O— or —$Z^{21}$—O—C(=O)—, wherein $Z^{21}$ is a $C_1$-$C_{12}$ alkanediyl group which may contain a carbonyl moiety, ester bond or ether bond. "A" is hydrogen or trifluoromethyl. $Z^3$ is a single bond, methylene, ethylene, phenylene, fluorinated phenylene.

—O—Z$^{31}$—, —C(=O)—O—Z$^{31}$—, or —C(=O)—NH—Z$^{31}$—, wherein Z$^{31}$ is a C$_1$-C$_6$ alkanediyl group, C$_2$-C$_6$ alkenediyl group, phenylene group, fluorinated phenylene group, or trifluoromethyl-substituted phenylene group, which may contain a carbonyl moiety, ester bond, ether bond or hydroxyl moiety. The alkanediyl and alkenediyl groups may be straight, branched or cyclic.

In formulae (f1) to (f3), R$^{21}$ to R$^{28}$ are each independently a C$_1$-C$_{20}$ monovalent hydrocarbon group which may contain a heteroatom. The monovalent hydrocarbon groups may be straight, branched or cyclic, and examples thereof include C$_1$-C$_{12}$ alkyl groups, C$_6$-C$_{12}$ aryl groups, and C$_7$-C$_{20}$ aralkyl groups. In these groups, some or all of the hydrogen atoms may be substituted by C$_1$-C$_{10}$ alkyl groups, halogen, trifluoromethyl, cyano, nitro, hydroxyl, mercapto, C$_1$-C$_{10}$ alkoxy groups, C$_2$-C$_{10}$ alkoxycarbonyl groups, or C$_2$-C$_{10}$ acyloxy groups, and some carbon atom may be replaced by a carbonyl moiety, ether bond or ester bond. Any two of R$^{23}$, R$^{24}$ and R$^{25}$ or any two of R$^{26}$, R$^{27}$ and R$^{28}$ may bond together to form a ring with the sulfur atom to which they are attached.

In formula (f1), M$^-$ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate: arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; methide ions such as tris(trifluoromethylsulfonyl)methide and tris(perfluoroethylsulfonyl)methide.

Also included are sulfonate ions having fluorine substituted at α-position as represented by the formula (f1-1) and sulfonate ions having fluorine substituted at α- and β-positions as represented by the formula (f1-2).

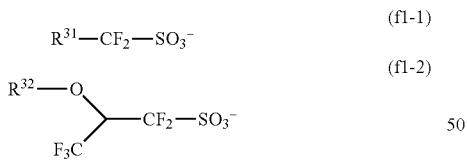

(f1-1)
(f1-2)

In formula (f1-1), R$^{31}$ is hydrogen, or a C$_1$-C$_{20}$ alkyl group, C$_2$-C$_{20}$ alkenyl group, or C$_6$-C$_{20}$ aryl group, which may contain an ether bond, ester bond, carbonyl moiety, lactone ring, or fluorine atom. The alkyl and alkenyl groups may be straight, branched or cyclic.

In formula (f1-2), R$^{32}$ is hydrogen, or a C$_1$-C$_{30}$ alkyl group. C$_2$-C$_{20}$ acyl group. C$_2$-C$_{20}$ alkenyl group, C$_6$-C$_{20}$ aryl group or C$_6$-C$_{20}$ aryloxy group, which may contain an ether bond, ester bond, carbonyl moiety or lactone ring. The alkyl, acyl and alkenyl groups may be straight, branched or cyclic.

Examples of the monomer from which recurring unit (f1) is derived are shown below, but not limited thereto. R$^A$ and M$^-$ are as defined above.

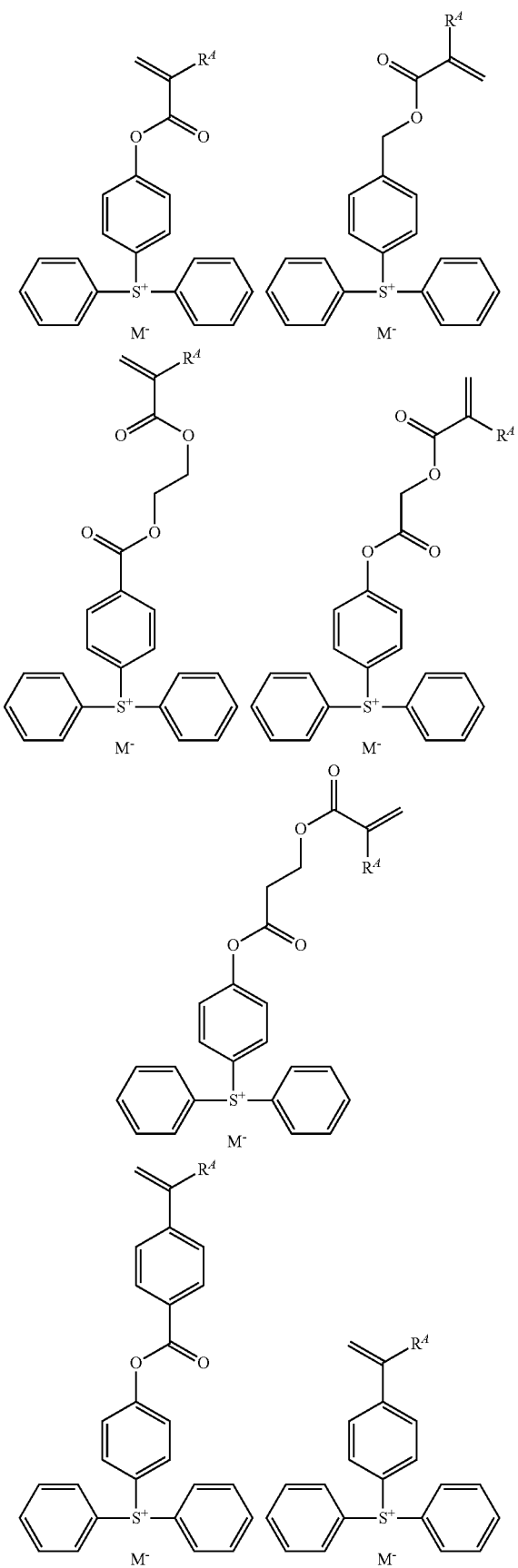

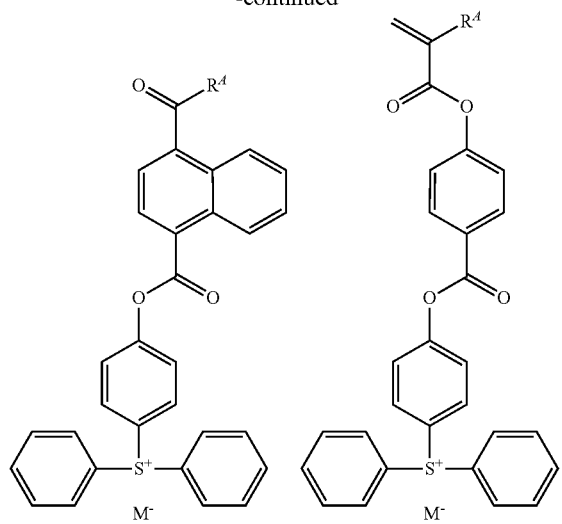
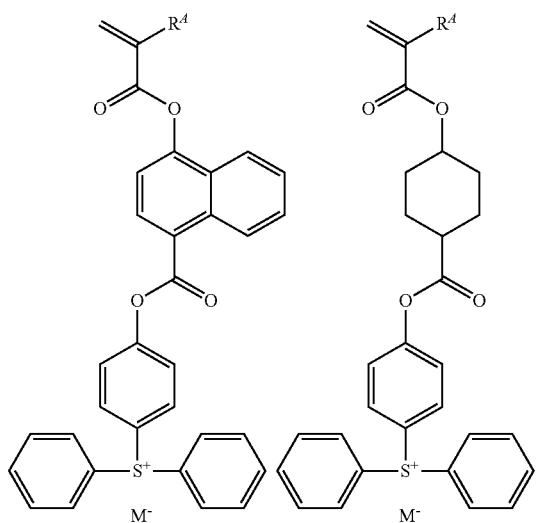
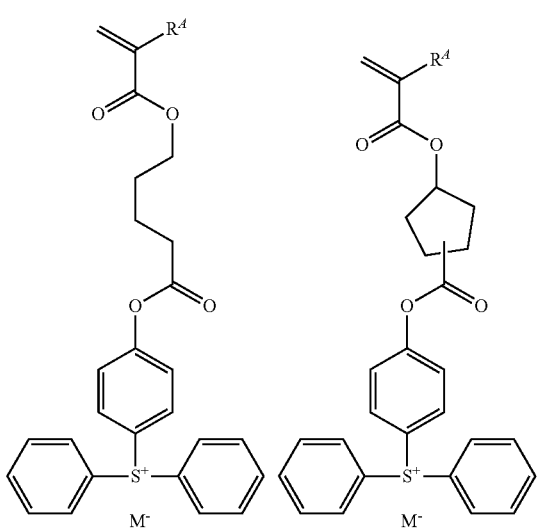
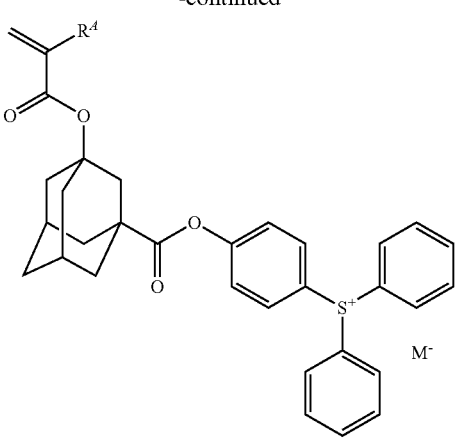
Examples of the monomer from which recurring unit (f2) is derived are shown below, but not limited thereto. $R^A$ is as defined above.
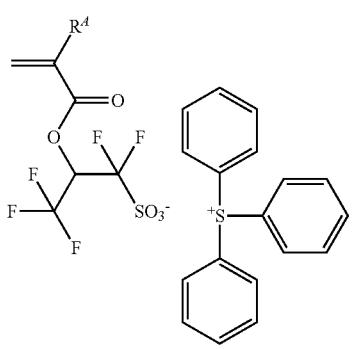
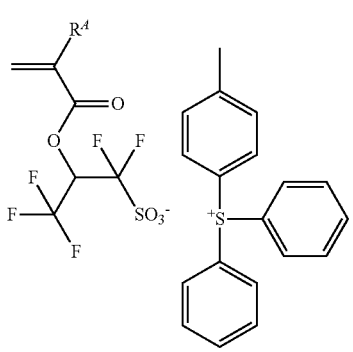
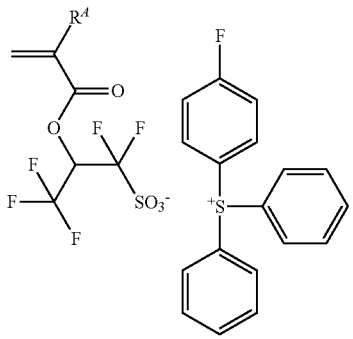

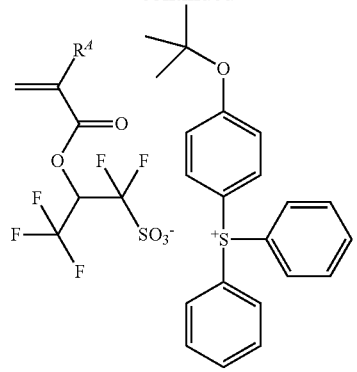
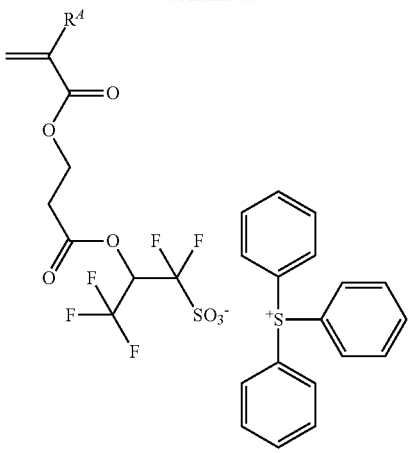
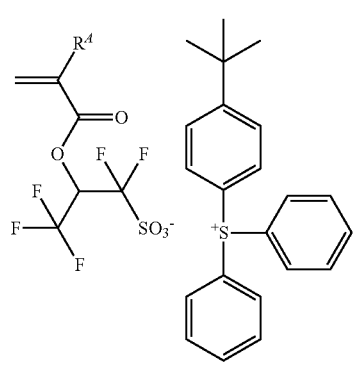
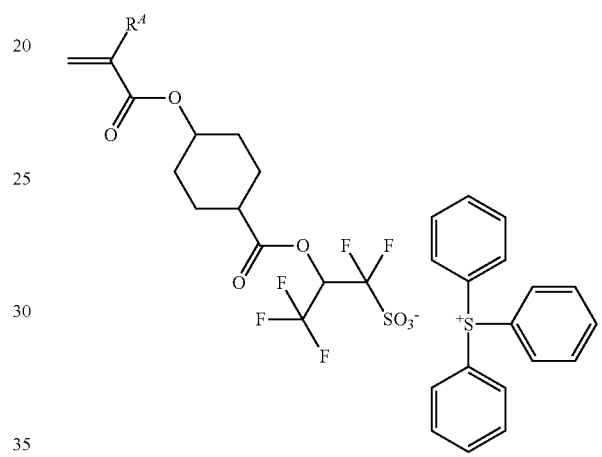
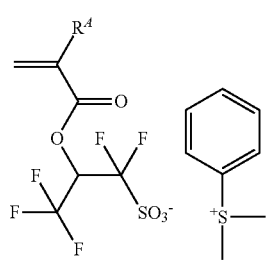
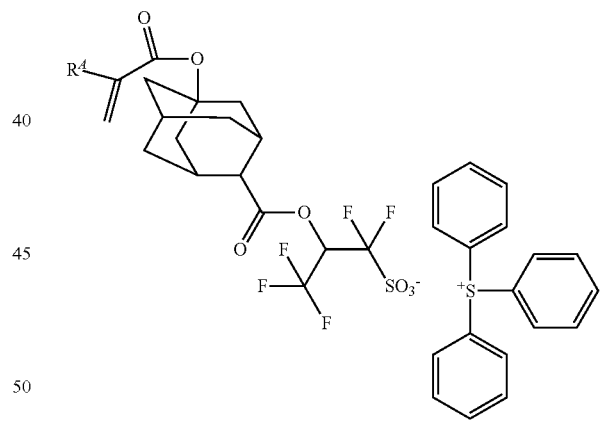
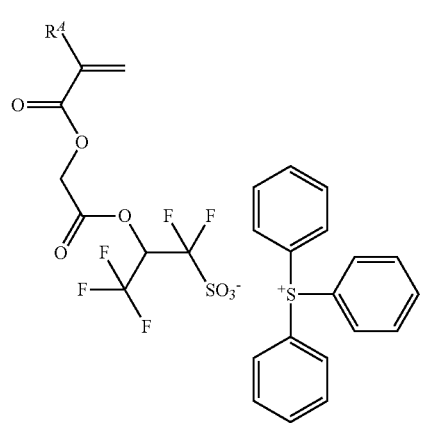
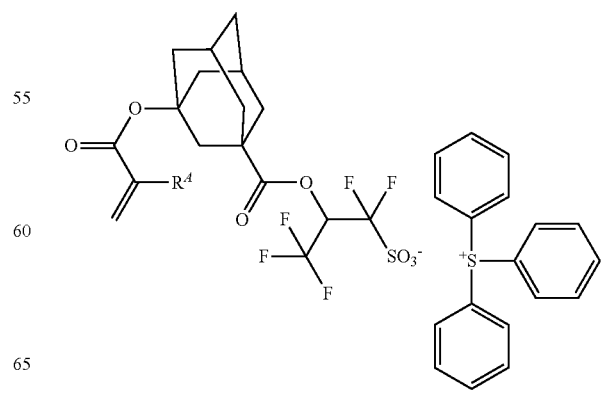

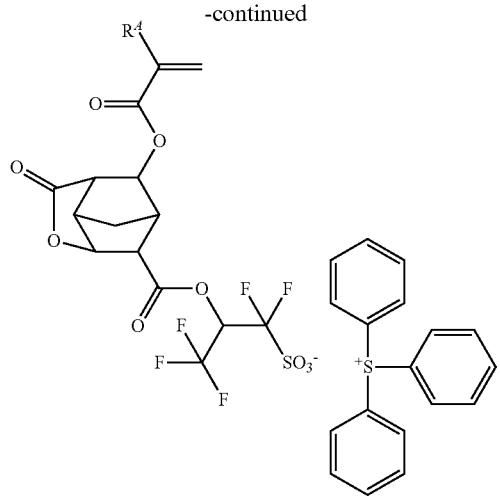
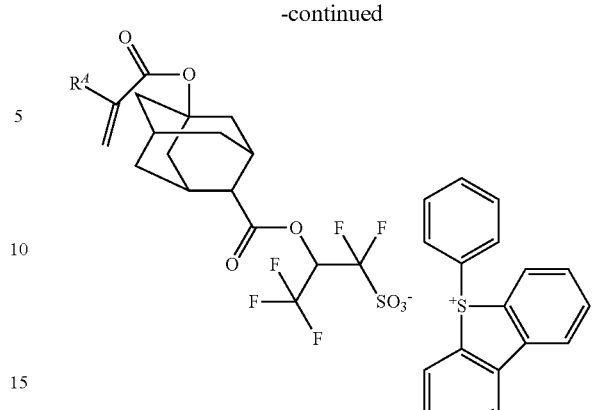
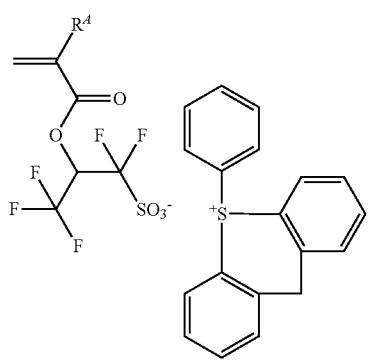
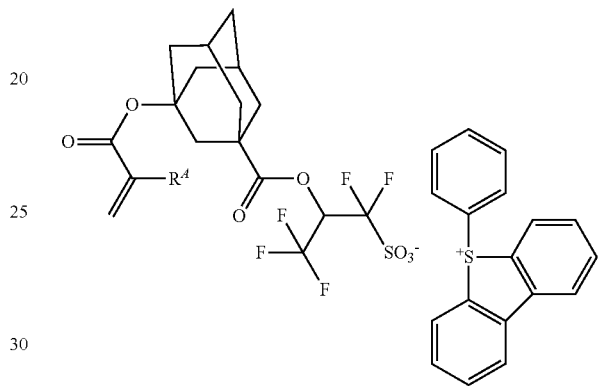
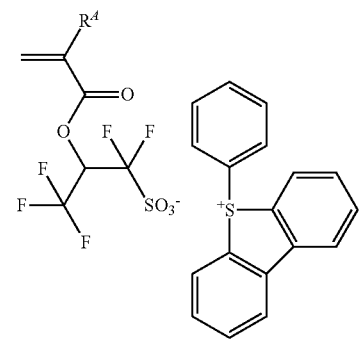
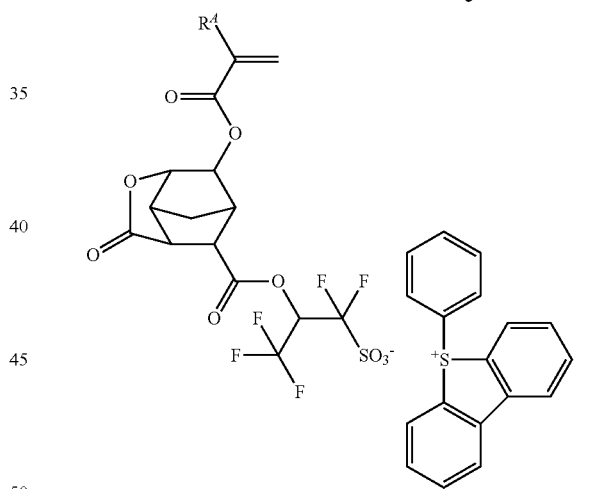
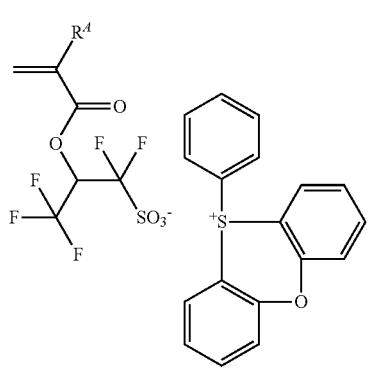
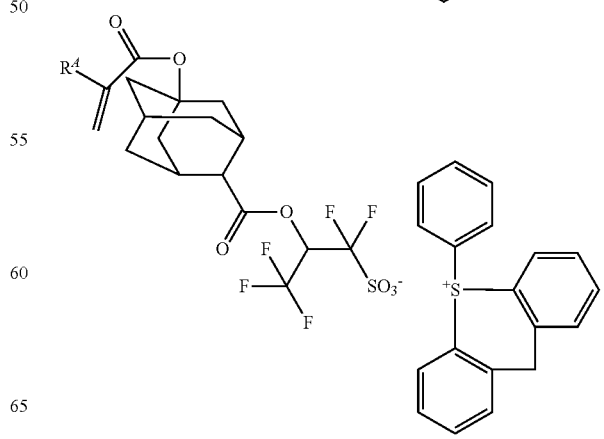

61
-continued
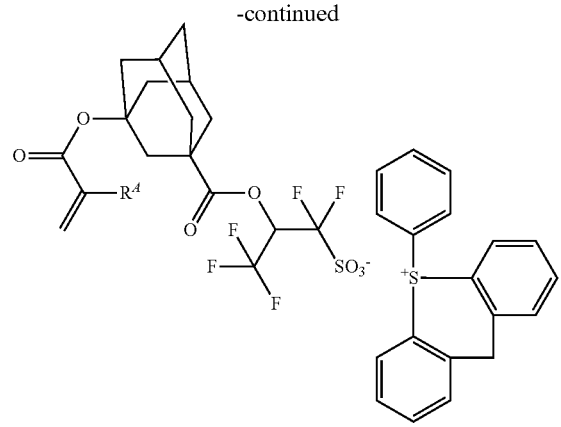
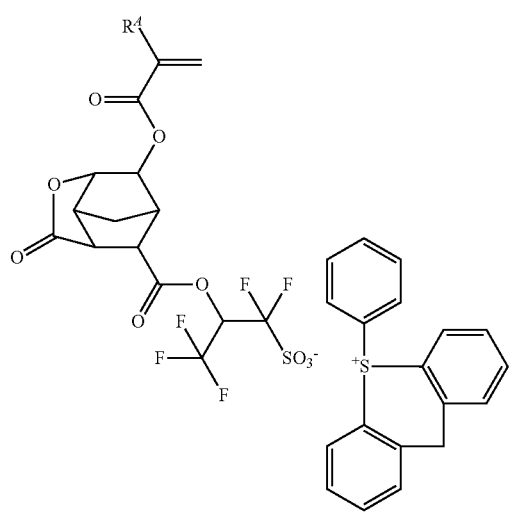
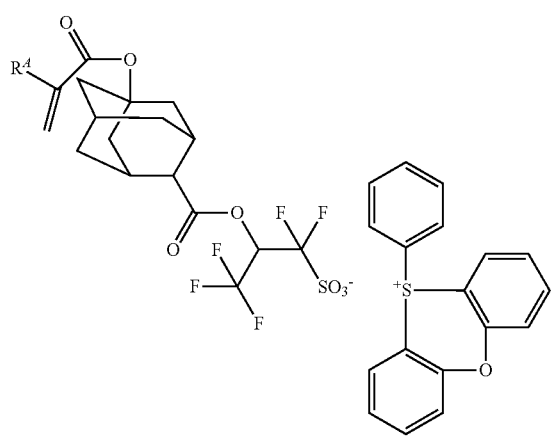
62
-continued
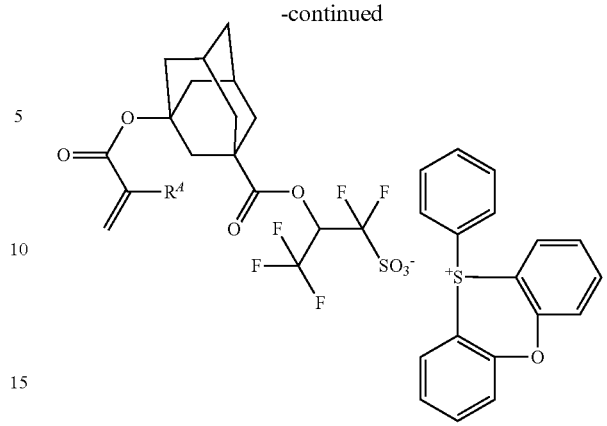
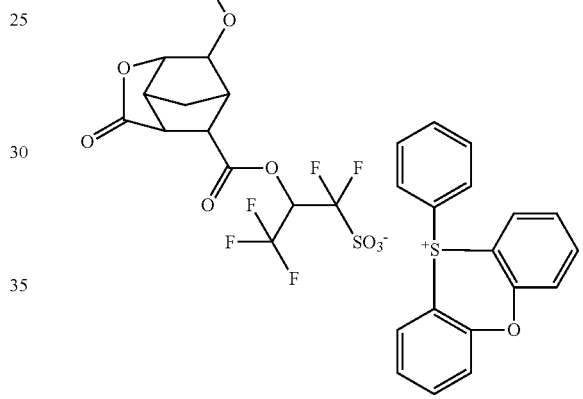
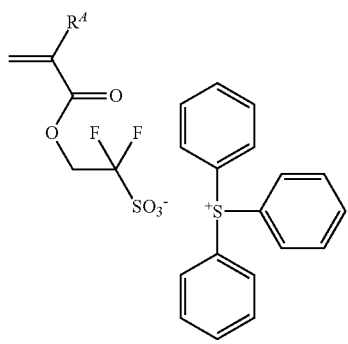
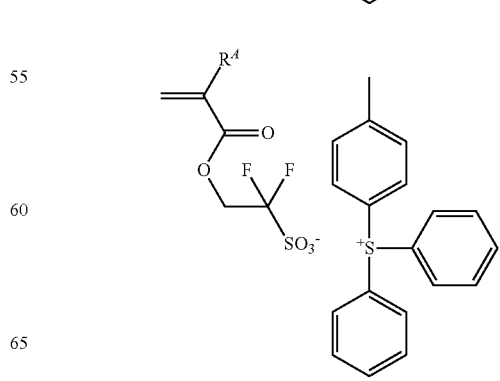

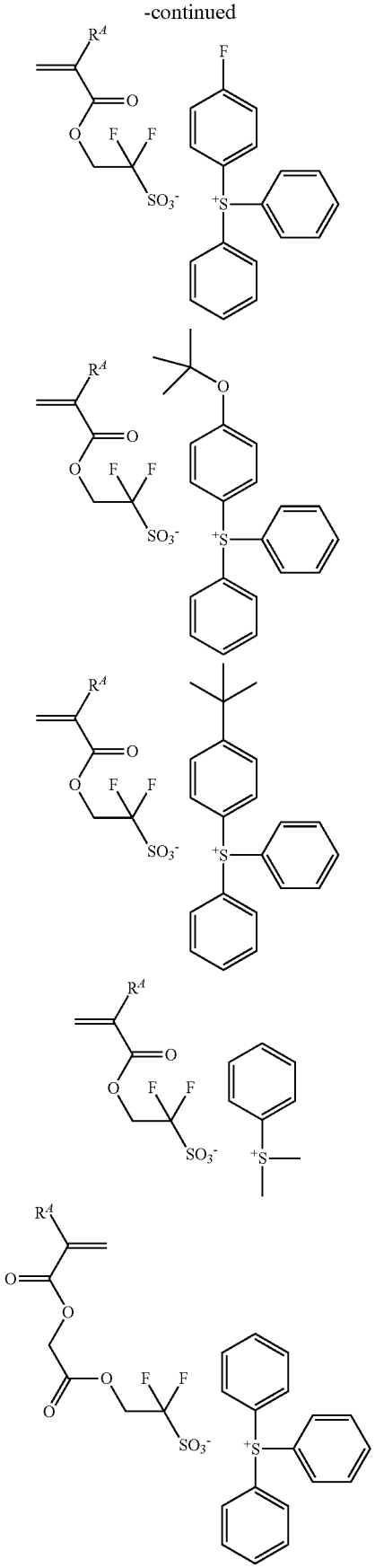
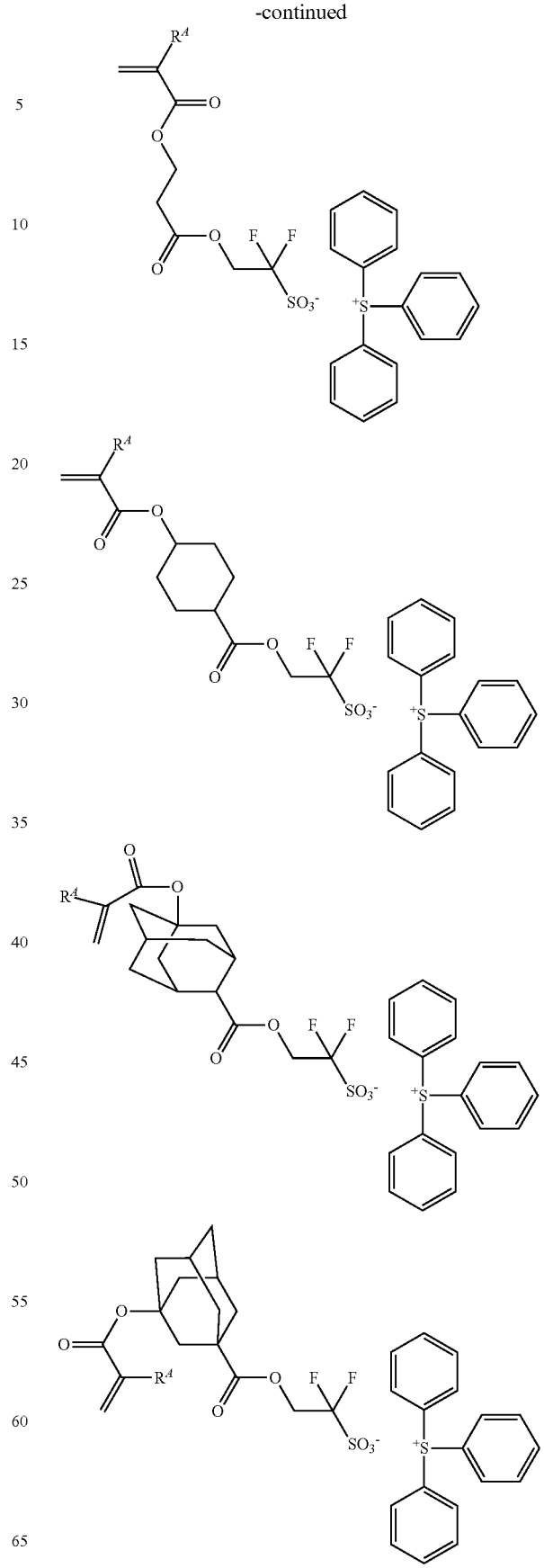

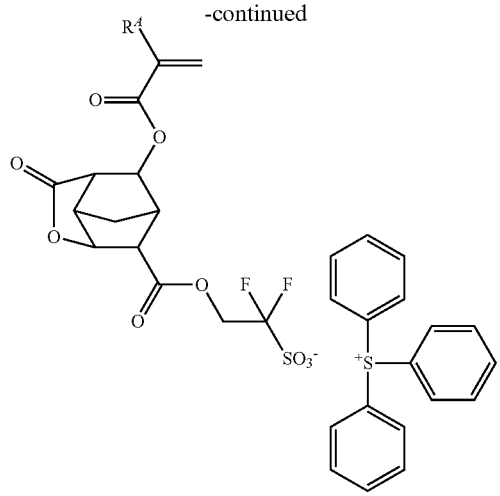
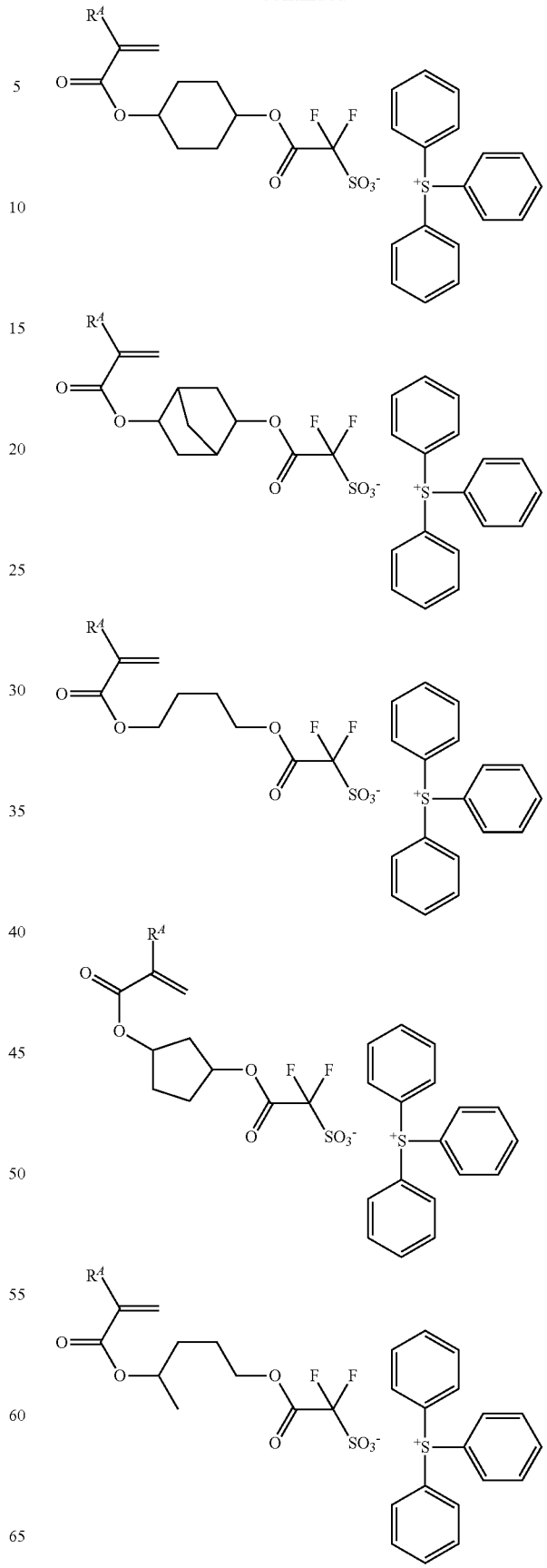
Examples of the monomer from which recurring unit (f3) is derived are shown below, but not limited thereto. $R^A$ is as defined above.
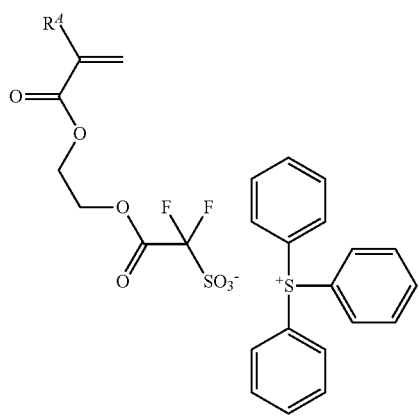

-continued
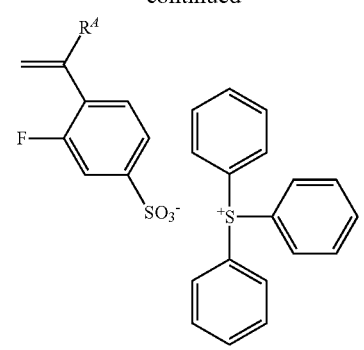
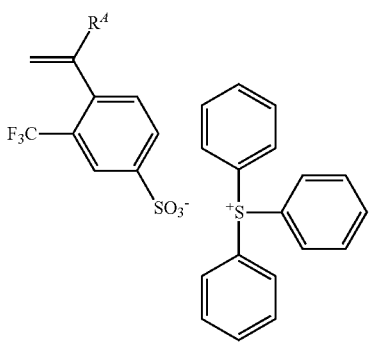
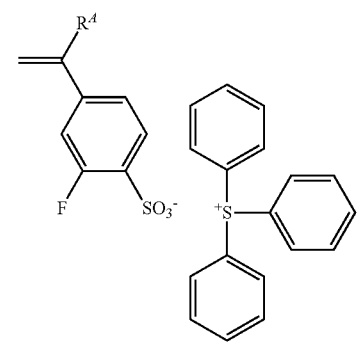
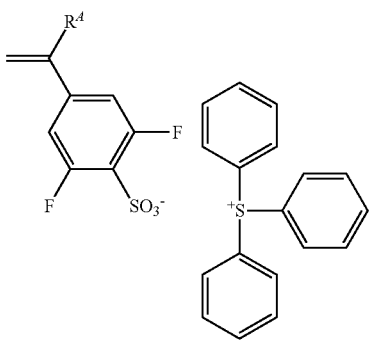
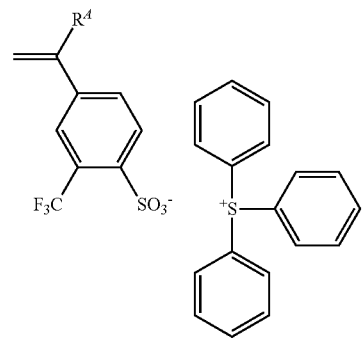
-continued
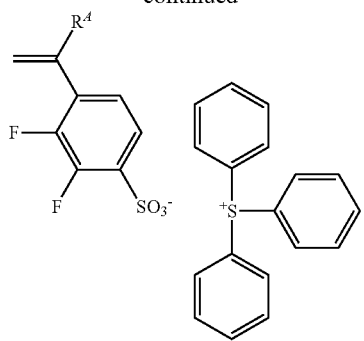
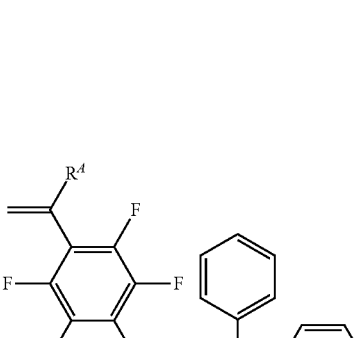
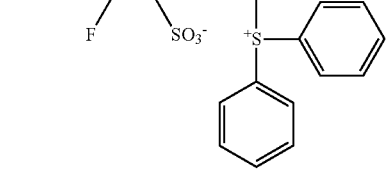
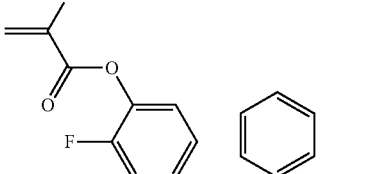

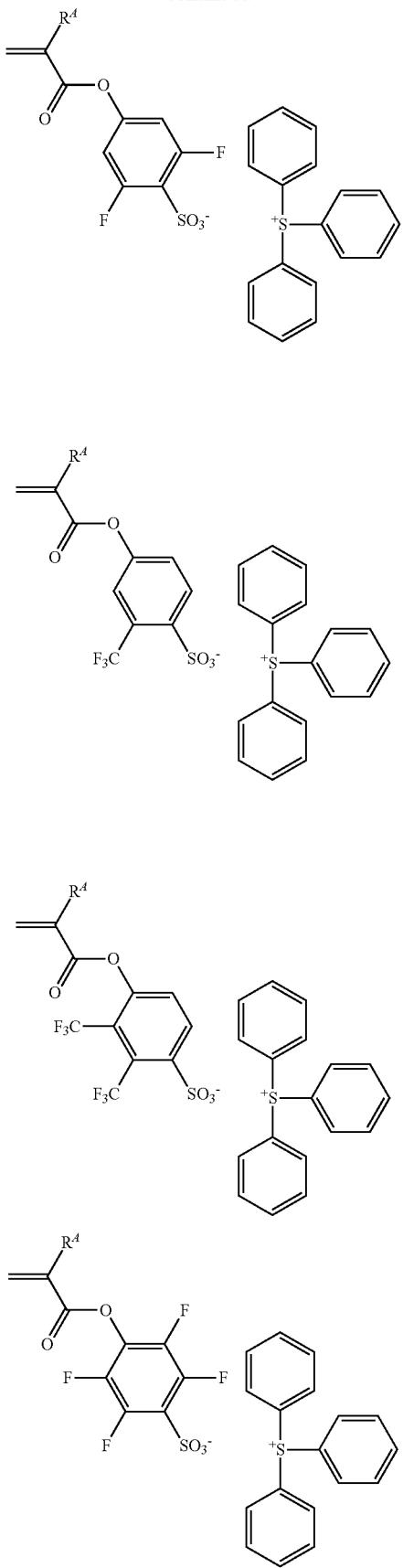

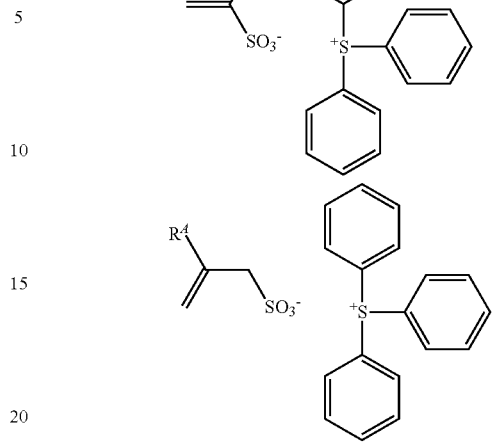

The attachment of an acid generator to the polymer main chain is effective in restraining acid diffusion, thereby preventing a reduction of resolution due to blur by acid diffusion. Also LWR is improved since the acid generator is uniformly distributed. Where a base polymer containing recurring units (f) is used, the blending of an acid generator of addition type may be omitted.

The base polymer for formulating the positive resist composition comprises recurring units (a1) or (a2) having an acid labile group as essential component and additional recurring units (b), (c), (d), (e), and (f) as optional components. A fraction of units (a1), (a2), (b), (c), (d), (e), and (f) is: preferably $0 \leq a1 < 1.0$, $0 \leq a2 < 1.0$, $0 < a1+a2 < 1.0$, $0 \leq b \leq 0.9$, $0 \leq c \leq 0.9$, $0 \leq d \leq 0.8$, $0 \leq e \leq 0.8$, and $0 \leq f \leq 0.5$; more preferably $0 \leq a1 \leq 0.9$, $0 \leq a2 \leq 0.9$, $0.1 \leq a1+a2 \leq 0.9$, $0 \leq b \leq 0.8$, $0 \leq c \leq 0.8$, $0 \leq d \leq 0.7$, $0 \leq e \leq 0.7$, and $0 \leq f \leq 0.4$; and even more preferably $0 \leq a1 \leq 0.8$, $0 \leq a2 \leq 0.8$, $0.1 \leq a1+a2 \leq 0.8$, $0 \leq b \leq 0.75$, $0 \leq c \leq 0.75$, $0 \leq d \leq 0.6$, $0 \leq e \leq 0.6$, and $0 \leq f \leq 0.3$. Notably, $f=f1+f2+f3$, meaning that unit (f) is at least one of units (f1) to (f3), and $a1+a2+b+c+d+e+f=1.0$.

For the base polymer for formulating the negative resist composition, an acid labile group is not necessarily essential. The base polymer comprises recurring units (b), and optionally recurring units (c), (d), (e), and/or (f). A fraction of these units is: preferably $0 < b \leq 1.0$, $0 \leq c \leq 0.9$, $0 \leq d \leq 0.8$, $0 \leq e \leq 0.8$, and $0 \leq f \leq 0.5$; more preferably $0.2 \leq b \leq 1.0$, $0 \leq c \leq 0.8$, $0 \leq d \leq 0.7$, $0 \leq e \leq 0.7$, and $0 \leq f \leq 0.4$; and even more preferably $0.3 \leq b \leq 1.0$, $0 \leq c \leq 0.75$, $0 \leq d \leq 0.6$, $0 \leq e \leq 0.6$, and $0 \leq f \leq 0.3$. Notably, $f=f1+f2+f3$, meaning that unit (f) is at least one of units (f1) to (f3), and $b+c+d+e+f=1.0$.

The base polymer may be synthesized by any desired methods, for example, by dissolving one or more monomers selected from the monomers corresponding to the foregoing recurring units in an organic solvent, adding a radical polymerization initiator thereto, and heating for polymerization. Examples of the organic solvent which can be used for polymerization include toluene, benzene, tetrahydrofuran, diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is preferably 2 to 100 hours, more preferably 5 to 20 hours.

Where a monomer having a hydroxyl group is copolymerized, the hydroxyl group may be replaced by an acetal group susceptible to deprotection with acid, typically ethoxyethoxy, prior to polymerization, and the polymerization be followed by deprotection with weak acid and water. Alternatively, the hydroxyl group may be replaced by an acetyl, formyl, pivaloyl or similar group prior to polymerization, and the polymerization be followed by alkaline hydrolysis.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran (THF) solvent. With too low a Mw, the resist composition may become less heat resistant. A polymer with too high a Mw may lose alkaline solubility and give rise to a footing phenomenon after pattern formation.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of Mw and Mw/Mn become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, Mw or Mw/Mn is acceptable.

Acid Generator

The resist composition may comprise an acid generator capable of generating a strong acid (referred to as acid generator of addition type, hereinafter). As used herein, the term "strong acid" refers to a compound having a sufficient acidity to induce deprotection reaction of an acid labile group on the base polymer in the case of a chemically amplified positive resist composition, or a compound having a sufficient acidity to induce acid-catalyzed polarity switch reaction or crosslinking reaction in the case of a chemically amplified negative resist composition. The inclusion of such an acid generator ensures that the amine compound functions as a quencher and the inventive resist composition functions as a chemically amplified positive or negative resist composition.

The acid generator is typically a compound (PAG) capable of generating an acid upon exposure to actinic ray or radiation. Although the PAG used herein may be any compound capable of generating an acid upon exposure to high-energy radiation, those compounds capable of generating sulfonic acid, imide acid (imidic acid) or methide acid are preferred. Suitable PAGs include sulfonium salts, iodonium salts, sulfonyldiazomethane, N-sulfonyloxyimide, and oxime-O-sulfonate acid generators. Exemplary PAGs are described in JP-A 2008-111103, paragraphs [0122]-[0142] (U.S. Pat. No. 7,537,880).

As the PAG used herein, sulfonium salts having the formula (1-1) and iodonium salts having the formula (1-2) are also preferred.

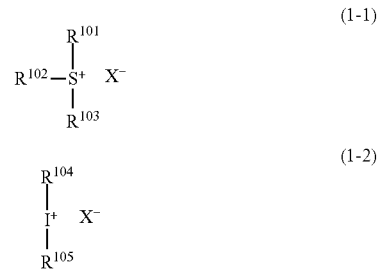

In formulae (1-1) and (1-2), $R^{101}$, $R^{102}$, $R^{103}$, $R^{104}$ and $R^{105}$ are each independently a $C_1$-$C_{20}$ monovalent hydrocarbon group which may contain a heteroatom. Any two of $R^{101}$, $R^{102}$ and $R^{103}$ may bond together to form a ring with the sulfur atom to which they are attached. The monovalent hydrocarbon group may be straight, branched or cyclic, and examples thereof include those exemplified above for $R^{21}$ to $R^{28}$ in formulae (f1) to (f3).

Example of the cation in the sulfonium salt having formula (1-1) are shown below, but not limited thereto.

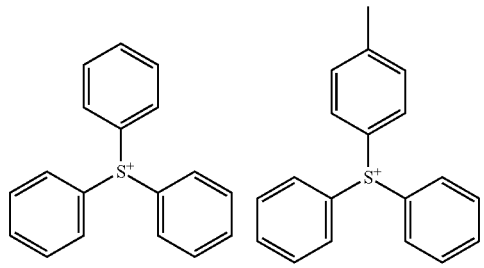

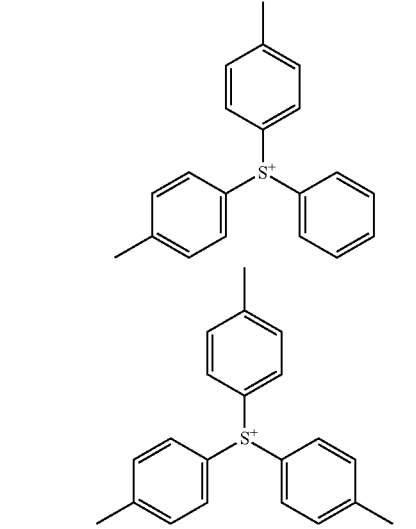

73
-continued
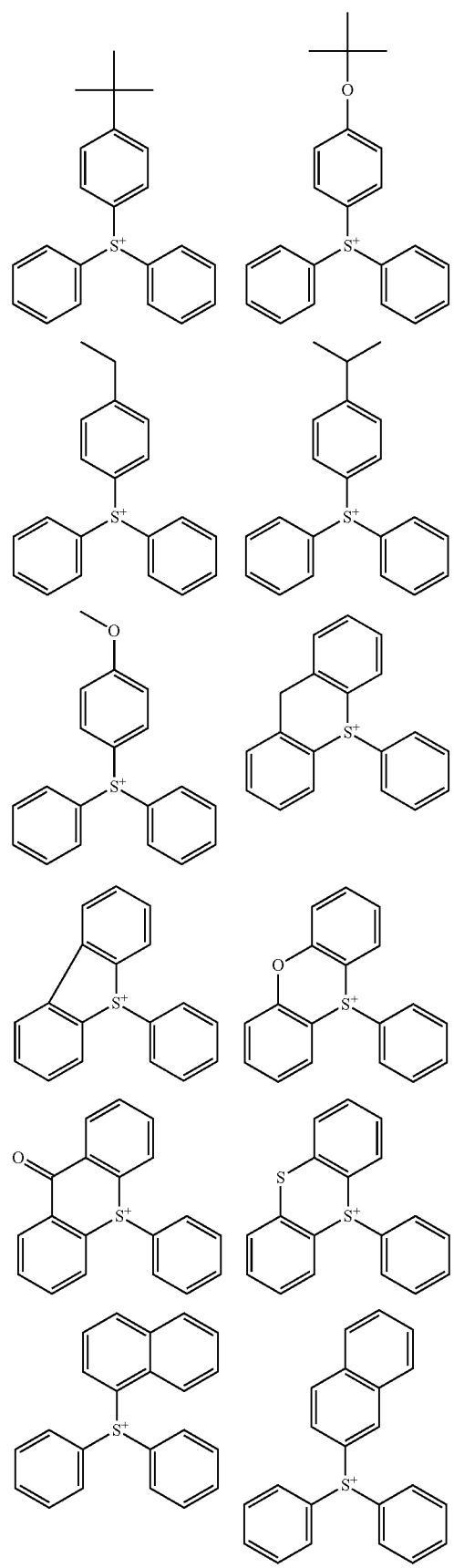
74
-continued
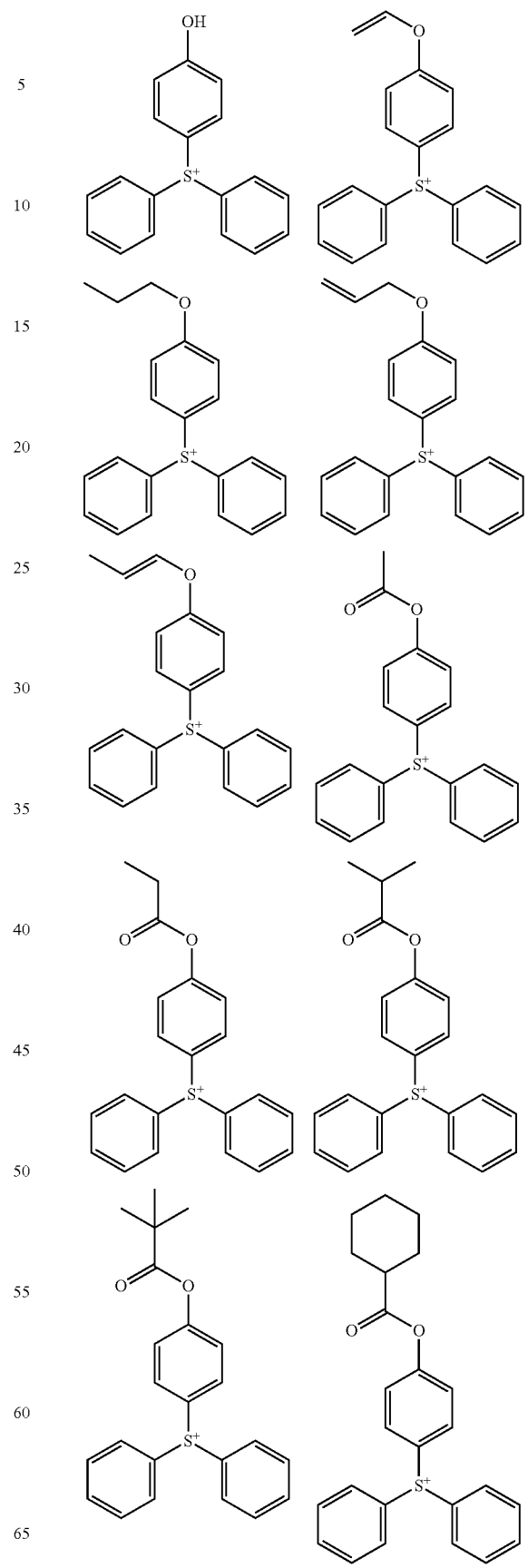

75
-continued
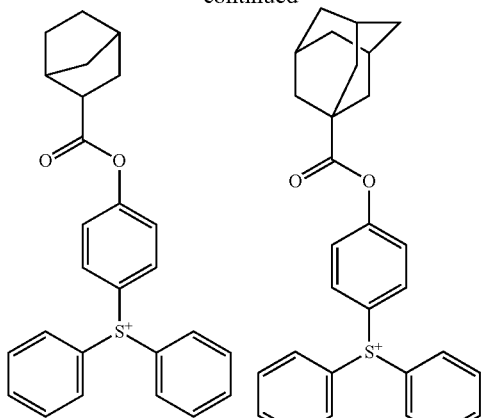
76
-continued
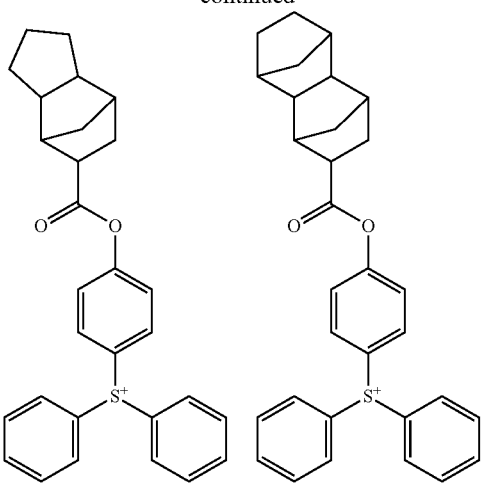
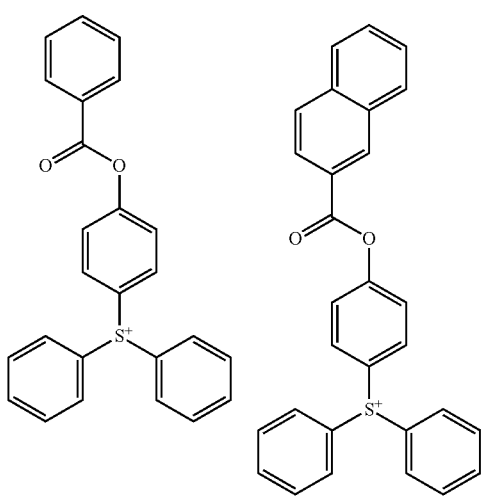
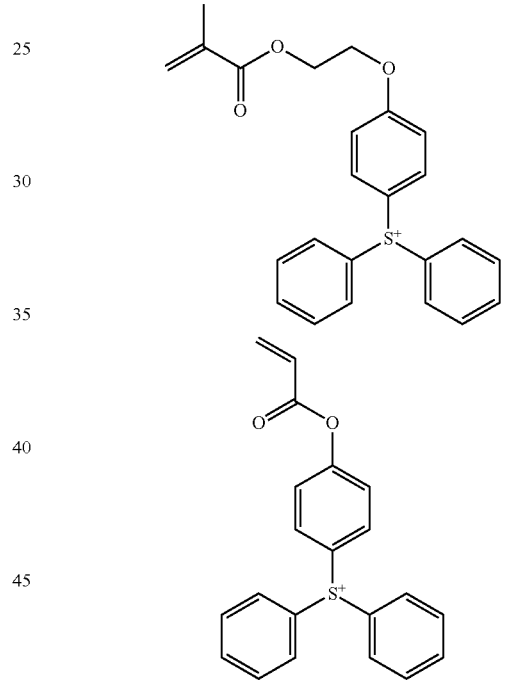
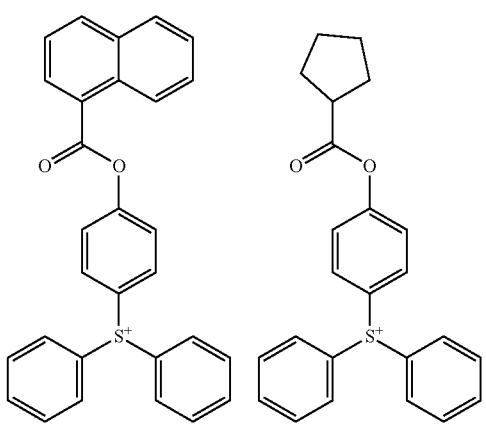
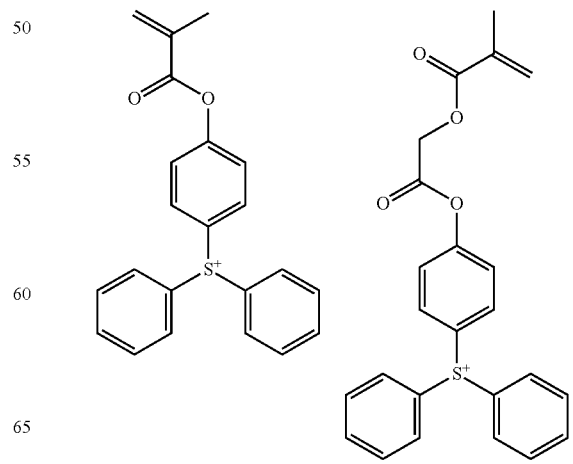

77
-continued
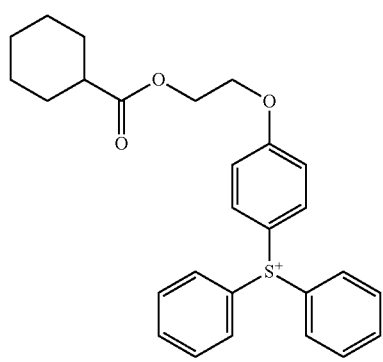
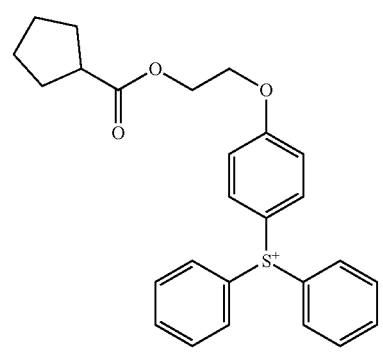
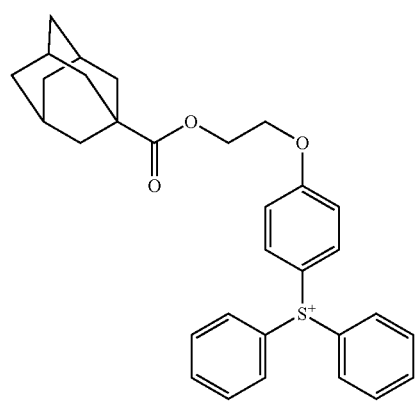
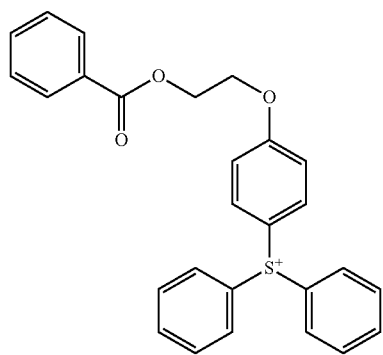
78
-continued
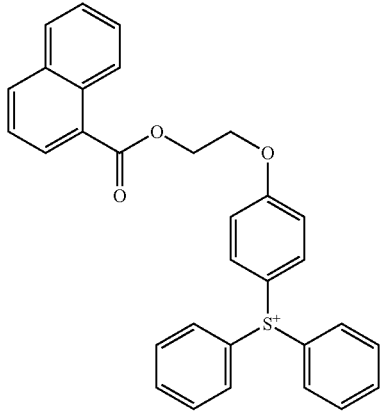
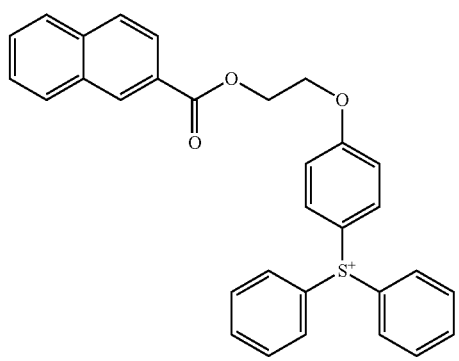
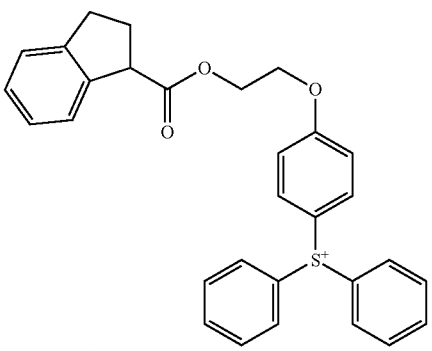
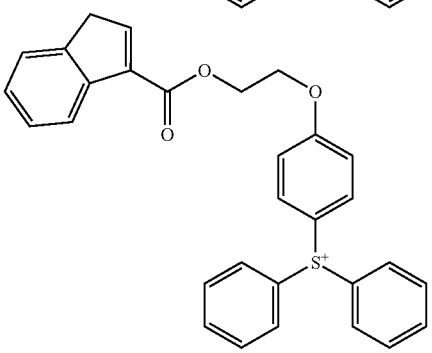

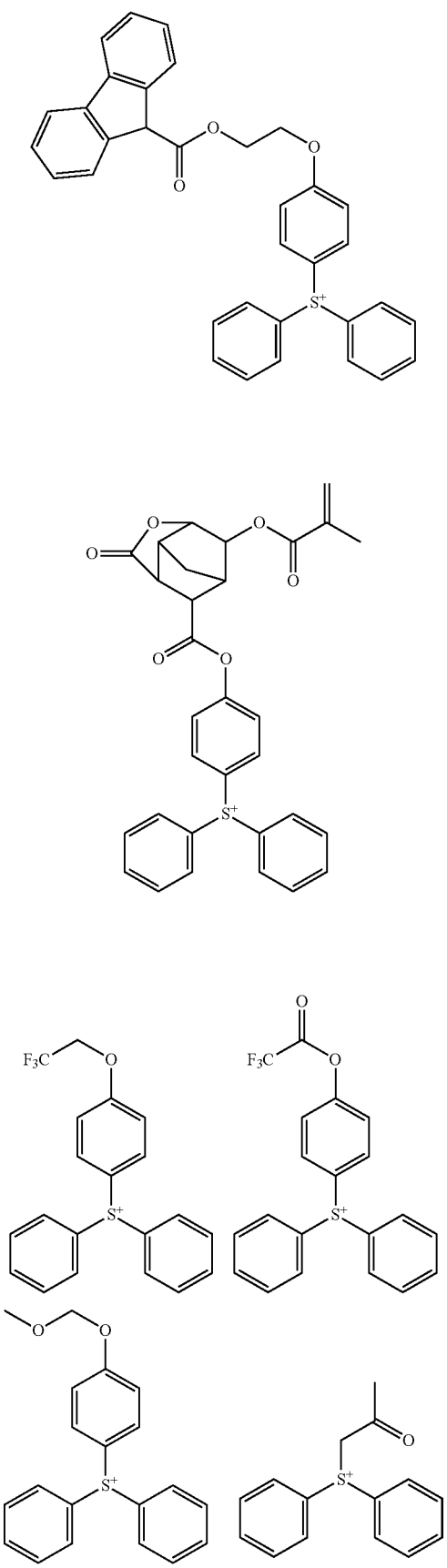
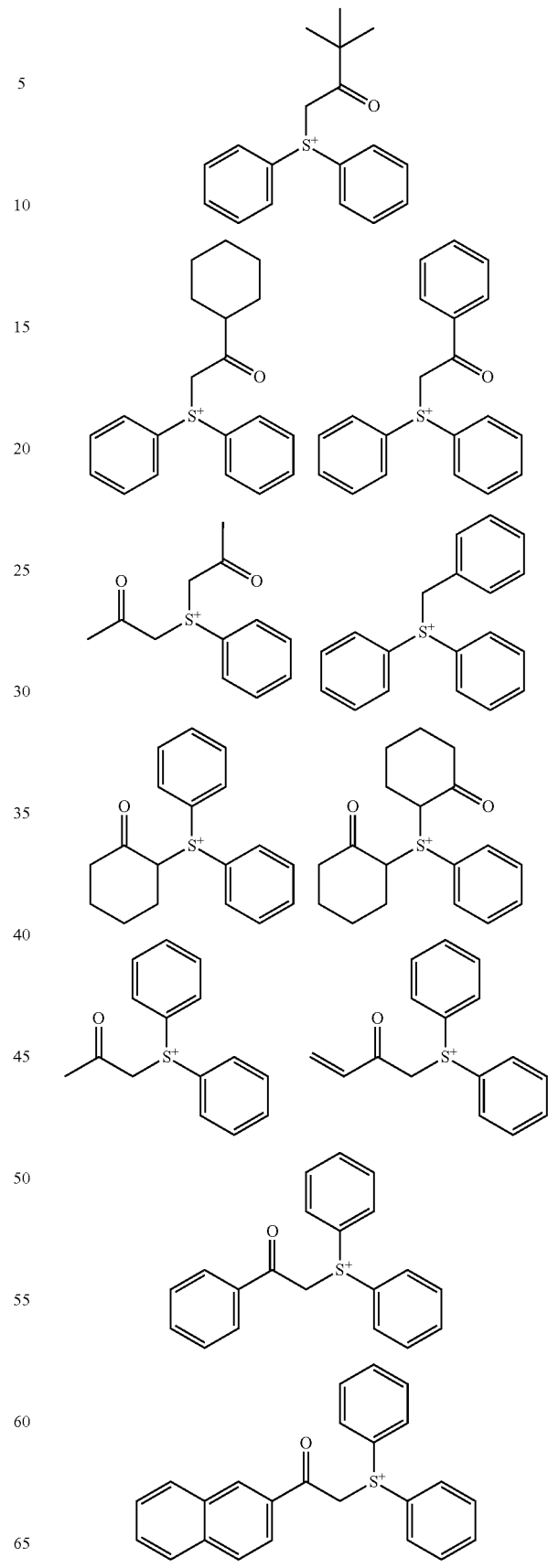

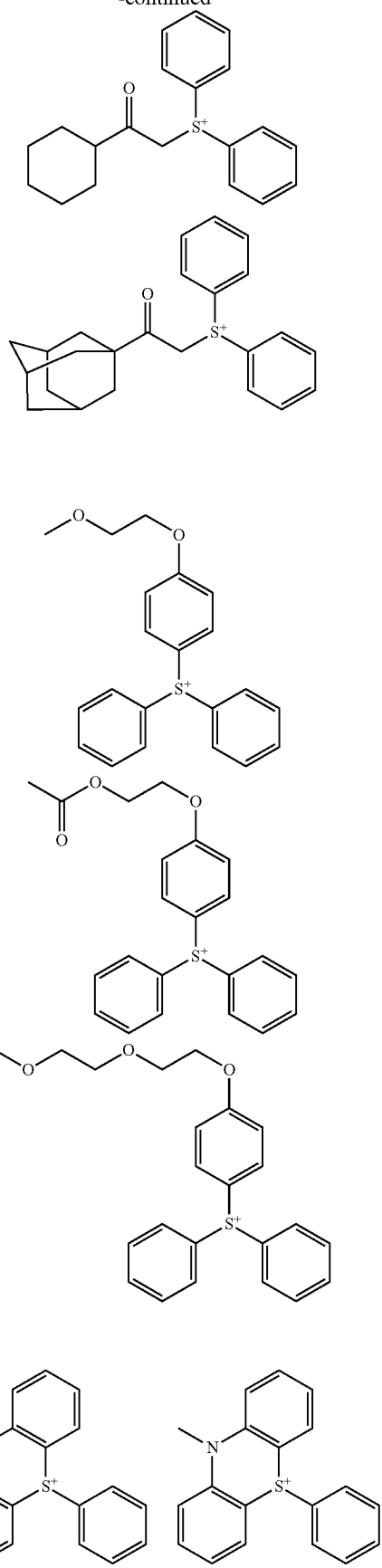
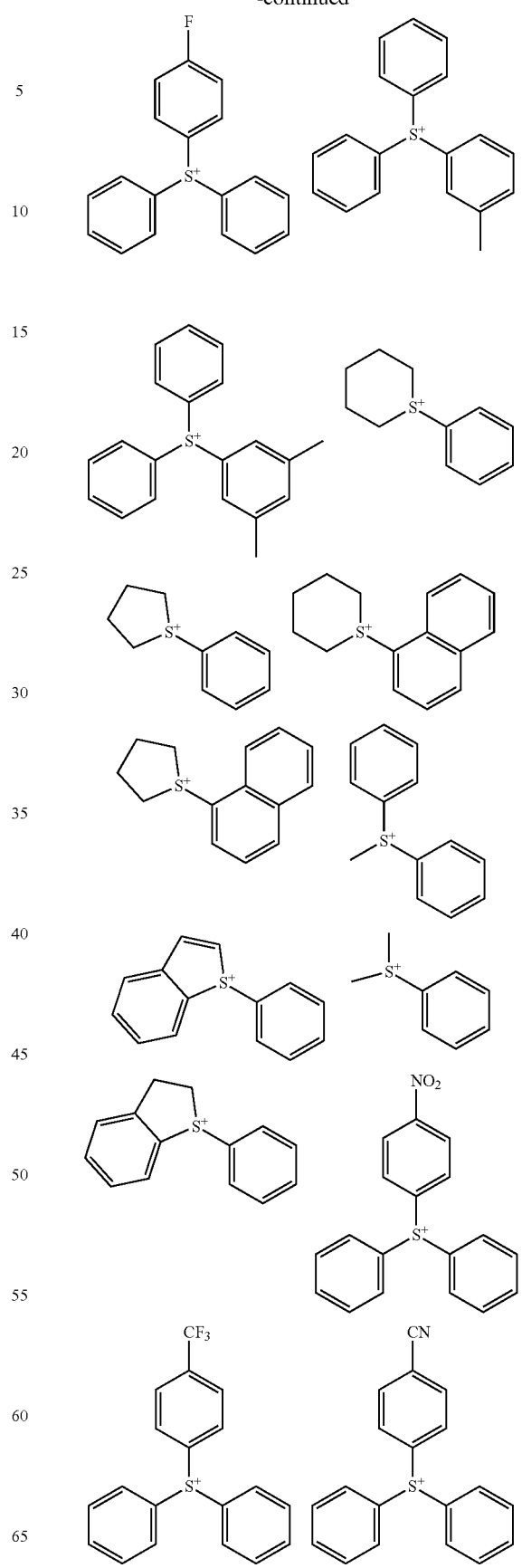

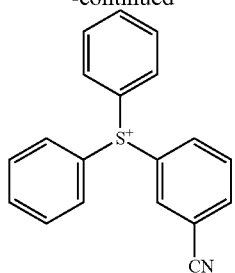
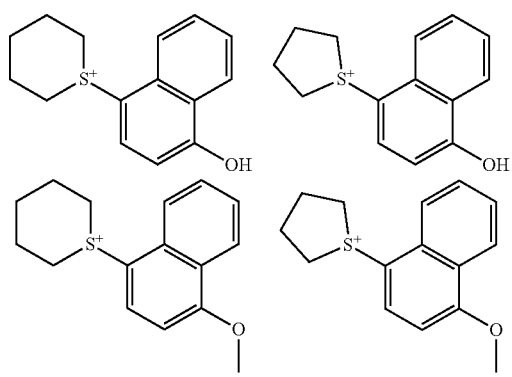
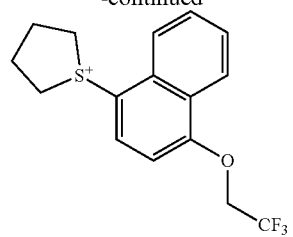
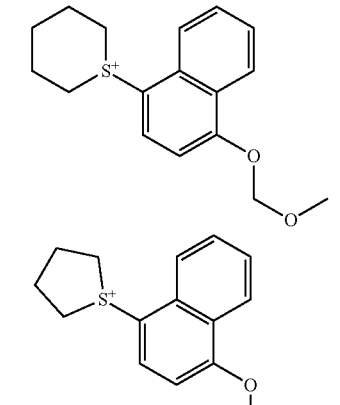
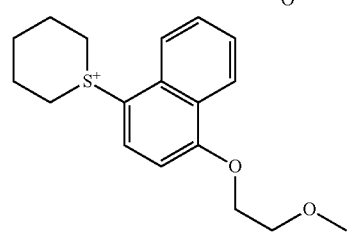
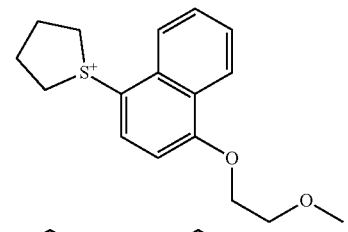
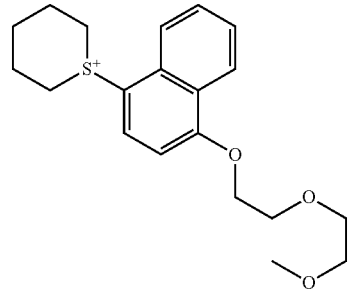
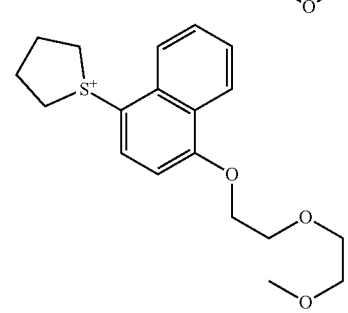

85
-continued
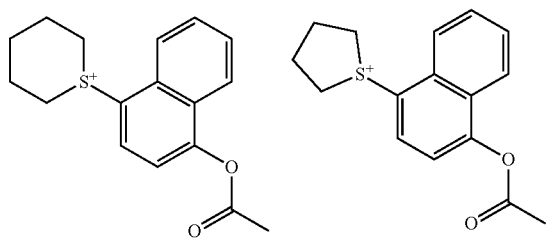
86
-continued
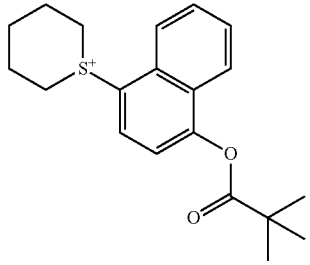
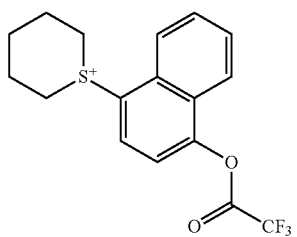
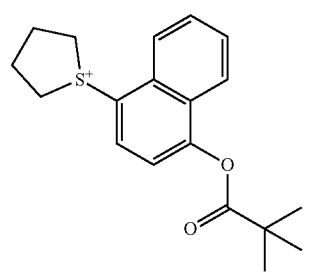
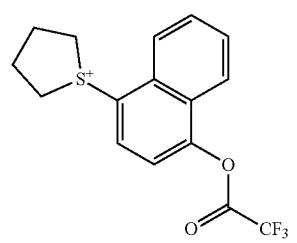
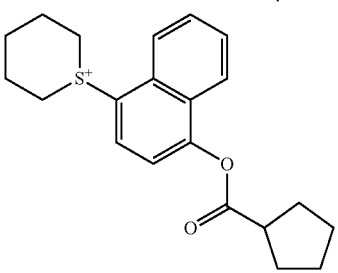
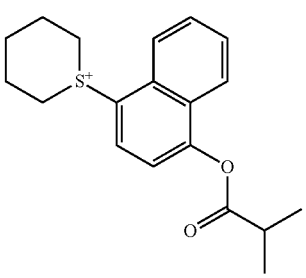
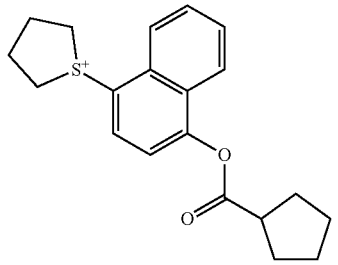
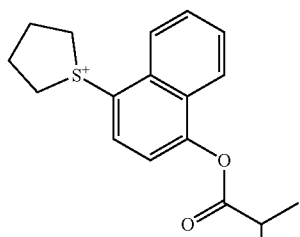
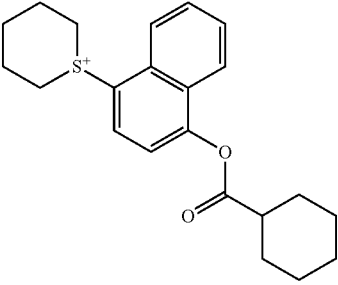
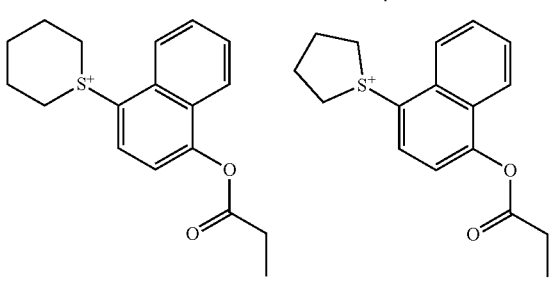
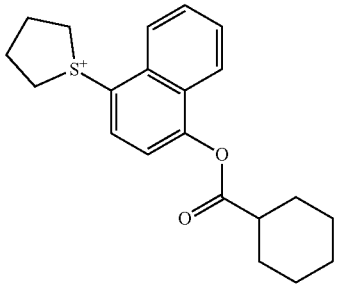

87
-continued
88
-continued
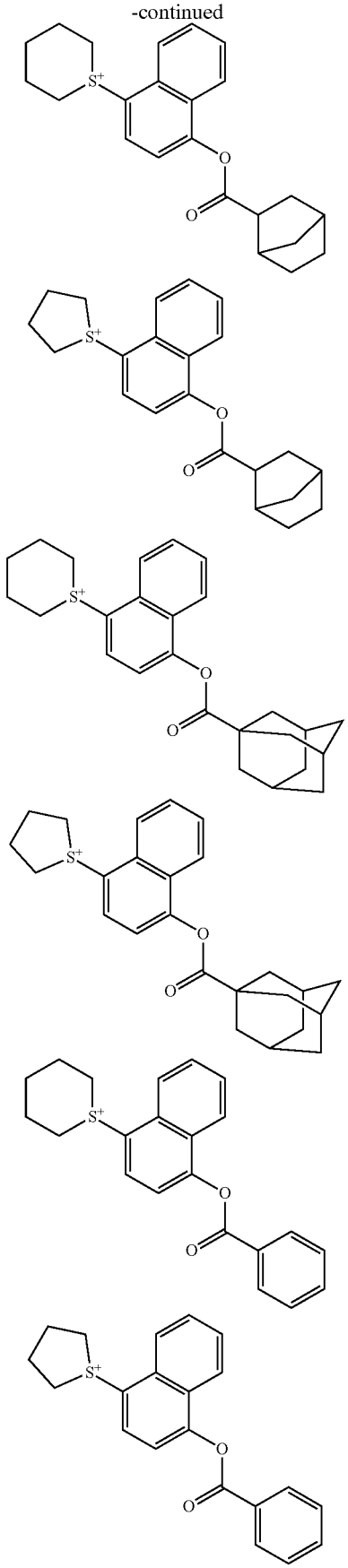

89
-continued
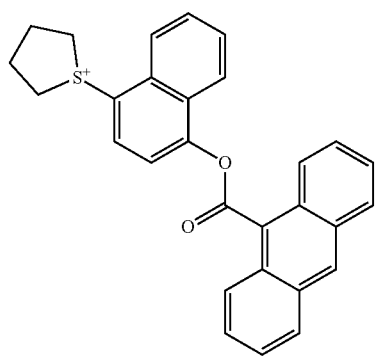
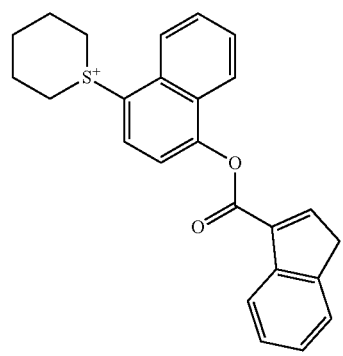
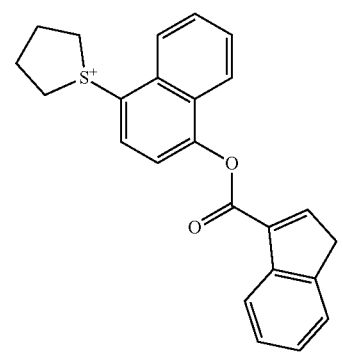
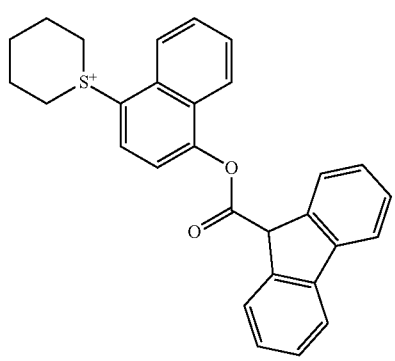
90
-continued
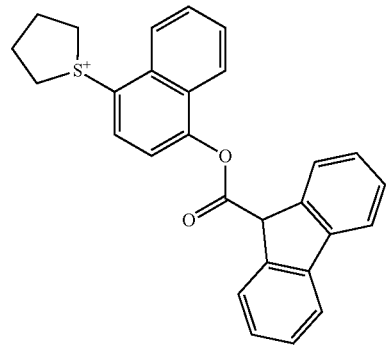
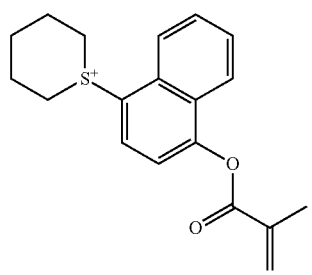
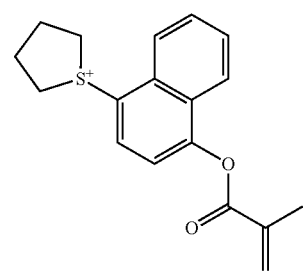
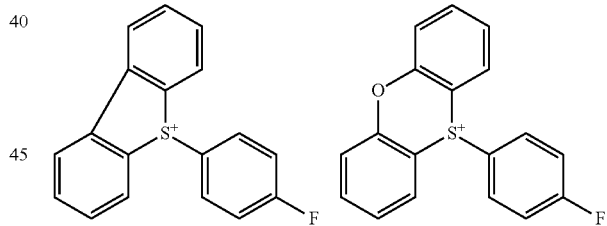
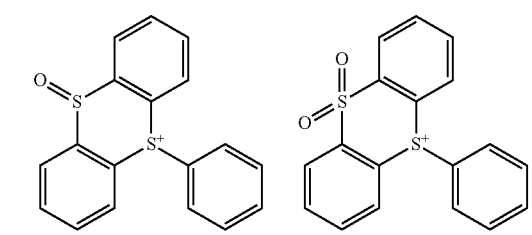
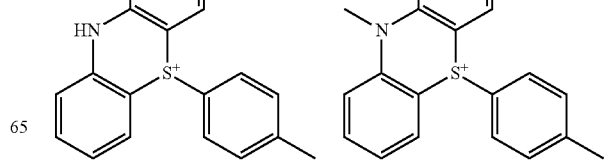

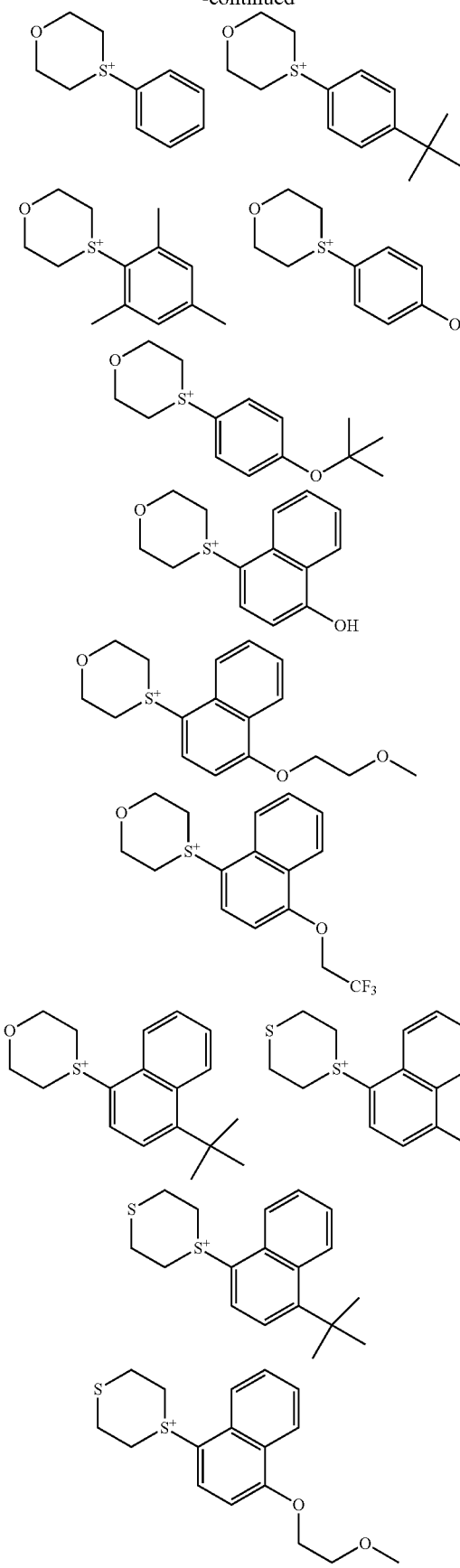
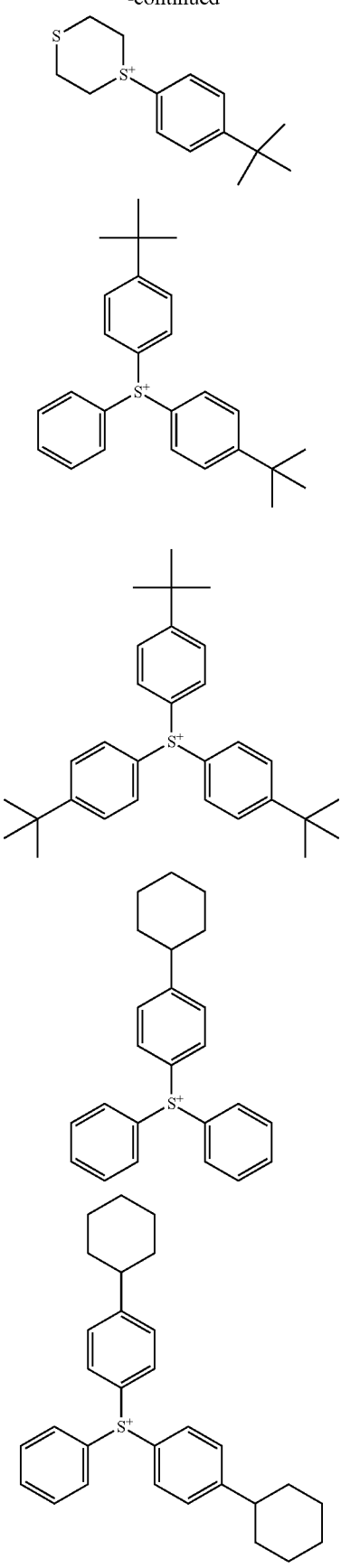

93
-continued
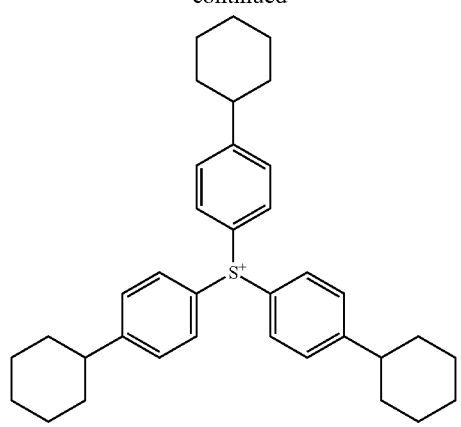
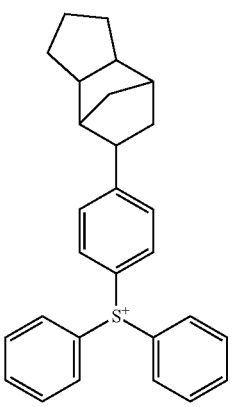
94
-continued
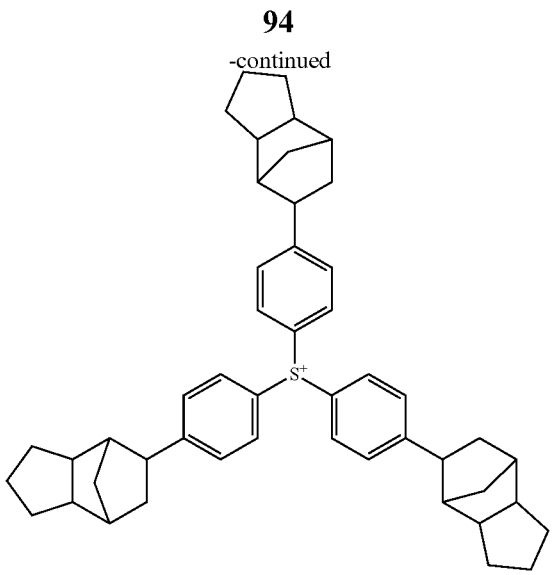
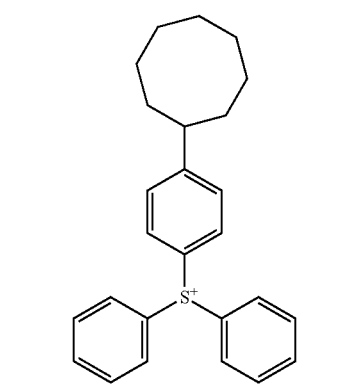
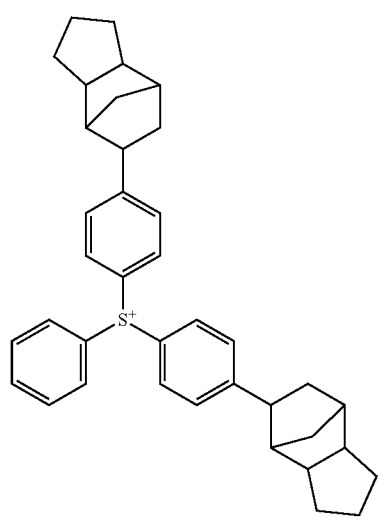
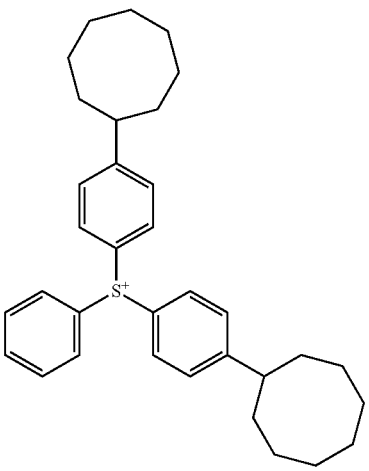

95
-continued
96
-continued
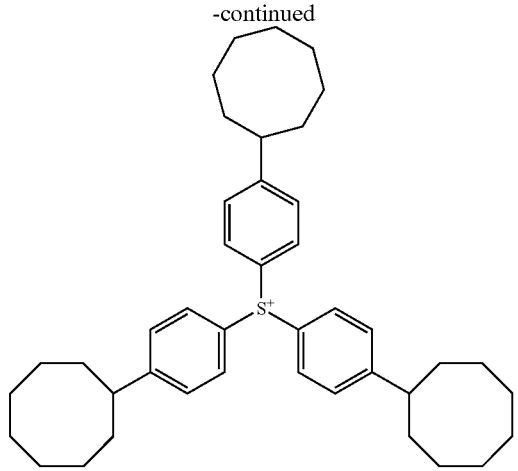
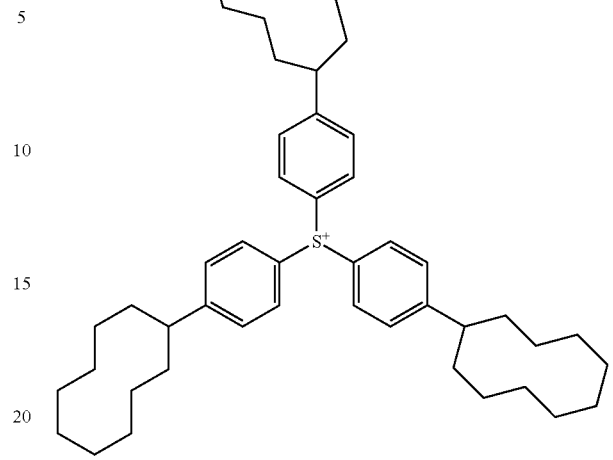
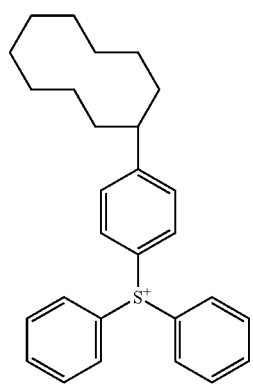
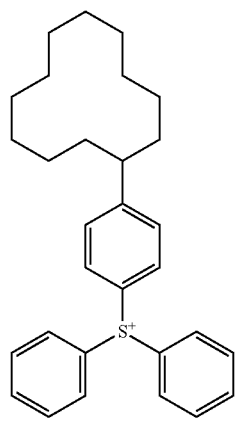
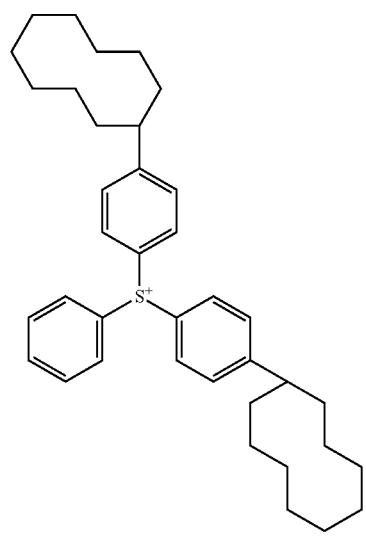
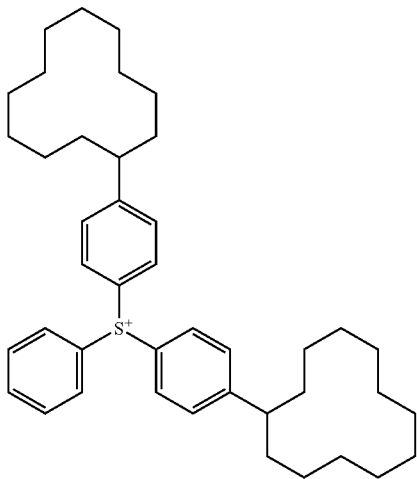

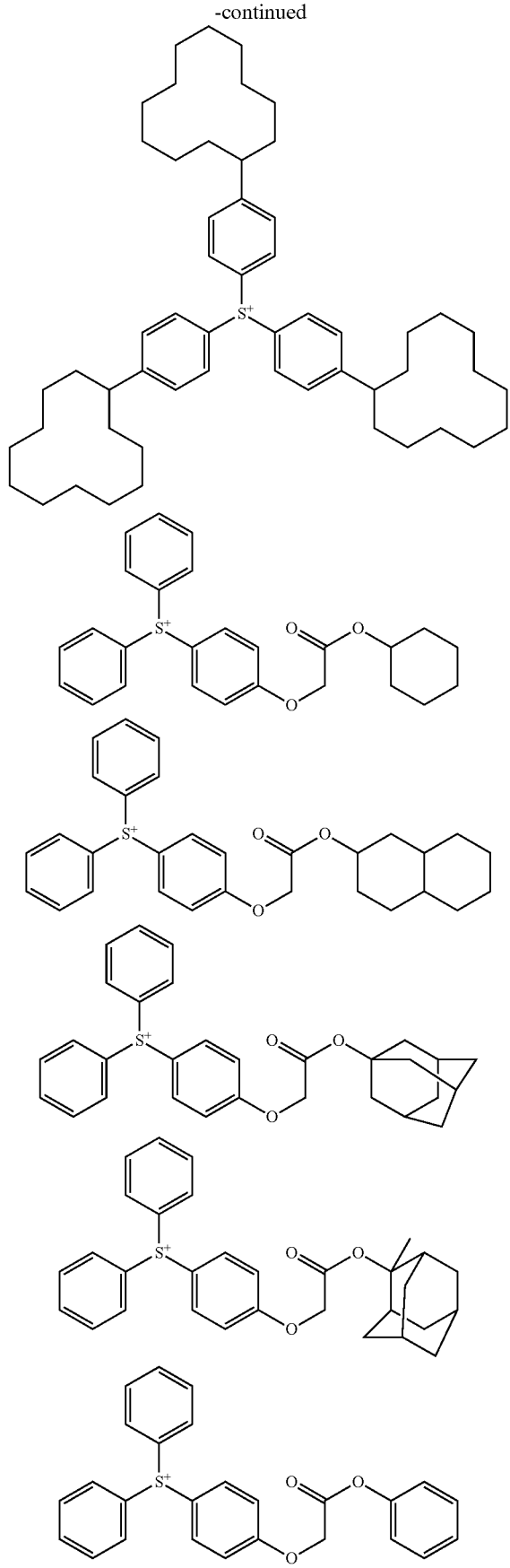
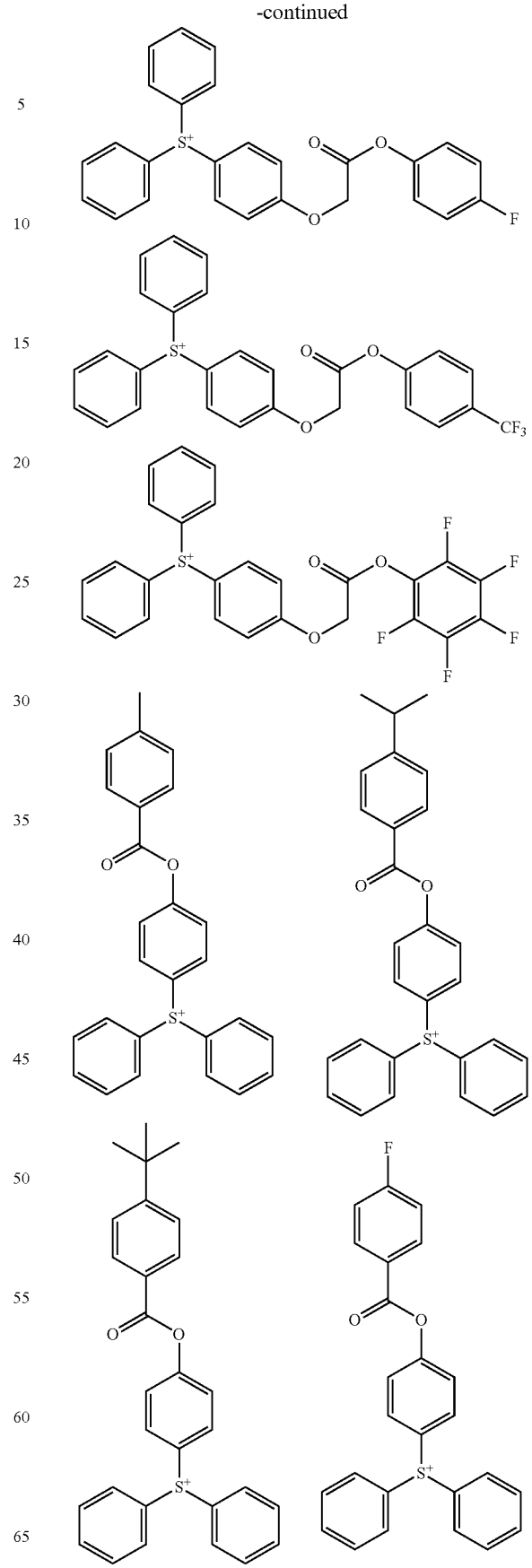

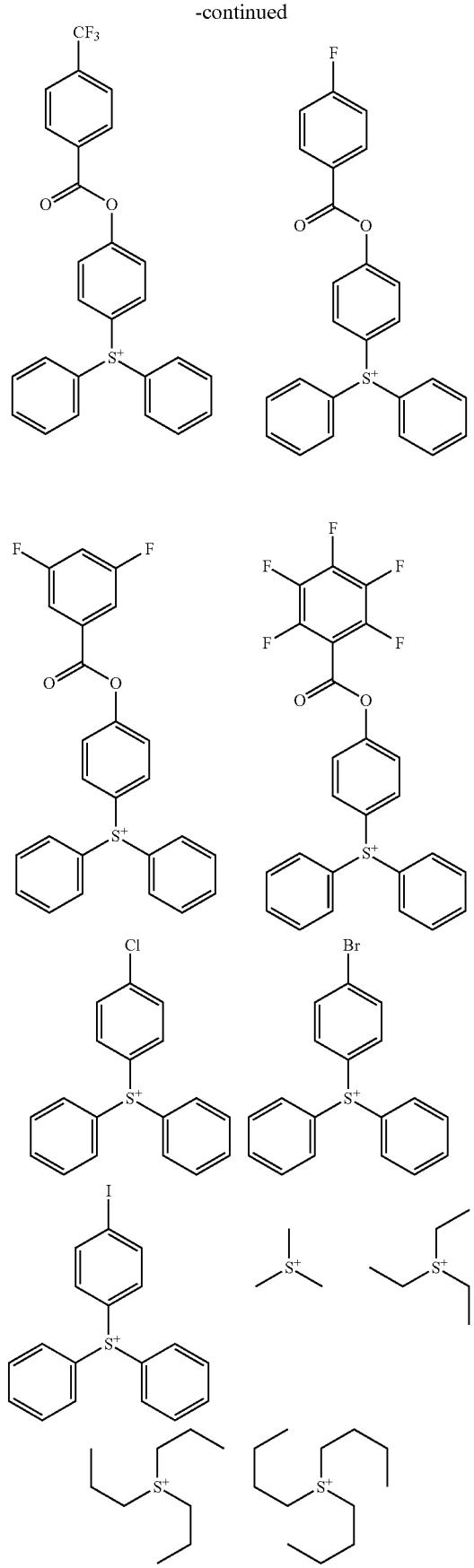
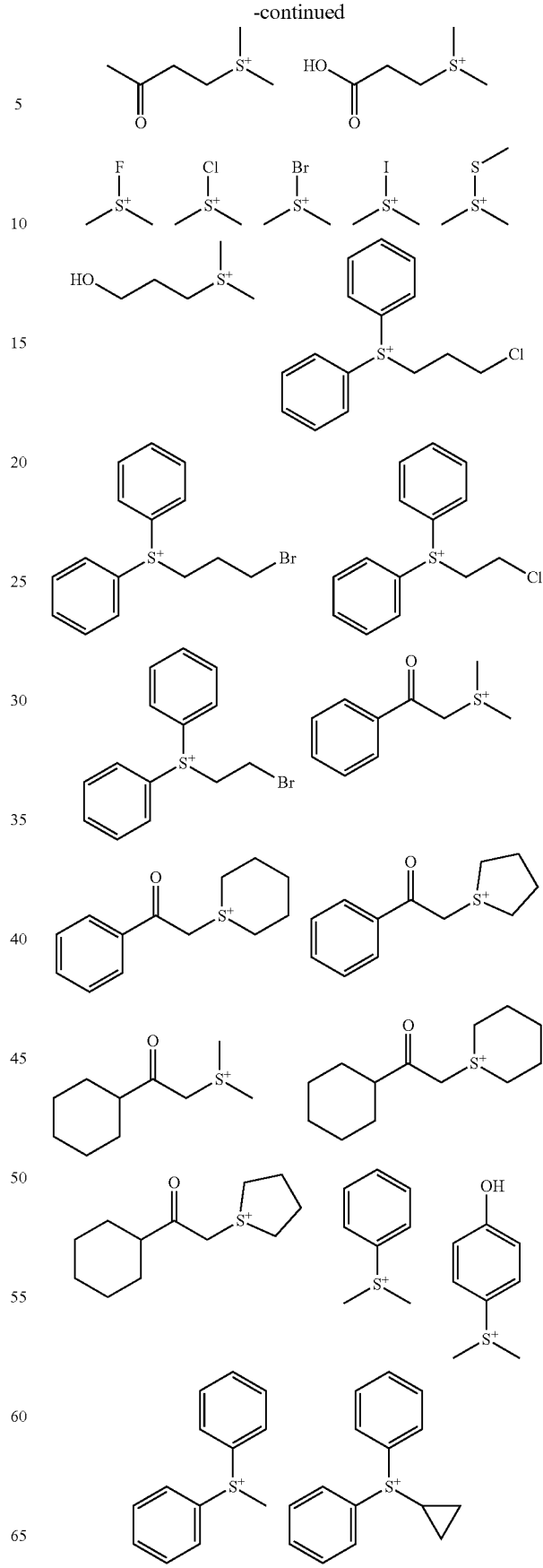

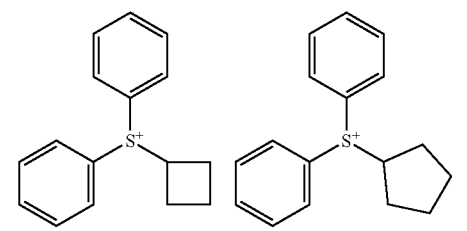
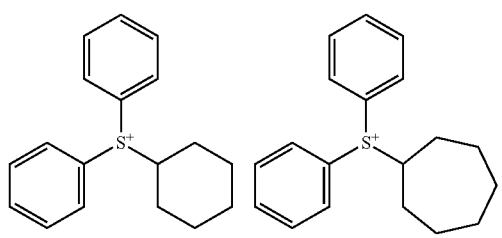
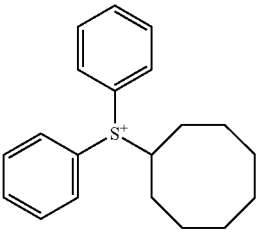
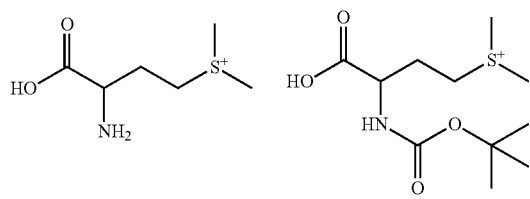
Examples of the cation in the iodonium salt having formula (1-2) are shown below, but not limited thereto.
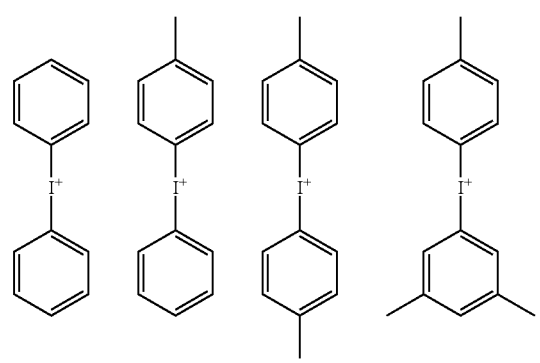
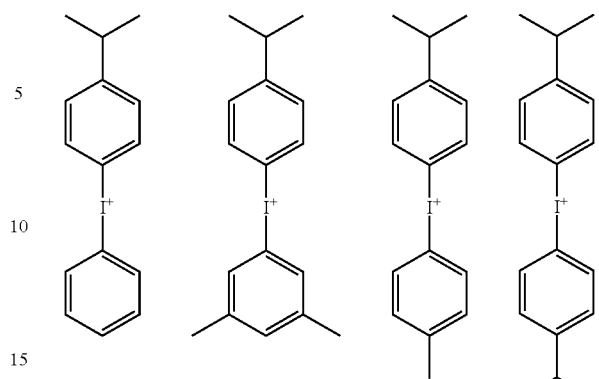
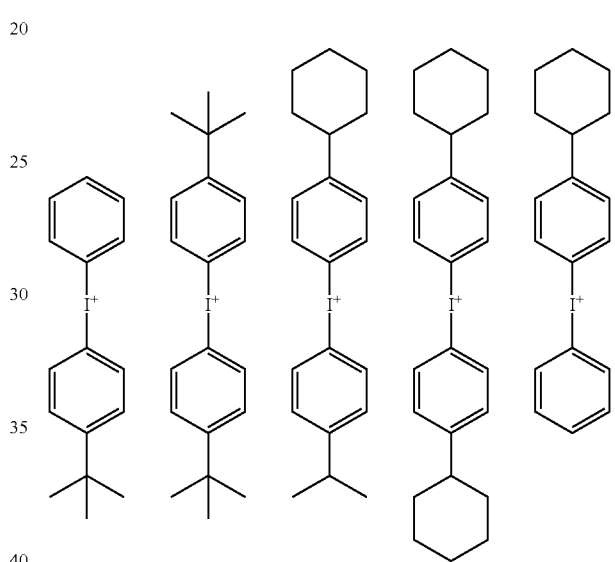
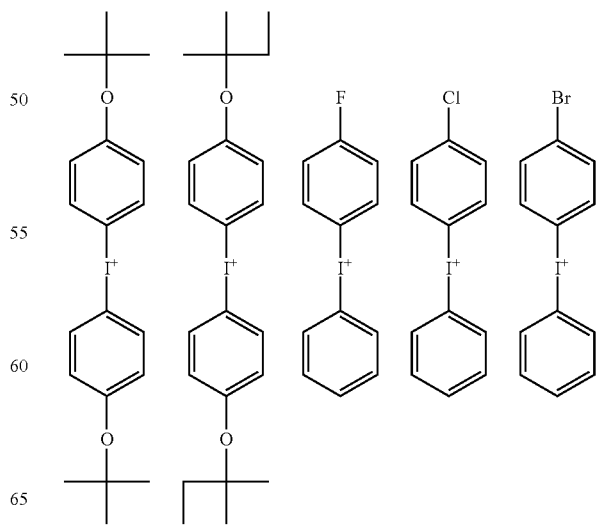

-continued

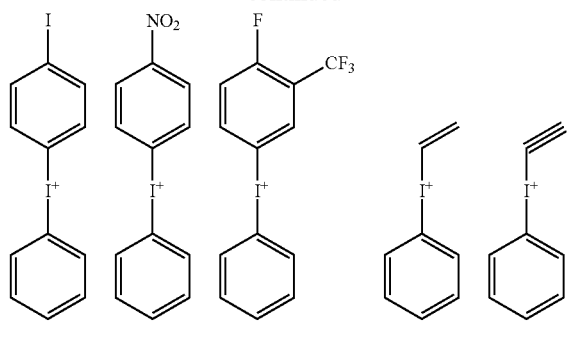

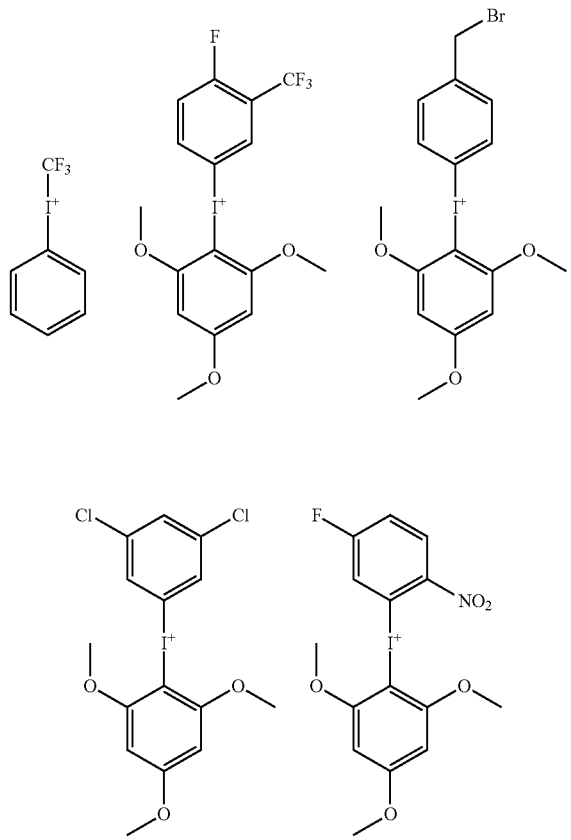

-continued

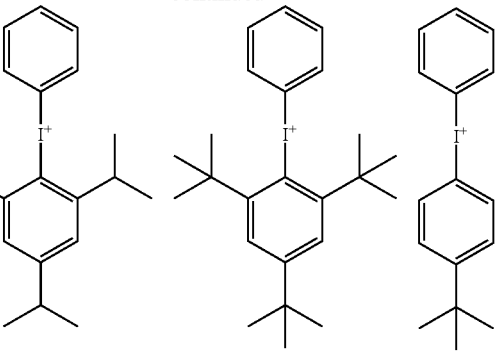

In formulae (1-1) and (1-2). $X^-$ is an anion of the following formula (1A), (1B), (1C) or (1D).

$$R^{fa}-CF_2-SO_3^- \quad (1A)$$

(1B)

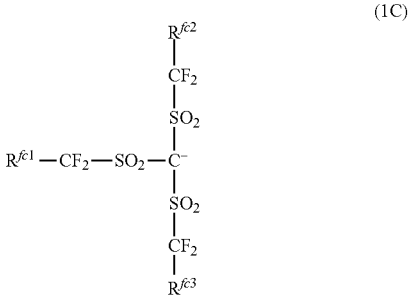

(1C)

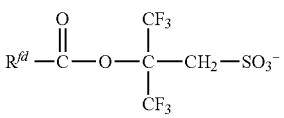

(1D)

In formula (1A). $R^{fa}$ is fluorine or a $C_1$-$C_{40}$ monovalent hydrocarbon group which may contain a heteroatom. The monovalent hydrocarbon group may be straight, branched or cyclic, and examples thereof include those exemplified later for $R^{107}$.

Of the anions of formula (1A), an anion having the formula (1A') is preferred.

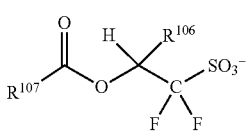

(1A')

In formula (1A'), $R^{106}$ is hydrogen or trifluoromethyl, preferably trifluoromethyl.

$R^{107}$ is a $C_1$-$C_{38}$ monovalent hydrocarbon group which may contain a heteroatom. As the heteroatom, oxygen, nitrogen, sulfur and halogen atoms are preferred, with oxygen being most preferred. Of the monovalent hydrocarbon groups represented by $R^{107}$, those groups of 6 to 30 carbon atoms are preferred from the aspect of achieving a

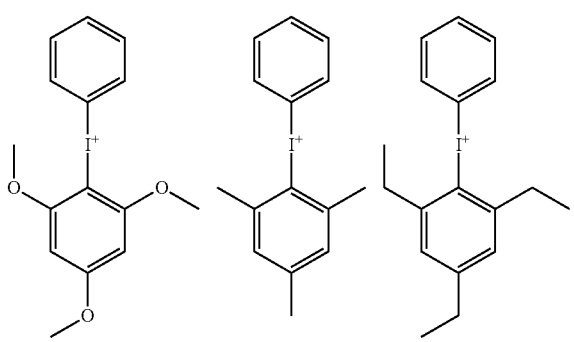

high resolution in forming patterns of fine feature size. The monovalent hydrocarbon groups may be straight, branched or cyclic. Examples thereof include, but are not limited to, straight or branched alkyl groups such as methyl, ethyl, propyl, isopropyl, butyl, isobutyl, sec-butyl, tert-butyl, pentyl, neopentyl, hexyl, heptyl, 2-ethylhexyl, nonyl, undecyl, tridecyl, pentadecyl, heptadecyl, eicosanyl, monovalent saturated alicyclic hydrocarbon groups such as cyclopentyl, cyclohexyl, 1-adamantyl, 2-adamantyl, 1-adamantylmethyl, norbornyl, norbornylmethyl, tricyclodecanyl, tetracyclodecanyl, tetracyclododecanylmethyl, and dicyclohexylmethyl: monovalent unsaturated aliphatic hydrocarbon groups such as allyl and 3-cyclohexenyl; aryl groups such as phenyl, 1-naphthyl and 2-naphthyl; and aralkyl groups such as benzyl and diphenylmethyl. Examples of the monovalent hydrocarbon group having a heteroatom include tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl. In these groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate moiety, lactone ring, sultone ring, carboxylic anhydride or haloalkyl moiety.

With respect to the synthesis of the sulfonium salt having an anion of formula (1A'), reference may be made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the anion having formula (1A) are shown below, but not limited thereto.

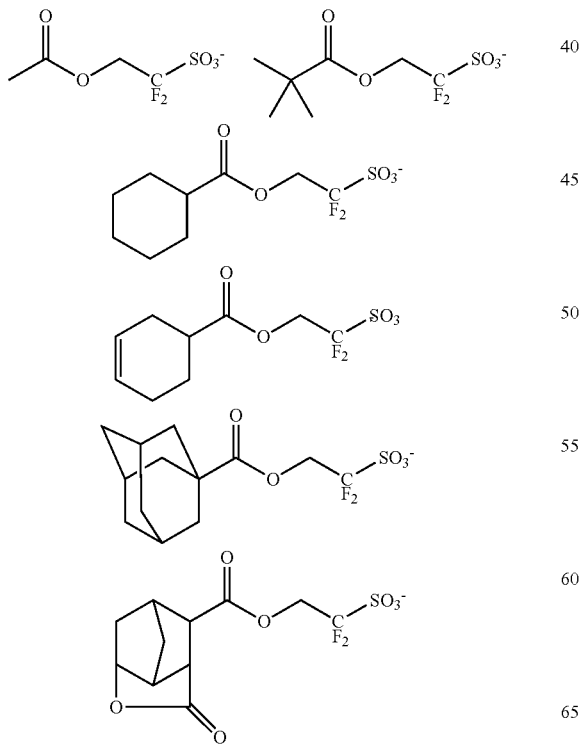

-continued

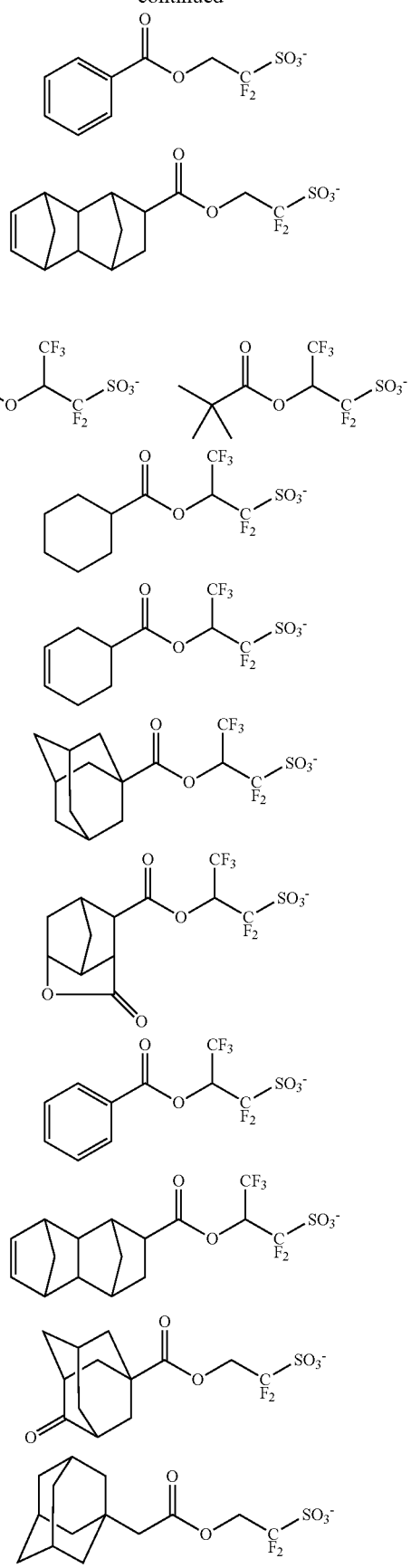

107

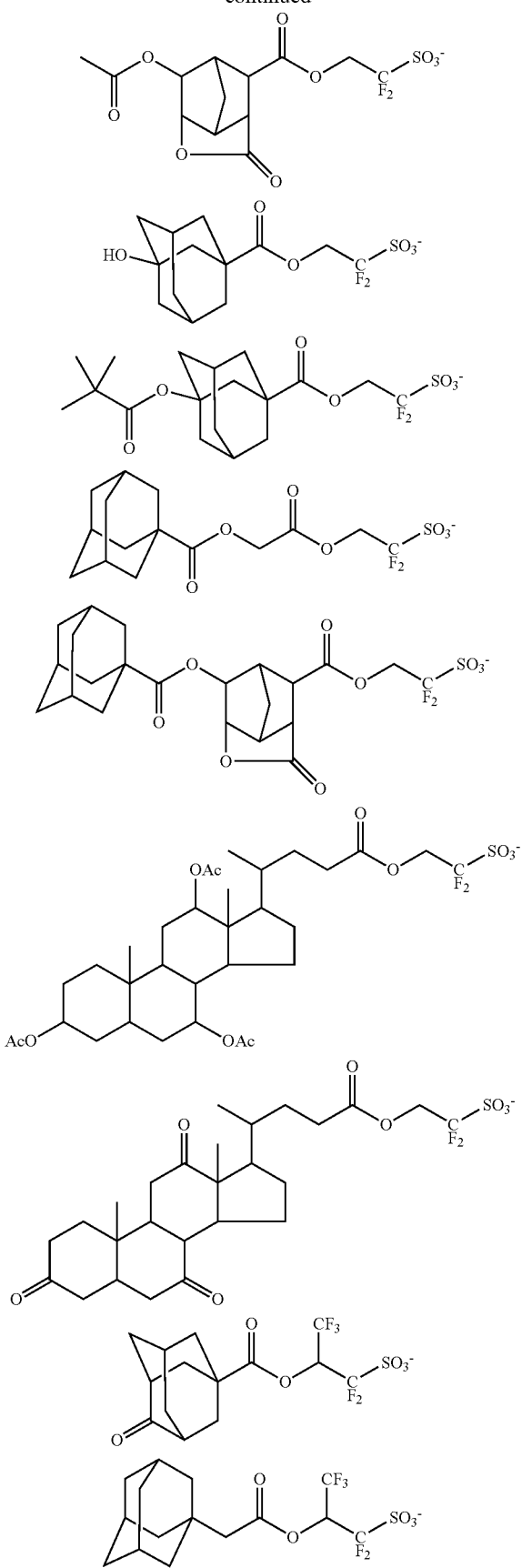

108

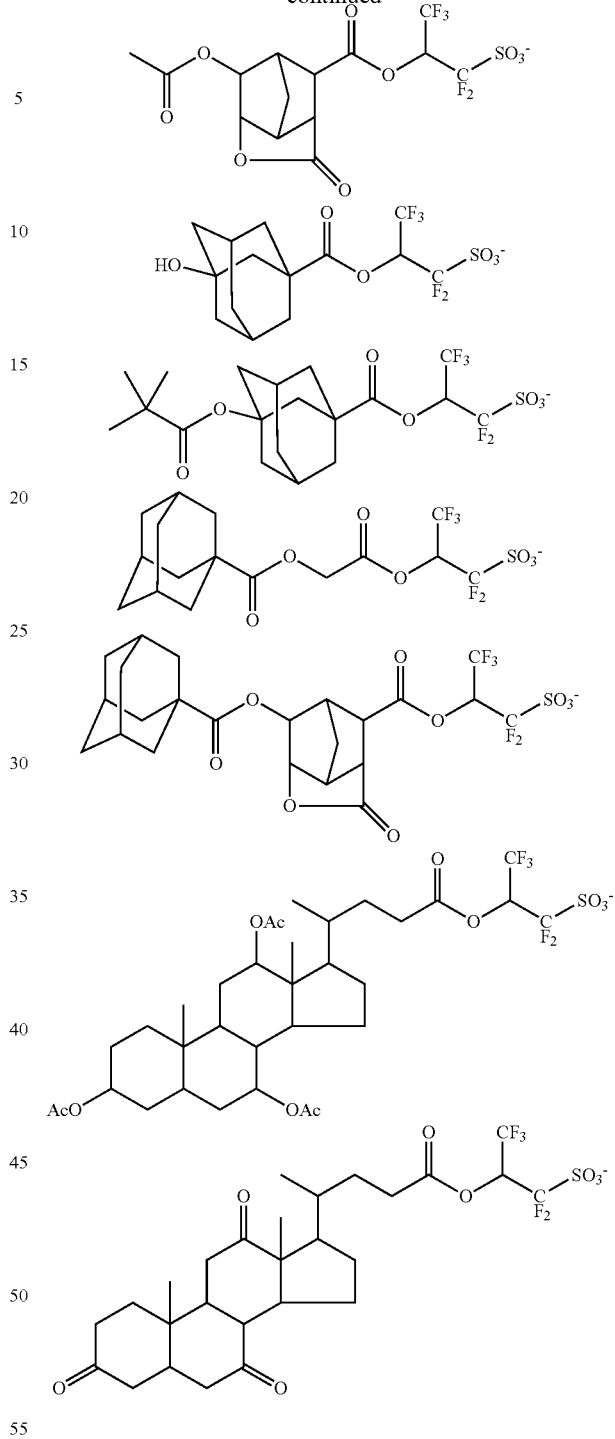

In formula (1B), $R^{fb1}$ and $R^{fb2}$ are each independently fluorine or a $C_1$-$C_{40}$ monovalent hydrocarbon group which may contain a heteroatom. The monovalent hydrocarbon group may be straight, branched or cyclic, and examples thereof are as exemplified for $R^{107}$. Preferably $R^{fb1}$ and $R^{fb2}$ are fluorine or $C_1$-$C_4$ straight fluorinated alkyl groups. Also, $R^{fb1}$ and $R^{fb2}$ may bond together to form a ring with the linkage: —$CF_2$—$SO_2$—$N^-$—$SO_2$—$CF_2$— to which they are attached. It is preferred that a combination of $R^{fb1}$ and $R^{fb2}$ be a fluorinated ethylene or fluorinated propylene group.

In formula (1C), $R^{fc1}$, $R^{fc2}$ and $R^{fc3}$ are each independently fluorine or a $C_1$-$C_{40}$ monovalent hydrocarbon group which may contain a heteroatom. The monovalent hydrocarbon group may be straight, branched or cyclic, and examples thereof are as exemplified for $R^{107}$. Preferably $R^{fc1}$, $R^{fc2}$ and $R^{fc3}$ are fluorine or $C_1$-$C_4$ straight fluorinated alkyl groups. Also, $R^{fc1}$ and $R^{fc2}$ may bond together to form a ring with the linkage: —$CF_2$—$SO_2$—$C^-$—$SO_2$—$CF_2$— to which they are attached. It is preferred that a combination of $R^{fc1}$ and $R^{fc2}$ be a fluorinated ethylene or fluorinated propylene group.

In formula (1D), $R^{fd}$ is a $C_1$-$C_{40}$ monovalent hydrocarbon group which may contain a heteroatom. The monovalent hydrocarbon group may be straight, branched or cyclic, and examples thereof are as exemplified above for $R^{107}$.

With respect to the synthesis of the sulfonium salt having an anion of formula (1D), reference may be made to JP-A 2010-215608 and JP-A 2014-133723.

Examples of the anion having formula (1D) are shown below, but not limited thereto.

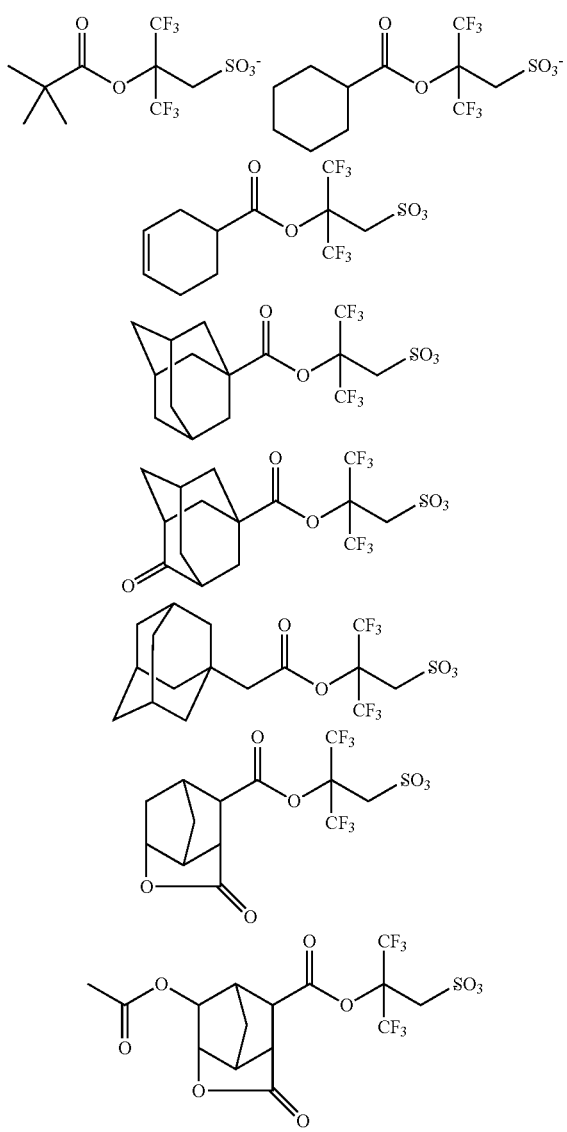

-continued

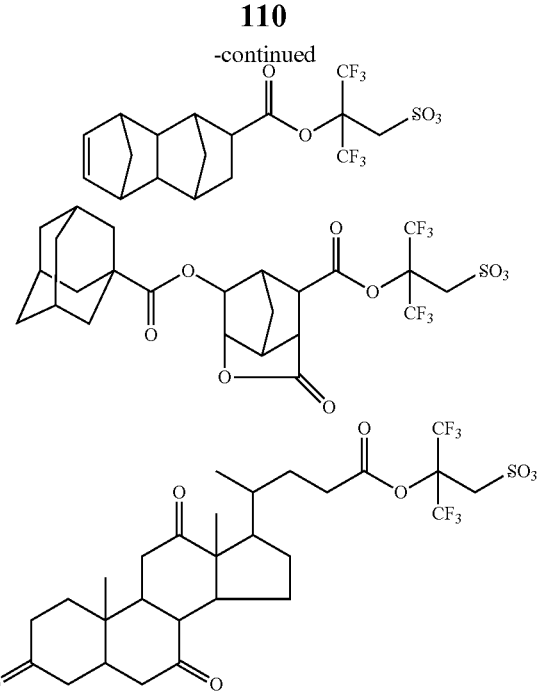

Notably, the compound having the anion of formula (1D) does not have fluorine at the α-position relative to the sulfo group, but two trifluoromethyl groups at the β-position. For this reason, it has a sufficient acidity to sever the acid labile groups in the resist polymer. Thus the compound is an effective PAG.

Another preferred PAG is a compound having the formula (2).

(2)

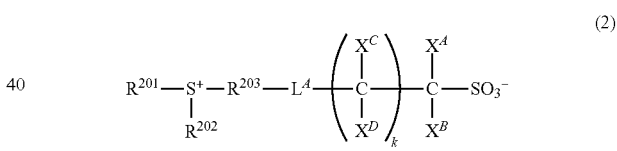

In formula (2), $R^{201}$ and $R^{202}$ are each independently a $C_1$-$C_{30}$ monovalent hydrocarbon group which may contain a heteroatom. $R^{203}$ is a $C_1$-$C_{30}$ divalent hydrocarbon group which may contain a heteroatom. Any two of $R^{201}$, $R^{202}$ and $R^{203}$ may bond together to form a ring with the sulfur atom to which they are attached. $L^A$ is a single bond, ether bond or a $C_1$-$C_{20}$ divalent hydrocarbon group which may contain a heteroatom. $X^A$, $X^B$, $X^C$ and $X^D$ are each independently hydrogen, fluorine or trifluoromethyl, with the proviso that at least one of $X^A$, $X^B$, $X^C$ and $X^D$ is fluorine or trifluoromethyl, and k is an integer of 0 to 3.

The monovalent hydrocarbon groups may be straight, branched or cyclic. Examples thereof include, but are not limited to, straight or branched alkyl groups such as methyl, ethyl, propyl, isopropyl, n-butyl, sec-butyl, tert-butyl, n-pentyl, tert-pentyl, n-hexyl, n-octyl, n-nonyl, n-decyl, and 2-ethylhexyl; monovalent saturated cyclic hydrocarbon groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, and adamantyl; and aryl groups such as phenyl, naphthyl and anthracenyl. In these groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate moiety, lactone ring, sultone ring, carboxylic anhydride or haloalkyl moiety.

The divalent hydrocarbon groups may be straight, branched or cyclic. Examples thereof include straight or branched alkanediyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; divalent saturated cyclic hydrocarbon groups such as cyclopentanediyl, cyclohexanediyl, norbornanediyl and adamantanediyl; and divalent unsaturated cyclic hydrocarbon groups such as phenylene and naphthylene. In these groups, some hydrogen may be substituted by an alkyl moiety such as methyl, ethyl, propyl, n-butyl or t-butyl: some hydrogen may be substituted by a moiety containing a heteroatom such as oxygen, sulfur, nitrogen or halogen; or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate, lactone ring, sultone ring, carboxylic anhydride or haloalkyl moiety. Of the heteroatoms, oxygen is preferred.

Of the PAGs having formula (2), those having formula (2') are preferred.

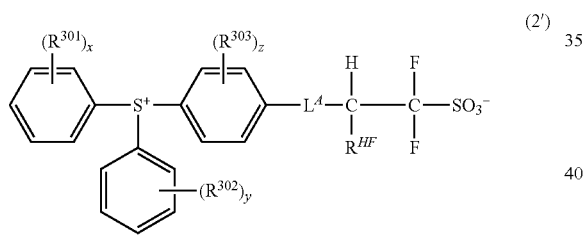

(2')

In formula (2'), $L^A$ is as defined above. $R^{HF}$ is hydrogen or trifluoromethyl, preferably trifluoromethyl. $R^{301}$, $R^{302}$ and $R^{303}$ are each independently hydrogen or a $C_1$-$C_{20}$ monovalent hydrocarbon group which may contain a heteroatom. The monovalent hydrocarbon groups may be straight, branched or cyclic, and examples thereof are as exemplified above for $R^{107}$. The subscripts x and y are each independently an integer of 0 to 5, and z is an integer of 0 to 4.

Examples of the PAG having formula (2) are shown below, but not limited thereto. Notably, $R^{HF}$ is as defined above.

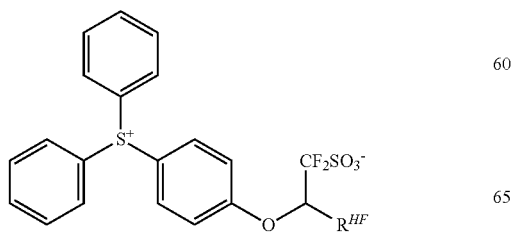

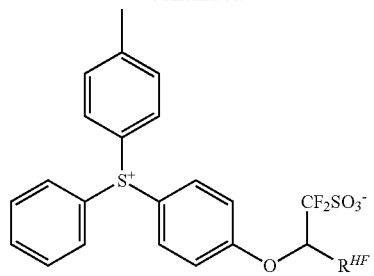

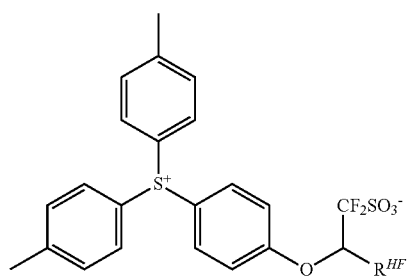

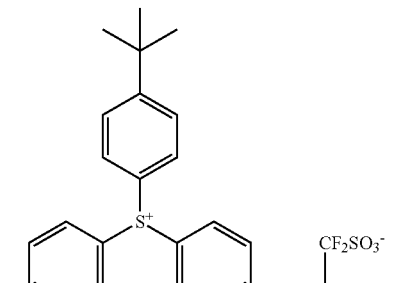

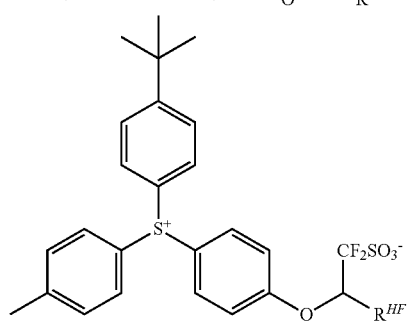

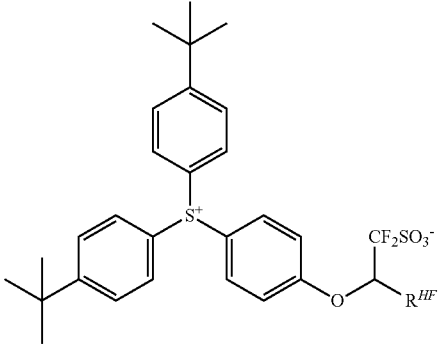

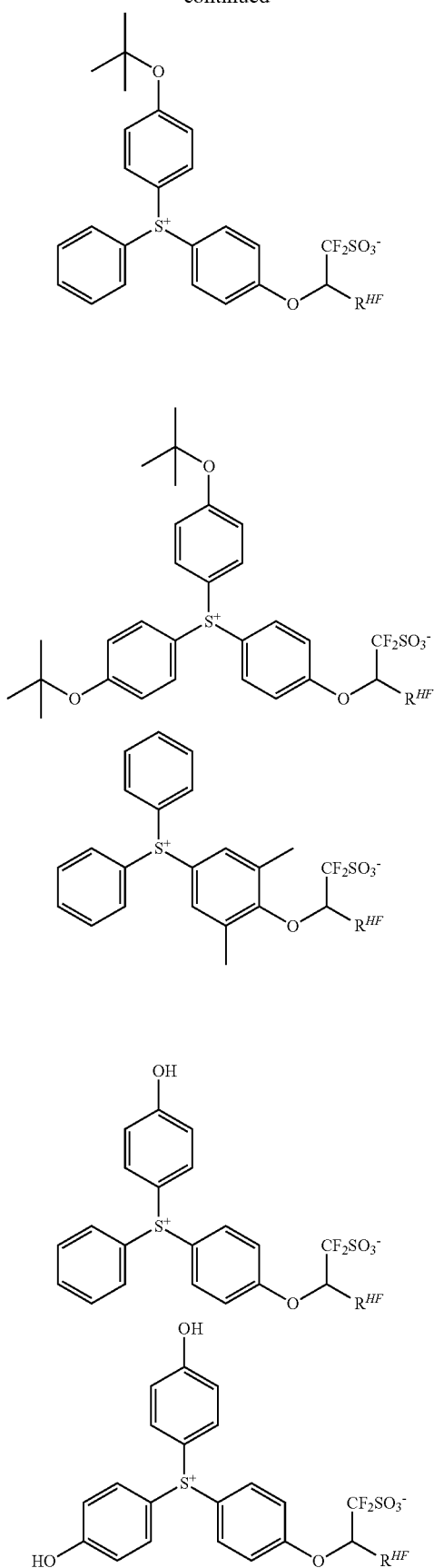

-continued
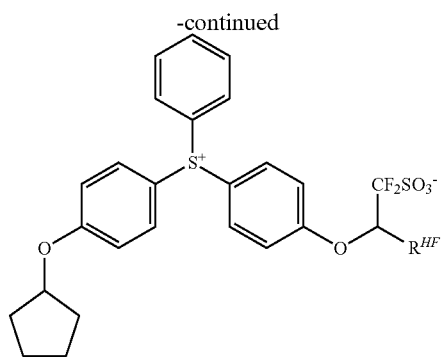
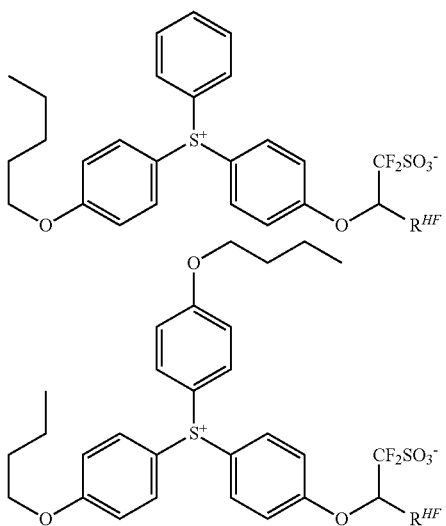
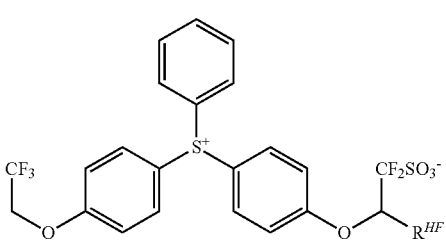
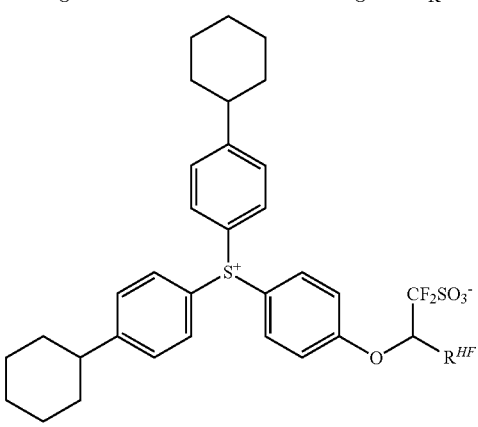
-continued
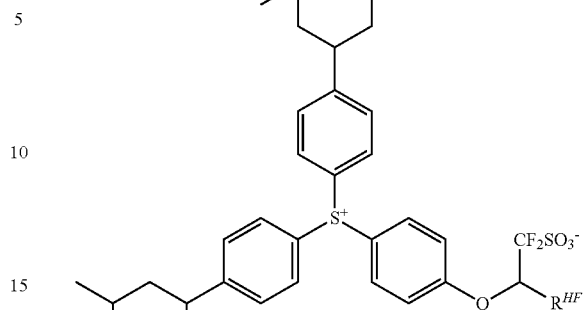
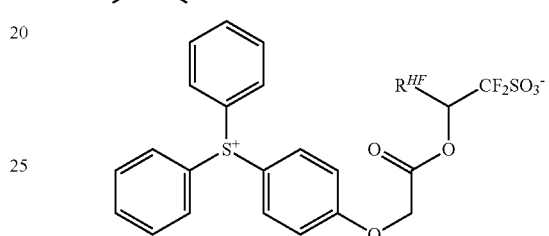
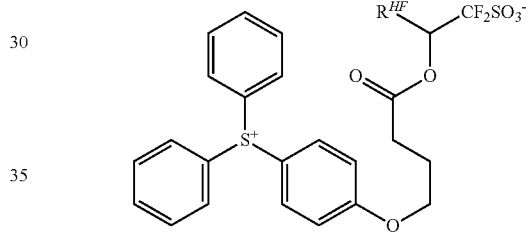
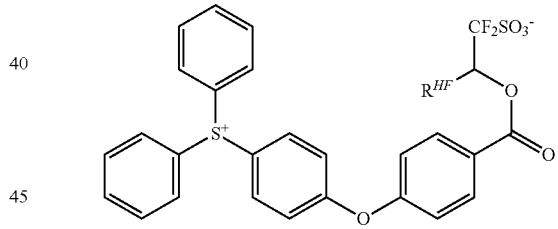
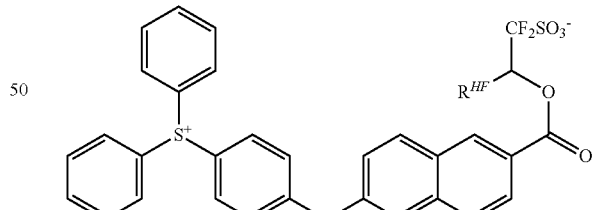
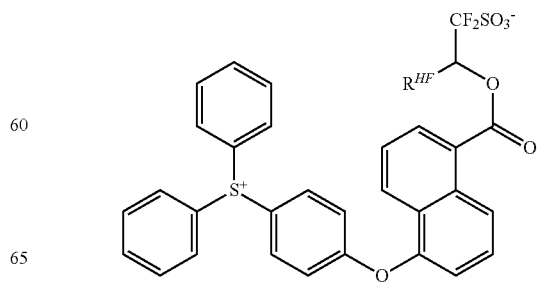

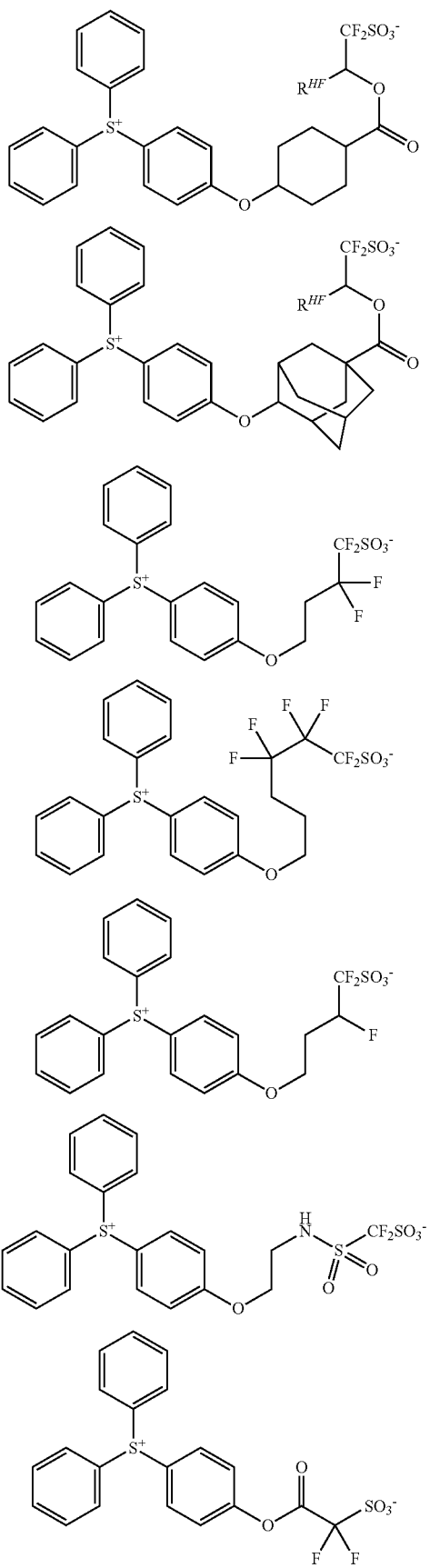

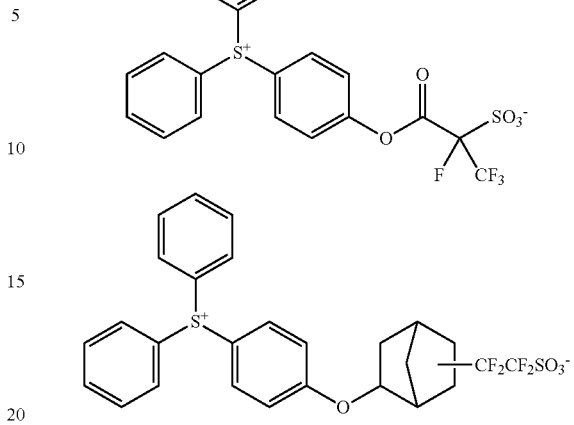

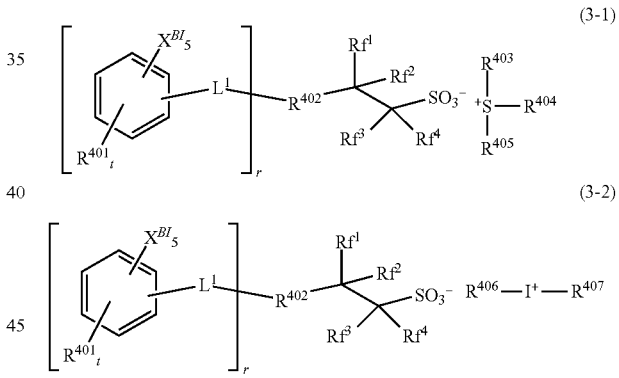

Of the foregoing PAGs, those having an anion of formula (1A') or (1D) are especially preferred because of reduced acid diffusion and high solubility in the resist solvent. Also those having an anion of formula (2') are especially preferred because of extremely reduced acid diffusion.

Also a sulfonium or iodonium salt having an iodized or brominated aromatic ring-containing anion may be used as the PAG. Suitable are sulfonium and iodonium salts having the formulae (3-1) and (3-2).

(3-1)

(3-2)

In formulae (3-1) and (3-2), $X^{BI}$ is iodine or bromine, and may be the same or different when s is 2 or more.

$L^1$ is a single bond, ether bond, ester bond, or a $C_1$-$C_6$ alkanediyl group which may contain an ether bond or ester bond. The alkanediyl group may be straight, branched or cyclic.

$R^{401}$ is a hydroxyl group, carboxyl group, fluorine, chlorine, bromine, amino group, or a $C_1$-$C_{20}$ alkyl, $C_1$-$C_{20}$ alkoxy, $C_2$-$C_{10}$ alkoxycarbonyl, $C_2$-$C_{20}$ acyloxy or $C_1$-$C_{20}$ alkylsulfonyloxy group, which may contain fluorine, chlorine, bromine, hydroxyl, amino or $C_1$-$C_{10}$ alkoxy moiety, or —NR$^{401A}$—C(=O)R$^{401B}$ or —NR$^{401A}$—C(=O)—O—R$^{401B}$, wherein R$^{401A}$ is hydrogen, or a $C_1$-$C_6$ alkyl group which may contain halogen, hydroxy, $C_1$-$C_6$ alkoxy. $C_2$-$C_6$ acyl or $C_2$-$C_6$ acyloxy moiety, R$^{401B}$ is a $C_1$-$C_{16}$ alkyl, $C_2$-$C_{16}$ alkenyl or $C_6$-$C_{12}$ aryl group, which may contain halogen, hydroxy. $C_1$-$C_6$ alkoxy, $C_2$-$C_6$ acyl or $C_2$-$C_6$ acyloxy moiety. The foregoing alkyl, alkoxy, alkoxycarbonyl, acyloxy, acyl and alkenyl groups may be straight, branched or cyclic. When t is 2 or more, groups $R^{401}$ may be the same or different. Of these, $R^{401}$ is preferably hydroxyl, $-NR^{401A}-C(=O)-R^{401B}$, $-NR^{401A}-C(=O)-O-R^{401B}$, fluorine, chlorine, bromine, methyl or methoxy.

$R^{402}$ is a single bond or a $C_1$-$C_{20}$ divalent linking group when r=1, or a $C_1$-$C_{20}$ tri- or tetravalent linking group when r=2 or 3, the linking group optionally containing an oxygen, sulfur or nitrogen atom.

$Rf^1$ to $Rf^4$ are each independently hydrogen, fluorine or trifluoromethyl, at least one of $Rf^1$ to $Rf^4$ is fluorine or trifluoromethyl, or $Rf^1$ and $Rf^2$, taken together, may form a carbonyl group. Preferably, both $Rf^3$ and $Rf^4$ are fluorine.

$R^{403}$, $R^{404}$, $R^{405}$, $R^{406}$ and $R^{407}$ are each independently a $C_1$-$C_{20}$ monovalent hydrocarbon group which may contain a heteroatom. Any two of $R^{403}$, $R^{404}$ and $R^{405}$ may bond together to form a ring with the sulfur atom to which they are attached. The monovalent hydrocarbon group may be straight, branched or cyclic, and examples thereof include $C_1$-$C_{20}$ alkyl, $C_2$-$C_{20}$ alkenyl, $C_2$-$C_{20}$ alkynyl, $C_6$-$C_{20}$ aryl, and $C_7$-$C_{20}$ aralkyl groups. In these groups, some or all of the hydrogen atoms may be substituted by hydroxyl, carboxyl, halogen, cyano, nitro, mercapto, sultone, sulfone, or sulfonium salt-containing moieties, and some carbon may be replaced by an ether bond, ester bond, carbonyl moiety, amide bond, carbonate moiety or sulfonic acid ester bond.

In formulae (3-1) and (3-2), r is an integer of 1 to 3, s is an integer of 1 to 5, and t is an integer of 0 to 3, and 1≤s+t≤5. Preferably, s is an integer of 1 to 3, more preferably 2 or 3, and t is an integer of 0 to 2.

Examples of the cation in the sulfonium salt having formula (3-1) include those exemplified above as the cation in the sulfonium salt having formula (1-1). Examples of the cation in the iodonium salt having formula (3-2) include those exemplified above as the cation in the iodonium salt having formula (1-2).

Examples of the anion in the onium salts having formulae (3-1) and (3-2) are shown below, but not limited thereto. Herein $X^{BI}$ is as defined above.

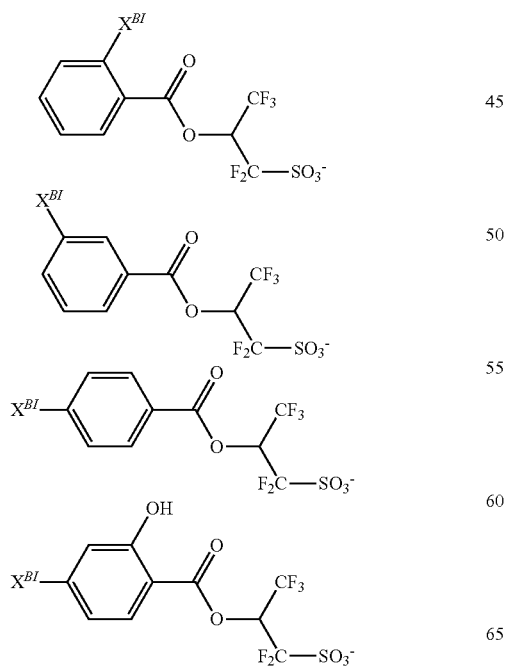

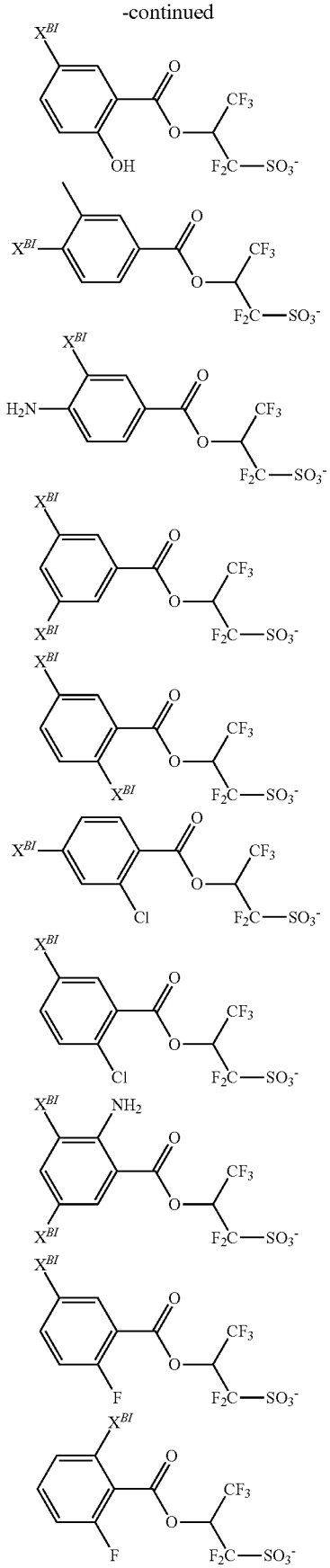

121
-continued
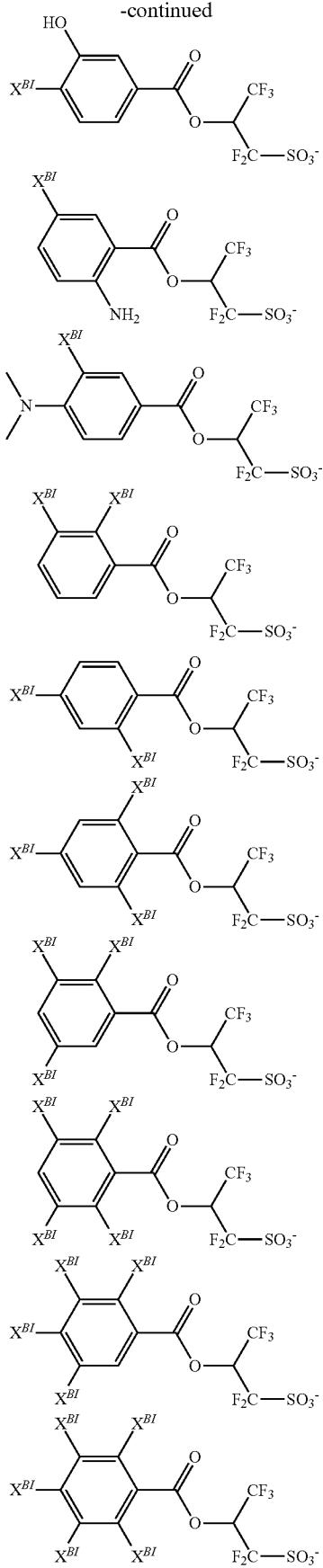
122
-continued
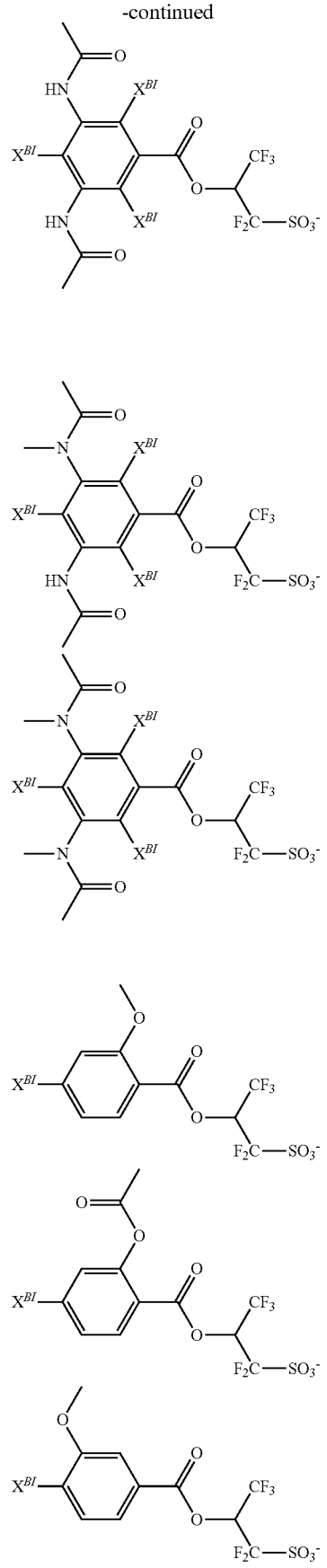

123
-continued
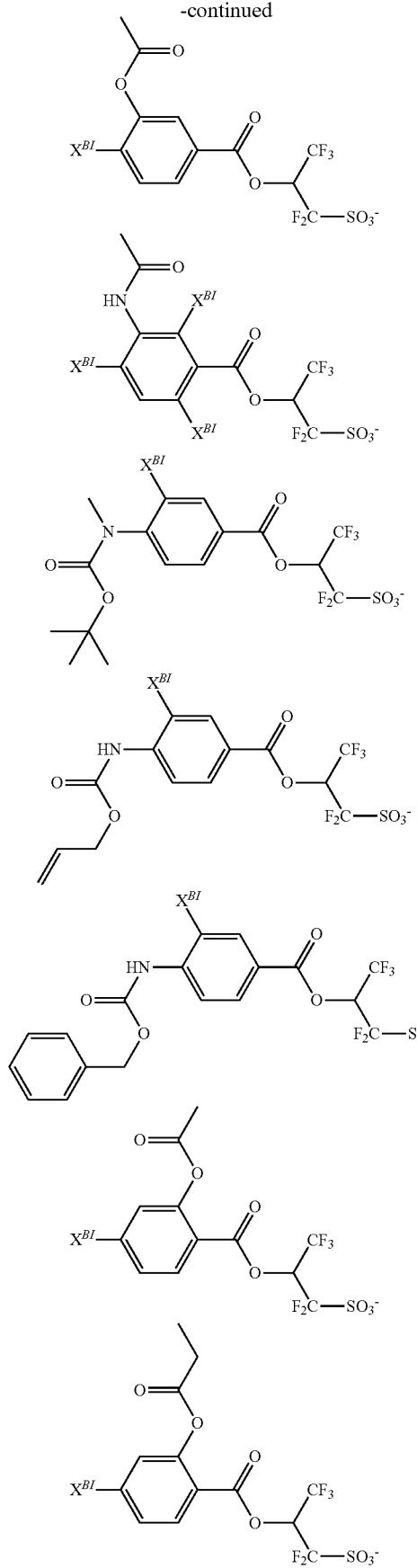
124
-continued
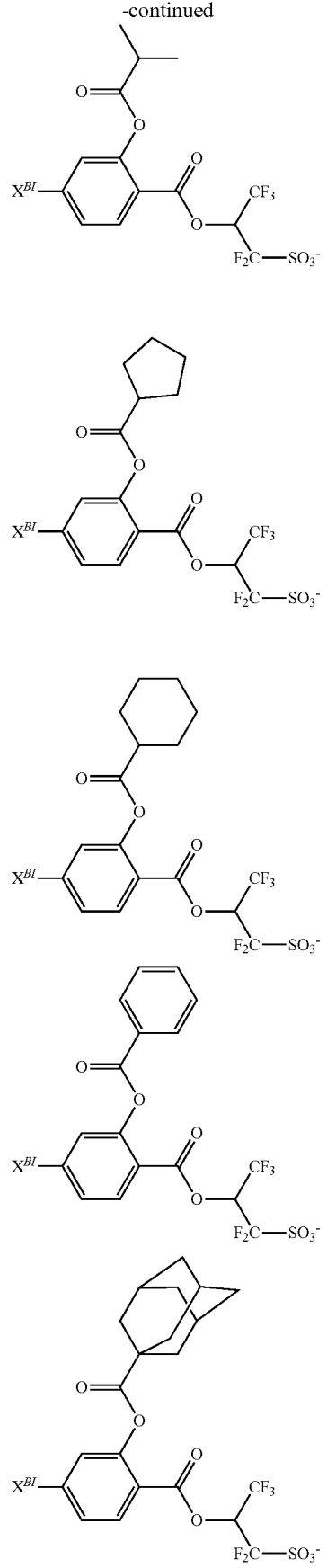

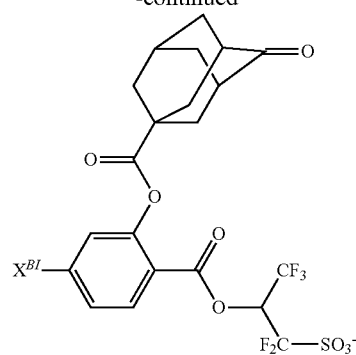
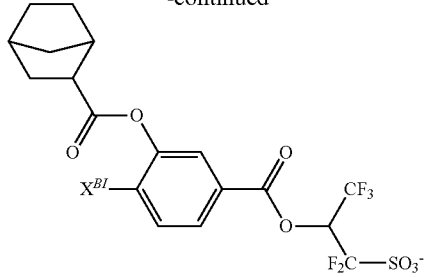
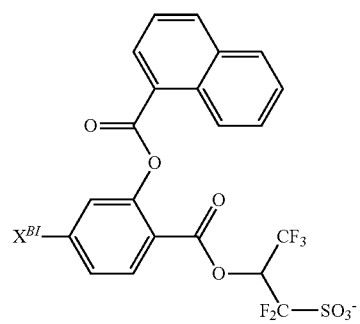
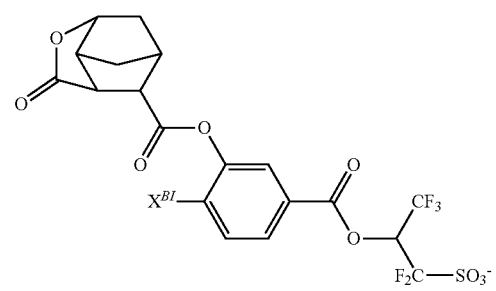
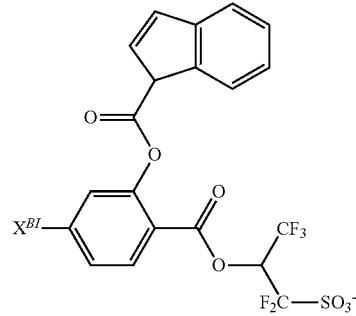
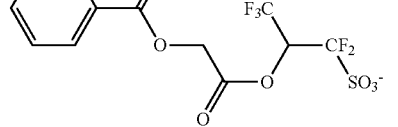
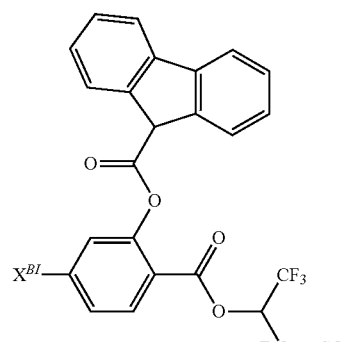
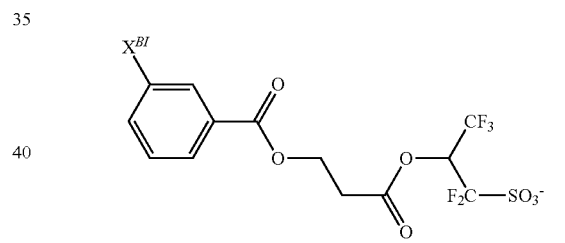
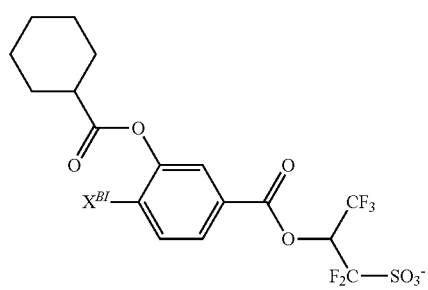
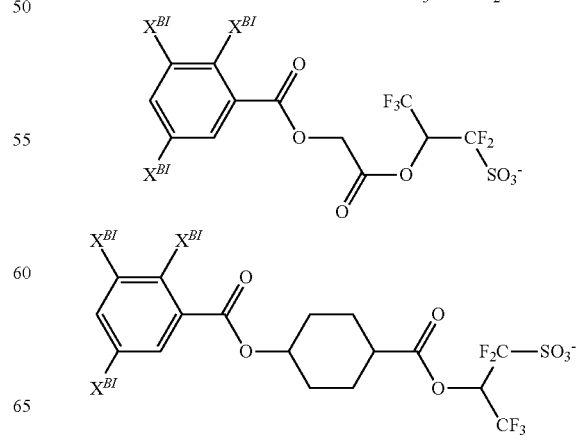

127
-continued
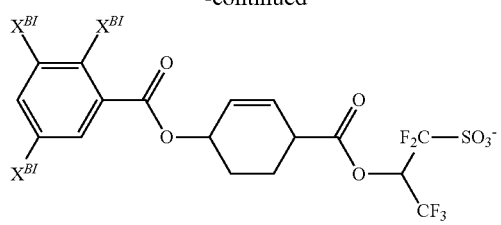
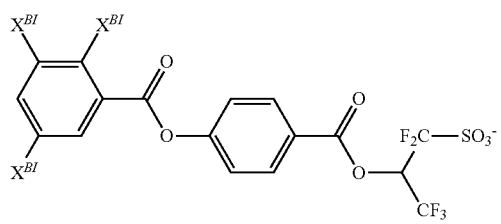
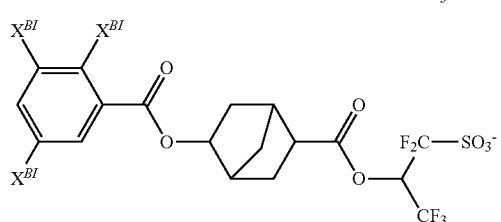
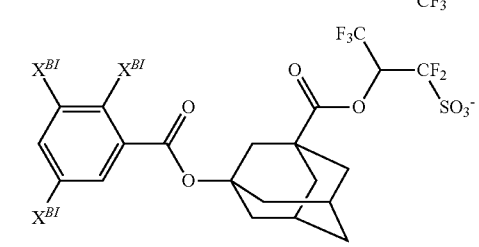
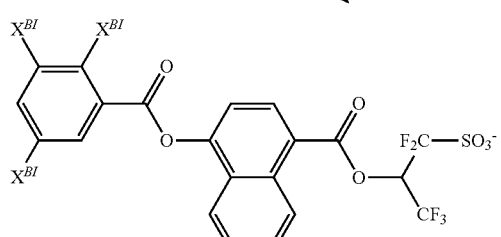
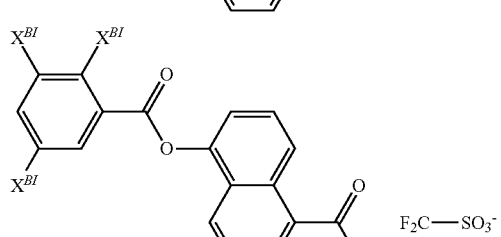
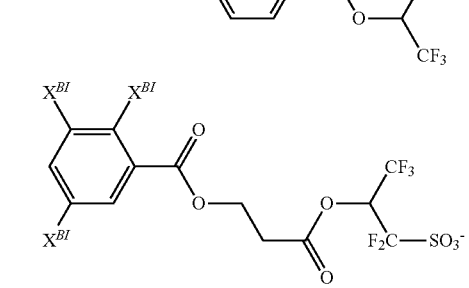
128
-continued
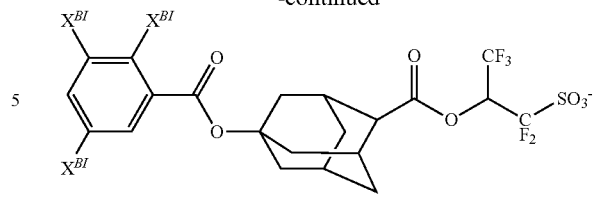
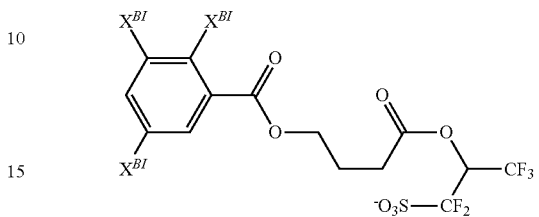
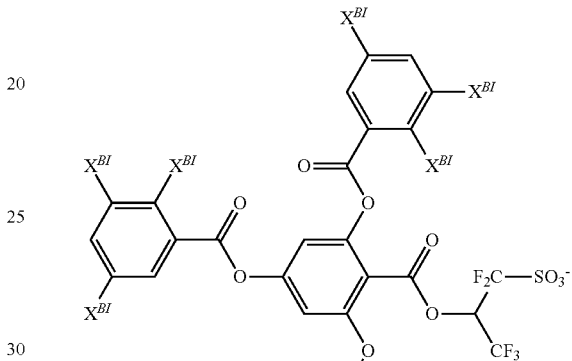
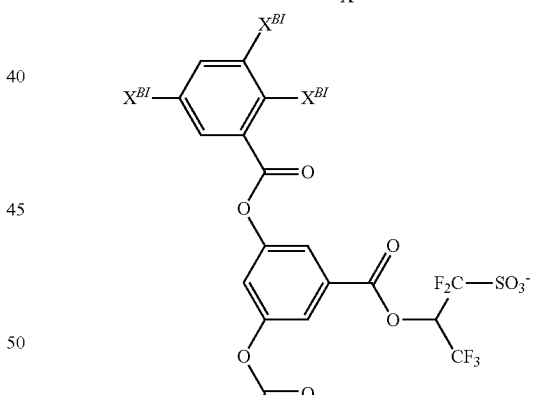
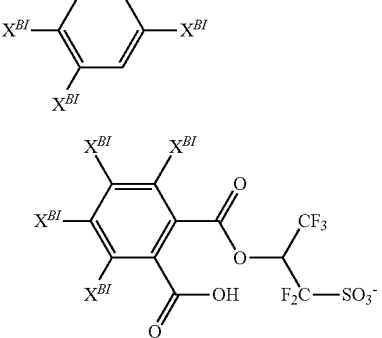

129 -continued
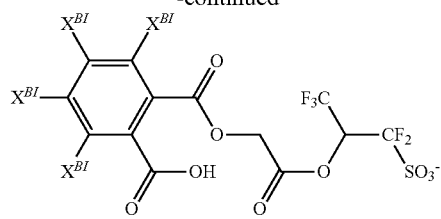
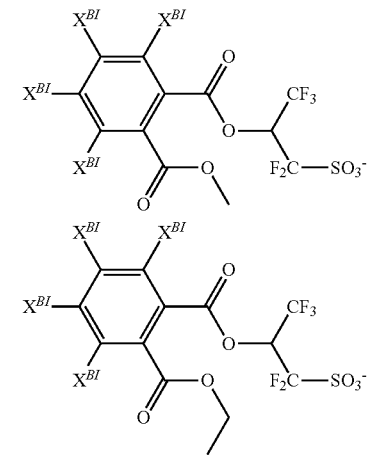
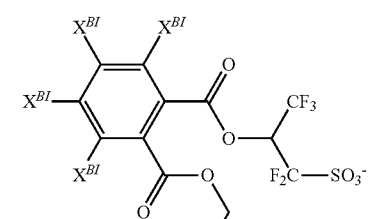
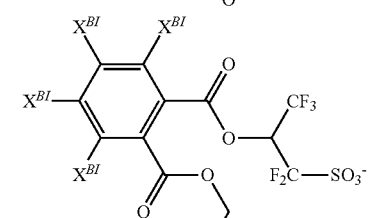
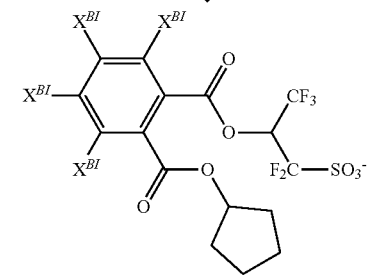
130 -continued
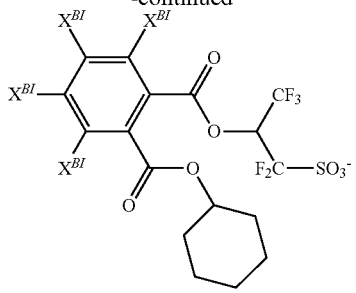

131
-continued
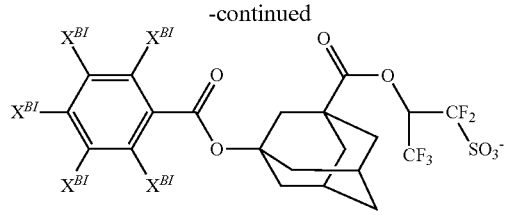
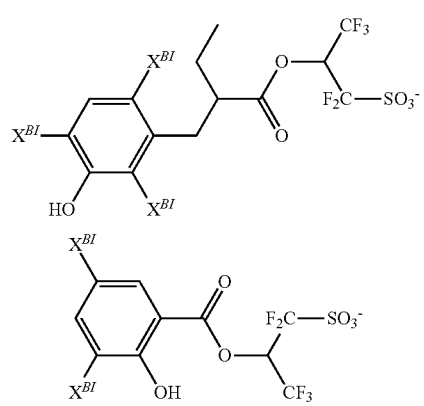
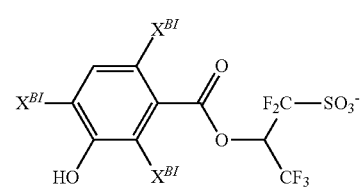
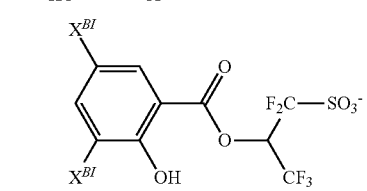
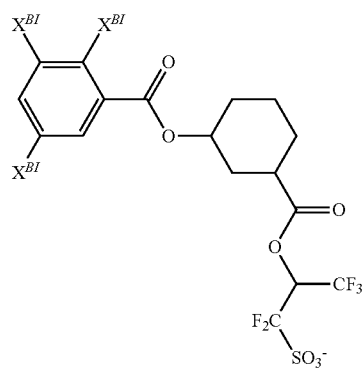
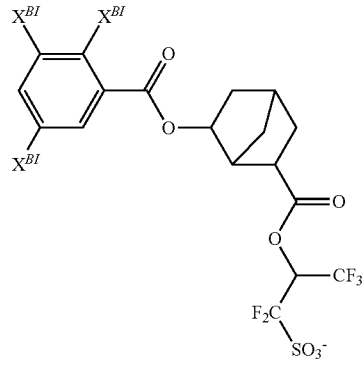
132
-continued
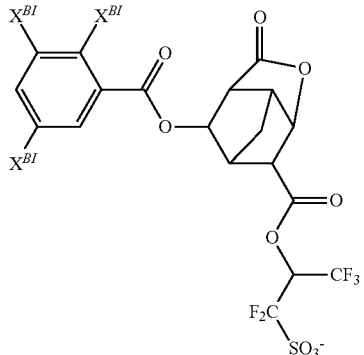
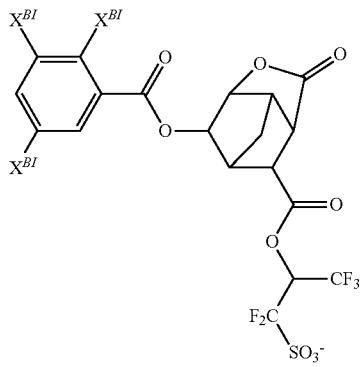
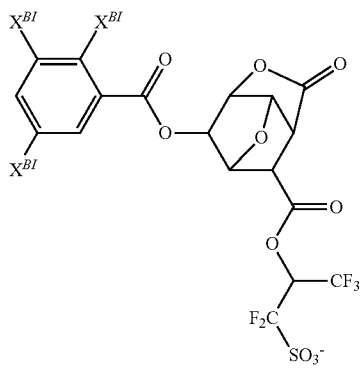
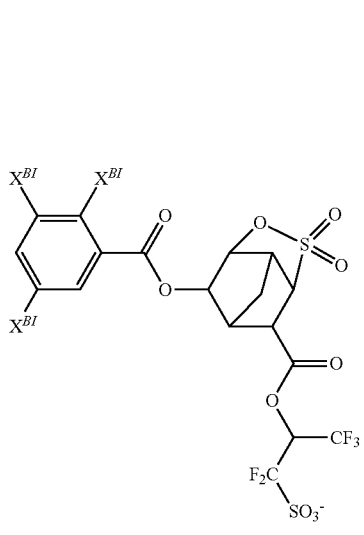

133
-continued
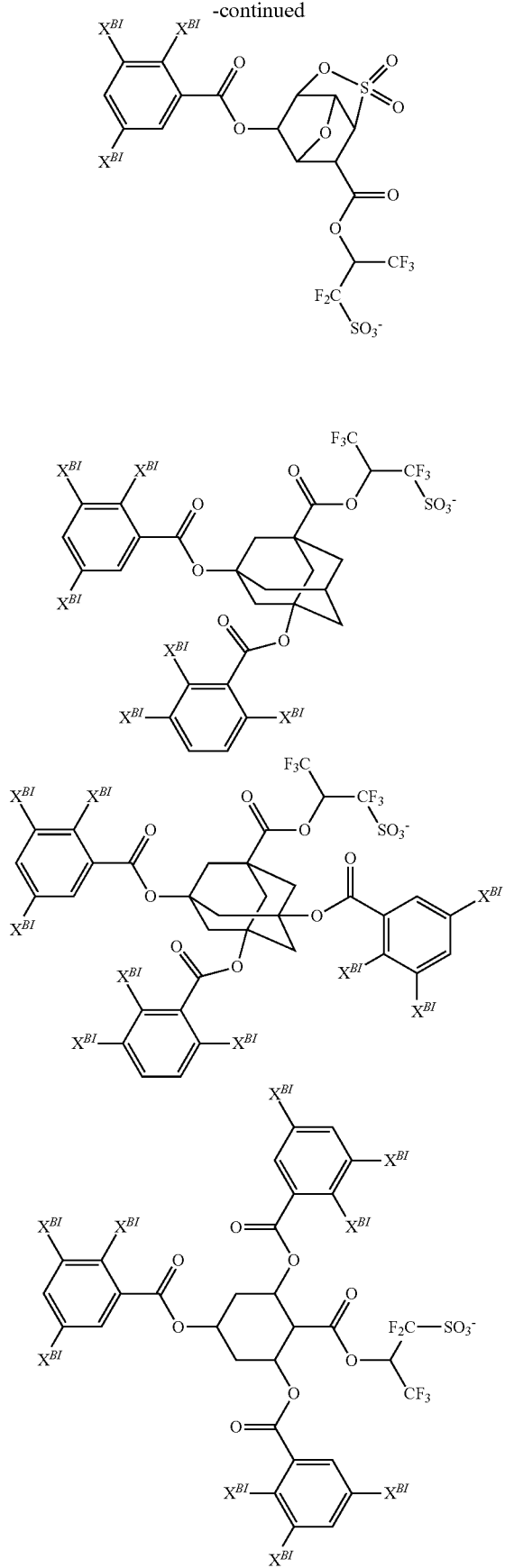
134
-continued
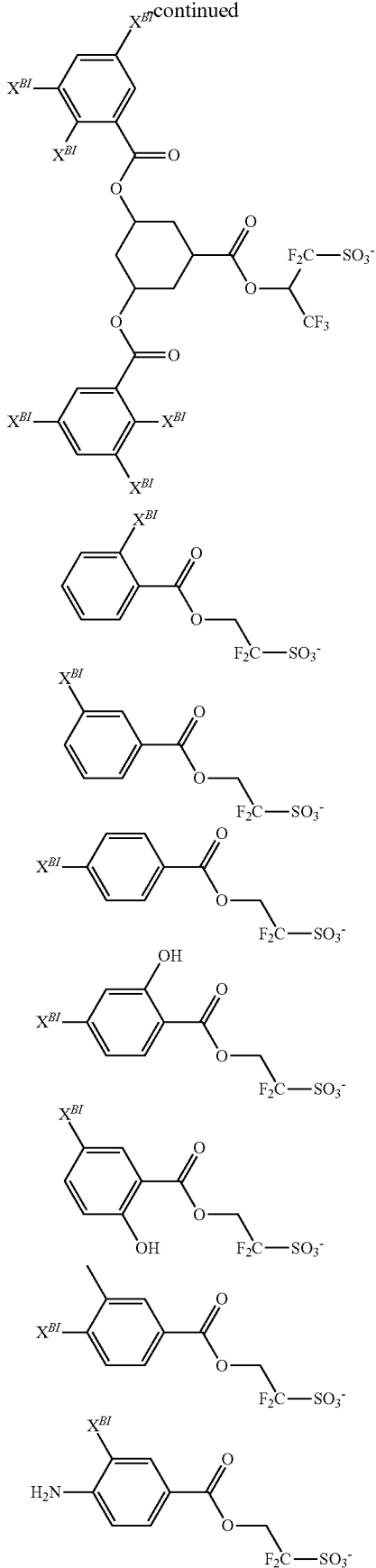

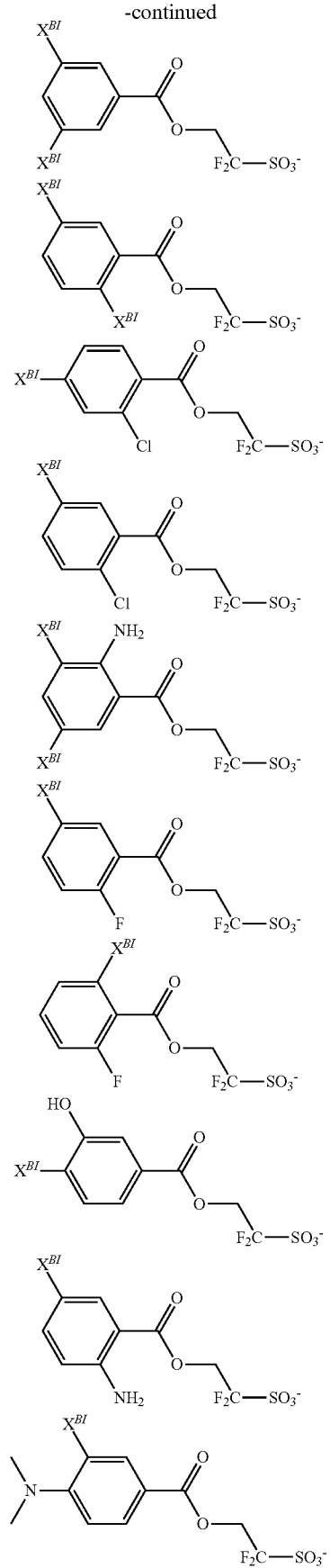
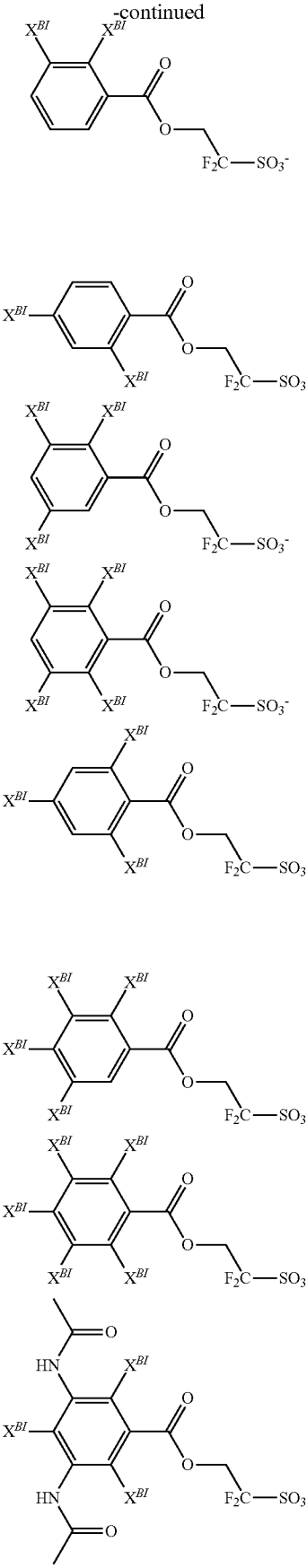

137
-continued
138
-continued
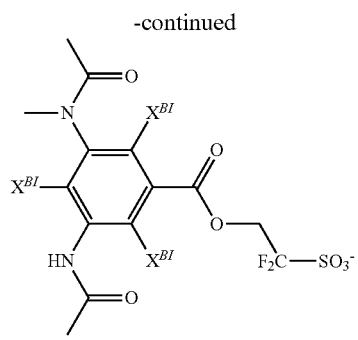
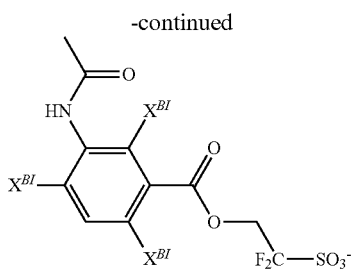

139
-continued
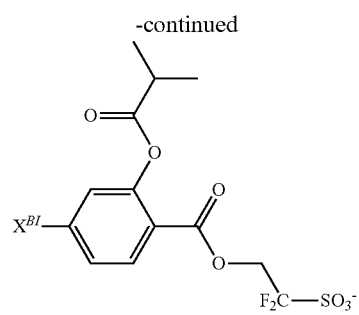
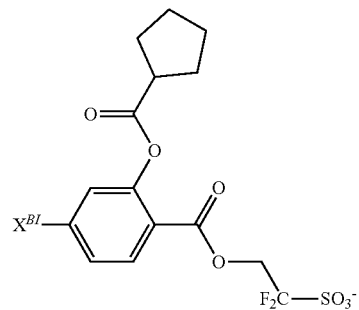
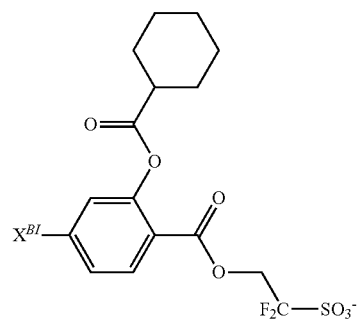
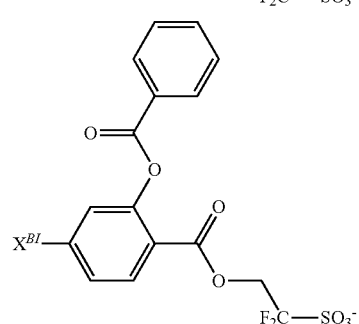
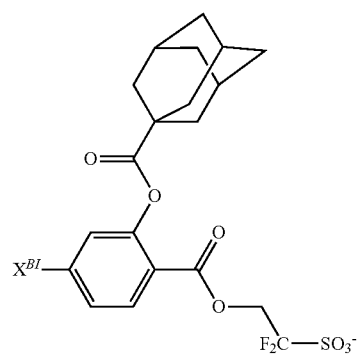
140
-continued
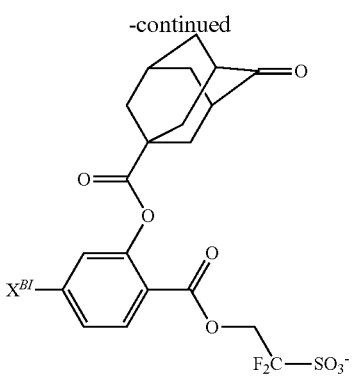
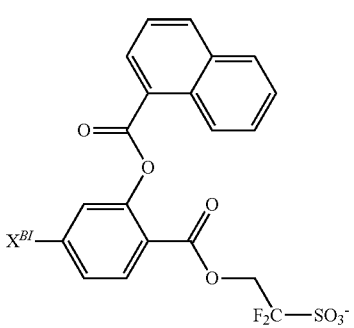
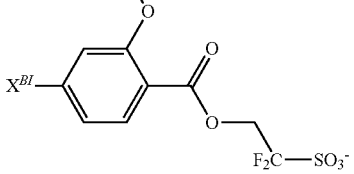
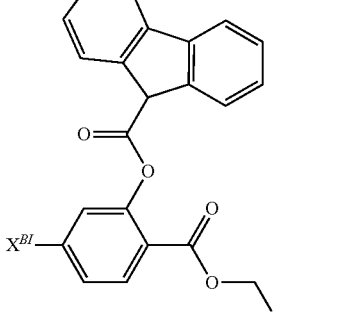
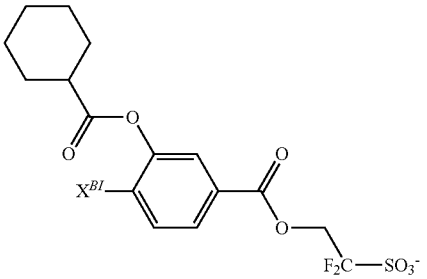

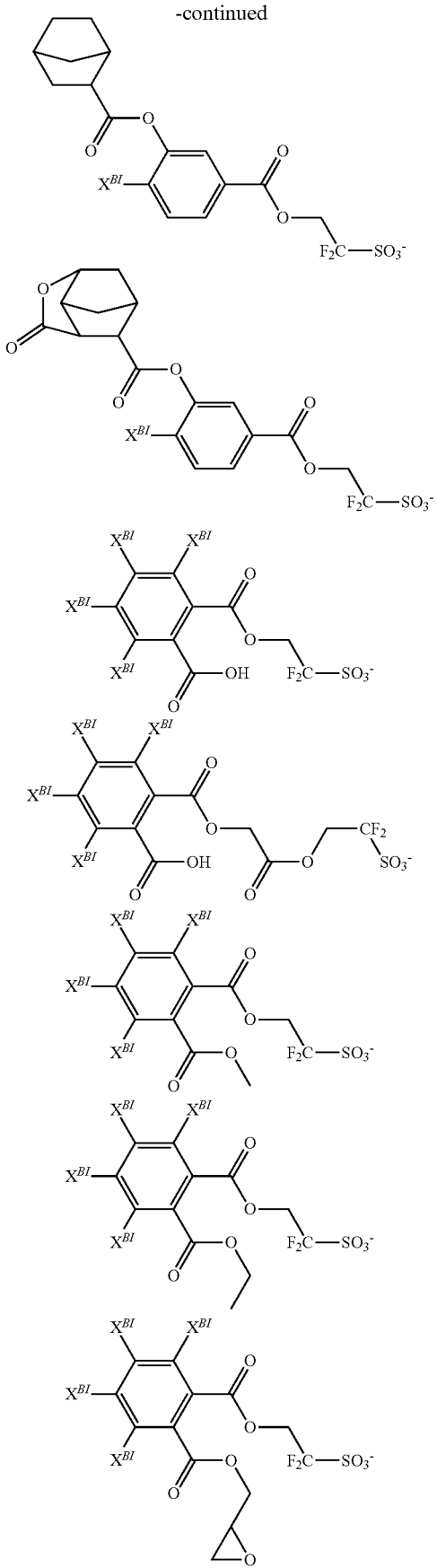
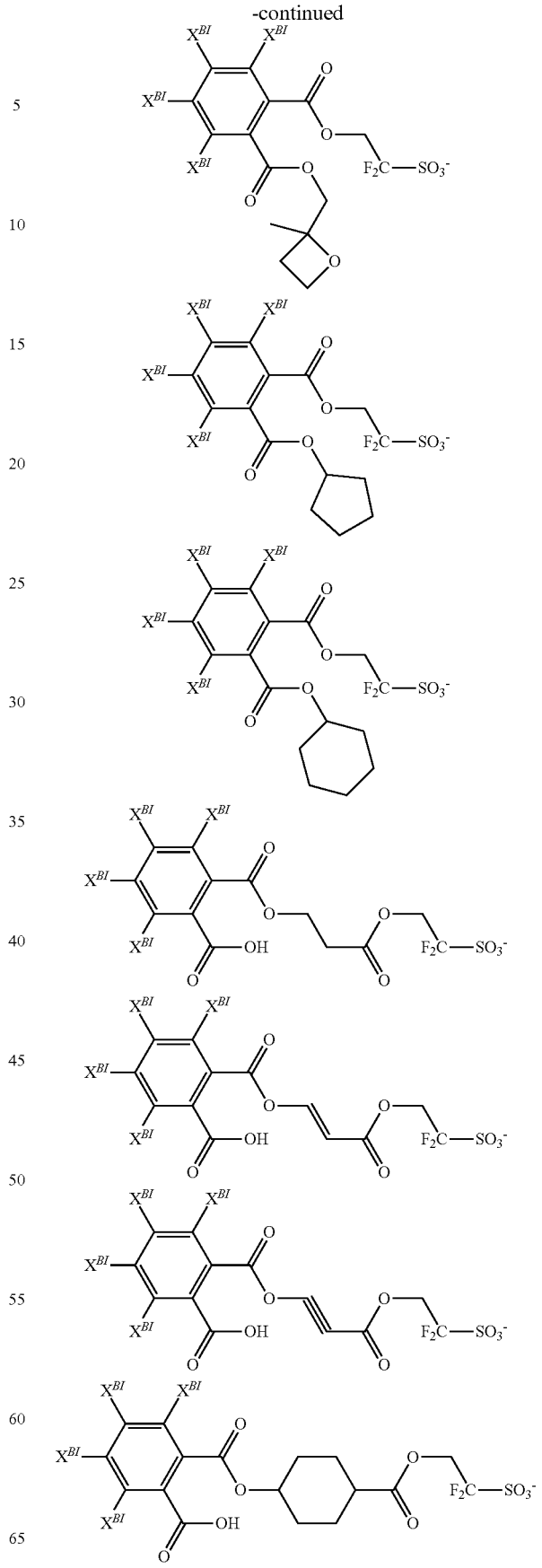

-continued
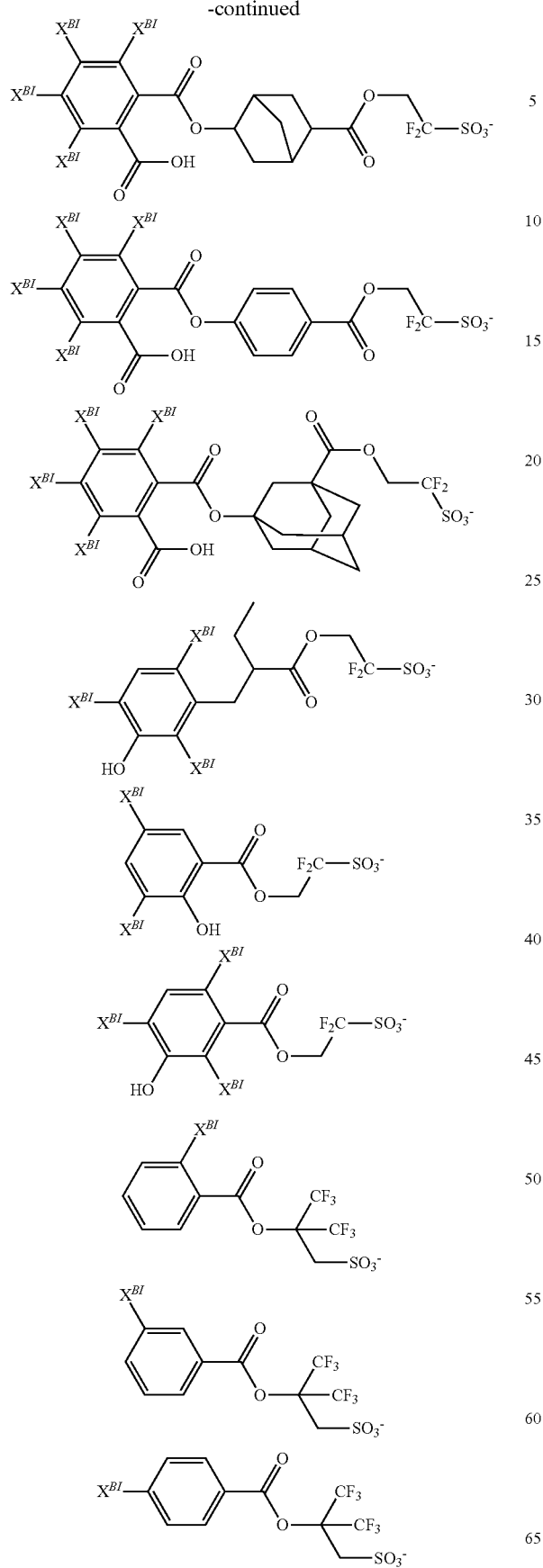
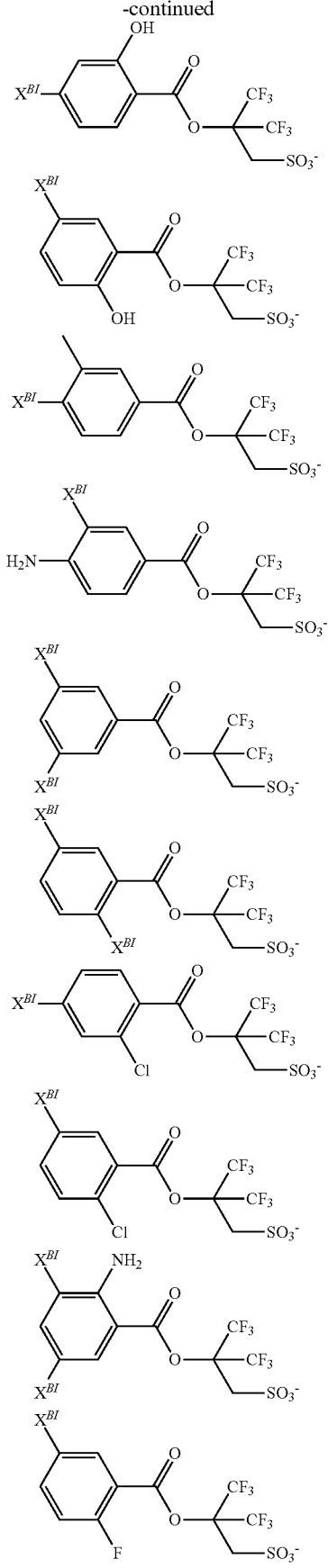

-continued
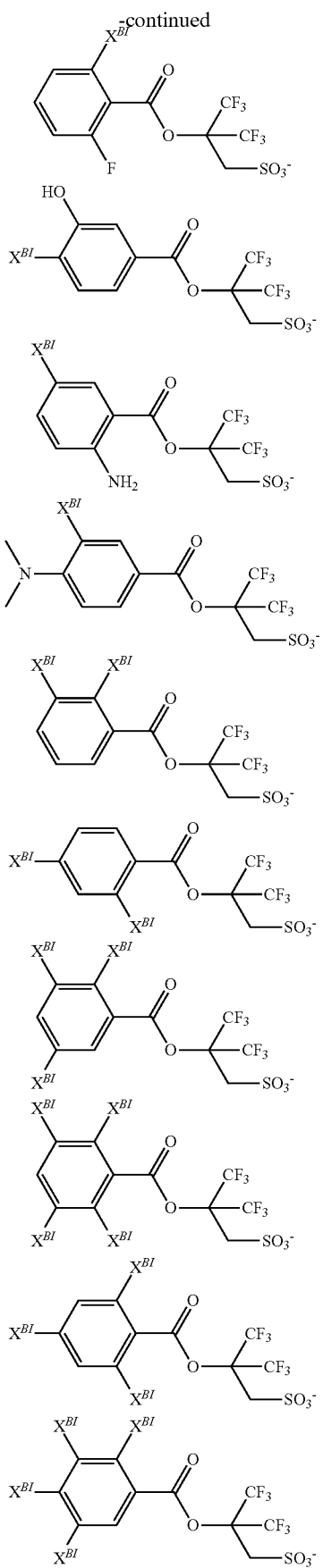
-continued
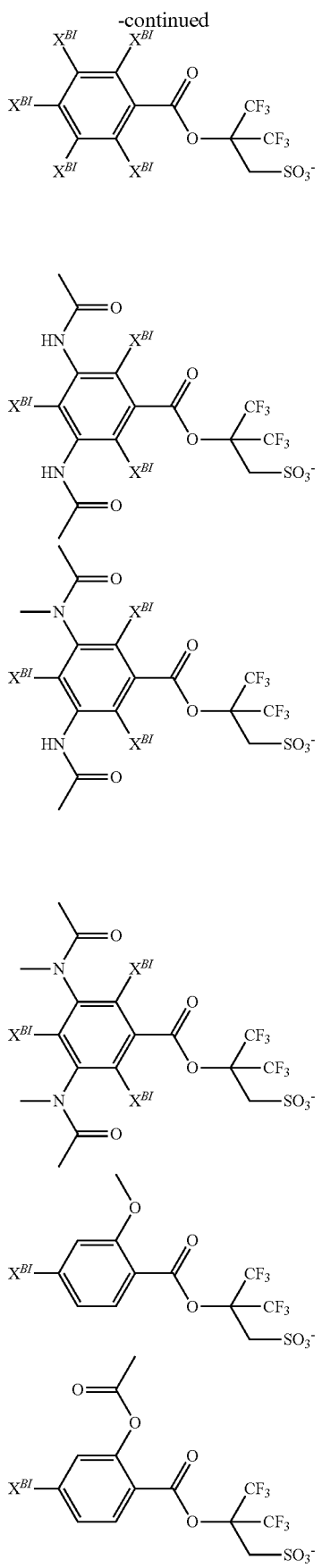

147
-continued
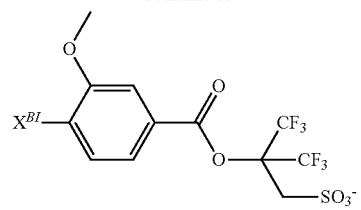
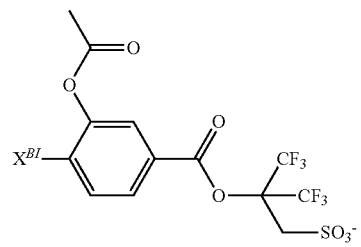
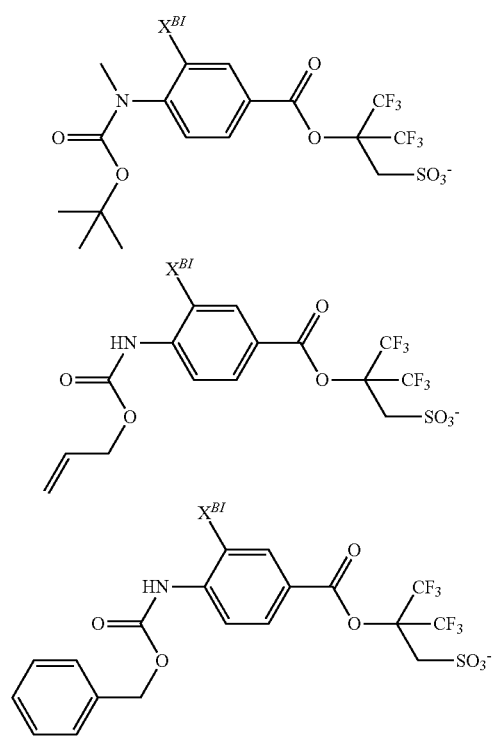
148
-continued
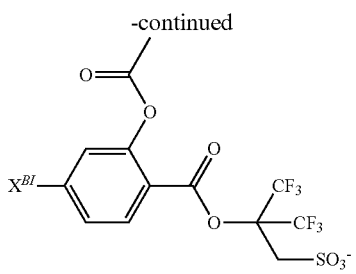
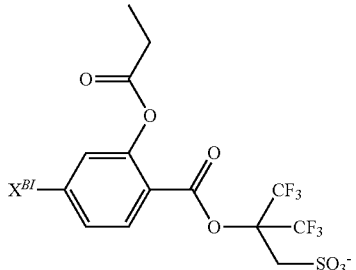
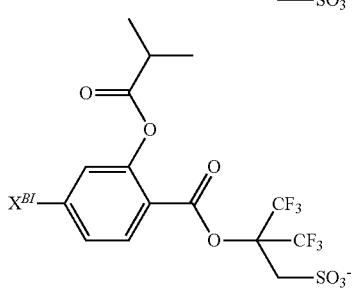
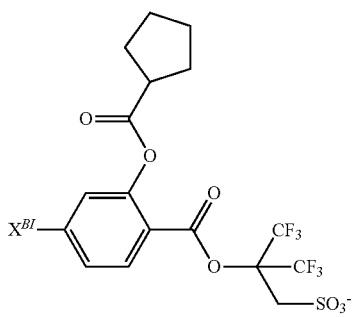
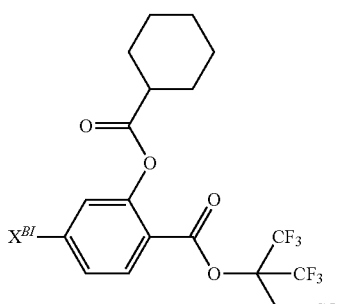

149
-continued
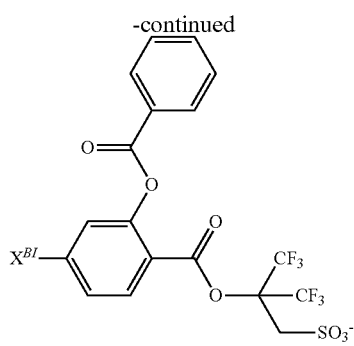
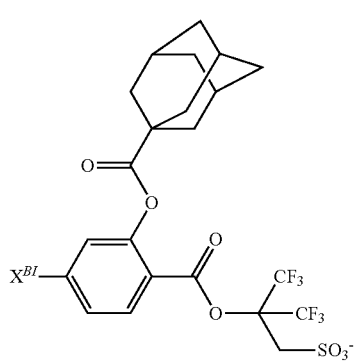
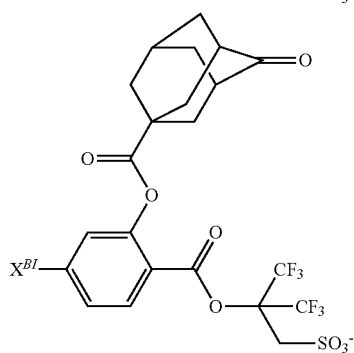
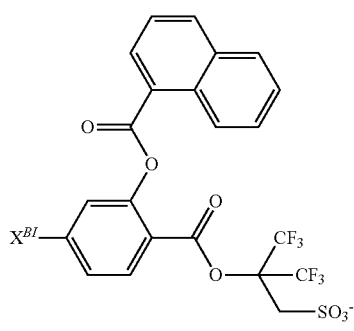
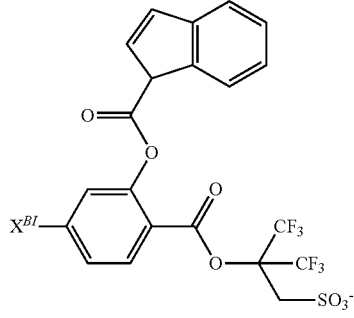
150
-continued
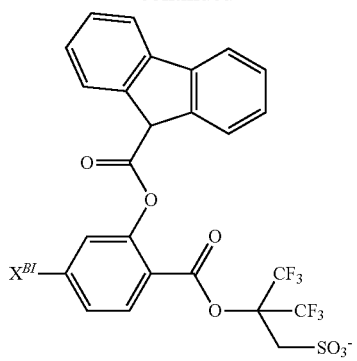
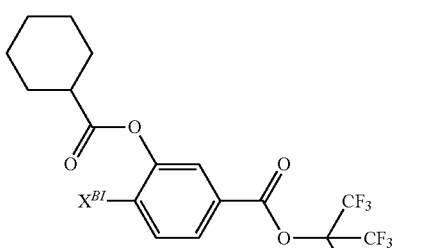
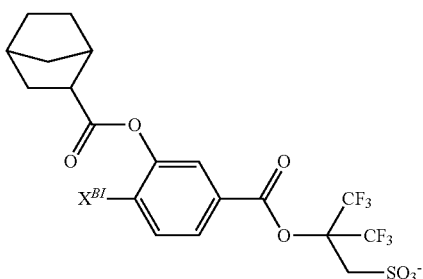
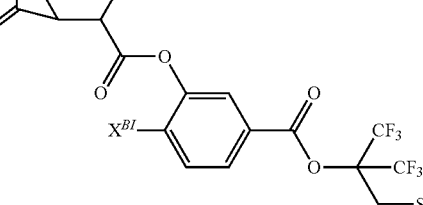
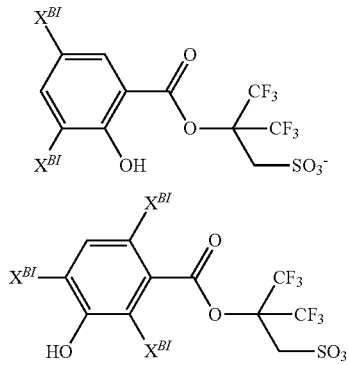

151
-continued
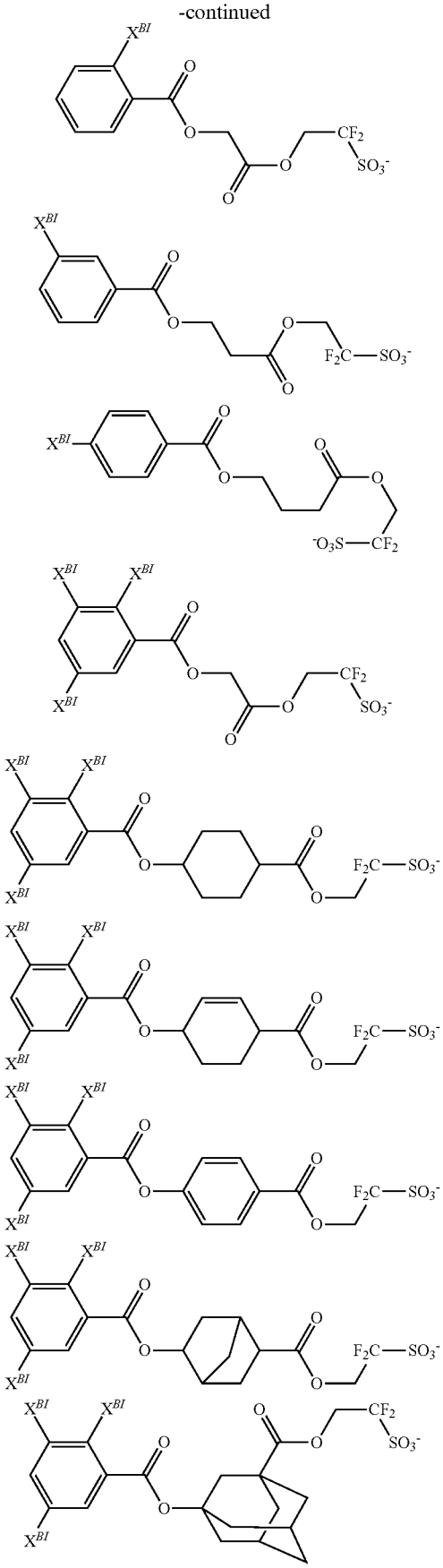
152
-continued
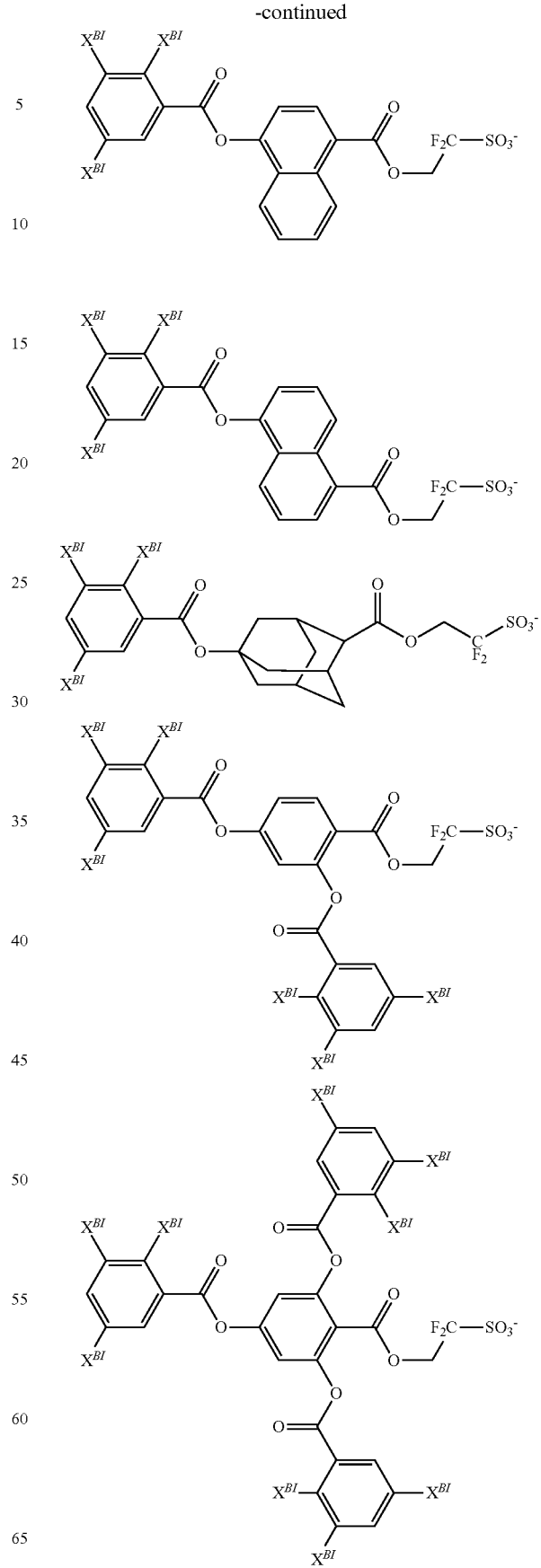

153 -continued
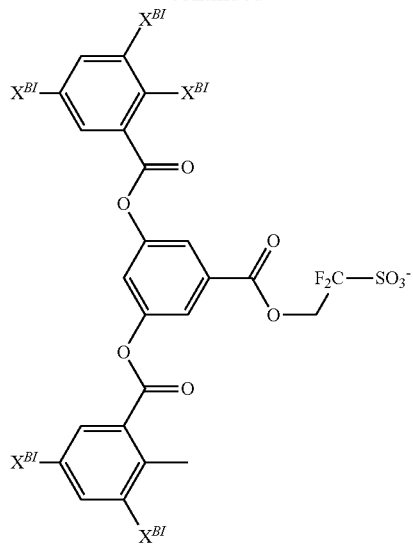
154 -continued
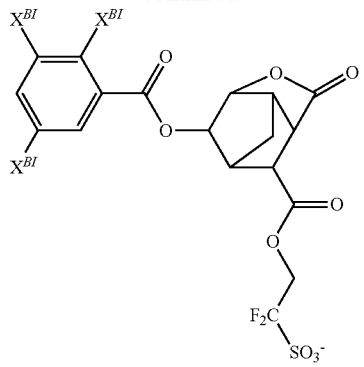
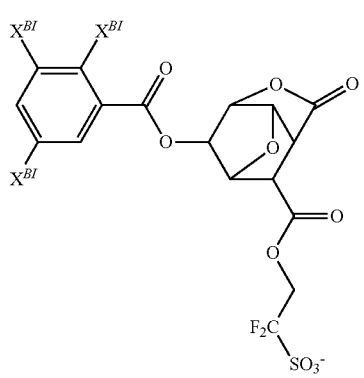
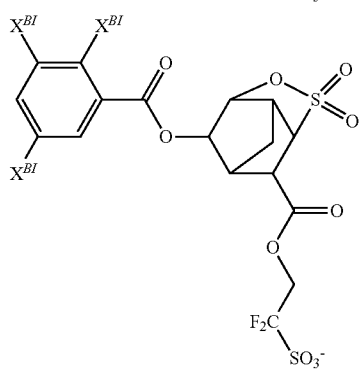
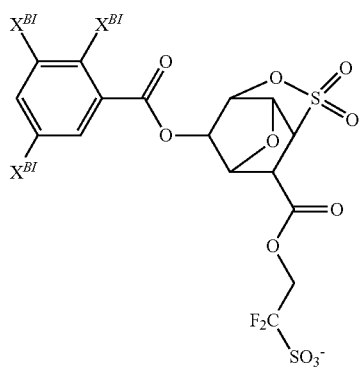

155
-continued
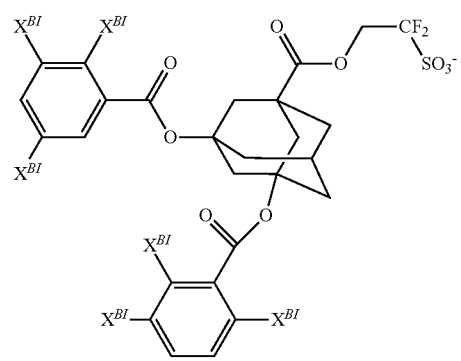
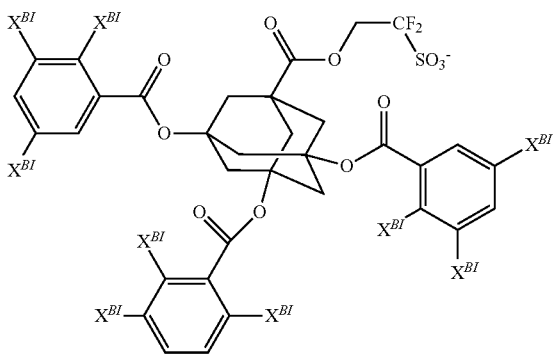
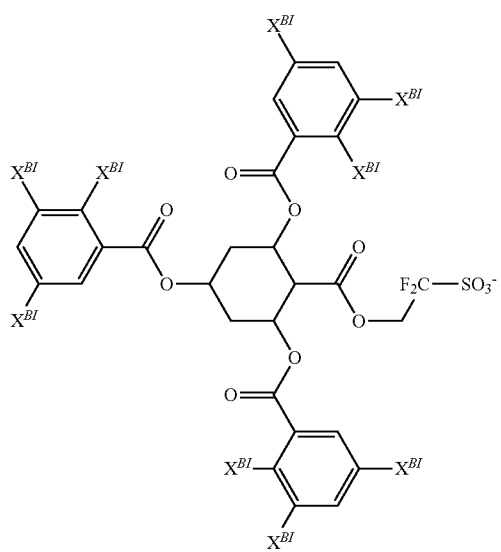
156
-continued
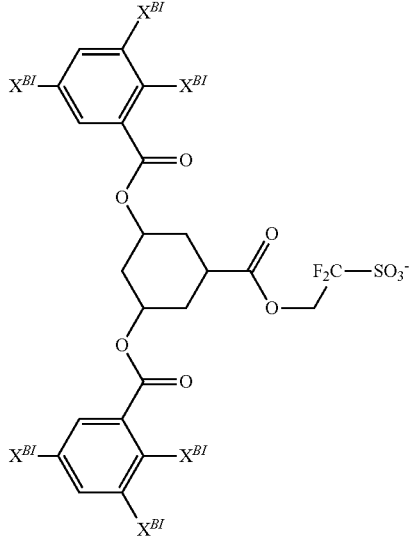
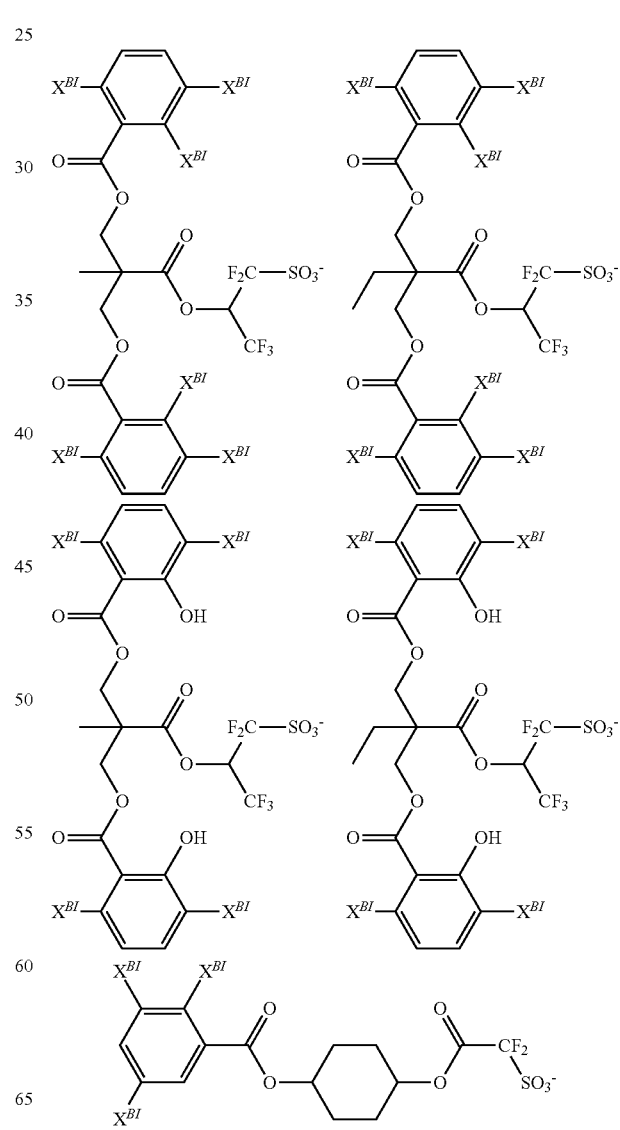

157
-continued
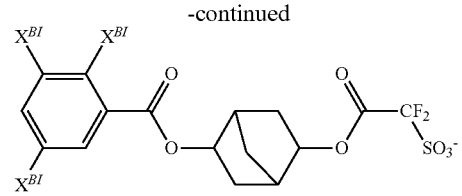
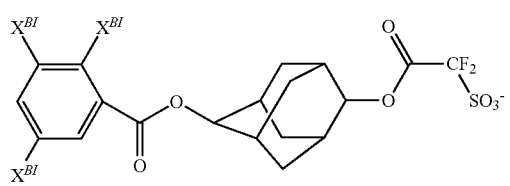
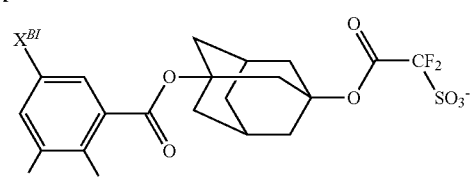
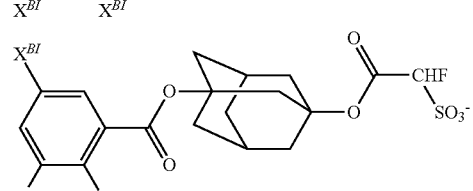
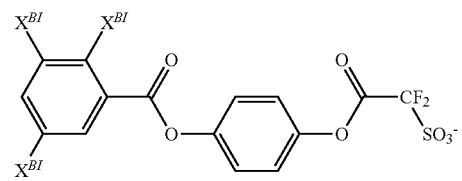
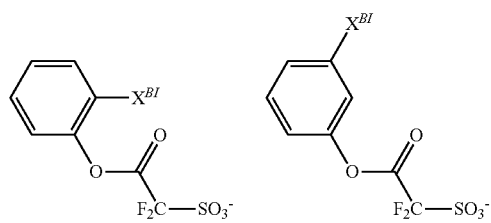
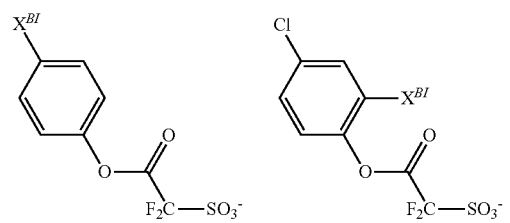
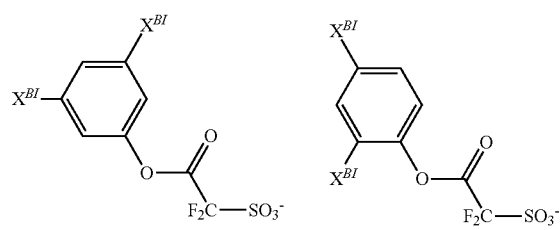
158
-continued
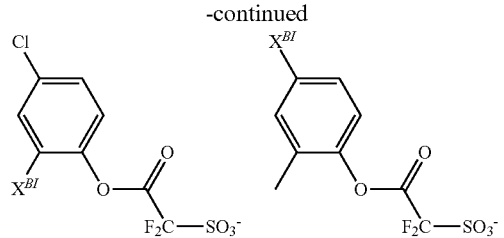
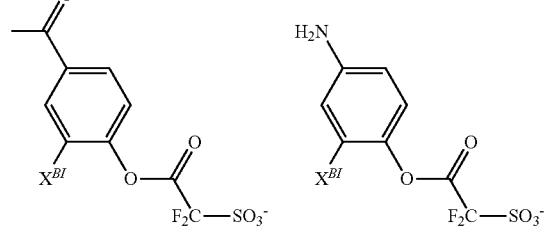
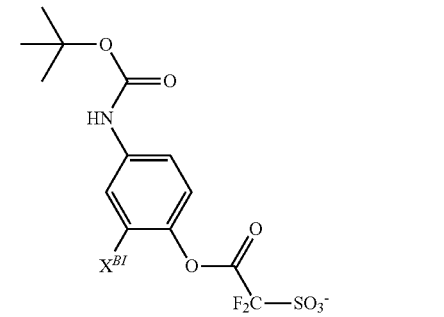
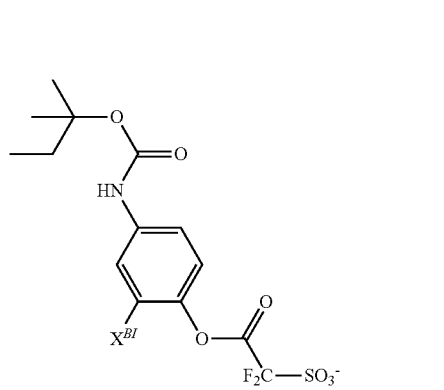
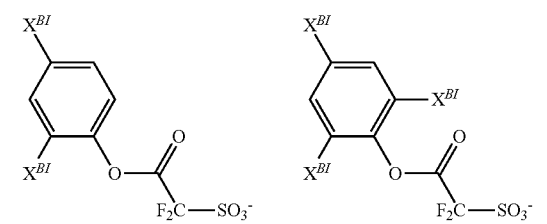
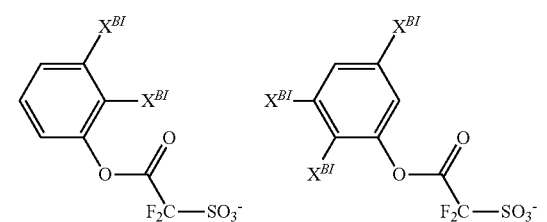

-continued
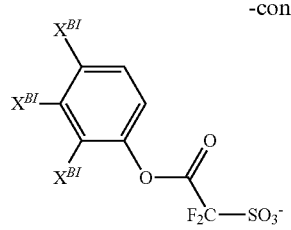
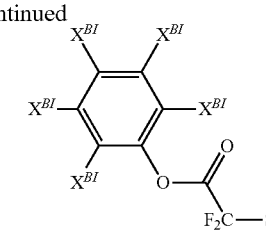
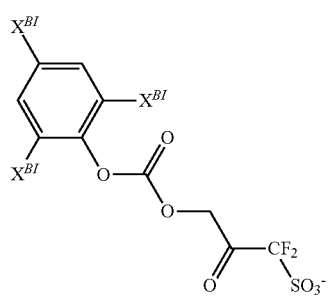
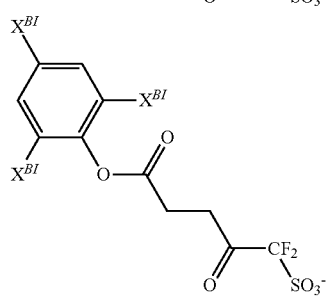
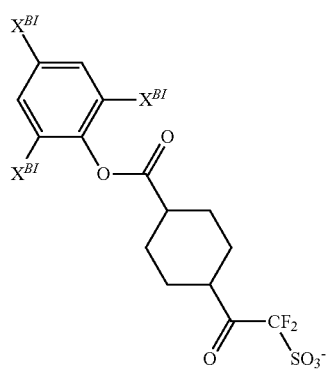
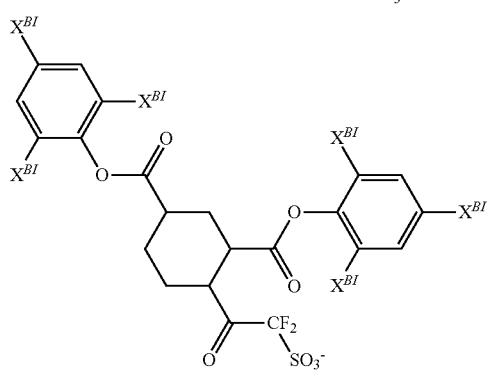
-continued
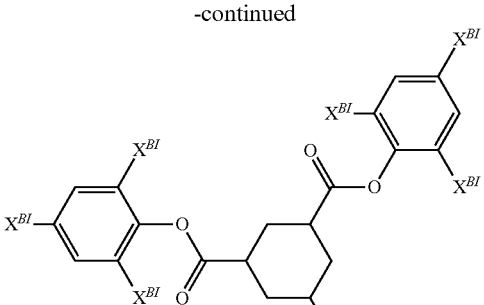
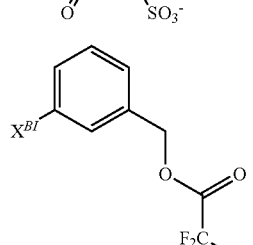
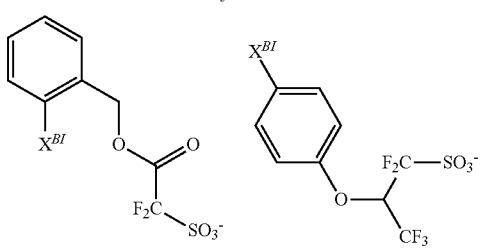
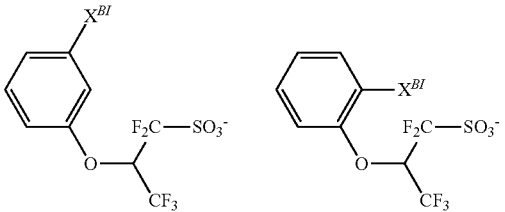
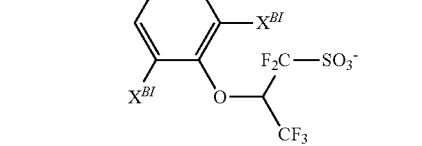
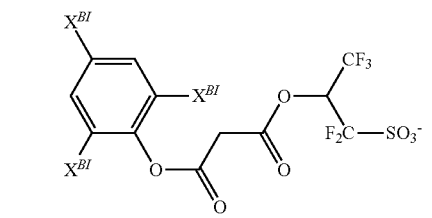
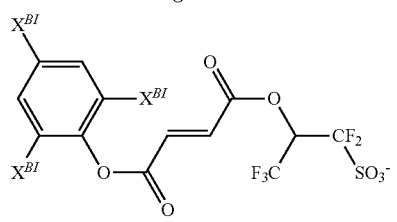

161
-continued
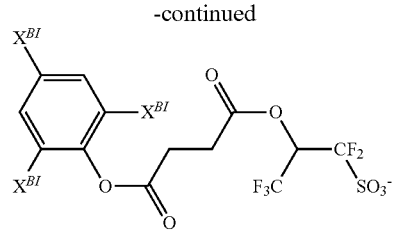
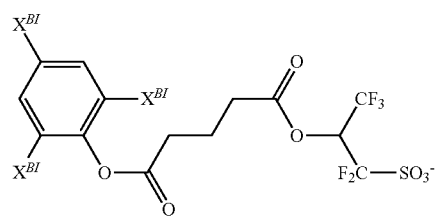
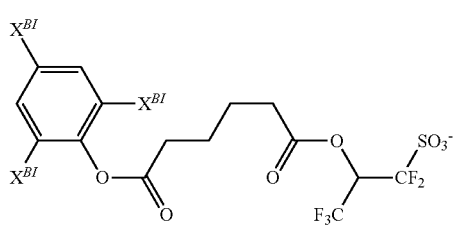
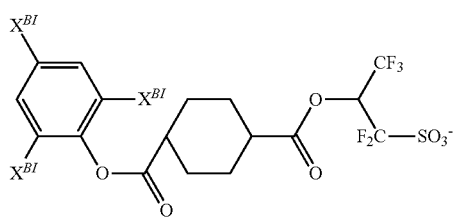
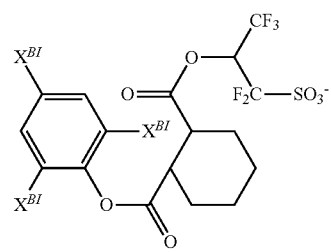
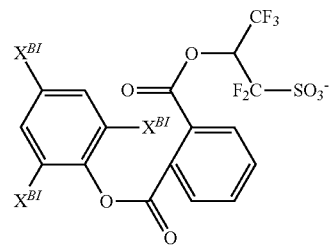
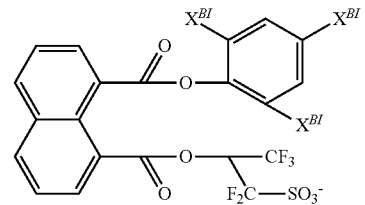
162
-continued
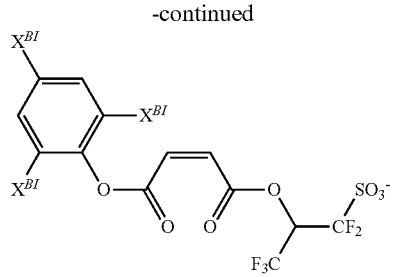
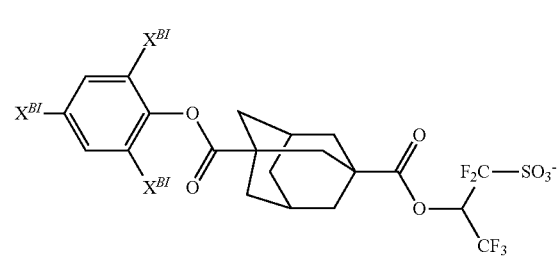
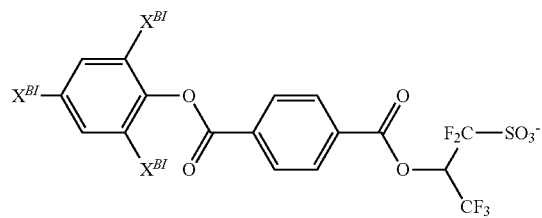
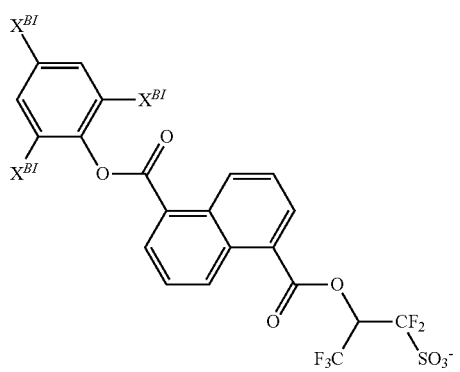
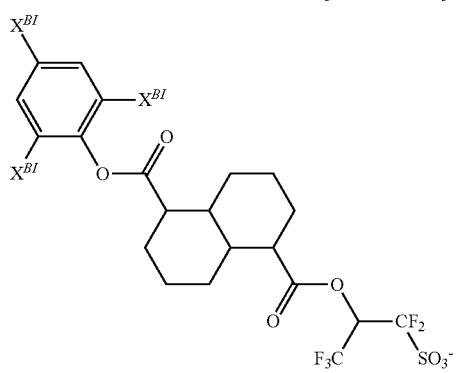
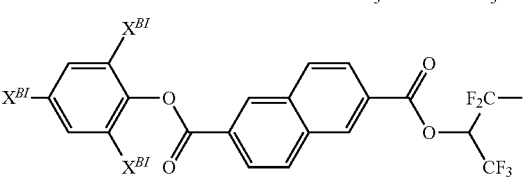

-continued
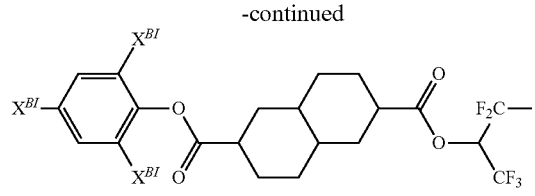
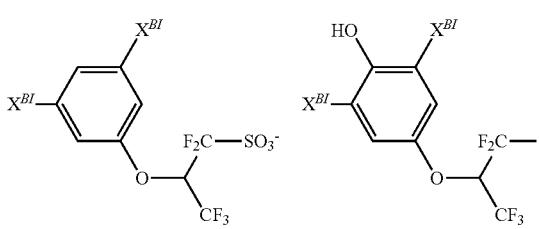
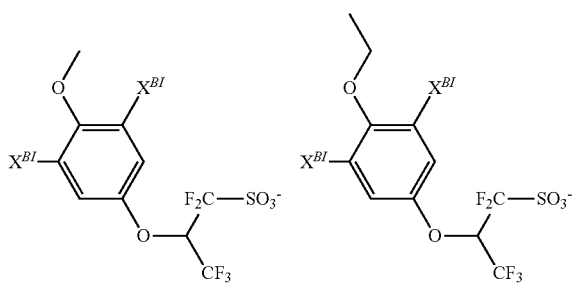
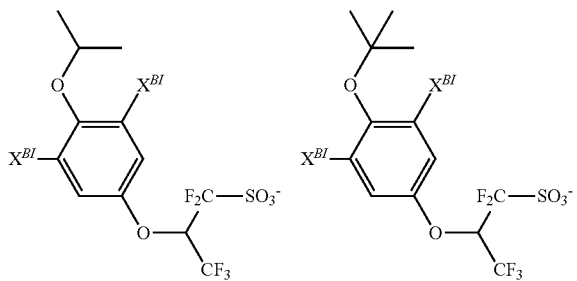
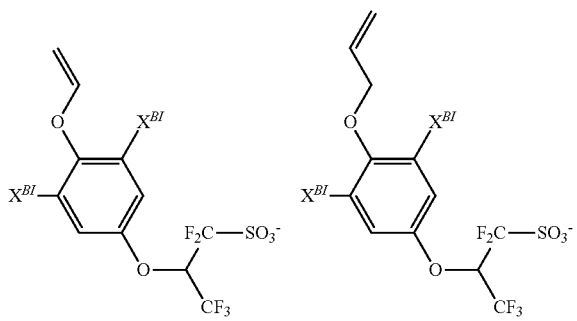
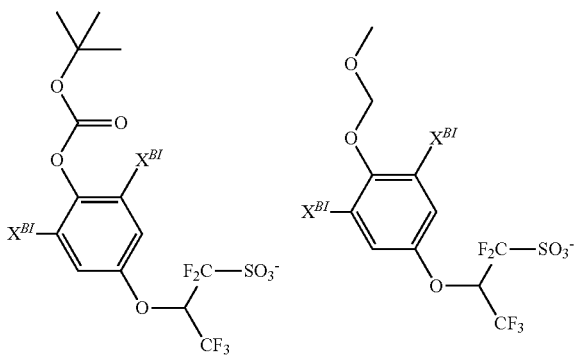
-continued
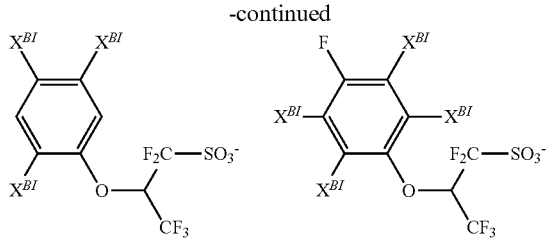
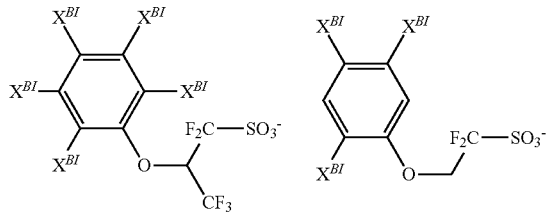
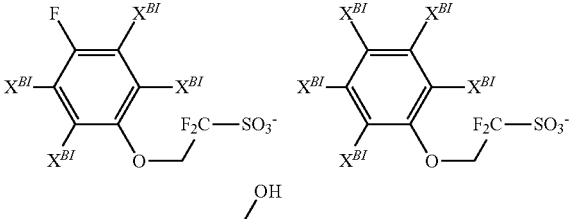
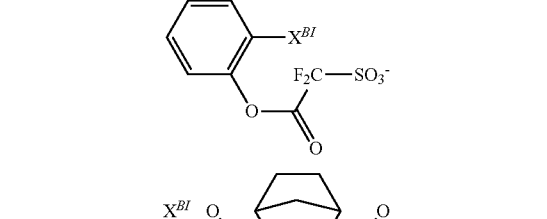
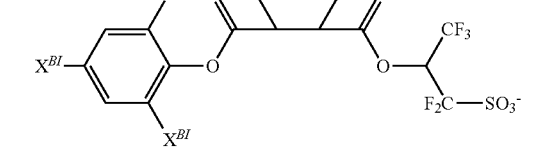
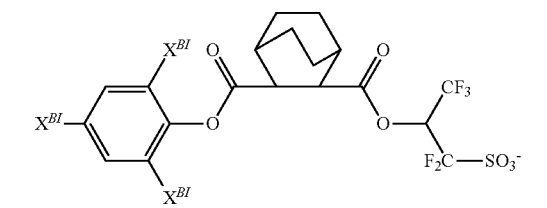
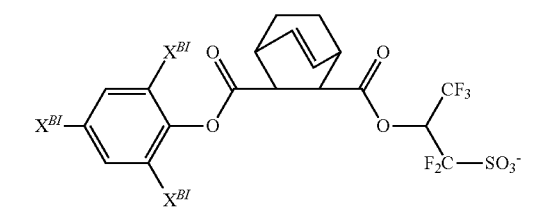
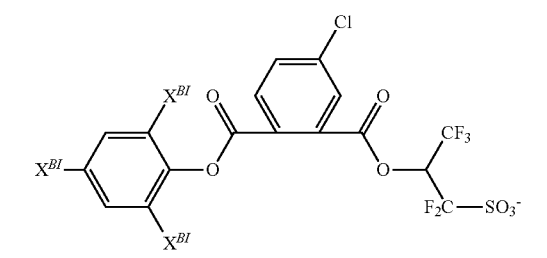

165
-continued
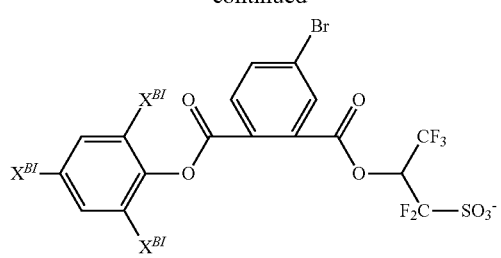
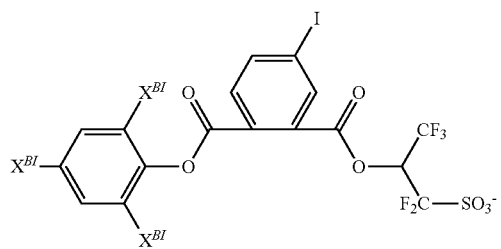
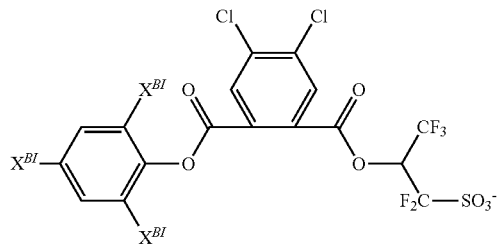
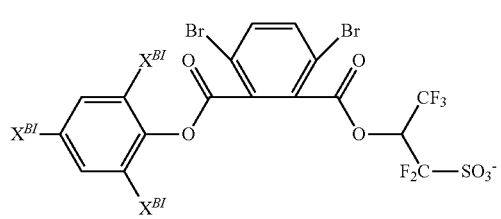
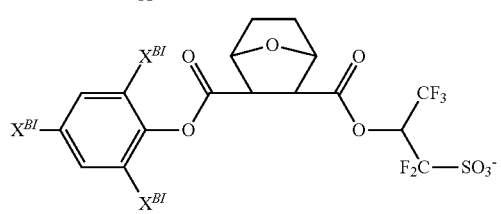
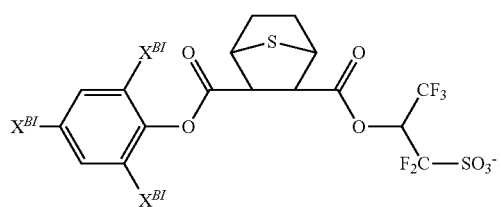
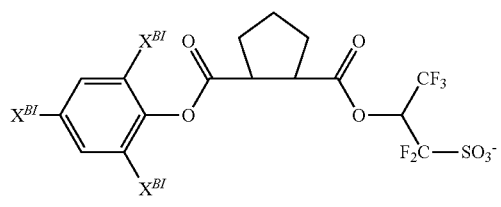
166
-continued
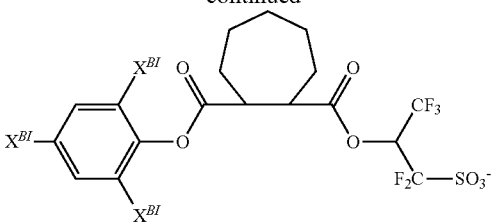
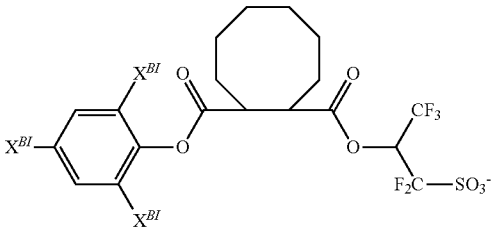
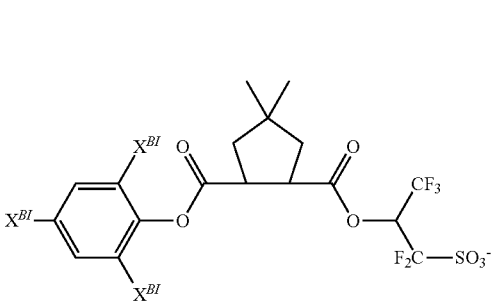
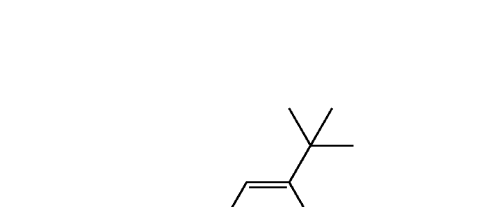
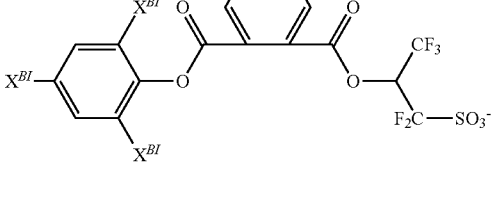
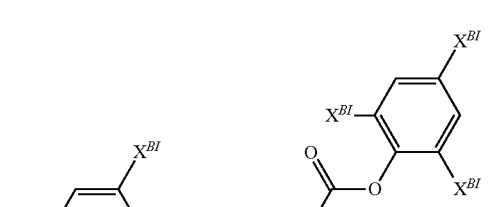
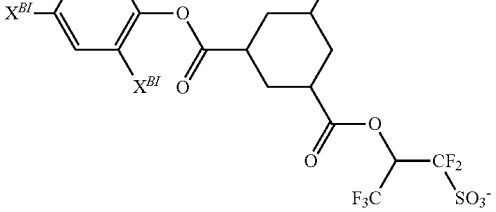

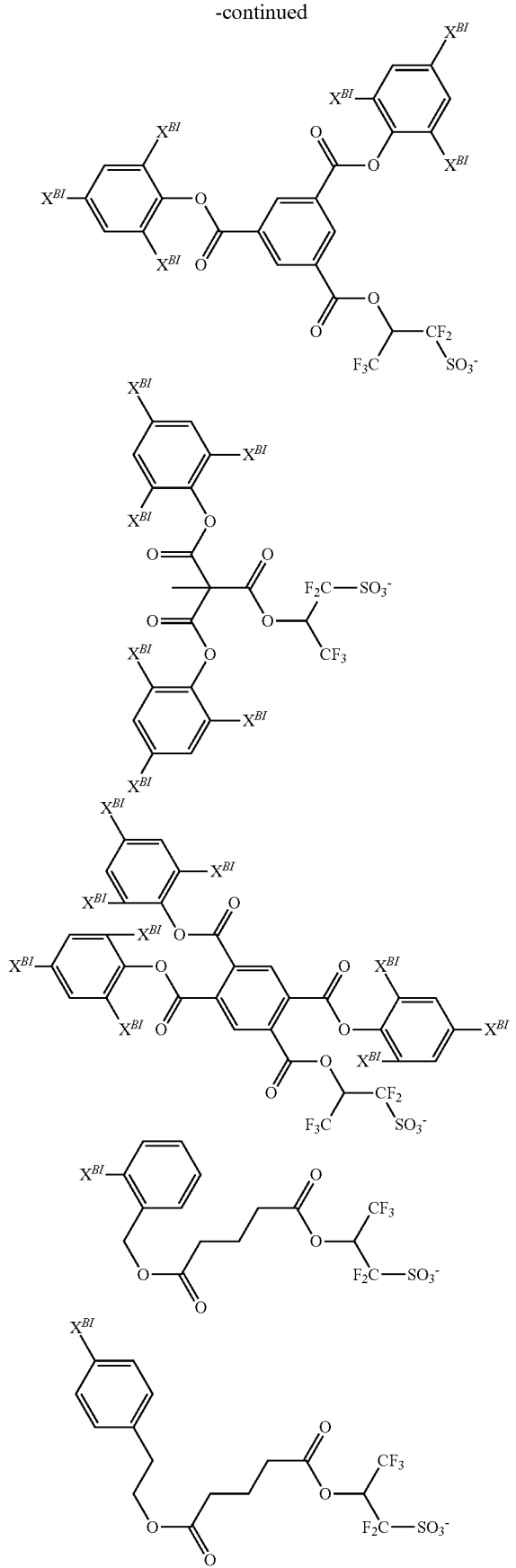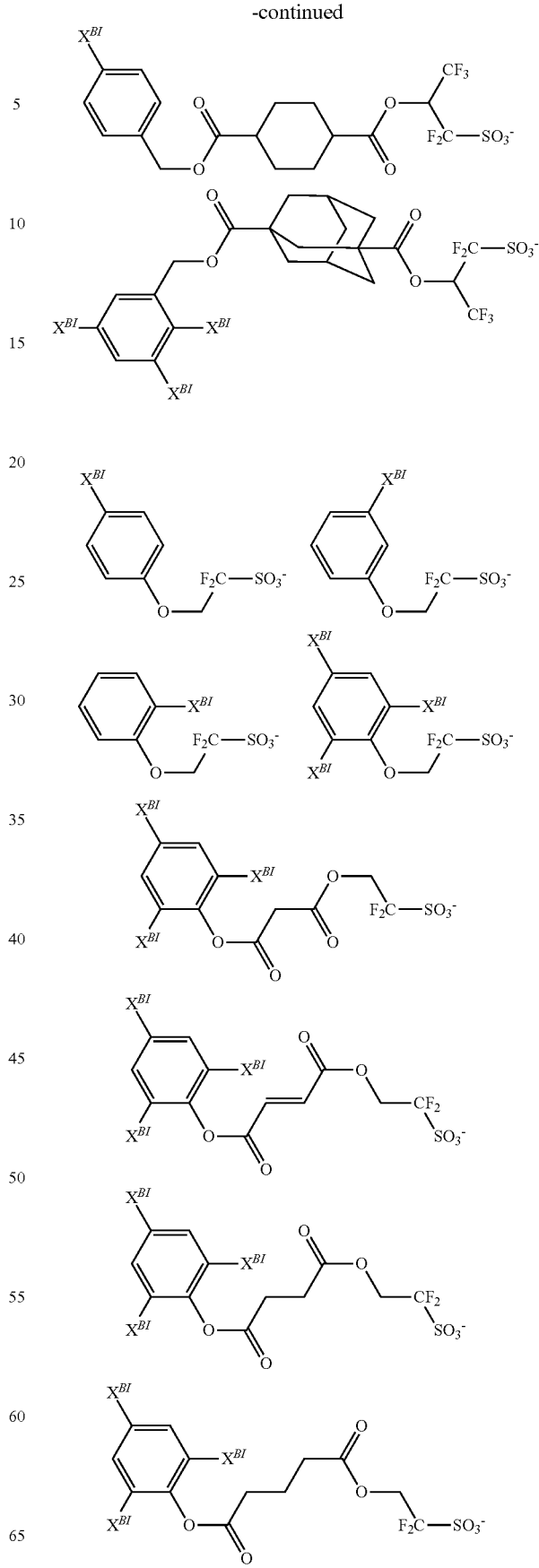

-continued
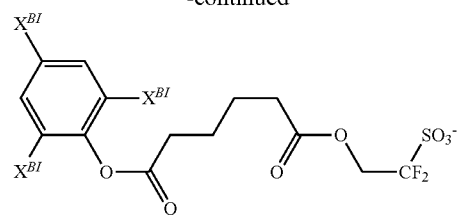
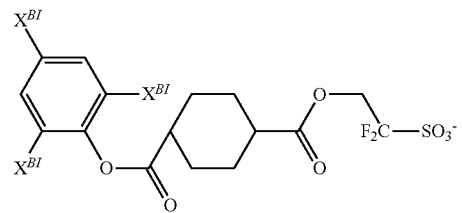
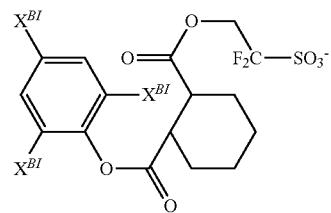
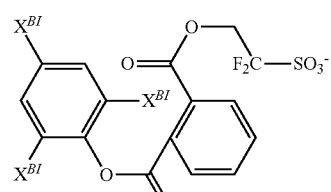
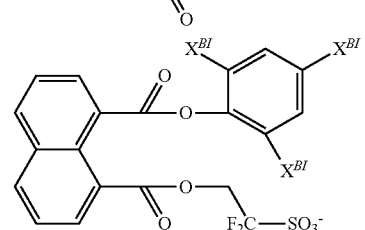
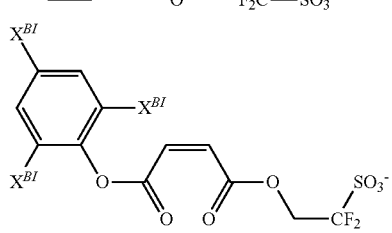
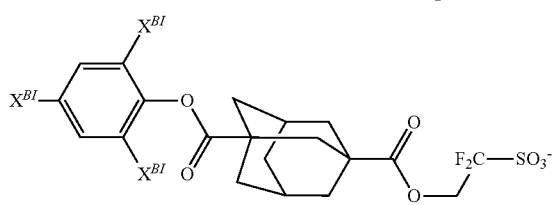
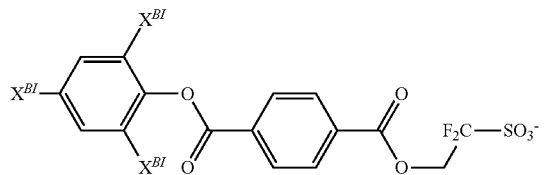
-continued
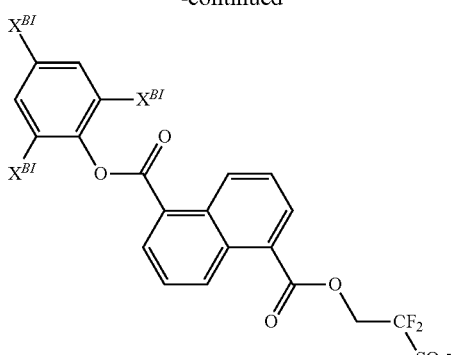
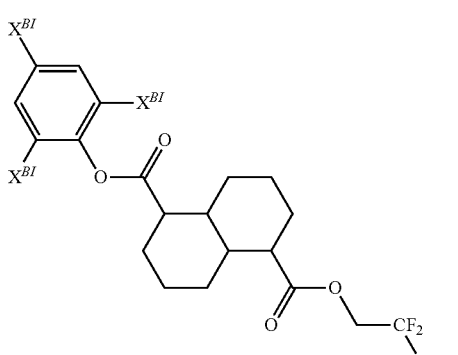
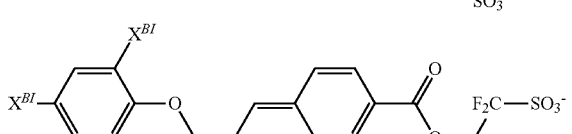
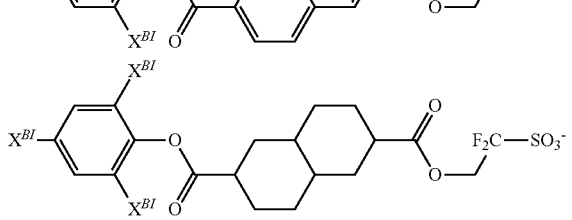
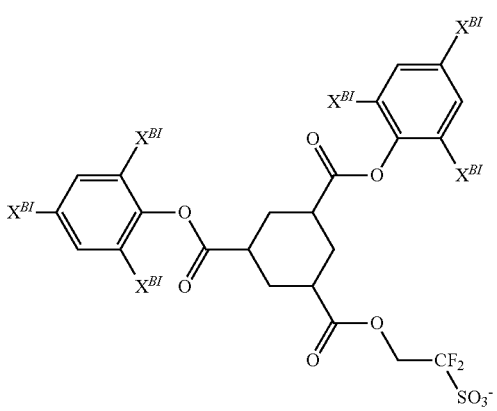

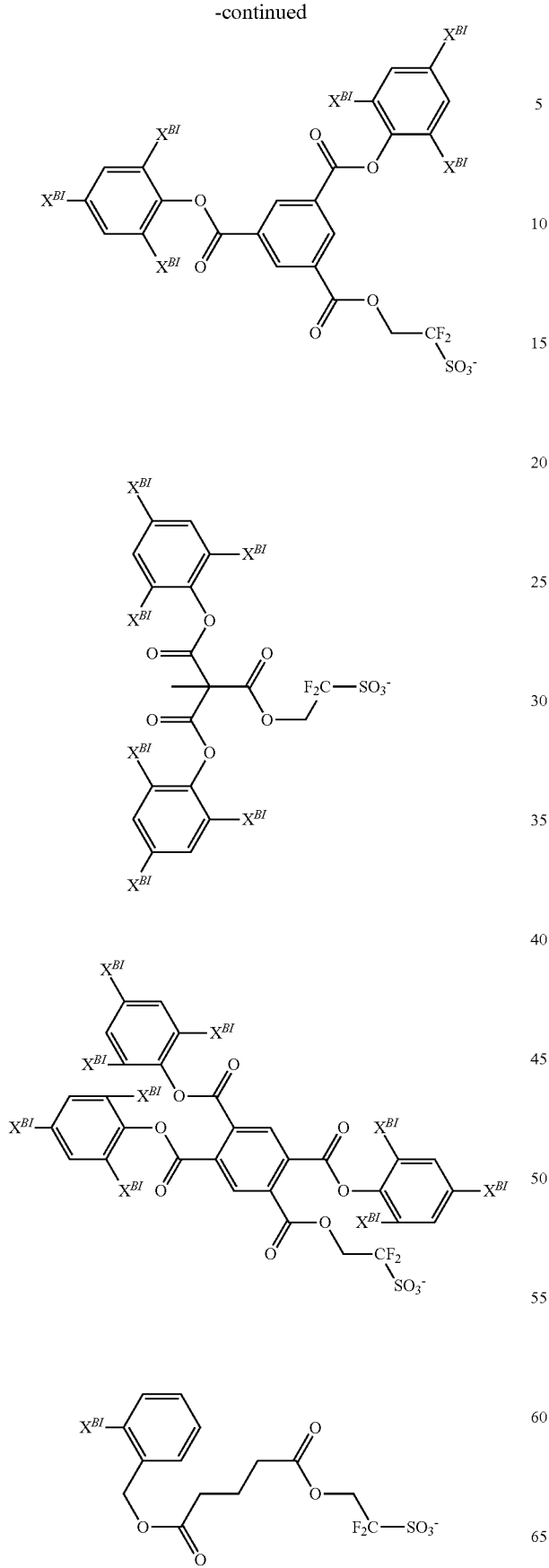
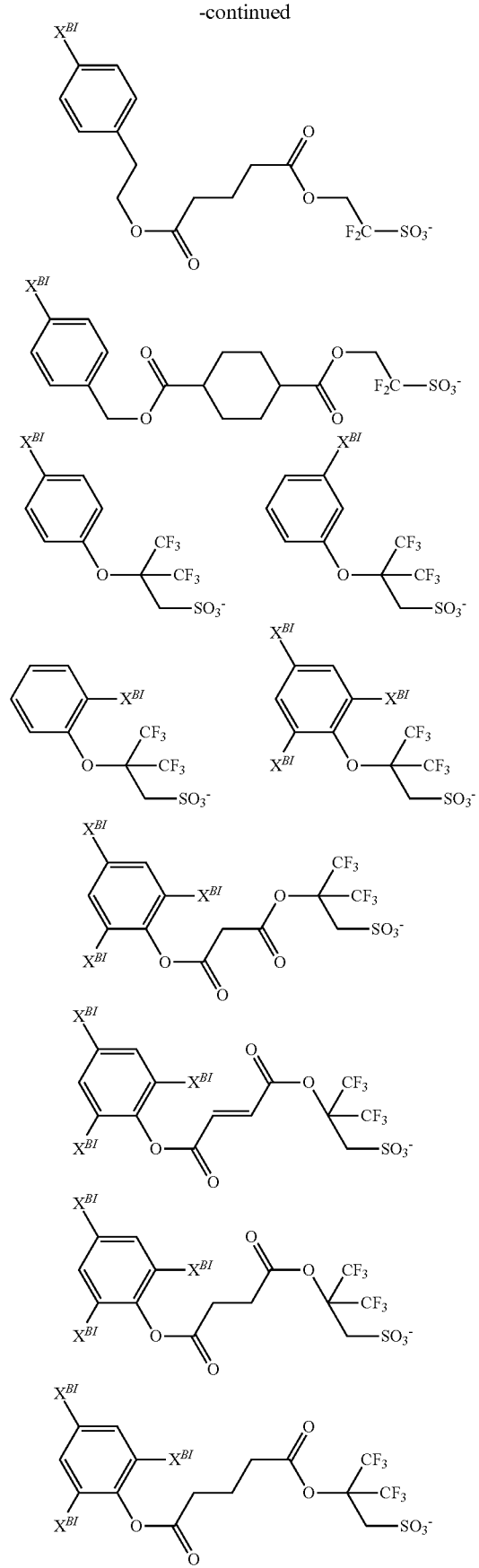

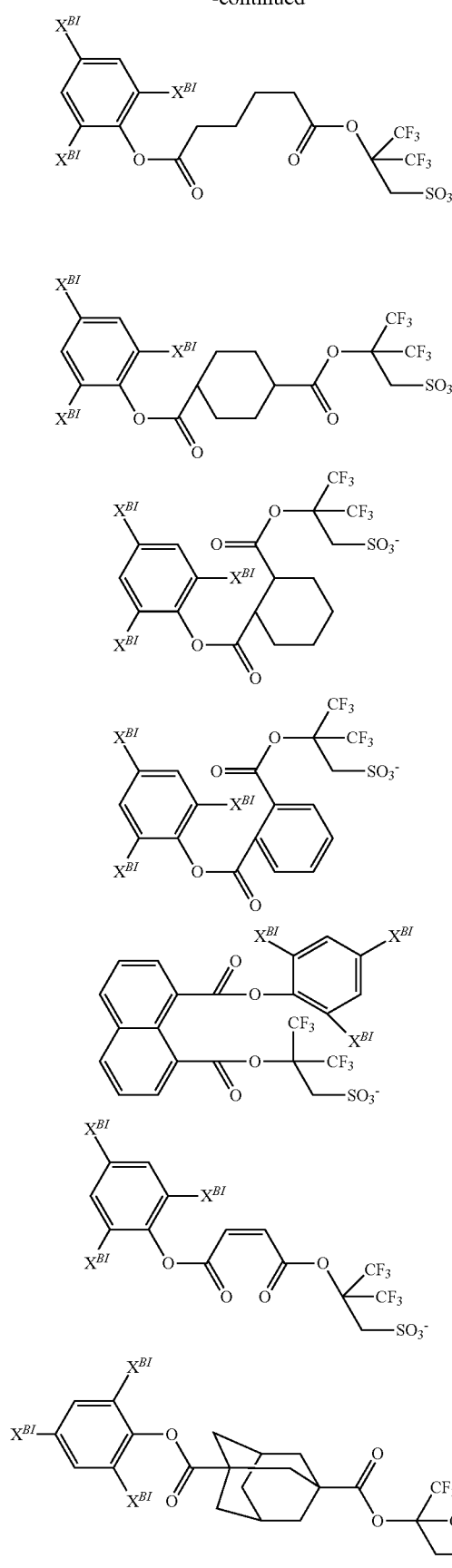
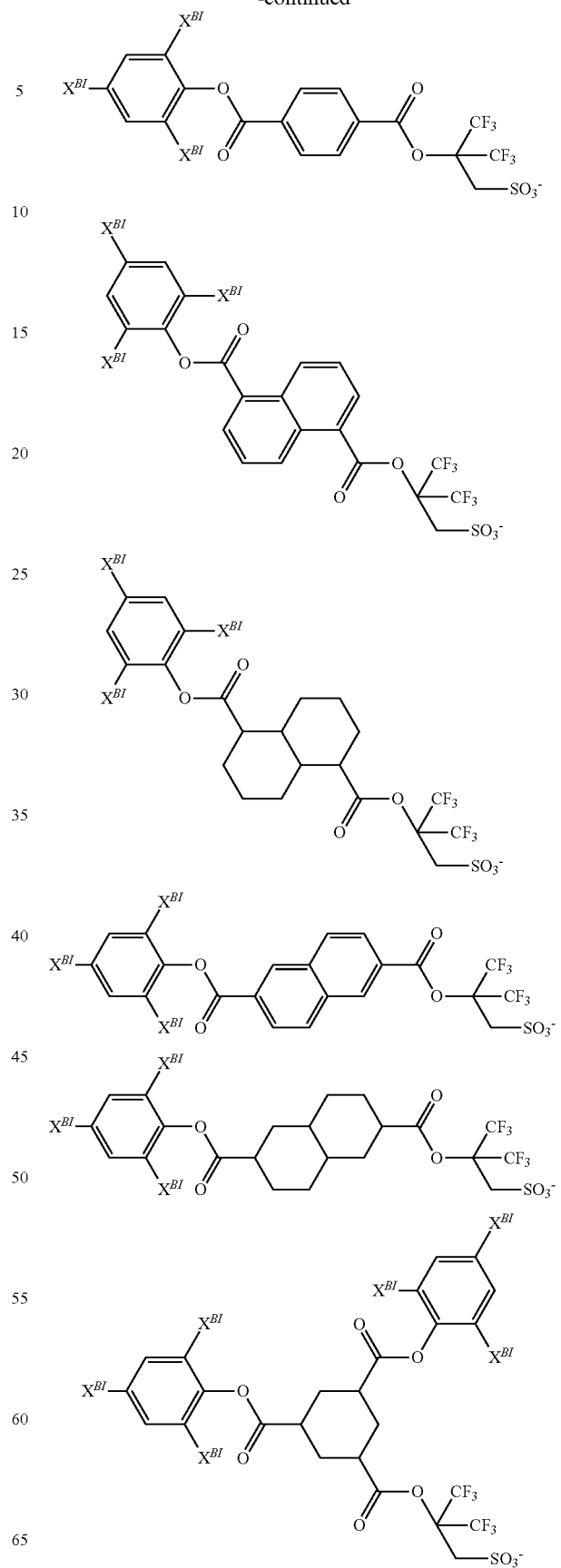

-continued

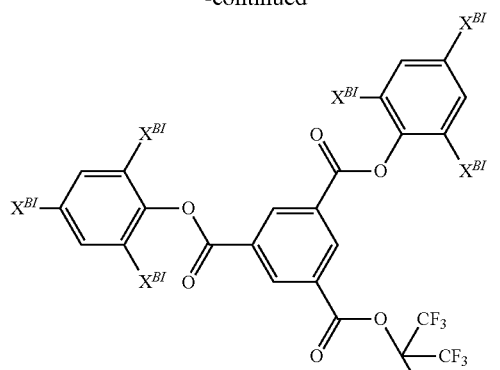

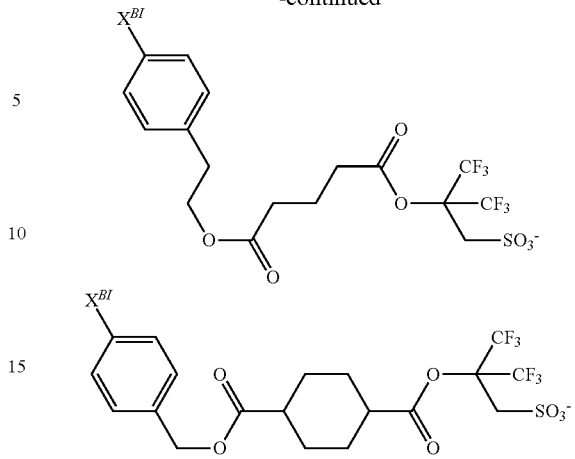

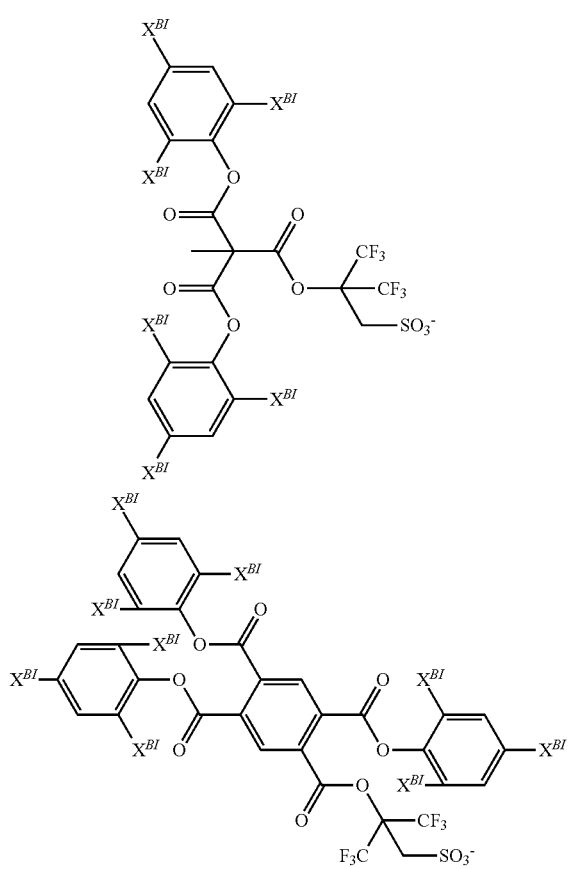

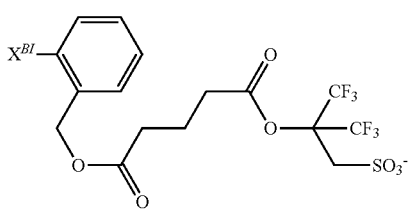

When used, the acid generator of addition type is preferably added in an amount of 0.1 to 50 parts, and more preferably 1 to 40 parts by weight per 100 parts by weight of the base polymer. When the base polymer has recurring units (f) incorporated therein and/or when the acid generator of addition type is added, the positive resist composition functions as a chemically amplified positive resist composition.

Organic Solvent

An organic solvent may be added to the resist composition. The organic solvent used herein is not particularly limited as long as the foregoing and other components are soluble therein. Examples of the organic solvent are described in JP-A 2008-111103, paragraphs [0144]-[0145] (U.S. Pat. No. 7,537,880). Exemplary solvents include ketones such as cyclohexanone, cyclopentanone and methyl-2-n-pentyl ketone; alcohols such as 3-methoxybutanol, 3-methyl-3-methoxybutanol, 1-methoxy-2-propanol, 1-ethoxy-2-propanol and diacetone alcohol (DAA); ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether, esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, which may be used alone or in admixture.

The organic solvent is preferably added in an amount of 100 to 10,000 parts, and more preferably 200 to 8,000 parts by weight per 100 parts by weight of the base polymer.

Other Components

With the foregoing components, other components such as a surfactant, dissolution inhibitor, and crosslinker may be blended in any desired combination to formulate a chemically amplified positive or negative resist composition. This positive or negative resist composition has a very high sensitivity in that the dissolution rate in developer of the base polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs.

Exemplary surfactants are described in JP-A 2008-111103, paragraphs [0165]-[0166]. Inclusion of a surfactant may improve or control the coating characteristics of the resist composition. While the surfactant may be used alone or in admixture, it is preferably added in an amount of 0.0001 to 10 parts by weight per 100 parts by weight of the base polymer.

In the case of positive resist compositions, inclusion of a dissolution inhibitor may lead to an increased difference in dissolution rate between exposed and unexposed areas and a further improvement in resolution. In the case of negative resist compositions, a negative pattern may be formed by adding a crosslinker to reduce the dissolution rate of a resist film in exposed area.

The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds having a molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in U.S. Pat. No. 7,771,914 (JP-A 2008-122932, paragraphs [0155]-[0178]).

In the positive resist composition, the dissolution inhibitor is preferably added in an amount of 0 to 50 parts, more preferably 5 to 40 parts by weight per 100 parts by weight of the base polymer. The dissolution inhibitor may be used alone or in admixture.

Suitable crosslinkers which can be used herein include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyl ether group. These compounds may be used as an additive or introduced into a polymer side chain as a pendant. Hydroxy-containing compounds may also be used as the crosslinker. The crosslinker may be used alone or in admixture.

Of the foregoing crosslinkers, examples of the epoxy compound include tris(2,3-epoxypropyl) isocyanurate, trimethylolethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycohluril, tetramethylol glycoluril compounds having 1 to 4 methylol groups methoxymethylated and mixtures thereof tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof; and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyl ether group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

In the negative resist composition, the crosslinker is preferably added in an amount of 0.1 to 50 parts, more preferably 1 to 40 parts by weight per 100 parts by weight of the base polymer.

In the resist composition of the invention, a quencher other than the inventive amine compound may be blended. The other quencher is typically selected from conventional basic compounds. Conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxyl group, ether bond, ester bond, lactone ring, cyano group, or sulfonic acid ester bond as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Onium salts such as sulfonium salts, iodonium salts and ammonium salts of sulfonic acids which are not fluorinated at α-position as described in U.S. Pat. No. 8,795,942 (JP-A 2008-158339) and similar onium salts of carboxylic acid may also be used as the other quencher. While an α-fluorinated sulfonic acid, imide acid, and methide acid are necessary to deprotect the acid labile group of carboxylic acid ester, an α-non-fluorinated sulfonic acid and a carboxylic acid are released by salt exchange with an α-non-fluorinated onium salt. An α-non-fluorinated sulfonic acid and a carboxylic acid function as a quencher because they do not induce deprotection reaction.

Also useful are quenchers of polymer type as described in U.S. Pat. No. 7,598,016 (JP-A 2008-239918). The polymeric quencher segregates at the resist surface after coating and thus enhances the rectangularity of resist pattern. When a protective film is applied as is often the case in the immersion lithography, the polymeric quencher is also effective for preventing a film thickness loss of resist pattern or rounding of pattern top.

The other quencher is preferably added in an amount of 0 to 5 parts, more preferably 0 to 4 parts by weight per 100 parts by weight of the base polymer. The other quencher may be used alone or in admixture.

To the resist composition, a polymeric additive or water repellency improver may also be added for improving the water repellency on surface of a resist film as spin coated. The water repellency improver may be used in the topcoatless immersion lithography. Suitable water repellency improvers include polymers having a fluoroalkyl group and polymers having a specific structure with a1,1,1,3,3,3-hexafluoro-2-propanol residue and are described in JP-A 2007-297590 and JP-A 2008-111103, for example. The water repellency improver to be added to the resist composition should be soluble in the alkaline developer and organic solvent developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, thus preventing any hole pattern opening failure after development. The water repellency improver may be used alone or in admixture. An appropriate amount of the water repellency improver is 0 to 20 parts, more preferably 0.5 to 10 parts by weight per 100 parts by weight of the base polymer.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer.

Pattern Forming Process

The resist composition is used in the fabrication of various integrated circuits. Pattern formation using the resist composition may be performed by well-known lithography processes. The process generally involves coating, exposure, and development. If necessary, any additional steps may be added.

For example, the positive resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hot plate at a temperature of 60 to 150° C. for 10 seconds to 30 minutes, preferably at 80 to 120° C. for 30 seconds to 20 minutes. The resulting resist film is generally 0.01 to 2 μm thick.

The resist film is then exposed to a desired pattern of high-energy radiation such as UV, deep-UV, EB, EUV, x-ray, soft x-ray, excimer laser light, γ-ray or synchrotron radiation. When UV, deep-UV, EUV, x-ray, soft x-ray, excimer laser light, γ-ray or synchrotron radiation is used as the high-energy radiation, the resist film is exposed thereto through a mask having a desired pattern in a dose of preferably about 1 to 200 $mJ/cm^2$, more preferably about 10 to 100 $mJ/cm^2$. When EB is used as the high-energy radiation, the resist film is exposed thereto through a mask having a desired pattern or directly in a dose of preferably about 0.1 to 100 $\mu C/cm^2$, more preferably about 0.5 to 50 $\mu C/cm^2$. It is appreciated that the inventive resist composition is suited in micropatterning using KrF excimer laser, ArF excimer laser, EB, EUV, x-ray, soft x-ray, γ-ray or synchrotron radiation, especially in micropatterning using EB or EUV.

After the exposure, the resist film may be baked (PEB) on a hot plate or in an oven at 30 to 150° C. for 10 seconds to 30 minutes, preferably at 50 to 120° C. for 30 seconds to 20 minutes.

After the exposure or PEB, in the case of positive resist, the resist film is developed in a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed area is dissolved in the developer whereas the resist film in the unexposed area is not dissolved. In this way, the desired positive pattern is formed on the substrate. Inversely in the case of negative resist, the exposed area of resist film is insolubilized and the unexposed area is dissolved in the developer.

In an alternative embodiment, a negative pattern may be formed via organic solvent development using a positive resist composition comprising a base polymer having an acid labile group. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-sec-butyl ether, di-n-pentyl ether, diisopentyl ether, di-sec-pentyl ether, di-tert-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, tert-butylbenzene and mesitylene. The solvents may be used alone or in admixture.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLES

Examples of the invention are given below by way of illustration and not by way of limitation. The abbreviation "pbw" is parts by weight.

Quenchers 1 to 25 used in resist compositions have the structure shown below.

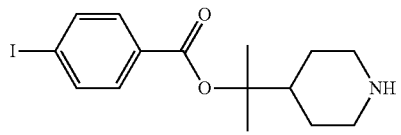

Quencher[1]

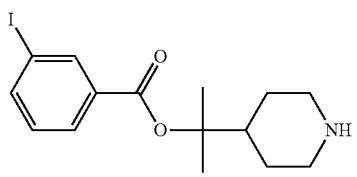

Quencher[2]

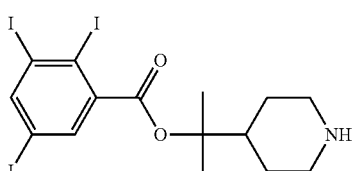

Quencher[3]

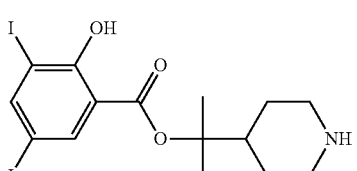

Quencher[4]

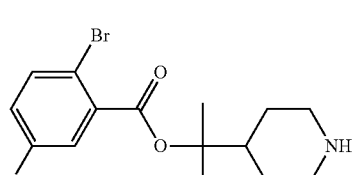

Quencher[5]

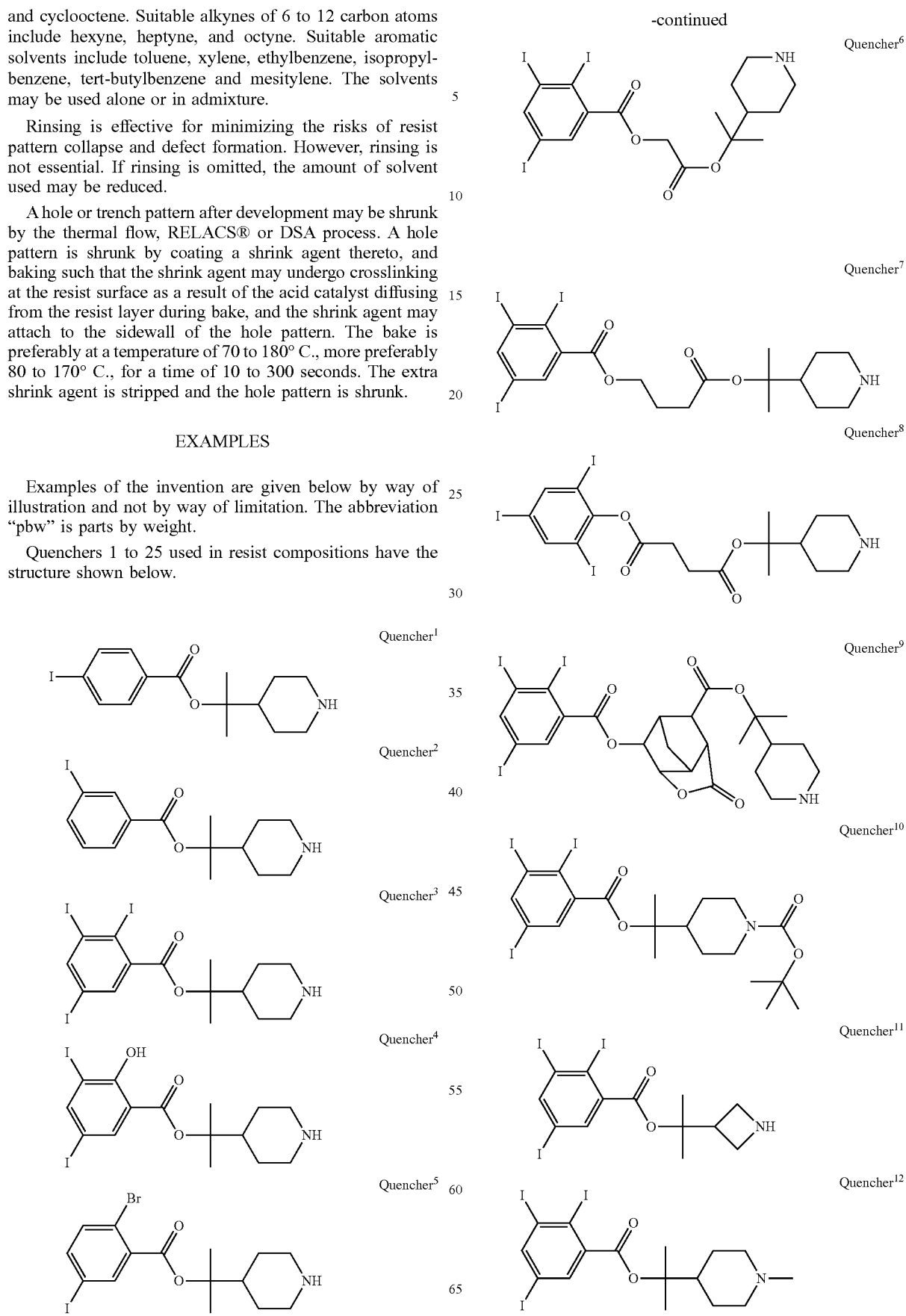

Quencher¹³
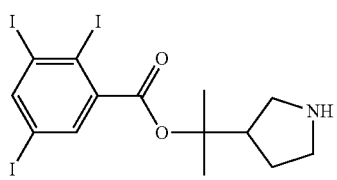
Quencher¹⁴
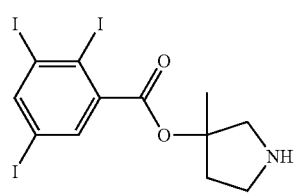
Quencher¹⁵
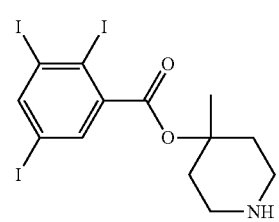
Quencher¹⁶
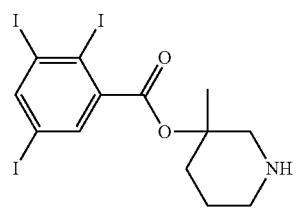
Quencher¹⁷
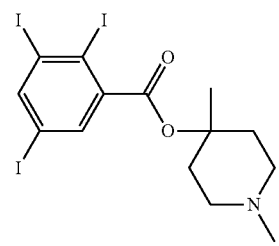
Quencher¹⁸
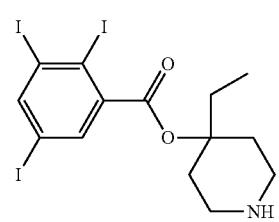
Quencher¹⁹
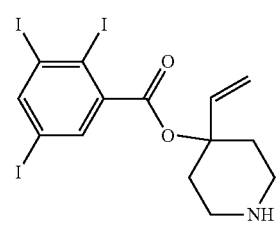
Quencher²⁰
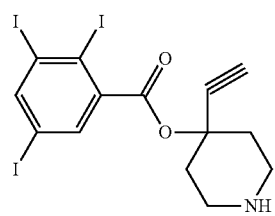
Quencher²¹
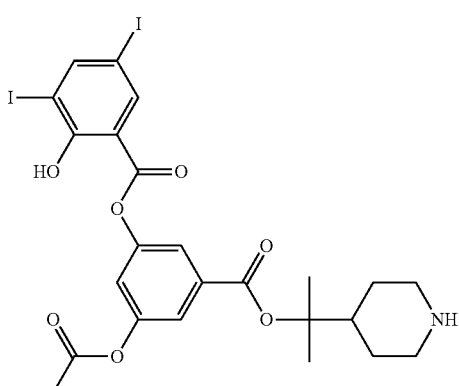
Quencher²²
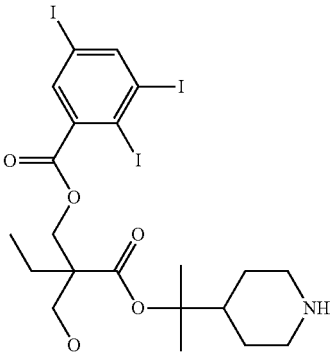
Quencher²³
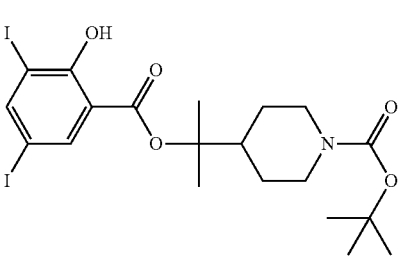

Quencher²⁴

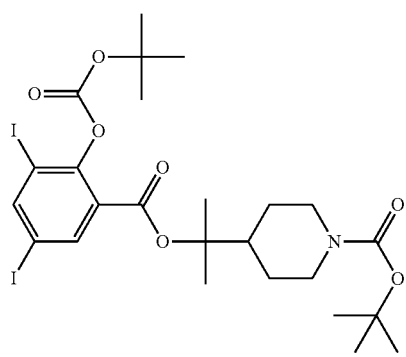

Quencher²⁵

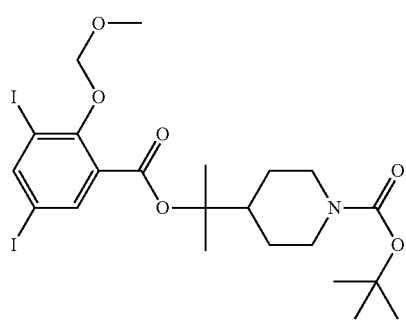

Synthesis Example

Synthesis of Base Polymers (Polymers 1 to 4)

Base polymers were prepared by combining suitable monomers, effecting copolymerization reaction thereof in tetrahydrofuran (THF) solvent, pouring the reaction solution into methanol for crystallization, repeatedly washing with hexane, isolation, and drying. The resulting polymers, designated Polymers 1 to 4, were analyzed for composition by ¹H-NMR spectroscopy, and for Mw and Mw/Mn by GPC versus polystyrene standards using THF solvent.

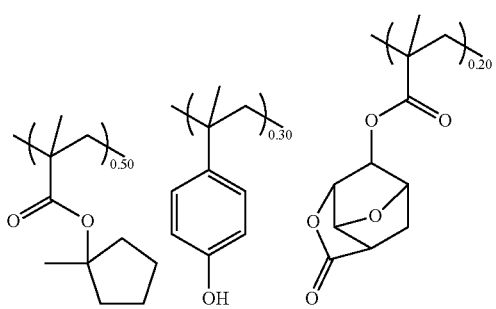

Polymer ¹
Mw = 8,600
Mw/Mn = 1.73

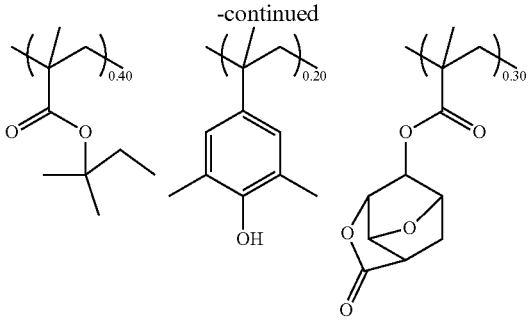

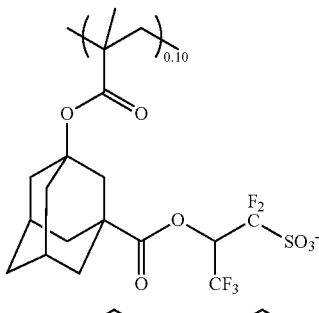

Polymer ²
Mw = 8,900
Mw/Mn = 1.89

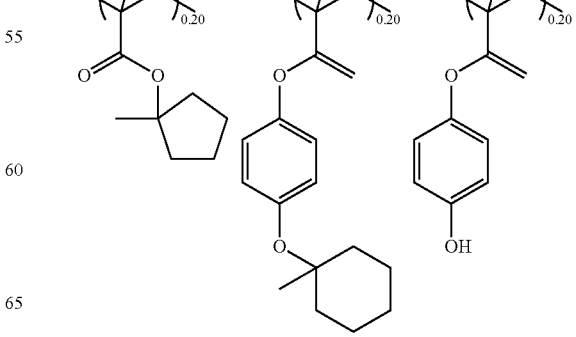

187
-continued

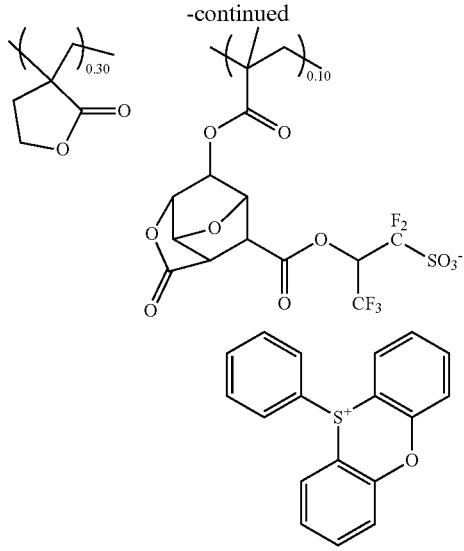

Polymer 3
Mw = 7,600
Mw/Mn = 1.73

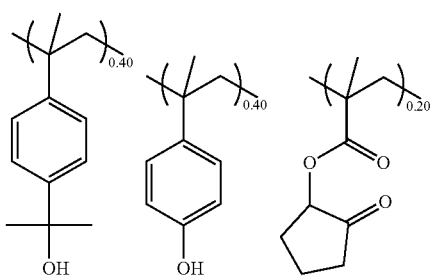

Polymer 4
Mw = 6,900
Mw/Mn = 1.62

Examples 1 to 30 and Comparative Examples 1 to 7

Resist compositions were prepared by dissolving various components in a solvent in accordance with the recipe shown in Tables 1 to 3, and filtering through a filter having a pore size of 0.2 μm. The solvent contained 100 ppm of surfactant Polyfox PF-636 (Omnova Solutions Inc.). The resist compositions of Examples 1 to 24, 26 to 30, and Comparative Examples 1 to 6 were of positive tone, while the resist compositions of Example 25 and Comparative Example 7 were of negative tone.

The components in Tables 1 to 3 are as identified below.

Organic Solvents:
  PGMEA (propylene glycol monomethyl ether acetate)
  CyH (cyclohexanone)
  PGME (propylene glycol monomethyl ether)
  DAA (diacetone alcohol)

188
Acid Generators PAG 1 to PAG 4

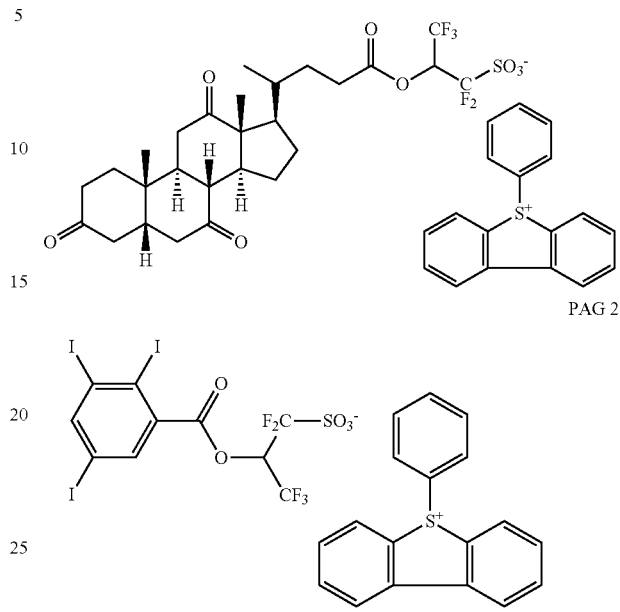

PAG 1

PAG 2

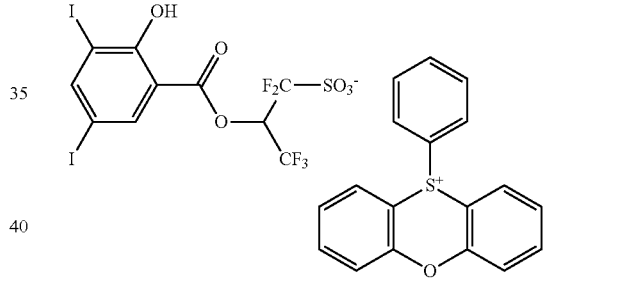

PAG 3

PAG 4

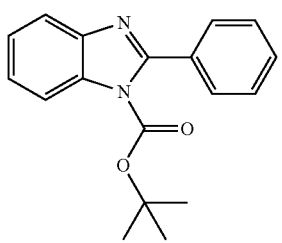

Comparative Quencher[1]

-continued

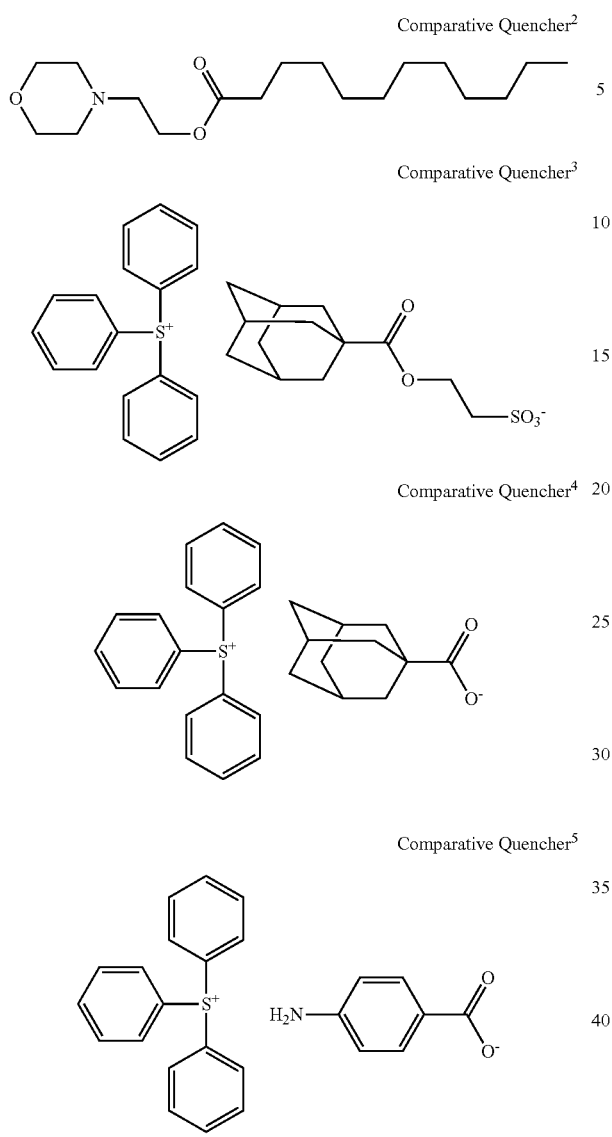

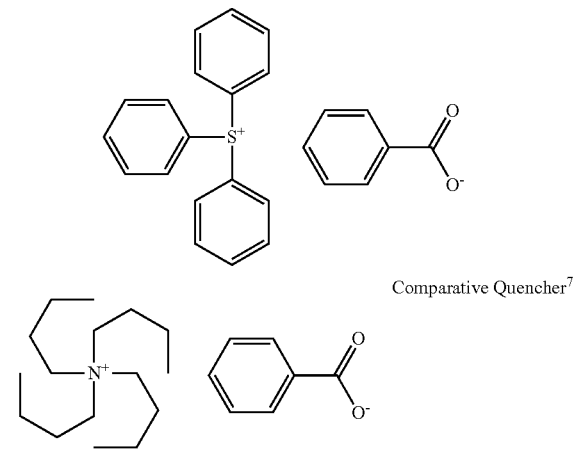

Comparative Quenchers 1 to 7
EUV Lithography Test

Each of the resist compositions in Tables 1 to 3 was spin coated on a silicon substrate having a 20-nm coating of silicon-containing spin-on hard mask SHB-A940 (Shin-Etsu Chemical Co., Ltd., silicon content 43 wt %) and prebaked on a hotplate at 105° C. for 60 seconds to form a resist film of 60 nm thick. Using an EUV scanner NXE3300 (ASML, NA 0.33, σ 0.9/0.6, quadrupole illumination), the resist film was exposed to EUV through a mask bearing a hole pattern at a pitch 46 nm (on-wafer size) and +20% bias. The resist film was baked (PEB) on a hotplate at the temperature shown in Tables 1 to 3 for 60 seconds and developed in a 2.38 wt % TMAH aqueous solution for 30 seconds to form a hole pattern having a size of 23 nm in Examples 1 to 24, 26 to 30, and Comparative Examples 1 to 6 or a dot pattern having a size of 23 nm in Example 25 and Comparative Example 7.

The resist pattern was evaluated using CD-SEM (CG-5000, Hitachi High-Technologies Corp.). The exposure dose that provides a hole or dot pattern having a size of 23 nm is reported as sensitivity. The size of 50 holes or dots in that dose was measured, from which a size variation (3σ) was computed and reported as CDU.

The resist composition is shown in Tables 1 to 3 together with the sensitivity and CDU of EUV lithography.

TABLE 1

|  |  | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Example | 1 | Polymer 1 (100) | PAG 1 (30) | Quencher 1 (3.73) | PGMEA (400) CyH (2,000) PGME (100) | 100 | 26 | 2.6 |
|  | 2 | Polymer 1 (100) | PAG 2 (30) | Quencher 2 (3.73) | PGMEA (400) CyH (2,000) PGME (100) | 100 | 26 | 2.7 |
|  | 3 | Polymer 1 (100) | PAG 2 (30) | Quencher 3 (6.24) | PGMEA (400) CyH (2,000) PGME (100) | 100 | 20 | 2.5 |
|  | 4 | Polymer 1 (100) | PAG 2 (30) | Quencher 4 (5.15) | PGMEA (400) CyH (2,000) PGME (100) | 100 | 22 | 2.4 |
|  | 5 | Polymer 1 (100) | PAG 2 (30) | Quencher 5 (4.52) | PGMEA (400) CyH (2,000) PGME (100) | 100 | 24 | 2.7 |
|  | 6 | Polymer 1 (100) | PAG 2 (30) | Quencher 6 (6.83) | PGMEA (400) CyH (2,000) PGME (100) | 100 | 24 | 2.4 |

TABLE 1-continued

|  | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|
| 7 | Polymer 1 (100) | PAG 2 (30) | Quencher 7 (7.11) | PGMEA (400) CyH (2,000) PGME (100) | 100 | 23 | 2.5 |
| 8 | Polymer 1 (100) | PAG 2 (30) | Quencher 8 (6.97) | PGMEA (400) CyH (2,000) PGME (100) | 100 | 23 | 2.4 |
| 9 | Polymer 1 (100) | PAG 2 (30) | Quencher 9 (8.05) | PGMEA (400) CyH (2,000) PGME (100) | 100 | 24 | 2.5 |
| 10 | Polymer 1 (100) | PAG 2 (30) | Quencher 10 (7.25) | PGMEA (400) CyH (2,000) PGME (100) | 100 | 23 | 2.5 |
| 11 | Polymer 1 (100) | PAG 2 (30) | Quencher 11 (5.97) | PGMEA (400) CyH (2,000) PGME (100) | 100 | 25 | 2.7 |
| 12 | Polymer 1 (100) | PAG 2 (30) | Quencher 12 (6.39) | PGMEA (400) CyH (2,000) PGME (100) | 100 | 25 | 2.3 |
| 13 | Polymer 1 (100) | PAG 2 (30) | Quencher 13 (6.10) | PGMEA (400) CyH (2,000) PGME (100) | 100 | 25 | 2.7 |
| 14 | Polymer 1 (100) | PAG 2 (30) | Quencher 14 (5.82) | PGMEA (400) CyH (2,000) PGME (100) | 100 | 25 | 2.6 |
| 15 | Polymer 1 (100) | PAG 2 (30) | Quencher 15 (5.97) | PGMEA (400) CyH (2,000) PGME (100) | 100 | 25 | 2.6 |
| 16 | Polymer 1 (100) | PAG 2 (30) | Quencher 16 (5.97) | PGMEA (400) CyH (2,000) PGME (100) | 100 | 24 | 2.6 |
| 17 | Polymer 1 (100) | PAG 2 (30) | Quencher 17 (6.11) | PGMEA (400) CyH (2,000) PGME (100) | 100 | 24 | 2.4 |

TABLE 2

|  |  | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Example | 18 | Polymer 1 (100) | PAG 1 (30) | Quencher 18 (6.11) | PGMEA (400) CyH (2,000) PGME (100) | 100 | 24 | 2.6 |
|  | 19 | Polymer 1 (100) | PAG 1 (30) | Quencher 19 (6.09) | PGMEA (400) CyH (2,000) PGME (100) | 100 | 25 | 2.6 |
|  | 20 | Polymer 1 (100) | PAG 1 (30) | Quencher 20 (6.07) | PGMEA (400) CyH (2,000) PGME (100) | 100 | 25 | 2.6 |
|  | 21 | Polymer 2 (100) | — | Quencher 7 (7.11) | PGMEA (2,000) DAA (500) | 100 | 25 | 2.1 |
|  | 22 | Polymer 3 (100) | — | Quencher 7 (7.11) | PGMEA (2,000) DAA (500) | 100 | 20 | 2.0 |
|  | 23 | Polymer 3 (100) | PAG 3 (15) | Quencher 7 (7.11) | PGMEA (2,000) DAA (500) | 95 | 21 | 2.4 |
|  | 24 | Polymer 3 (100) | PAG 4 (15) | Quencher 7 (7.11) | PGMEA (2,000) DAA (500) | 95 | 22 | 2.3 |
|  | 25 | Polymer 4 (100) | PAG 1 (20) | Quencher 7 (7.11) | PGMEA (400) CyH (2,000) PGME (100) | 120 | 29 | 3.3 |
|  | 26 | Polymer 2 (100) | — | Quencher 21 (10.22) | PGMEA (2,000) DAA (500) | 100 | 23 | 2.3 |
|  | 27 | Polymer 2 (100) | — | Quencher 22 (12.37) | PGMEA (2,000) DAA (500) | 100 | 22 | 2.4 |
|  | 28 | Polymer 2 (100) | — | Quencher 23 (6.15) | PGMEA (2,000) DAA (500) | 100 | 26 | 2.3 |
|  | 29 | Polymer 2 (100) | — | Quencher 24 (7.15) | PGMEA (2,000) DAA (500) | 100 | 25 | 2.4 |
|  | 30 | Polymer 2 (100) | — | Quencher 25 (6.59) | PGMEA (2,000) DAA (500) | 100 | 26 | 2.4 |

TABLE 3

| | | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Comparative Example | 1 | Polymer 1 (100) | PAG 2 (30) | Comparative Quencher 1 (1.20) | PGMEA (400) CyH (2,000) PGME (100) | 100 | 28 | 3.5 |
| | 2 | Polymer 1 (100) | PAG 2 (30) | Comparative Quencher 2 (1.20) | PGMEA (400) CyH (2,000) PGME (100) | 100 | 28 | 3.2 |
| | 3 | Polymer 1 (100) | PAG 2 (30) | Comparative Quencher 3 (3.20) | PGMEA (400) CyH (2,000) PGME (100) | 100 | 30 | 2.9 |
| | 4 | Polymer 1 (100) | PAG 2 (30) | Comparative Quencher 4 (3.20) | PGMEA (400) CyH (2,000) PGME (100) | 100 | 28 | 2.8 |
| | 5 | Polymer 1 (100) | PAG 2 (30) | Comparative Quencher 5 (3.20) | PGMEA (400) CyH (2,000) PGME (100) | 100 | 38 | 3.0 |
| | 6 | Polymer 1 (100) | PAG 2 (30) | Comparative Quencher 6 (3.20) | PGMEA (400) CyH (2,000) PGME (100) | 100 | 30 | 3.0 |
| | 7 | Polymer 4 (100) | PAG 2 (30) | Comparative Quencher 7 (3.65) | PGMEA (400) CyH (2,000) PGME (100) | 120 | 30 | 4.9 |

It is demonstrated in Tables 1 to 3 that resist compositions comprising amine compounds containing an iodized aromatic ring and a tertiary ester structure form patterns having a high sensitivity and a reduced value of CDU.

Japanese Patent Application No. 2019-010892 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising a base polymer and a quencher, the quencher containing at least one compound selected from amine compounds having the formula (A-1) and amine compounds having the formula (A-2):

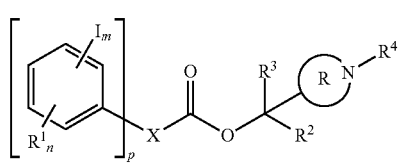

(A-1)

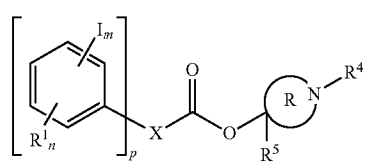

(A-2)

wherein X is a single bond or a $C_1$-$C_{20}$ divalent linking group which may contain an ether bond, carbonyl moiety, ester bond, amide bond, sultone ring, lactam ring, carbonate bond, halogen, hydroxyl moiety or carboxyl moiety, $R^1$ is hydrogen, hydroxyl, an optionally halo-substituted $C_1$-$C_6$ alkyl group, optionally halo-substituted $C_1$-$C_6$ alkoxy group, optionally halo-substituted $C_2$-$C_6$ acyloxy group, optionally halo-substituted $C_1$-$C_4$ alkylsulfonyloxy group, fluorine, chlorine, bromine, amino, nitro, cyano, —NR$^{14}$—C(=O)—R$^{1B}$, or —NR$^{14}$—C(=O)—O—R$^{1B}$, R$^{14}$ is hydrogen or a $C_1$-$C_6$ alkyl group, R$^{1B}$ is a $C_1$-$C_6$ alkyl group or $C_2$-$C_8$ alkenyl group, $R^2$ and $R^3$ are each independently a $C_1$-$C_6$ alkyl group, $R^2$ and $R^3$ may bond together to form a ring with the carbon atom to which they are attached, $R^4$ and $R^6$ are each independently hydrogen, a $C_1$-$C_4$ straight or branched alkyl group, $C_2$-$C_{12}$ straight or branched alkoxycarbonyl group, $C_6$-$C_{15}$ aryloxycarbonyl group, or $C_6$-$C_{14}$ aralkyloxycarbonyl group, $R^5$ is a $C_1$-$C_6$ alkyl group, $C_2$-$C_6$ alkenyl group, $C_2$-$C_6$ alkynyl group, or $C_6$-$C_{12}$ aryl group, R is a $C_2$-$C_{10}$ alicyclic group to form a ring with the nitrogen atom, m is an integer of 1 to 5, n is an integer of 0 to 4, and 1≤m+n≤5, and p is 1 or 2.

2. The resist composition of claim 1, further comprising an acid generator capable of generating a sulfonic acid, imide acid or methide acid.

3. The resist composition of claim 1, further comprising an organic solvent.

4. The resist composition of claim 1 wherein the base polymer comprises recurring units having the formula (a1) or recurring units having the formula (a2):

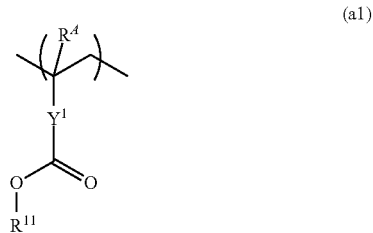

(a1)

(a2)

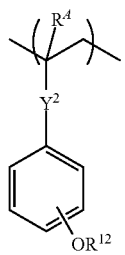

wherein $R^A$ is each independently hydrogen or methyl, $R^{11}$ and $R^{12}$ each are an acid labile group, $Y^1$ is a single bond, phenylene group, naphthylene group, or $C_1$-$C_{12}$ linking group containing at least one moiety selected from ester bond and lactone ring, and $Y^2$ is a single bond or ester bond.

5. The resist composition of claim 4 which is a chemically amplified positive resist composition.

6. The resist composition of claim 1 wherein the base polymer is free of an acid labile group.

7. The resist composition of claim 6 which is a chemically amplified negative resist composition.

8. The resist composition of claim 1, further comprising a surfactant.

9. The resist composition of claim 1 wherein the base polymer further comprises recurring units of at least one type selected from recurring units having the formulae (f1) to (f3):

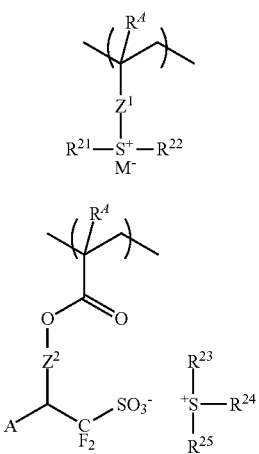

(f3)

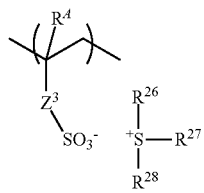

wherein $R^A$ is each independently hydrogen or methyl, $Z^1$ is a single bond, phenylene group, —O—$Z^{11}$—, —C(=O)—O—$Z^{11}$— or —C(=O)—NH—$Z^{11}$—, $Z^{11}$ is a $C_1$-$C_6$ alkanediyl group, $C_2$-$C_6$ alkenediyl group, or phenylene group, which may contain a carbonyl, ester bond, ether bond or hydroxyl moiety, $Z^2$ is a single bond, —$Z^{21}$—C(=O)—O—, —$Z^{21}$—O— or —$Z^{21}$—O—C(=O)—, $Z^{21}$ is a $C_1$-$C_{12}$ alkanediyl group which may contain a carbonyl moiety, ester bond or ether bond, $Z^3$ is a single bond, methylene, ethylene, phenylene, fluorinated phenylene, —O—$Z^{31}$—, —C(=O)—O—$Z^{31}$—, or —C(=O)—NH—$Z^{31}$—, $Z^{31}$ is a $C_1$-$C_6$ alkanediyl group, $C_2$-$C_6$ alkenediyl group, phenylene group, fluorinated phenylene group, or trifluoromethyl-substituted phenylene group, which may contain a carbonyl moiety, ester bond, ether bond or hydroxyl moiety, $R^{21}$ to $R^{28}$ are each independently a $C_1$-$C_{20}$ monovalent hydrocarbon group which may contain a heteroatom, any two of $R^{23}$, $R^{24}$ and $R^{25}$ or any two of $R^{26}$, $R^{27}$ and $R^{28}$ may bond together to form a ring with the sulfur atom to which they are attached, A is hydrogen or trifluoromethyl, and $M^-$ is a non-nucleophilic counter ion.

10. A process for forming a pattern comprising the steps of applying the resist composition of claim 1 to form a resist film on a substrate, exposing the resist film to high-energy radiation, and developing the exposed resist film in a developer.

11. The process of claim 10 wherein the high-energy radiation is ArF excimer laser radiation of wavelength 193 nm or KrF excimer laser radiation of wavelength 248 nm.

12. The process of claim 10 wherein the high-energy radiation is EB or EUV of wavelength 3 to 15 nm.

* * * * *